(12) United States Patent
Chen et al.

(10) Patent No.: US 11,578,079 B2
(45) Date of Patent: Feb. 14, 2023

(54) SUMO INHIBITOR COMPOUNDS AND USES THEREOF

(71) Applicants: CITY OF HOPE, Duarte, CA (US); Suvalent Therapeutics, Inc., Thousand Oaks, CA (US)

(72) Inventors: Yuan Chen, Arcadia, CA (US); Xiaohu Ouyang, Rosemead, CA (US); Sung Wook Yi, Los Angeles, CA (US); Ted Charles Judd, Granada Hills, CA (US)

(73) Assignees: City of Hope, Duarte, CA (US); Suvalent Therapeutics, Inc., Thousand Oaks, CA (US)

( * ) Notice: Subject to any disclaimer, the term of this patent is extended or adjusted under 35 U.S.C. 154(b) by 0 days.

(21) Appl. No.: 17/263,487

(22) PCT Filed: Jul. 31, 2019

(86) PCT No.: PCT/US2019/044404
§ 371 (c)(1),
(2) Date: Jan. 26, 2021

(87) PCT Pub. No.: WO2020/028525
PCT Pub. Date: Feb. 6, 2020

(65) Prior Publication Data
US 2022/0298171 A1 Sep. 22, 2022

Related U.S. Application Data

(60) Provisional application No. 62/712,822, filed on Jul. 31, 2018.

(51) Int. Cl.
*C07D 493/08* (2006.01)
*C07D 493/18* (2006.01)
*A61P 35/00* (2006.01)

(52) U.S. Cl.
CPC ......... *C07D 493/08* (2013.01); *C07D 493/18* (2013.01)

(58) Field of Classification Search
CPC .......................... C07D 493/08; C07D 493/18
See application file for complete search history.

(56) References Cited

U.S. PATENT DOCUMENTS

| | | |
|---|---|---|
| 9,238,654 B2 | 1/2016 | Chen et al. |
| 9,447,240 B2 | 9/2016 | Suzuki et al. |
| 2016/0355504 A1 | 12/2016 | Duffey et al. |
| 2017/0360940 A1 | 12/2017 | Finn et al. |

FOREIGN PATENT DOCUMENTS

WO    WO-2012/064898 A1    5/2012

OTHER PUBLICATIONS

Hong et al. (J. Am. Chem. Soc., 2009, 131, 9986-9994).*
International Search Report dated Oct. 25, 2019, for PCT Application No. PCT/US2019/044404, filed Jul. 31, 2019, 3 pages.
Written Opinion dated Oct. 25, 2019, for PCT Application No. PCT/US2019/044404, filed Jul. 31, 2019, 6 pages.
Xu, W. et al. (2013). "Targeting the ubiquitin E1 as a novel anti-cancer strategy," *Current Pharmaceutical Design* 19(18):3201-3209.

* cited by examiner

*Primary Examiner* — Susanna Moore
(74) *Attorney, Agent, or Firm* — Mintz, Levin, Cohn, Ferris, Glovsky and Popeo, P.C.

(57) ABSTRACT

There are disclosed, inter alia, methods of inhibiting an E1 enzyme, and compounds useful for inhibiting an E1 enzyme.

19 Claims, 1 Drawing Sheet
Specification includes a Sequence Listing.

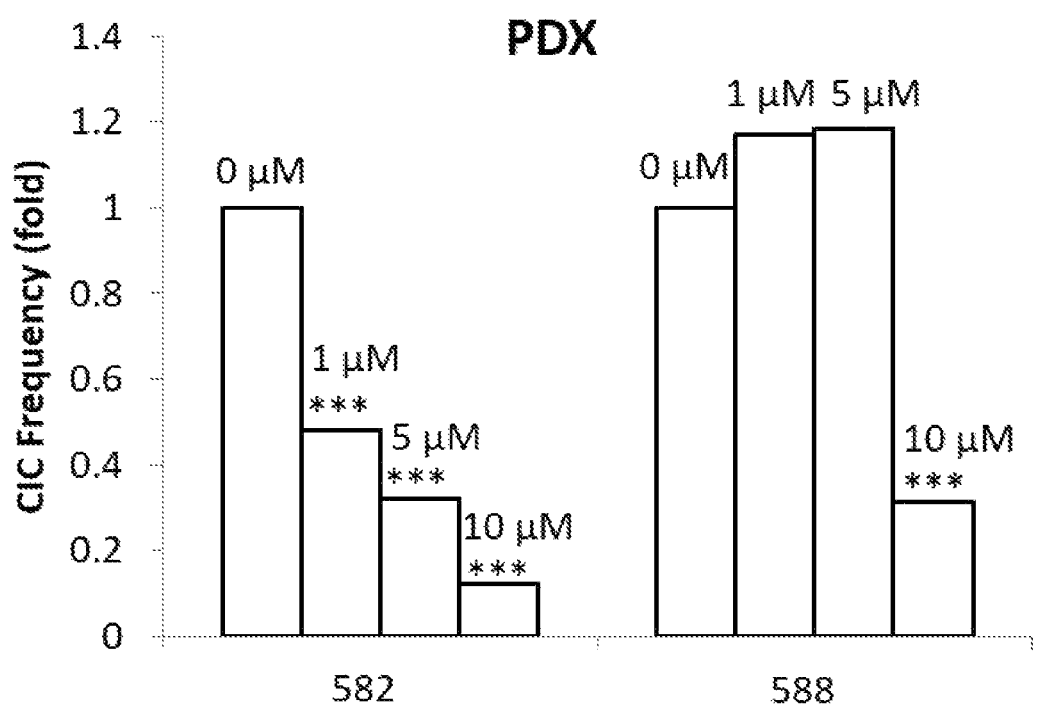

SUMO INHIBITOR COMPOUNDS AND USES THEREOF

CROSS-REFERENCES TO RELATED APPLICATIONS

This application is the national stage filing under 35 U.S.C. § 371 of International Application No. PCT/US2019/044404 filed Jul. 31, 2019, which claims the benefit of U.S. Provisional Application No. 62/712,822, filed Jul. 31, 2018, which is incorporated herein by reference in its entirety and for all purposes.

This invention was made with government support under grant numbers 2R44CA189499 and GM102538, awarded by the National Institutes of Health. The government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440-501NO1US_Sequence_Listing_ST25.txt, created Jan. 11, 2021, 7,323 bytes, machine format IBM-PC, MS Windows operating system, is hereby incorporated by reference.

BACKGROUND

Post-translational modifications of cellular proteins by the small ubiquitin-like modifier (SUMO) family of proteins are important epigenetic mechanisms for regulating various cellular functions. Aberrations in post-translational modification of cellular proteins by the small ubiquitin-like modifier (SUMO) family of proteins are associated with the pathogenesis of life-threatening diseases, such as cancer, neurodegenerative disorders, and viral infection. Indeed, the enzymes catalyzing SUMO-modification (e.g., E1 disclosed herein) are present in higher levels in cancer tissues versus normal tissues and in metastasized tumors versus normal cells, and play an important role in cancer proliferation and metastasis. Without wishing to be bound by any theory, it is believed that E1 is a target for the development of therapeutics (e.g., cancer therapeutics). Thus, there are disclosed herein methods of inhibiting an E1 enzyme, and compounds useful for inhibiting an E1 enzyme.

SUMMARY

In an aspect is provided a method of treating cancer in a subject in need thereof, said method including administering to the subject a pharmaceutically acceptable excipient and a therapeutically effective amount of a compound of formula:

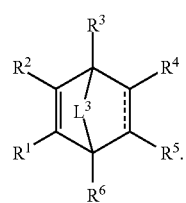

(I)

═══ is a single bond or double bond.

$L^3$ is —O—, —S—, —N—, —S(O)—, —S(O)$_2$—, —C(O)—, —N($R^7$)—, substituted or unsubstituted alkylene, or substituted or unsubstituted heteroalkylene.

$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1A}$, —$SO_{v1}NR^{1A}R^{1B}$, —NHC(O)$NR^{1A}R^{1B}$, —N(O)$_{m1}$, —$NR^{1A}R^{1B}$, —$NH^{1A}R^{1B}$, —C(O)$R^{1A}$, —C(O)—$OR^{1A}$, —C(O)$NR^{1A}R^{1B}$, —C(O)$NHNR^{1A}R^{1B}$, —$OR^{1A}$, —$NR^{1A}SO_2R^{1B}$, —$NR^{1A}C(O)R^{1B}$, —$NR^{1A}C(O)OR^{1B}$, —$NR^{1A}OR^{1B}$, —$N_3$, -$L^1$-$E^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2A}$, —$SO_{v2}NR^{2A}R^{2B}$, —NHC(O)$NR^{2A}R^{2B}$, —N(O)$_{m2}$, —$NR^{2A}R^{2B}$, —$NHNR^{2A}R^{2B}$, —C(O)$R^{2A}$, —C(O)—$OR^{2A}$, —C(O)$NR^{2A}R^{2B}$, —C(O)$NHNR^{2A}R^{2B}$, —$OR^{2A}$, —$NR^{2A}SO_2R^{2B}$, —$NR^{2A}C(O)R^{2B}$, —$NR^{2A}C(O)OR^{2B}$, —$NR^{2A}OR^{2B}$, —$N_3$, -$L^2$-$E^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3A}$, —$SO_{v3}NR^{3A}R^{3B}$, —NHC(O)$NR^{3A}R^{3B}$, —N(O)$_{m3}$, —$NR^{3A}R^{3B}$, —$R^{3A}R^{3B}$, —C(O)$R^{3A}$, —C(O)—$OR^{3A}$, —C(O)$NR^{3A}R^{3B}$, —$OR^{3A}$, —$NR^{3A}SO_2R^{3B}$, —$NR^{3A}C(O)R^{3B}$, —$NR^{3A}C(O)OR^{3B}$, —$NR^{3A}OR^{3B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4A}$, —$SO_{v4}NR^{4A}R^{4B}$, —NHC(O)$NR^{4A}R^{4B}$, —N(O)$_{m4}$, —$NR^{4A}R^{4B}$, —$NHNR^{4A}R^{4B}$, —C(O)$R^{4A}$, —C(O)—$OR^{4A}$, —C(O)$NR^{4A}R^{4B}$, —C(O)$NHNR^{4A}R^{4B}$, —$OR^{4A}$, —$NR^{4A}SO_2R^{4B}$, —$NR^{4A}C(O)R^{4B}$, —$NR^{4A}C(O)OR^{4B}$, —$NR^{4A}OR^{4B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5A}$, —$SO_{v5}NR^{5A}R^{5B}$, —NHC(O)$NR^{5A}R^{5B}$, —N(O)$_{m5}$, —$NR^{5A}R^{5B}$, —$NHNR^{5A}R^{5B}$, —C(O)$R^{5A}$, —C(O)—$OR^{5A}$, —C(O)$NR^{5A}R^{5B}$, —C(O)$NHNR^{5A}R^{5B}$, —$OR^{5A}$, —$NR^{5A}SO_2R^{5B}$, —$NR^{5A}C(O)R^{5B}$, —$NR^{5A}C(O)OR^{5B}$, —$NR^{5A}OR^{5B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6A}$, —$SO_{v6}NR^{6A}R^{6B}$, —NHC(O)$NR^{6A}R^{6B}$, —N(O)$_{m6}$, —$NR^{6A}R^{6B}$, —$NHNR^{6A}R^{6B}$, —C(O)$R^{6A}$, —C(O)—$OR^{6A}$, —C(O)$NR^{6A}R^{6B}$, —C(O)$NHNR^{6A}R^{6B}$, —$OR^{6A}$, —$NR^{6A}SO_2R^{6B}$, —$NR^{6A}C(O)R^{6B}$, —$NR^{6A}C(O)OR^{6B}$, —$NR^{6A}OR^{6B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7A}$, $-SO_{v7}NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)-OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$E^1$ and $E^2$ are independently an electron-withdrawing moiety.

Each $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, $R^{7A}$, and $R^{7B}$ is independently hydrogen, $-CX_3$, $-CHX_2$, $-CH_2X$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl.

m1, m2, m3, m4, m5, m6, and m7 are independently 1 or 2.

v1, v2, v3, v4, v5, v6, and v7 are independently 1 or 2.

n1, n2, n3, n4, n5, n6, and n7, are independently an integer from 0 to 4.

X, $X^1$, $X^2$, $X^3$, $X^4$, $X^5$, $X^6$, and $X^7$ are independently $-Cl$, $-Br$, $-I$ or $-F$.

$L^1$ and $L^2$ are independently a bond, $-O-$, $-S-$, $-S(O)-$, $-S(O)_2-$, $-NH-$, $-C(O)-$, $-C(O)O-$, $-C(O)NH-$, $-C(O)NHNH-$, $-OC(O)-$, $-NHC(O)-$, $-NH-C(O)-NH-$, $-OC(O)NH-$, $-NHC(O)O-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ and $R^2$ may optionally be joined to form a substituted or unsubstituted cycloalkyl, substituted or unsubstituted heterocycloalkyl, substituted or unsubstituted aryl, or substituted or unsubstituted heteroaryl.

$R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl.

Wherein the compound is administered at a rate approximately equal to the half-life of an E1 enzyme.

In an aspect is provided a compound of Formula:

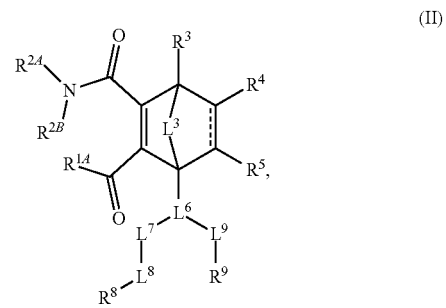

(II)

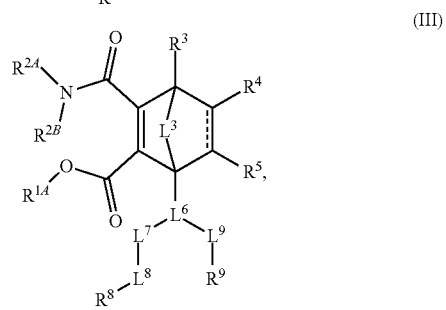

(III)

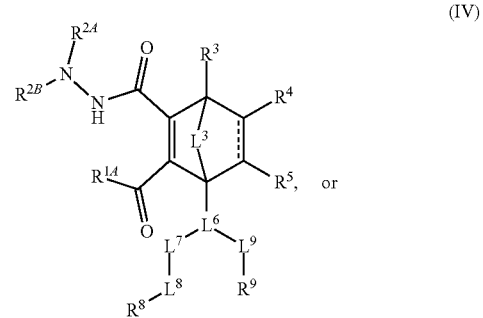

(IV)

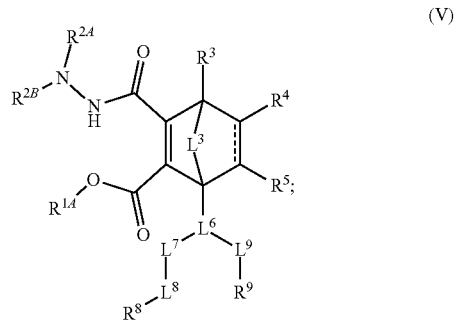

(V)

$L^3$ is $-O-$, $-S-$, or $-N(R^7)-$.

$L^7$ is $-O-$ or $-N(R^{10})-$.

$R^{14}$ is hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-CN$, $-SO_{n14}R^{1AA}$, $-SO_{v14}NR^{1AA}R^{1AB}$, $-NHC(O)NR^{1AA}R^{1AB}$, $-N(O)_{m1A}$, $-NR^{1AA}R^{1AB}$, $-NHNR^{1AA}R^{1AB}$, $-C(O)R^{1AA}$, $-C(O)-OR^{1AA}$, $-C(O)NR^{1AA}R^{1AB}$, $-OR^{1AA}$, $-NR^{1AA}SO_2R^{1AB}$, $-NR^{1AA}C(O)R^{1AB}$, $-NR^{1AA}C(O)OR^{1AB}$, $-NR^{1AA}OR^{1AB}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ is hydrogen, halogen, $-CX^{2A}_3$, $-CHX^{2A}_2$, $-CH_2X^{2A}$, $-OCX^{2A}_3$, $-OCH_2X^{2A}$, $-OCHX^{2A}_2$, $-CN$, $-SO_{n2A}R^{2AA}$, $-SO_{v2A}NR^{2AA}R^{2AB}$, $-NHC(O)NR^{2AA}R^{2AB}$, $-N(O)_{m2A}$, $-NR^{2AA}R^{2AB}$, $-NHNR^{2AA}R^{2AB}$, $-C(O)R^{2AA}$, $-C(O)-OR^{2AA}$, $-C(O)NR^{2AA}R^{2AB}$, $-OR^{2AA}$, $-NR^{2AA}SO_2R^{2AB}$, $-NR^{2AA}C(O)R^{2AB}$, $-NR^{2AA}C(O)OR^{2AB}$, $-NR^{2AA}OR^{2AB}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2B}$ is hydrogen, halogen, $-CX^{2B}_3$, $-CHX^{2B}_2$, $-CH_2X^{2B}$, $-OCX^{2B}_3$, $-OCH_2X^{2B}$, $-OCHX^{2B}_2$, $-CN$, $-SO_{n2B}R^{2BA}$, $-SO_{v2B}NR^{2BA}R^{2BB}$, $-NHC(O)NR^{2BA}R^{2BB}$, $-N(O)_{m2B}$, $-NR^{2BA}R^{2BB}$, $-NHNR^{2BA}R^{2BB}$, $-C(O)R^{2BA}$, $-C(O)-OR^{2BA}$, $-C(O)NR^{2BA}R^{2BB}$, $-OR^{2BA}$, $-NR^{2BA}SO_2R^{2BB}$, $-NR^{2BA}C(O)R^{2BB}$, $-NR^{2BA}C(O)OR^{2BB}$, $-NR^{2BA}OR^{2BB}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3A}$, $-SO_{v3}NR^{3A}R^{3B}$, $-NHC(O)NR^{3A}R^{3B}$, $-N(O)_{m3}$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4A}$, $-SO_{v4}NR^{4A}R^{4B}$, $-NHC(O)NR^{4A}R^{4B}$, $-N(O)_{m4}$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5A}$, $-SO_{v5}NR^{5A}R^{5B}$, $-NHC(O)NR^{5A}R^{5B}$, $-N(O)_{m5}$, $-NR^{5A}R^{5B}$, $-NHNR^{5A}R^{5B}$, $-C(O)R^{5A}$, $-C(O)-OR^{5A}$, $-C(O)NR^{5A}R^{5B}$, $-C(O)NHNR^{5A}R^{5B}$, $-OR^{5A}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7A}$, $SO_{v7}NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)-OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is hydrogen, halogen, $-CX^8_3$, $-CHX^8_2$, $-CH_2X^8$, $-OCX^8_3$, $-OCH_2X^8$, $-OCHX^8_2$, $-CN$, $-SO_{n8}R^{8A}$, $-SO_{v8}NR^{8A}R^{8B}$, $-NHC(O)NR^{8A}R^{8B}$, $-N(O)_{m8}$, $-NR^{8A}R^{8B}$, $-NHNR^{8A}R^{8B}$, $-C(O)R^{8A}$, $-C(O)-OR^{8A}$, $-C(O)NR^{8A}R^{8B}$, $-C(O)NHNR^{8A}R^{8B}$, $-OR^{8A}$, $-NR^{8A}SO_2R^{8B}$, $-NR^{8A}C(O)R^{8B}$, $-NR^{8A}C(O)OR^{8B}$, $-NR^{8A}OR^{8B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is hydrogen, halogen, $-CX^9_3$, $-CHX^9_2$, $-CH_2X^9$, $-OCX^9_3$, $-OCH_2X^9$, $-OCHX^9_2$, $-CN$, $-SO_{n9}R^{9A}$, $-SO_{v9}NR^{9A}R^{9B}$, $-NHC(O)NR^{9A}R^{9B}$, $-N(O)_{m9}$, $-NR^{9A}R^{9B}$, $-NHNR^{9A}R^{9B}$, $-C(O)R^{9A}$, $-C(O)-OR^{9A}$, $-C(O)NR^{9A}R^{9B}$, $-C(O)NHNR^{9A}R^{9B}$, $-OR^{9A}$, $-NR^{9A}SO_2R^{9B}$, $-NR^{9A}C(O)R^{9B}$, $-NR^{9A}C(O)OR^{9B}$, $-NR^{9A}OR^{9B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-CN$, $-SO_{n10}R^{10A}$, $-SO_{v10}NR^{10A}R^{10B}$, $-NHC(O)NR^{10A}R^{10B}$, $-N(O)_{m10}$, $-NR^{10A}R^{10B}$, $-NHNR^{10A}R^{10B}$, $-C(O)R^{10A}$, $-C(O)-OR^{10A}$, $-C(O)NR^{10A}R^{10B}$, $-C(O)NHNR^{10A}R^{10B}$, $-OR^{10A}$, $-NR^{10A}SO_2R^{10B}$, $-NR^{10A}C(O)R^{10B}$, $-NR^{10A}C(O)OR^{10B}$, $-NR^{10A}OR^{10B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each $R^{1AA}$, $R^{1AB}$, $R^{2AA}$, $R^{2AB}$, $R^{2BA}$, $R^{2BB}$, $R^{3A}$, $R^{3B}$, $R^{4A}$, $R^{4B}$, $R^{5A}$, $R^{5B}$, $R^{7A}$, $R^{7B}$, $R^{8A}$, $R^{8B}$, $R^{9A}$, $R^{9B}$, $R^{10A}$, and $R^{10B}$ is independently hydrogen, $-CX_3$, $-CHX_2$, $-CH_2X$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1AA}$ and $R^{1AB}$ substituents bonded to the same nitrogen atom may optionally be joined to form a substituted or unsubstituted heterocycloalkyl or substituted or unsubstituted heteroaryl; $R^{2AA}$ and $R^{2AB}$ substituents bonded to the same nitrogen atom may optionally be joined to form a substituted or unsubstituted heterocycloalkyl or substituted or unsubstituted heteroaryl; $R^{2BA}$ and $R^{2BB}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl.

m1A, m2A, m2B, m3, m4, m5, m7, m8, m9, and m10 are independently 1 or 2.

v1A, v2A, v2B, v3, v4, v5, v7, v8, v9, and v10 are independently 1 or 2.

n1A, n2A, n2B, n3, n4, n5, n7, n8, n9, and n10 are independently an integer from 0 to 4.

X, $X^{1A}$, $X^{2A}$, $X^{2B}$, $X^3$, $X^4$, $X^5$, $X^7$, $X^8$, $X^9$, and $X^{10}$ are independently —Cl, —Br, —I, or —F.

$L^6$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$L^8$ is a bond, —C(O)—, —C(O)NH—, —C(O)O—, —S—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$L^9$ is a bond, —O—, —S—, —NH—, —C(O)—, —C(O)O—, —C(O)NH—, —OC(O)—, —NHC(O)—, —NHC(O)NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Wherein $R^{2A}$ and $R^{2B}$ may optionally be joined to form a substituted or unsubstituted heterocycloalkyl or substituted or unsubstituted heteroaryl.

$R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl.

In an aspect is provided a pharmaceutical composition including a compound described herein, or pharmaceutically acceptable salt thereof, and a pharmaceutically acceptable excipient.

In an aspect is provided a method of treating cancer, the method including administering to a subject in need thereof an effective amount of a compound described herein.

In an aspect is provided a method of inhibiting cell proliferation, the method including contacting the cell with a compound described herein.

BRIEF DESCRIPTION OF THE DRAWINGS

FIG. 1. Examination of the effect of compounds 582 and 588 to reduce cancer stem cell (CSC) populations in patient derived xenograft (PDX) models using limited dilution assays. Compound 582 showed dose-dependent inhibition on PDX cancer-initiating-cell (CIC) frequency, even at 1 μM. Compound 588 only showed inhibition on CIC at high dose 10 μM.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, S, B, As, or Si), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A heteroaryl group can be attached to the remainder of the molecule through a carbon or heteroatom. An "arylene" and a "heteroarylene," alone or as part of another substituent, mean a divalent radical derived from an aryl and heteroaryl, respectively.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〰〰" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

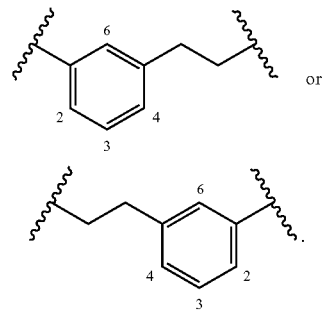

Each of the above terms (e.g., "alkyl," "heteroalkyl," "cycloalkyl," "heterocycloalkyl," "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR"R', —NRSO$_2$R', —NR'NR"R", —ONR'R", —NR'C(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), Boron (B), and silicon (Si).

A "substituent group," as used herein, means a group selected from the following moieties:

(A) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (B) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (ii) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_4$-$C_6$, or $C_5$-$C_6$), unsubstituted heterocycloalkyl (e.g., 3 to 10 membered, 3 to 8 membered, 3 to 6 membered, 4 to 6 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted aryl ene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted aryl ene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

The term "pharmaceutically acceptable salts" is meant to include salts of the active compounds that are prepared with relatively nontoxic acids or bases, depending on the particular substituents found on the compounds described herein. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. As used herein, the term "cancer" refers to all types of cancer, neoplasm or malignant tumors found in mammals (e.g. humans), including leukemia, carcinomas and sarcomas. The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease) means that the disease (e.g. cancer) is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixmab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e.

R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Gurin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "SUMO protein" or "small ubiquitin-like modifier protein" is a family of proteins that are covalently attached to other proteins to modify their function. SUMO proteins are members of the ubiquitin-like protein family. SUMO modification is involved in various cellular processes, for example, nuclear-cytosolic transport, transcriptional regulation, apoptosis, and protein stability.

The term "Ubiquitin-activating enzyme" or "E1 enzyme" or "E1" refers to a protein (including homologs, isoforms, and functional fragments thereof) that catalyzes the first step in the ubiquitination reaction, which can target a protein for degradation. E1 enzymes are capable of catalyzing SUMO modification. In embodiments, the E1 enzyme is encoded by UBA1. In embodiments, the E1 enzyme is encoded by UBA2. In embodiments, the E1 enzyme is encoded by UBA3. In embodiments, the E1 enzyme is encoded by UBA4. In embodiments, the E1 enzyme is encoded by UBA5. In embodiments, the E1 enzyme is encoded by UBA6. In embodiments, the E1 enzyme is encoded by UBA7. In embodiments, the E1 enzyme is encoded by ATG7. In embodiments, the E1 enzyme is encoded by NAE1. In embodiments, the E1 enzyme is encoded by SAE1.

The term "SUMO-activating enzyme subunit 2" or "UBA2" or "UBA2 subunit 2" is a protein involved in SUMO modification. The term "UBA2" refers to the nucleotide sequences or proteins of human UBA2. The term "UBA2" includes both the wild type form of the nucleotide sequences or proteins as well as any mutants thereof. In some embodiments, "UBA2" is wild-type UBA2. In some embodiments, "UBA2" is one or more mutant forms. The term "UBA2" XYZ refers to a nucleotide sequence or protein of a mutant UBA2 wherein the Y numbered amino acid of UBA2 has an X amino acid in the wild type instead has a Z amino acid in the mutant. In embodiments, UBA2 is a functional fragment thereof. In embodiments, UBA2 refers to RefSeq (mRNA) NM 005499.2 or RefSeq (Protein) NP 005490.1. In some embodiments, UBA2 refers to UniProt Q9UBT2, having the sequence:

(SEQ ID NO: 1)
MALSRGLPRELAEAVAGGRVLVVGAGGIGCELLKNLVLTGFSHIDLID

LDTIDVSNLNRQFLFQKKHVGRSKAQVAKESVLQFYPKANIVAYHDSI

MNPDYNVEFFRQFILVMNALDNRAARNHVNRMCLAADVPLIESGTAGY

LGQVTTIKKGVTECYECHPKPTQRTFPGCTIRNTPSEPIHCIVWAKYL

FNQLFGEEDADQEVSPDRADPEAAWEPTEAEARARASNEDGDIKRIST

KEWAKSTGYDPVKLFTKLFKDDIRYLLTMDKLWRKRKPPVPLDWAEVQ

SQGEETNASDQQNEPQLGLKDQQVLDVKSYARLFSKSIETLRVHLAEK

GDGAELIWDKDDPSAMDFVTSAANLRMHIFSMNMKSRFDIKSMAGNII

PAIATTNAVIAGLIVLEGLKILSGKIDQCRTIFLNKQPNPRKKLLVPC

ALDPPNPNCYVCASKPEVTVRLNVHKVTVLTLQDKIVKEKFAMVAPDV

QIEDGKGTILISSEEGETEANNHKKLSEFGIRNGSRLQADDFLQDYTL

LINILHSEDLGKDVEFEVVGDAPEKVGPKQAEDAAKSITNGSDDGAQP

STSTAQEQDDVLIVDSDEEDSSNNADVSEEERSRKRKLDEKENLSAKR

SRIEQKEELDDVIALD.

II. Compounds

In an aspect is provided a compound having the formula:

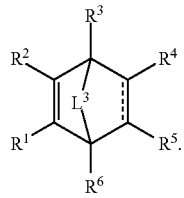

(I)

$\stackrel{\text{===}}{}$ is a single bond or double bond.

$L^1$ and $L^2$ are independently a bond, —O—, —S—, —S(O)—, —S(O)$_2$—, —NH—, —C(O)—, —C(O)O—, —C(O)NH—, —C(O)NHNH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

$L^3$ is —O—, —S—, —N—, —S(O)—, —S(O)$_2$—, —C(O)—, —N(R$^7$)—, substituted or unsubstituted alkylene (e.g., $C_1$-$C_8$, $C_1$-$C_6$, $C_1$-$C_4$, or $C_1$-$C_2$) or substituted or unsubstituted heteroalkylene (e.g., 2 to 8 membered, 2 to 6 membered, 4 to 6 membered, 2 to 3 membered, or 4 to 5 membered).

$L^6$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

$L^7$ is —O— or —N(R$^{10}$)—.

$L^8$ is a bond, —C(O)—, —C(O)NH—, —C(O)O—, —S—, —S(O)—, —S(O)$_2$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

$L^9$ is a bond, —O—, —S—, —NH—, —C(O)—, —C(O)O—, —C(O)NH—, —OC(O)—, —NHC(O)—, —NHC(O)NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

$R^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, -L$^1$-E$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2A}$, —SO$_{v2}$NR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, -L$^2$-E$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ and $R^2$ may optionally be joined to form a substituted or unsubstituted cycloalkyl, substituted or unsubstituted heterocycloalkyl, substituted or unsubstituted aryl, or substituted or unsubstituted heteroaryl.

$R^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)

$R^{3B}$, —$NR^{3A}C(O)OR^{3B}$, —$NR^{3A}OR^{3B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4A}$, —$SO_{v4}NR^{4A}R^{4B}$, —$NHC(O)NR^{4A}R^{4B}$, —$N(O)_{m4}$, —$NR^{4A}R^{4B}$, —$NHNR^{4A}R^{4B}$, —$C(O)R^{4A}$, —$C(O)$—$OR^{4A}$, —$C(O)NR^{4A}R^{4B}$, —$C(O)NHNR^{4A}R^{4B}$, —$OR^{4A}$, —$NR^{4A}SO_2R^{4B}$, —$NR^{4A}C(O)R^{4B}$, —$NR^{4A}C(O)OR^{4B}$, —$NR^{4A}OR^{4B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5A}$, —$SO_{v5}NR^{5A}R^{5B}$, —$NHC(O)NR^{5A}R^{5B}$, —$N(O)_{m5}$, —$NR^{5A}R^{5B}$, —$NHNR^{5A}R^{5B}$, —$C(O)R^{5A}$, —$C(O)$—$OR^{5A}$, —$C(O)NR^{5A}R^{5B}$, —$C(O)NHNR^{5A}R^{5B}$, —$OR^{5A}$, —$NR^{5A}SO_2R^{5B}$, —$NR^{5A}C(O)R^{5B}$, —$NR^{5A}C(O)OR^{5B}$, —$NR^{5A}OR^{5B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ and $R^5$ may optionally be joined to form a substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^4$ and $R^5$ are joined to form a substituted or unsubstituted phenyl. In embodiments, $R^4$ and $R^5$ are joined to form an unsubstituted phenyl.

$R^6$ is hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6A}$, —$SO_{v6}NR^{6A}R^{6B}$, —$NHC(O)NR^{6A}R^{6B}$, —$N(O)_{m6}$, —$NR^{6A}R^{6B}$, —$NHNR^{6A}R^{6B}$, —$C(O)R^{6A}$, —$C(O)$—$OR^{6A}$, —$C(O)NR^{6A}R^{6B}$, —$C(O)NHNR^{6A}R^{6B}$, —$OR^{6A}$, —$NR^{6A}SO_2R^{6B}$, —$NR^{6A}C(O)R^{6B}$, —$NR^{6A}C(O)OR^{6B}$, —$NR^{6A}OR^{6B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^6$(-$L^7$-$L^8$-$R^8$)(-$L^9$-$R^9$).

$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7A}$, $SO_{v7}NR^{7A}R^{7B}$, —$NHC(O)NR^{7A}R^{7B}$, —$N(O)_{m7}$, —$NR^{7A}R^{7B}$, —$NHNR^{7A}R^{7B}$, —$C(O)R^{7A}$, —$C(O)$—$OR^{7A}$, —$C(O)NR^{7A}R^{7B}$, —$C(O)NHNR^{7A}R^{7B}$, —$OR^{7A}$, —$NR^{7A}SO_2R^{7B}$, —$NR^{7A}C(O)R^{7B}$, —$NR^{7A}C(O)OR^{7B}$, —$NR^{7A}OR^{7B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8A}$, $SO_{v8}NR^{8A}R^{8B}$, —$NHC(O)NR^{8A}R^{8B}$, —$N(O)_{m8}$, —$NR^{8A}R^{8B}$, —$NHNR^{8A}R^{8B}$, —$C(O)R^{8A}$, —$C(O)$—$OR^{8A}$, —$C(O)NR^{8A}R^{8B}$, —$C(O)NHNR^{8A}R^{8B}$, —$OR^{8A}$, —$NR^{8A}SO_2R^{8B}$, —$NR^{8A}C(O)R^{8B}$, —$NR^{8A}C(O)OR^{8B}$, —$NR^{8A}OR^{8B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9A}$, —$SO_{v9}NR^{9A}R^{9B}$, —$NHC(O)NR^{9A}R^{9B}$, —$N(O)_{m9}$, —$NR^{9A}R^{9B}$, —$NHNR^{9A}R^{9B}$, —$C(O)R^{9A}$, —$C(O)$—$OR^{9A}$, —$C(O)NR^{9A}R^{9B}$, —$C(O)NHNR^{9A}R^{9B}$, —$OR^{9A}$, —$NR^{9A}SO_2R^{9B}$, —$NR^{9A}C(O)R^{9B}$, —$NR^{9A}C(O)OR^{9B}$, —$NR^{9A}OR^{9B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10A}$, —$SO_{v10}NR^{10A}R^{10B}$, —$NHC(O)NR^{10A}R^{10B}$, —$N(O)_{m10}$, —$NR^{10A}R^{10B}$, —$NHNR^{10A}R^{10B}$, —$C(O)R^{10A}$, —$C(O)$—$OR^{10A}$, —$C(O)NR^{10A}R^{10B}$, —$C(O)NHNR^{10A}R^{10B}$, —$OR^{10A}$, —$NR^{10A}SO_2R^{10B}$, —$NR^{10A}C(O)R^{10B}$, —$NR^{10A}C(O)OR^{10B}$, —$NR^{10A}OR^{10B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$E^1$ and $E^2$ are independently an electron-withdrawing moiety.

$R^{1A}$ is hydrogen, halogen, —$CX^{1A}_3$, —$CHX^{1A}_2$, —$CH_2X^{1A}$, —$OCX^{1A}_3$, —$OCH_2X^{1A}$, —$OCHX^{1A}_2$, —CN, —$SO_{n1A}R^{1AA}$, —$SO_{v1A}NR^{1AA}R^{1AB}$, —$NHC(O)NR^{1AA}R^{1AB}$, —$N(O)_{m1A}$, —$NR^{1AA}R^{1AB}$, —$NHNR^{1AA}R^{1AB}$, —$C(O)R^{1AA}$, —$C(O)$—$OR^{1AA}$, —$C(O)NR^{1AA}R^{1AB}$, —$OR^{1AA}$, —$NR^{1AA}SO_2R^{1AB}$, —$NR^{1AA}C(O)R^{1AB}$, —$NR^{1AA}C(O)OR^{1AB}$, —$NR^{1AA}OR^{1AB}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ is hydrogen, halogen, —$CX^{2A}_3$, —$CHX^{2A}_2$, —$CH_2X^{2A}$, —$OCX^{2A}_3$, —$OCH_2X^{2A}$, —$OCHX^{2A}_2$, —CN, —$SO_{n2A}R^{2AA}$, —$SO_{v2A}NR^{2AA}R^{2AB}$, —$NHC(O)NR^{2AA}R^{2AB}$, —$N(O)_{m2A}$, —$NR^{2AA}R^{2AB}$, —$NHNR^{2AA}R^{2AB}$, —$C(O)R^{2AA}$, —$C(O)$—$OR^{2AA}$, —$C(O)NR^{2AA}R^{2AB}$, —$OR^{2AA}$, —$NR^{2AA}SO_2R^{2AB}$, —$NR^{2AA}C(O)R^{2AB}$, —$NR^{2AA}C(O)OR^{2AB}$, —$NR^{2AA}OR^{2AB}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2B}$ is hydrogen, halogen, —$CX^{2B}_3$, —$CHX^{2B}_2$, —$CH_2X^{2B}$, —$OCX^{2B}_3$, —$OCH_2X^{2B}$, —$OCHX^{2B}_2$, —CN, —$SO_{n2B}R^{2BA}$, —$SO_{v2B}NR^{2BA}R^{2BB}$, —$NHC(O)NR^{2BA}R^{2BB}$, —$N(O)_{m2B}$, —$NR^{2BA}R^{2BB}$, —$NHNR^{2BA}R^{2BB}$, —$C(O)R^{2BA}$, —$C(O)$—$OR^{2BA}$, —$C(O)NR^{2BA}R^{2BB}$, —$OR^{2BA}$, —$NR^{2BA}SO_2R^{2BB}$, —$NR^{2BA}C(O)R^{2BB}$, —$NR^{2BA}C(O)OR^{2BB}$, —$NR^{2BA}OR^{2BB}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each $R^{1B}$, $R^{3A}$, $R^{3B}$, $R^{4A}$, $R^{4B}$, $R^{5A}$, $R^{5B}$, $R^{6A}$, $R^{6B}$, $R^{7A}$, $R^{7B}$, $R^{1AA}$, $R^{1A}$, $R^{2AA}$, $R^{2AB}$, $R^{2BA}$, $R^{2BB}$, $R^{8A}$, $R^{8B}$, $R^{9A}$, $R^{9B}$, $R^{10A}$, and $R^{10B}$ is independently hydrogen, —$CX_3$, —$CHX_2$, —$CH_2X$, —$C(O)OH$, —$C(O)NH_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)

NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{8A}$ and R$^{8B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl; R$^{1AA}$ and R$^{1AB}$ substituents bonded to the same nitrogen atom may optionally be joined to form a substituted or unsubstituted heterocycloalkyl or substituted or unsubstituted heteroaryl; R$^{2AA}$ and R$^{2A}$ substituents bonded to the same nitrogen atom may optionally be joined to form a substituted or unsubstituted heterocycloalkyl or substituted or unsubstituted heteroaryl; R$^{2BA}$ and R$^{2BB}$ substituents bonded to the same nitrogen atom may optionally be joined to form a substituted or unsubstituted heterocycloalkyl or substituted or unsubstituted heteroaryl.

m1, m2, m3, m4, m5, m6, m7, m8, m9, m10, m1A, m2A, and m2B are independently 1 or 2.

v1, v2, v3, v4, v5, v6, v7, v8, v9, v10, v1A, v2A, and v2B are independently 1 or 2.

n1, n2, n3, n4, n5, n6, n7, n8, n9, n10, n1A, n2A, and n2B are independently an integer from 0 to 4.

X, X$^1$, X$^2$, X$^3$, X$^4$, X$^5$, X$^6$, X$^7$, X$^8$, X$^9$, X$^{10}$, X$^{1A}$, X$^{2A}$, and X$^{2B}$ are independently —Cl, —Br, —I or —F.

In embodiments, L$^1$ and L$^2$ are independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{12}$, C$_6$-C$_{10}$, or phenylene), or substituted or unsubstituted heteroarylene (e.g., 5 to 12 membered, 5 to 10 membered, 5 to 9 membered, or 5 to 6 membered).

In embodiments, L$^7$ is independently —O—. In embodiments, L$^7$ is independently —N(R$^{10}$)—.

In embodiments, L$^8$ is a bond, —C(O)—, —C(O)NH—, —C(O)O—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{12}$, C$_6$-C$_{10}$, or phenylene), or substituted or unsubstituted heteroarylene (e.g., 5 to 12 membered, 5 to 10 membered, 5 to 9 membered, or 5 to 6 membered). In embodiments, L$^8$ is independently a bond. In embodiments, L$^8$ is independently an unsubstituted phenylene.

In embodiments, R$^6$ is independently -L$^6$(-L$^7$-L$^8$-R$^8$)(-L$^9$-R$^9$). In embodiments R$^6$ is

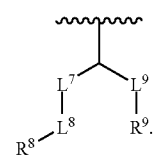

In an aspect is provided a compound having the formula:

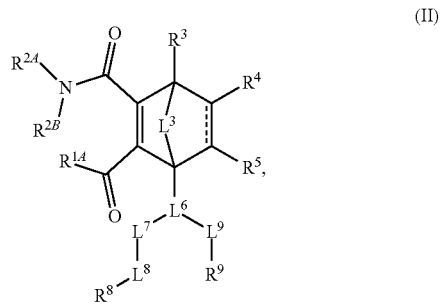

(II)

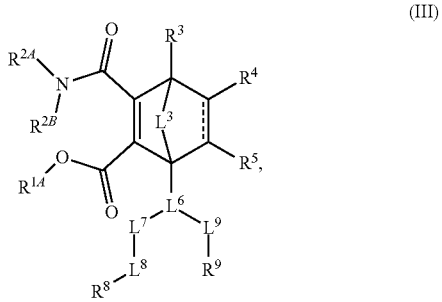

(III)

-continued

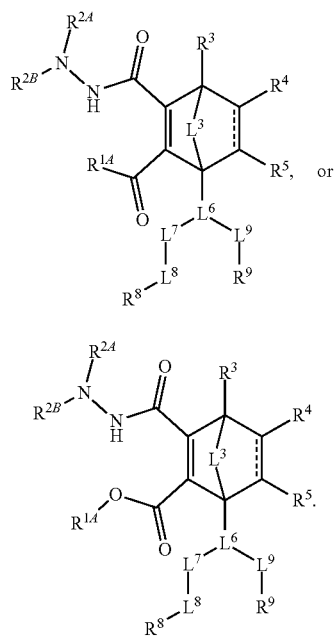
(IV)

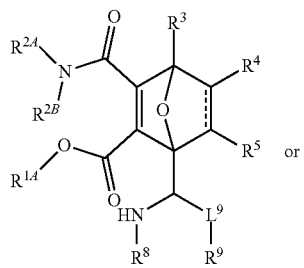
(V)

$R^3$, $R^4$, $R^5$, $R^8$, $R^9$, $R^{1A}$, $R^{2A}$, $R^{2B}$, $L^3$, $L^6$, $L^7$, $L^8$, and $L^9$ are as described herein. $R^8$ and $R^9$ substituents may optionally be joined to form a substituted or unsubstituted cycloalkyl, a substituted or unsubstituted heterocycloalkyl, a substituted or unsubstituted aryl, or a substituted or unsubstituted heteroaryl.

In embodiments, the compound has the formula.

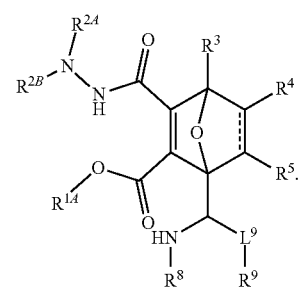
(IIIa)

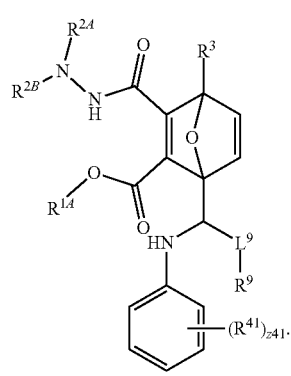
(Va)

$R^{1A}$, $R^{2A}$, $R^{2B}$, $R^3$, $R^4$, $R^5$, $R^8$, $R^9$, and $L^9$ are as described herein. $R^8$ and $R^9$ substituents may optionally be joined to form a substituted or unsubstituted heterocycloalkyl, or a substituted or unsubstituted heteroaryl.

In embodiments, the compound has the formula:

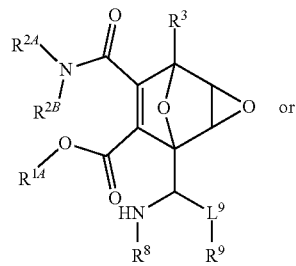
(IIIb)

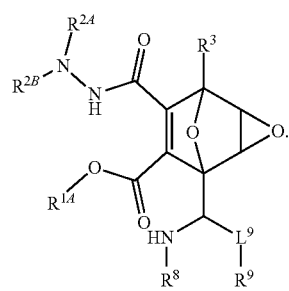
(Vb)

$R^{1A}$, $R^{2A}$, $R^{2B}$, $R^3$, $R^8$, $R^9$, and $L^9$ are as described herein. $R^8$ and $R^9$ substituents may optionally be joined to form a substituted or unsubstituted heterocycloalkyl, or a substituted or unsubstituted heteroaryl.

In embodiments, the compound has the formula:

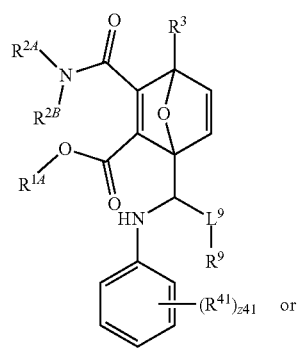
(IIIc)

(Vc)

$R^{1A}$, $R^{2A}$, $R^{2B}$, $R^3$, $R^9$, and $L^9$ are as described herein.
$R^{41}$ is independently halogen, $-CX^{41}_3$, $-CHX^{41}_2$, $-CH_2X^{41}$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{41}_3$, —OCHX$^{41}_2$, —OCH$_2$X$^{41}$, —OPh, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^{41}$ substituents may optionally be joined to form a substituted or unsubstituted cycloalkyl, substituted or unsubstituted heterocycloalkyl, substituted or unsubstituted aryl, or substituted or unsubstituted heteroaryl.

z41 is an integer from 0 to 5.

X$^{41}$ is independently —Cl, —Br, —I, or —F.

In embodiments, the compound has the formula:

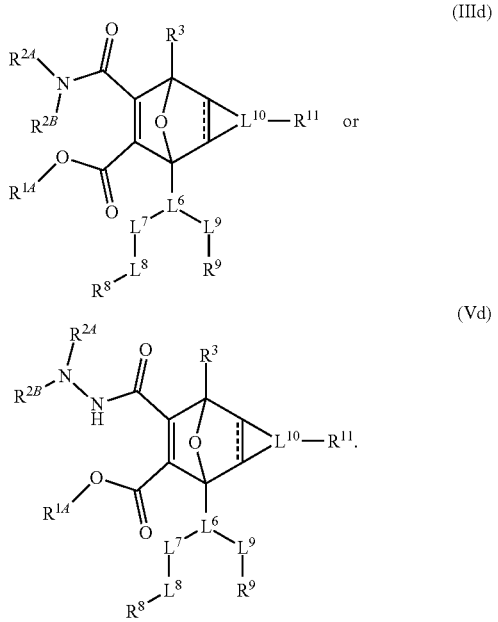

R$^{1A}$, R$^{2A}$, R$^{2B}$, R$^3$, R$^1$, R$^9$, L$^6$, L$^7$, L$^8$ and L$^9$ are as described herein. R$^8$ and R$^9$ substituents may optionally be joined to form a substituted or unsubstituted cycloalkyl, a substituted or unsubstituted heterocycloalkyl, a substituted or unsubstituted aryl, or a substituted or unsubstituted heteroaryl.

L$^{10}$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

R$^{11}$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, L$^{10}$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{12}$, C$_6$-C$_{10}$, or phenylene), or substituted or unsubstituted heteroarylene (e.g., 5 to 12 membered, 5 to 10 membered, 5 to 9 membered, or 5 to 6 membered).

In embodiments, a substituted L$^{10}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted L$^{10}$ is substituted with a plurality of groups selected from substituent groups, size-limited substituent groups, and lower substituent groups; each substituent group, size-limited substituent group, and/or lower substituent group may optionally be different. In embodiments, when L$^{10}$ is substituted, it is substituted with at least one substituent group. In embodiments, when L$^{10}$ is substituted, it is substituted with at least one size-limited substituent group. In embodiments, when L$^{10}$ is substituted, it is substituted with at least one lower substituent group.

In embodiments, R$^{11}$ is hydrogen, halogen, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered).

In embodiments, a substituted R$^{11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{11}$ is substituted with a plurality of groups selected from substituent groups, size-limited substituent groups, and lower substituent groups; each substituent group, size-limited substituent group, and/or lower substituent group may optionally be different. In embodiments, when R$^{11}$ is substituted, it is substituted with at least one substituent group. In embodiments, when R$^{11}$ is substituted, it is substituted with at least one size-limited substituent group. In embodiments, when R$^{11}$ is substituted, it is substituted with at least one lower substituent group.

In an aspect is provided a compound of Formula:

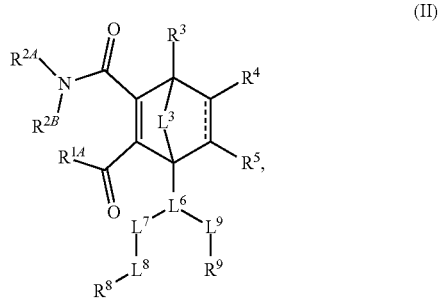

-continued

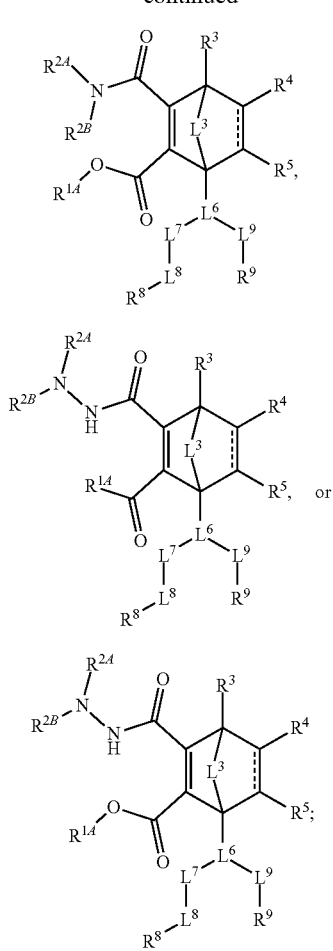

(III)

(IV)

(V)

L$^3$ is —O—, —S—, or —N(R$^7$)—.
L$^7$ is —O— or —N(R$^{10}$)—.
R$^{1A}$ is hydrogen, halogen, —CX$^{1A}_3$, —CHX$^{1A}_2$, —CH$_2$X$^{1A}$, —OCX$^{1A}_3$, —OCH$_2$X$^{1A}$—OCHX$^{1A}_2$, —CN, —SO$_{n1A}$R$^{1AA}$, —SO$_{v1A}$NR$^{1AA}$R$^{1AB}$, —NHC(O)NR$^{1AA}$R$^{1AB}$, —N(O)$_{m1A}$, —NR$^{1AA}$R$^{1AB}$, —NHNR$^{1AA}$R$^{1AB}$, —C(O)R$^{1AA}$, —C(O)—OR$^{1AA}$, —C(O)NR$^{1AA}$R$^{1AB}$, —OR$^{1AA}$, —NR$^{1AA}$SO$_2$R$^{1AB}$, —NR$^{1AA}$C(O)R$^{1AB}$, —NR$^{1AA}$C(O)OR$^{1AB}$, —NR$^{1AA}$OR$^{1AB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{2A}$ is hydrogen, halogen, —CX$^{2A}_3$, —CHX$^{2A}_2$, —CH$_2$X$^{2A}$, —OCX$^{2A}_3$, —OCH$_2$X$^{2A}$, —OCHX$^{2A}_2$, —CN, —SO$_{n2A}$R$^{2AA}$, —SO$_{v2A}$NR$^{2AA}$R$^{2AB}$, —NHC(O)NR$^{2AA}$R$^{2AB}$, —N(O)$_{m2A}$, —NR$^{2AA}$R$^{2AB}$, —NHNR$^{2AA}$R$^{2AB}$, —C(O)R$^{2AA}$, —C(O)—OR$^{2AA}$, —C(O)NR$^{2AA}$R$^{2AB}$, —OR$^{2AA}$, —NR$^{2AA}$SO$_2$R$^{2AB}$, —NR$^{2AA}$C(O)R$^{2AB}$, —NR$^{2AA}$C(O)OR$^{2AB}$, —NR$^{2AA}$OR$^{2AB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{2B}$ is hydrogen, halogen, —CX$^{2B}_3$, —CHX$^{2B}_2$, —CH$_2$X$^{2B}$, —OCX$^{2B}_3$, —OCH$_2$X$^{2B}$—OCHX$^{2B}_2$, —CN, —SO$_{n2B}$R$^{2BA}$, —SO$_{v2B}$NR$^{2BA}$R$^{2BB}$, —NHC(O)NR$^{2BA}$R$^{2BB}$, —N(O)$_{m2B}$, —NR$^{2BA}$R$^{2BB}$, —NHNR$^{2BA}$R$^{2BB}$, —C(O)R$^{2BA}$, —C(O)—OR$^{2BA}$, —C(O)NR$^{2BA}$R$^{2BB}$, —OR$^{2BA}$, —NR$^{2BA}$SO$_2$R$^{2BB}$, —NR$^{2BA}$C(O)R$^{2BB}$, —NR$^{2BA}$C(O)OR$^{2BB}$, —NR$^{2BA}$OR$^{2BB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4A}$, —SO$_{v4}$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5A}$, —SO$_{v5}$NR$^{5A}$R$^{5B}$, —NHC(O)NR$^{5A}$R$^{5B}$, —N(O)$_{m5}$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7A}$, SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —CN, —SO$_{n8}$R$^{8A}$, SO$_{v8}$NR$^{8A}$R$^{8B}$, —NHC(O)NR$^{8A}$R$^{8B}$, —N(O)$_{m8}$, —NR$^{8A}$R$^{8B}$, —NHNR$^{8A}$R$^{8B}$, —C(O)R$^{8A}$, —C(O)—OR$^{8A}$, —C(O)NR$^{8A}$R$^{8B}$, —C(O)NHNR$^{8A}$R$^{8B}$, —OR$^{8A}$, —NR$^{8A}$SO$_2$R$^{8B}$, —NR$^{8A}$C(O)R$^{8B}$, —NR$^{8A}$C(O)OR$^{8B}$, —NR$^{8A}$OR$^{8B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —CN, —SO$_{n9}$R$^{9A}$, —SO$_{v9}$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)—OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^8$ and R$^9$ substituents may optionally be joined to form a substituted or unsubstituted cycloalkyl, a substituted or unsubstituted heterocycloalkyl, a substituted or unsubstituted aryl, or a substituted or unsubstituted heteroaryl.

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{1A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each R$^{1AA}$, R$^{1AB}$, R$^{2AA}$, R$^{2AB}$, R$^{2BA}$, R$^{2BB}$, R$^{3A}$, R$^{3B}$, R$^{4A}$, R$^{4B}$, R$^{5A}$, R$^{5B}$, R$^{7A}$, R$^{7B}$, R$^{8A}$, R$^{8B}$, R$^{9A}$, R$^{9B}$, R$^{10A}$, and R$^{10B}$ is independently hydrogen, —CX$_3$, —CHX$_2$, —CH$_2$X, —C(O)OH, —C(O)NH$_2$, —CN, —OH, —C(O), —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1AA}$ and R$^{1AB}$ substituents bonded to the same nitrogen atom may optionally be joined to form a substituted or unsubstituted heterocycloalkyl or substituted or unsubstituted heteroaryl; R$^{2AA}$ and R$^{2A}$ substituents bonded to the same nitrogen atom may optionally be joined to form a substituted or unsubstituted heterocycloalkyl or substituted or unsubstituted heteroaryl; R$^{2BA}$ and R$^{2BB}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{8A}$ and R$^{8B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl.

m1A, m2A, m2B, m3, m4, m5, m7, m8, m9, and m10 are independently 1 or 2.

v1A, v2A, v2B, v3, v4, v5, v7, v8, v9, and v10 are independently 1 or 2.

n1A, n2A, n2B, n3, n4, n5, n7, n8, n9, and n10 are independently an integer from 0 to 4.

X, X$^{1A}$, X$^{2A}$, X$^{2B}$, X$^3$, X$^4$, X$^5$, X$^7$, X$^8$, X$^9$, and X$^{10}$ are independently —Cl, —Br, —I, or —F.

L$^6$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

L$^8$ is a bond, —C(O)—, —C(O)NH—, —C(O)O—, —S—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^8$ is a bond, —C(O)—, —C(O)NH—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L$^8$ is unsubstituted phenylene.

L$^9$ is a bond, —O—, —S—, —NH—, —C(O)—, —C(O)O—, —C(O)NH—, —OC(O)—, —NHC(O)—, —NHC(O)NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Wherein R$^{2A}$ and R$^{2B}$ may optionally be joined to form a substituted or unsubstituted heterocycloalkyl or substituted or unsubstituted heteroaryl.

R$^4$ and R$^5$ may optionally be joined to form a substituted or unsubstituted cycloalkyl, substituted or unsubstituted heterocycloalkyl, substituted or unsubstituted aryl, or substituted or unsubstituted heteroaryl. In embodiments, R$^4$ and R$^5$ are joined to form a substituted or unsubstituted phenyl.

R$^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, -L$^1$-E$^1$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered).

In embodiments, E$^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $E^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{14}$, —$SO_{v1}NR^{14}R^{1B}$, —NHC(O)$NR^{14}R^{1B}$, —N(O)$_{m1}$, —$NR^{14}R^{1B}$, —$NHNR^{14}R^{1B}$, —C(O)$R^{14}$, —C(O)—$OR^{14}$, —C(O)$NR^{14}R^{1B}$, —C(O)$NHNR^{14}R^{1B}$, —$OR^{14}$, —$NR^{14}SO_2R^{1B}$, —$NR^{14}C(O)R^{1B}$, —$NR^{14}C(O)OR^{1B}$, —$NR^{14}OR^{1B}$, —$N_3$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{12}$, $C_6$-$C_{10}$, or phenyl), or $R^{20}$-substituted or unsubstituted heteroaryl (e.g., 5 to 12 membered, 5 to 10 membered, 5 to 9 membered, or 5 to 6 membered).

In embodiments, $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{12}$, $C_6$-$C_{10}$, or phenyl), or $R^{20}$-substituted or unsubstituted heteroaryl (e.g., 5 to 12 membered, 5 to 10 membered, 5 to 9 membered, or 5 to 6 membered). In embodiments, $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^1$ is independently —F, —Cl, —Br, or —I.

In embodiments, $R^1$ is independently hydrogen. In embodiments, $R^1$ is independently —COOH. In embodiments, $R^1$ is independently —C(O)O($C_1$-$C_4$ alkyl). In embodiments, $R^1$ is independently —$CF_3$. In embodiments, $R^1$ is independently —$CH_2OH$. In embodiments, $R^1$ is independently —C(O)$CH_3$. In embodiments, $R^1$ is independently

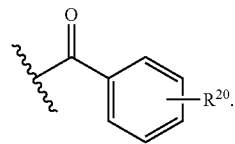

In embodiments, $R^1$ is independently.

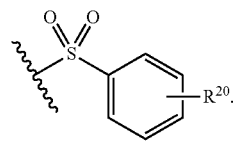

In embodiments, $R^{20}$ is hydrogen, —F, —Cl, or unsubstituted $C_1$-$C_4$ alkyl.

$R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHC(O)—OH, —NHOH, —$N_3$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{12}$, $C_6$-$C_{10}$, or phenyl), or $R^{21}$-substituted or unsubstituted heteroaryl (e.g., 5 to 12 membered, 5 to 10 membered, 5 to 9 membered, or 5 to 6 membered). In embodiments, $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20}$ is independently —F, —Cl, —Br, or —I. In embodiments, $R^{20}$ is independently unsubstituted methyl. In embodiments, $R^{20}$ is independently unsubstituted ethyl.

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(=O)$NHNH_2$, —NHC(=O)$NH_2$, —$NHSO_2H$, —NHC(=O)H, —NHC(O)—OH, —NHOH, —$N_3$, $R^2_2$-substituted or unsubstituted alkyl (e.g., $C_1$-$C_8$, $C_1$-$C_6$, $C_1$-$C_4$, or $C_1$-$C_2$), $R^2_2$-substituted or unsubstituted heteroalkyl (e.g., 2 to 8 membered, 2 to 6 membered, 4 to 6 membered, 2 to 3 membered, or 4 to 5 membered), $R^2_2$-substituted or unsubstituted cycloalkyl (e.g., $C_3$-$C_8$, $C_3$-$C_6$, $C_4$-$C_6$, or $C_5$-$C_6$), $R^2{}_2$-substituted or unsubstituted heterocycloalkyl (e.g., 3 to 8 membered, 3 to 6 membered, 4 to 6 membered, 4 to 5 membered, or 5 to 6 membered), $R^2{}_2$-substituted or unsubstituted aryl (e.g., $C_6$-$C_{12}$, $C_6$-$C_{10}$, or phenyl), or $R^2{}_2$-substituted or unsubstituted heteroaryl (e.g., 5 to 12 membered, 5 to 10 membered, 5 to 9 membered, or 5 to 6 membered). In embodiments, $R^{21}$ is independently oxo, halogen, —$CX^{21}{}_3$, —$CHX^{21}{}_2$, —$CH_2X^{21}$, —$OCX^{21}{}_3$, —$OCH_2X^{21}$, —$OCHX^{21}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21}$ is independently —F, —Cl, —Br, or —I. In embodiments, $R^{21}$ is independently unsubstituted methyl. In embodiments, $R^{21}$ is independently unsubstituted ethyl.

$R^2{}_2$ is independently oxo, halogen, —$CX^{22}{}_3$, —$CHX^{22}{}_2$, —$CH_2X^{22}$, —$OCX^{22}{}_3$, —$OCH_2X^{22}$, —$OCHX^{22}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^2{}_2$ is independently —F, —Cl, —Br, or —I. In embodiments, $R^2{}_2$ is independently unsubstituted methyl. In embodiments, $R^2{}_2$ is independently unsubstituted ethyl.

$R^{1A}$ is hydrogen, halogen, —$CX^{1A}{}_3$, —$CHX^{1A}{}_2$, —$CH_2X^{1A}$, —$OCX^{1A}{}_3$, —$OCH_2X^{1A}$ —$OCHX^{1A}{}_2$, —CN, —$SO_{n1A}R^{1AA}$, —$SO_{v1A}NR^{1AA}R^{1AB}$, —NHC(O)$NR^{1AA}R^{1AB}$, —N(O)$^{m1A}$, —$NR^{1AA}R^{1AB}$, —$NHNR^{1AA}R^{1AB}$, —C(O)$R^{1AA}$, —C(O)—$OR^{1AA}$, —C(O)$NR^{1AA}R^{1AB}$, —$OR^{1AA}$, —$NR^{1AA}SO_2R^{1AB}$, —$NR^{1AA}C(O)R^{1AB}$, —$NR^{1AA}C(O)OR^{1AB}$, —$NR^{1AA}OR^{1AB}$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $R^{1A}$ is independently hydrogen. In embodiments, $R^{1A}$ is independently —$CX^{1A}{}_3$. In embodiments, $R^{1A}$ is independently —$CHX^{1A}{}_2$. In embodiments, $R^{1A}$ is independently —$CH_2X^{1A}$. In embodiments, $R^{1A}$ is independently —CN. In embodiments, $R^{1A}$ is independently —COOH. In embodiments, $R^{1A}$ is independently —$CONH_2$. In embodiments, $X^{1A}$ is independently —F, —Cl, —Br, or —I.

In embodiments, $R^{1A}$ is independently hydrogen, —$CX^{1A}{}_3$, —$CHX^{1A}{}_2$, —$CH_2X^{1A}$, —CN, —COOH, —$CONH_2$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 to 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 8 membered, 3 to 6 membered, 4 to 6 membered, 4 to 5 membered, or 5 to 6 membered), $R^{20A}$-substituted or unsubstituted aryl (e.g., $C_6$-$C_{12}$, $C_6$-$C_{10}$, or phenyl), or $R^{20A}$-substituted or unsubstituted heteroaryl (e.g., 5 to 12 membered, 5 to 10 membered, 5 to 9 membered, or 5 to 6 membered). In embodiments, $R^{1A}$ is independently hydrogen, —$CX^{1A3}$, —$CHX^{1A}{}_2$, —$CH_2X^{1A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{1A}$ is independently —F, —Cl, —Br, or —I. In embodiments, $R^{1A}$ is independently hydrogen. In embodiments, $R^{1A}$ is independently unsubstituted methyl. In embodiments, $R^{1A}$ is independently unsubstituted ethyl.

In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered) or $R^{20A}$-substituted or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20A}$ is independently oxo, halogen, —$CX^{20A}{}_3$, —$CHX^{20A}{}_2$, —$CH_2X^{20A}$, —$OCX^{20A}{}_3$, —$OCH_2X^{20A}$, —$OCHX^{20A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 8 membered, 3 to 6 membered, 4 to 6 membered, 4 to 5 membered, or 5 to 6 membered), $R^{21A}$-substituted or unsubstituted aryl (e.g., $C_6$-$C_{12}$, $C_6$-$C_{10}$, or phenyl), or $R^{21A}$-substituted or unsubstituted heteroaryl (e.g., 5 to 12 membered, 5 to 10 membered, 5 to 9 membered, or 5 to 6 membered). In embodiments, $R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20A}$ is independently —F, —Cl, —Br, or —I. In embodiments, $R^{20A}$ is independently unsubstituted methyl. In embodiments, $R^{20A}$ is independently unsubstituted ethyl.

$R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{22A}$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 to 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_{12}$, $C_6$-$C_{10}$, or phenyl), or $R^{22A}$-substituted or unsubstituted heteroaryl (e.g., 5 to 12 membered, 5 to 10 membered, 5 to 9 membered, or 5 to 6 membered). In embodiments, $R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21A}$ is independently —F, —Cl, —Br, or —I. In embodiments, $R^{21A}$ is independently unsubstituted methyl. In embodiments, $R^{21A}$ is independently unsubstituted ethyl.

$R^{22A}$ is independently oxo, halogen, —$CX^{22A}_3$, —$CHX^{22A}_2$, —$CH_2X^{22A}$, —$OCX^{22A}_3$, —$OCH_2X^{22A}$, —$OCHX^{22A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22A}$ is independently —F, —Cl, —Br, or —I. In embodiments, $R^{22A}$ is independently unsubstituted methyl. In embodiments, $R^{22A}$ is independently unsubstituted ethyl.

In embodiments, $R^{1A}$ is independently hydrogen. In embodiments, $R^{1A}$ is independently —OH. In embodiments, $R^{1A}$ is independently unsubstituted methyl. In embodiments, $R^{1A}$ is independently —$OCH_3$. In embodiments, $R^{1A}$ is independently —NH—($C_1$-$C_4$ alkyl). In embodiments, $R^{1A}$ is independently

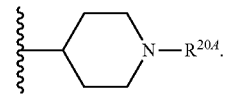

In embodiments, $R^{1A}$ is independently —NH—NH-Ph. In embodiments, $R^{1A}$ is independently $R^{20A}$-substituted or unsubstituted 5 membered heteroalkyl. In embodiments, $R^{1A}$ is independently $R^{20A}$-substituted or unsubstituted 6 membered heteroalkyl. In embodiments, $R^{1A}$ is independently $R^{20A}$-substituted or unsubstituted 7 membered heteroalkyl. In embodiments, $R^{20A}$ is independently —F, —$CF_3$, or unsubstituted $C_1$-$C_4$ alkyl.

In embodiments, RB is independently hydrogen, halogen, —$CX^{1B}_3$, —$CHX^{1B}_2$, —$CH_2X^{1B}$, —C(O)OH, —C(O)$NH_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{1B}_3$, —$OCHX^{1B}_2$, —$OCH_2X^{1B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{1B}$ are independently —Cl, —Br, —I, or —F.

In embodiments, a substituted $R^{1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{1B}$ is substituted, it is substituted with at least one lower substituent group.

In embodiments, $R^{1AA}$ is independently hydrogen, halogen, $-CX^{1AA}{}_3$, $-CHX^{1AA}{}_2$, $-CH_2X^{1AA}$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{1AA}{}_3$, $-OCHX^{1AA}{}_2$, $-OCH_2X^{1AA}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{1AA}$ is independently $-Cl$, $-Br$, $-I$, or $-F$.

In embodiments, a substituted $R^{1AA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1AA}$ is substituted with a plurality of groups selected from substituent groups, size-limited substituent groups, and lower substituent groups; each substituent group, size-limited substituent group, and/or lower substituent group may optionally be different. In embodiments, when $R^{1AA}$ is substituted, it is substituted with at least one substituent group. In embodiments, when $R^{1AA}$ is substituted, it is substituted with at least one size-limited substituent group. In embodiments, when $R^{1AA}$ is substituted, it is substituted with at least one lower substituent group.

In embodiments, $R^{1AB}$ is independently hydrogen, halogen, $-CX^{1A}{}_3$, $-CHX^{1AB}{}_2$, $-CH_2X^{1AB}$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{1AB}{}_3$, $-OCHX^{1A}B_2$, $-OCH_2X^{1AB}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{1AB}$ is independently $-Cl$, $-Br$, $-I$, or $-F$.

In embodiments, a substituted $R^{1AB}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1AB}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, $R^{1AA}$ and $R^{1AB}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12 membered, 5 to 10 membered, 5 to 9 membered, or 5 to 6 membered). In embodiments, a substituted heterocycloalkyl or substituted heteroaryl formed by the joining of $R^{1AA}$ and $R^{1AB}$ substituents bonded to the same nitrogen atom is substituted with at least one substituent group, size-limited substituent group, or lower substituent group; wherein if the substituted heterocycloalkyl or substituted heteroaryl is substituted with a plurality of groups selected from substituent groups, size-limited substituent groups, and lower substituent groups; each substituent group, size-limited substituent group, and/or lower substituent group may optionally be different. In embodiments, when a heterocycloalkyl formed by the joining of $R^{1AA}$ and $R^{1A}$ substituents bonded to the same nitrogen atom is substituted, it is substituted with at least one substituent group. In embodiments, when a heterocycloalkyl formed by the joining of $R^{1AA}$ and $R^{1AB}$ substituents bonded to the same nitrogen atom is substituted, it is substituted with at least one size-limited substituent group. In embodiments, when a heterocycloalkyl formed by the joining of $R^{1AA}$ and $R^{1AB}$ substituents bonded to the same nitrogen atom is substituted, it is substituted with at least one lower substituent group. In embodiments, when a heteroaryl formed by the joining of $R^{1AA}$ and $R^{1AB}$ substituents bonded to the same nitrogen atom is substituted, it is substituted with at least one substituent group. In embodiments, when a heteroaryl formed by the joining of $R^{1AA}$ and $R^{1AB}$ substituents bonded to the same nitrogen atom is substituted, it is substituted with at least one size-limited substituent group. In embodiments, when a heteroaryl formed by the joining of $R^{1AA}$ and $R^{1AB}$ substituents bonded to the same nitrogen atom is substituted, it is substituted with at least one lower substituent group.

$R^2$ is hydrogen, halogen, $-CX^2{}_3$, $-CHX^2{}_2$, $-CH_2X^2$, $-OCX^2{}_3$, $-OCH_2X^2$, $-OCHX^2{}_2$, $-CN$, $-SO_{n2}R^{2A}$, $-SO_{v2}NR^{2A}R^{2B}$, $-NHC(O)NR^{2A}R^{2B}$, $-N(O)_{m2}$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, $-L^2$-$E^2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $E^2$ is independently halogen, $-CX^2{}_3$, $-CHX^2{}_2$, $-CH_2X^2$, $-OCX^2{}_3$, $-OCH_2X^2$, $-OCHX^2{}_2$, $-CN$, $-SO_{n2}R^{2A}$, $SO_{v1}NR^{2A}R^{2B}$, $-NHC(O)NR^{2A}R^{2B}$, $-N(O)_{m2}$, $-NR^{2A}R^{2B}$, $-NHNR^{2A}R^{2B}$, $-C(O)R^{2A}$, $-C(O)-OR^{2A}$, $-C(O)NR^{2A}R^{21B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $E^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2A}$, $SO_{v1}NR^{2A}R^{2B}$, $-NHC(O)NR^{2A}R^{2B}$, $-N(O)_{m2}$, $-NR^{2A}R^{2B}$, $-NHNR^{2A}R^{2B}$, $-C(O)R^{2A}$, $-C(O)-OR^{2A}$, $-C(O)NR^{2A}R^{21B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, $R^2_3$-substituted or unsubstituted alkyl (e.g., $C_1$-$C_8$, $C_1$-$C_6$, $C_1$-$C_4$, or $C_1$-$C_2$), $R^2_3$-substituted or unsubstituted heteroalkyl (e.g., 2 to 8 membered, 2 to 6 membered, 4 to 6 membered, 2 to 3 membered, or 4 to 5 membered), $R^2_3$-substituted or unsubstituted cycloalkyl (e.g., $C_3$-$C_8$, $C_3$-$C_6$, $C_4$-$C_6$, or $C_5$-$C_6$), $R^2_3$-substituted or unsubstituted heterocycloalkyl (e.g., 3 to 8 membered, 3 to 6 membered, 4 to 6 membered, 4 to 5 membered, or 5 to 6 membered), $R^2_3$-substituted or unsubstituted aryl (e.g., $C_6$-$C_{12}$, $C_6$-$C_{10}$, or phenyl), or $R^2_3$-substituted or unsubstituted heteroaryl (e.g., 5 to 12 membered, 5 to 10 membered, 5 to 9 membered, or 5 to 6 membered).

In embodiments, $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^2_3$-substituted or unsubstituted alkyl (e.g., $C_1$-$C_8$, $C_1$-$C_6$, $C_1$-$C_4$, or $C_1$-$C_2$), $R^2_3$-substituted or unsubstituted heteroalkyl (e.g., 2 to 8 membered, 2 to 6 membered, 4 to 6 membered, 2 to 3 membered, or 4 to 5 membered), $R^2_3$-substituted or unsubstituted cycloalkyl (e.g., $C_3$-$C_8$, $C_3$-$C_6$, $C_4$-$C_6$, or $C_5$-$C_6$), $R^2_3$-substituted or unsubstituted heterocycloalkyl (e.g., 3 to 8 membered, 3 to 6 membered, 4 to 6 membered, 4 to 5 membered, or 5 to 6 membered), $R^2_3$-substituted or unsubstituted aryl (e.g., $C_6$-$C_{12}$, $C_6$-$C_{10}$, or phenyl), or $R^2_3$-substituted or unsubstituted heteroaryl (e.g., 5 to 12 membered, 5 to 10 membered, 5 to 9 membered, or 5 to 6 membered). In embodiments, $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^2$ is independently $-F$, $-Cl$, $-Br$, or $-I$.

$R^2_3$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{12}$, $C_6$-$C_{10}$, or phenyl), or $R^{24}$-substituted or unsubstituted heteroaryl (e.g., 5 to 12 membered, 5 to 10 membered, 5 to 9 membered, or 5 to 6 membered). In embodiments, $R^2_3$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^2_3$ is independently $-F$, $-Cl$, $-Br$, or $-I$. In embodiments, $R^2_3$ is independently unsubstituted methyl. In embodiments, $R^2_3$ is independently unsubstituted ethyl.

$R^{24}$ is independently oxo, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$-$C_{12}$, $C_6$-$C_{10}$, or phenyl), or $R^{25}$-substituted or unsubstituted heteroaryl (e.g., 5 to 12 membered, 5 to 10 membered, 5 to 9 membered, or 5 to 6 membered). In embodiments, $R^{24}$ is independently oxo, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24}$ is independently $-F$, $-Cl$, $-Br$, or $-I$. In embodiments, $R^{24}$ is independently unsubstituted methyl. In embodiments, $R^{24}$ is independently unsubstituted ethyl.

$R^{25}$ is independently oxo, halogen, $-CX^{25}{}_3$, $-CHX^{25}{}_2$, $-CH_2X^{25}$, $-OCX^{25}{}_3$, $-OCH_2X^{25}$, $-OCHX^{25}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25}$ is independently $-F$, $-Cl$, $-Br$, or $-I$. In embodiments, $R^{25}$ is independently unsubstituted methyl. In embodiments, $R^{25}$ is independently unsubstituted ethyl.

In embodiments, $R^2$ is independently hydrogen. In embodiments, $R^2$ is independently $-COOH$. In embodiments, $R^2$ is independently $-C(O)O(C_1$-$C_4$ alkyl). In embodiments, $R^2$ is independently $-CF_3$. In embodiments, $R^2$ is independently $-CH_2OH$. In embodiments, $R^2$ is independently $-C(O)CH_3$. In embodiments, $R^2$ is independently

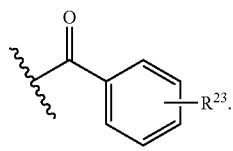

In embodiments, $R^1$ is independently.

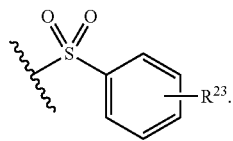

In embodiments, $R^2{}_3$ is hydrogen, $-F$, $-Cl$, or unsubstituted $C_1$-$C_4$ alkyl.

$R^{2A}$ is hydrogen, halogen, $-CX^{2A}{}_3$, $-CHX^{2A}{}_2$, $-CH_2X^{2A}$, $-OCX^{2A}{}_3$, $-OCH_2X^{2A}$, $-OCHX^{2A}{}_2$, $-CN$, $-SO_{n2}{}^AR^{2AA}$, $-SO_{v2A}NR^{2AA}R^{2AB}$, $-NHC(O)NR^{2AA}R^{2AB}$, $-N(O)_{m2A}$, $-NR^{2AA}R^{2AB}$, $-NR^{2AA}R^{2AB}$, $-C(O)R^{2AA}$, $-C(O)-OR^{2AA}$, $-C(O)NR^{2AA}R^{2AB}$, $-OR^{2AA}$, $-NR^{2AA}SO_2R^{2AB}$, $-NR^{2AA}C(O)R^{2AB}$, $-NR^{2AA}C(O)OR^{2AB}$, $-NR^{2AA}OR^{2AB}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). In embodiments, $R^{2A}$ is independently hydrogen, $-CX^{2A}{}_3$, $-CHX^{2A}{}_2$, $-CH_2X^{2A}$, $-CN$, $-COOH$, $-CONH_2$, $R^{23A}$-substituted or unsubstituted alkyl (e.g., $C_1$-$C_8$, $C_1$-$C_6$, $C_1$-$C_4$, or $C_1$-$C_2$), $R^{23A}$-substituted or unsubstituted heteroalkyl (e.g., 2 to 12 membered, 2 to 8 membered, 2 to 6 membered, 4 to 6 membered, 2 to 3 membered, or 4 to 5 membered), $R^{23A}$-substituted or unsubstituted cycloalkyl (e.g., $C_3$-$C_8$, $C_3$-$C_6$, $C_4$-$C_6$, or $C_5$-$C_6$), $R^{23A}$-substituted or unsubstituted heterocycloalkyl (e.g., 3 to 8 membered, 3 to 6 membered, 4 to 6 membered, 4 to 5 membered, or 5 to 6 membered), $R^{23A}$-substituted or unsubstituted aryl (e.g., $C_6$-$C_{12}$, $C_6$-$C_{10}$, or phenyl), or $R^{23A}$-substituted or unsubstituted heteroaryl (e.g., 5 to 12 membered, 5 to 10 membered, 5 to 9 membered, or 5 to 6 membered). In embodiments, $R^{2A}$ is independently hydrogen, $-CX^{2A}{}_3$, $-CHX^{2A}{}_2$, $-CH_2X^{2A}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{2A}$ is independently $-F$, $-Cl$, $-Br$, or $-I$. In embodiments, $R^{2A}$ is independently hydrogen. In embodiments, $R^{2A}$ is independently unsubstituted methyl. In embodiments, $R^{2A}$ is independently unsubstituted ethyl.

In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered) or $R^{23A}$-substituted or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen and the nitrogen they are both bonded to are joined to form

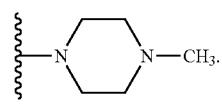

$R^{23A}$ is independently oxo, halogen, $-CX^{23A}{}_3$, $-CHX^{23A}{}_2$, $-CH_2X^{23A}$, $-OCX^{23A}{}_3$, $-OCH_2X^{23A}$, $-OCHX^{23A}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $-OPh$, $R^{24A}$-substituted or unsubstituted alkyl (e.g., $C_1$-$C_8$, $C_1$-$C_6$, $C_1$-$C_4$, or $C_1$-$C_2$), $R^{24A}$-substituted or unsubstituted heteroalkyl (e.g., 2 to 8 membered, 2 to 6 membered, 4 to 6 membered, 2 to 3 membered, or 4 to 5 membered), $R^{24A}$-substituted or unsubstituted cycloalkyl (e.g., $C_3$-$C_8$, $C_3$-$C_6$, $C_4$-$C_6$, or $C_5$-$C_6$), $R^{24A}$-substituted or unsubstituted heterocycloalkyl (e.g., 3 to 8 membered, 3 to 6 membered, 4 to 6 membered, 4 to 5 membered, or 5 to 6 membered), $R^{24A}$-substituted or unsubstituted aryl (e.g., $C_6$-$C_{14}$, $C_6$-$C_{12}$, $C_6$-$C_{10}$, or phenyl), or $R^{24A}$-substituted or unsubstituted heteroaryl (e.g., 5 to 12 membered, 5 to 10 membered, 5 to 9 membered, or 5 to 6 membered). In embodiments, $R^{23A}$ is independently oxo, halogen, —$CX^{23A}_3$, —$CHX^{23A}_2$, —$CH_2X^{23A}$, —$OCX^{23A}_3$, —$OCH_2X^{23A}$—$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{23A}$ is independently —F, —Cl, —Br, or —I. In embodiments, $R^{23A}$ is independently unsubstituted methyl. In embodiments, $R^{23A}$ is independently unsubstituted ethyl. In embodiments, two adjacent $R^{23A}$ substituents may optionally be joined to form an $R^{24A}$-substituted or unsubstituted cycloalkyl, $R^{24A}$-substituted or unsubstituted heterocycloalkyl, $R^{24A}$-substituted or unsubstituted aryl, or $R^{24A}$-substituted or unsubstituted heteroaryl.

$R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{25A}$-substituted or unsubstituted alkyl (e.g., $C_1$-$C_8$, $C_1$-$C_6$, $C_1$-$C_4$, or $C_1$-$C_2$), $R^{25A}$-substituted or unsubstituted heteroalkyl (e.g., 2 to 8 membered, 2 to 6 membered, 4 to 6 membered, 2 to 3 membered, or 4 to 5 membered), $R^{25A}$-substituted or unsubstituted cycloalkyl (e.g., $C_3$-$C_8$, $C_3$-$C_6$, $C_4$-$C_6$, or $C_5$-$C_6$), $R^{25A}$-substituted or unsubstituted heterocycloalkyl (e.g., 3 to 8 membered, 3 to 6 membered, 4 to 6 membered, 4 to 5 membered, or 5 to 6 membered), $R^{25A}$-substituted or unsubstituted aryl (e.g., $C_6$-$C_{12}$, $C_6$-$C_{10}$, or phenyl), or $R^{25A}$-substituted or unsubstituted heteroaryl (e.g., 5 to 12 membered, 5 to 10 membered, 5 to 9 membered, or 5 to 6 membered). In embodiments, $R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24A}$ is independently —F, —Cl, —Br, or —I.

In embodiments, $R^{24A}$ is independently unsubstituted methyl. In embodiments, $R^{24A}$ is independently unsubstituted ethyl.

$R^{25A}$ is independently oxo, halogen, —$CX^{25A}_3$, —$CHX^{25A}_2$, —$CH_2X^{25A}$, —$OCX^{25A}_3$, —$OCH_2X^{25A}$, —$OCHX^{25A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25A}$ is independently —F, —Cl, —Br, or —I. In embodiments, $R^{25A}$ is independently unsubstituted methyl. In embodiments, $R^{25A}$ is independently unsubstituted ethyl.

In embodiments, $R^{2A}$ is independently hydrogen. In embodiments, $R^{2A}$ is independently unsubstituted $C_1$-$C_4$ alkyl. In embodiments, $R^{2A}$ is independently —$CH_2CH_2OH$. In embodiments, $R^{2A}$ is independently unsubstituted $C_5$-$C_6$ cycloalkyl. In embodiments, $R^{2A}$ is independently $R^{23A}$-substituted or unsubstituted phenyl. In embodiments, $R^{2A}$ is independently unsubstituted phenyl. In embodiments, $R^{2A}$ is independently

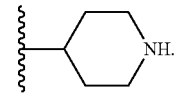

In embodiments, $R^{2A}$ is independently

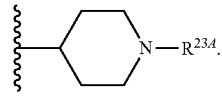

In embodiments, $R^{2A}$ is independently —NHPh. In embodiments, $R^{2A}$ is independently —NH-pyridyl. In embodiments, $R^{2A}$ is independently an $R^{23A}$-substituted or unsubstituted 4 to 9 membered heteroalkyl. In embodiments, $R^{2A}$ is independently an unsubstituted 4 to 9 membered heteroalkyl. In embodiments, $R^{2A}$ is independently an $R^{23A}$-substituted or unsubstituted 5 to 9 membered heteroaryl. In embodiments, $R^{2A}$ is independently an unsubstituted 5 to 9 membered heteroaryl. In embodiments, $R^{23A}$ is independently —F or —Cl. In embodiments, $R^{23A}$ is independently —$OCH_3$. In embodiments, $R^{23A}$ is independently —$OCF_3$. In embodiments, $R^{23A}$ is independently —C(O)-tert-butyl. In embodiments, $R^{23A}$ is independently —$CONH_2$. In embodiments, $R^{23A}$ is independently

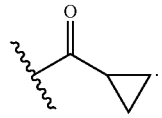 [SMILES: *C(=O)C1CC1]

In embodiments, $R^{23A}$ is independently —COCH$_3$. In embodiments, $R^{23A}$ is independently —CH$_2$CH$_2$OH. In embodiments, $R^{23A}$ is independently an unsubstituted C$_1$-C$_4$ alkyl. In embodiments, $R^{23A}$ is independently an unsubstituted C$_2$ alkynyl. In embodiments, $R^{23A}$ is independently an $R^{24A}$-substituted or unsubstituted phenyl. In embodiments, $R^{23A}$ is independently an unsubstituted phenyl. In embodiments, $R^{23A}$ is independently an unsubstituted C$_{13}$ aryl. In embodiments, $R^{23A}$ is independently an $R^{24A}$-substituted or unsubstituted pyridyl. In embodiments, $R^{23A}$ is independently an unsubstituted pyridyl. In embodiments, $R^{23A}$ is independently —SO$_2$CH$_3$. In embodiments, $R^{23A}$ is independently —SO$_2$Ph. In embodiments, $R^{23A}$ is independently

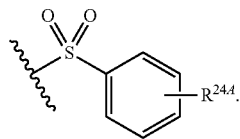

In embodiments, $R^{23A}$ is independently —OPh. In embodiments, $R^{23A}$ is independently

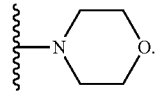

In embodiments, $R^{23A}$ is independently an $R^{24A}$-substituted or unsubstituted 6 membered heteroalkyl. In embodiments, $R^{23A}$ is independently

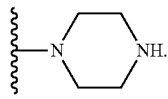 [SMILES: *N1CCNCC1]

In embodiments, $R^{23A}$ is independently

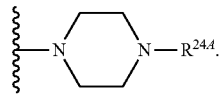

In embodiments, $R^{23A}$ is independently an unsubstituted 6 membered heteroalkyl. In embodiments, $R^{24A}$ is independently oxo. In embodiments, $R^{24A}$ is independently unsubstituted methyl. In embodiments, $R^{24A}$ is independently an $R^{25A}$-substituted or unsubstituted phenyl. In embodiments, $R^{24A}$ is independently unsubstituted phenyl. In embodiments, $R^{24A}$ is independently an $R^{25A}$-substituted or unsubstituted 5 to 6 membered heterocycloalkyl. In embodiments, $R^{24A}$ is independently an unsubstituted 5 to 6 membered heterocycloalkyl. In embodiments, $R^{24A}$ is independently an $R^{25A}$-substituted or unsubstituted 5 to 6 membered heteroaryl. In embodiments, $R^{24A}$ is independently an unsubstituted 5 to 6 membered heteroaryl. In embodiments, $R^{24A}$ is independently an $R^{25A}$-substituted thienyl. In embodiments, $R^{24A}$ is independently an unsubstituted thienyl. In embodiments, $R^{24A}$ is independently an $R^{25A}$-substituted pyridyl. In embodiments, $R^{24A}$ is independently an unsubstituted pyridyl. In embodiments, $R^{24A}$ is independently an $R^{25A}$-substituted pyrimidinyl. In embodiments, $R^{24A}$ is independently an unsubstituted pyrimidinyl. In embodiments, $R^{25A}$ is independently —F, —Cl, —CN, or unsubstituted methyl.

$R^{2B}$ is hydrogen, halogen, —CX$^{2B}$$_3$, —CHX$^{2B}$$_2$, —CH$_2$X$^{2B}$, —OCX$^{2B}$$_3$, —OCH$_2$X$^{2B}$, —OCHX$^{2B}$$_2$, —CN, —SO$_{n2B}$R$^{2BA}$, —SO$_{v2B}$NR$^{2BA}$R$^{2BB}$, —NHC(O)NR$^{2BA}$R$^{2BB}$, —N(O)$_{m2B}$, —NR$^{2BA}$R$^{2BB}$, —NHNR$^{2BA}$R$^{2BB}$, —C(O)R$^{2BA}$, —C(O)—OR$^{2BA}$, —C(O)NR$^{2BA}$R$^{2BB}$, —OR$^{2BA}$, —NR$^{2BA}$SO$_2$R$^{2BB}$, —NR$^{2BA}$C(O)R$^{2BB}$, —NR$^{2BA}$C(O)OR$^{2BB}$ NR$^{2BA}$OR$^{2BB}$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered).

In embodiments, $R^{2B}$ is independently hydrogen, —CX$^{2B}$$_3$, —CHX$^{2B}$$_2$, —CH$_2$X$^{2B}$, —CN, —COOH, —CONH$_2$, $R^{23B}$-substituted or unsubstituted alkyl (e.g., C$_1$-C$_8$, C$_1$-C$_6$, C$_1$-C$_4$, or C$_1$-C$_2$), $R^{23B}$-substituted or unsubstituted heteroalkyl (e.g., 2 to 8 membered, 2 to 6 membered, 4 to 6 membered, 2 to 3 membered, or 4 to 5 membered), $R^{23B}$-substituted or unsubstituted cycloalkyl (e.g., C$_3$-C$_8$, C$_3$-C$_6$, C$_4$-C$_6$, or C$_5$-C$_6$), $R^{23B}$-substituted or unsubstituted heterocycloalkyl (e.g., 3 to 8 membered, 3 to 6 membered, 4 to 6 membered, 4 to 5 membered, or 5 to 6 membered), $R^{23B}$-substituted or unsubstituted aryl (e.g., C$_6$-C$_{12}$, C$_6$-C$_{10}$, or phenyl), or $R^{23B}$-substituted or unsubstituted heteroaryl (e.g., 5 to 12 membered, 5 to 10 membered, 5 to 9 membered, or 5 to 6 membered). In embodiments, $R^{2B}$ is independently hydrogen, —CX$^{2B}$$_3$, —CHX$^{2B}$$_2$, —CH$_2$X$^{2B}$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). $X^{2B}$ is independently —F, —Cl, —Br, or —I. In embodiments, $R^{2B}$ is independently hydrogen. In embodiments, $R^{2B}$ is independently an unsubstituted methyl. In embodiments, $R^{2B}$ is independently unsubstituted ethyl.

$R^{23B}$ is independently oxo, halogen, —CX$^{23B}$$_3$, —CHX$^{23B}$$_2$, —CH$_2$X$^{23B}$, —OCX$^{23B}$$_3$, —OCH$_2$X$^{23B}$, —OCHX$^{23B}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, —OPh, $R^{24B}$-substituted or unsubstituted alkyl (e.g., C$_1$-C$_8$, C$_1$-C$_6$, C$_1$-C$_4$, or C$_1$-C$_2$), $R^{24B}$-substituted or unsubstituted heteroalkyl (e.g., 2 to 8 membered, 2 to 6 membered, 4 to 6 membered, 2 to 3 membered, or 4 to 5 membered), $R^{24B}$-substituted or unsubstituted cycloalkyl (e.g., C$_3$-C$_8$, C$_3$-C$_6$, C$_4$-C$_6$, or C$_5$-C$_6$), $R^{24B}$-substituted or unsubstituted heterocycloalkyl (e.g., 3 to 8 membered, 3 to 6 membered, 4 to 6 membered, 4 to 5 membered, or 5 to 6 membered), $R^{24B}$-substituted or unsubstituted aryl (e.g., C$_6$-C$_{12}$, C$_6$-C$_{10}$, or phenyl), or $R^{24B}$-substituted or unsubstituted heteroaryl (e.g., 5 to 12 membered, 5 to 10 membered, 5 to 9 membered, or 5 to 6 membered). In embodiments, $R^{23B}$ is independently oxo, halogen, —$CX^{23B}_3$, —$CHX^{23B}_2$, —$CH_2X^{23B}$, —$OCX^{23B}_3$, —$OCH_2X^{23B}$, —$OCHX^{23B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{23B}$ is independently —F, —Cl, —Br, or —I. In embodiments, $R^{23B}$ is independently unsubstituted methyl. In embodiments, $R^{23B}$ is independently unsubstituted ethyl. In embodiments, two adjacent $R^{23B}$ substituents may optionally be joined to form an $R^{24B}$-substituted or unsubstituted cycloalkyl, $R^{24B}$-substituted or unsubstituted heterocycloalkyl, $R^{24B}$-substituted or unsubstituted aryl, or $R^{24B}$-substituted or unsubstituted heteroaryl.

$R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{25B}$-substituted or unsubstituted alkyl (e.g., $C_1$-$C_8$, $C_1$-$C_6$, $C_1$-$C_4$, or $C_1$-$C_2$), $R^{25B}$-substituted or unsubstituted heteroalkyl (e.g., 2 to 8 membered, 2 to 6 membered, 4 to 6 membered, 2 to 3 membered, or 4 to 5 membered), $R^{25B}$-substituted or unsubstituted cycloalkyl (e.g., $C_3$-$C_8$, $C_3$-$C_6$, $C_4$-$C_6$, or $C_5$-$C_6$), $R^{25B}$-substituted or unsubstituted heterocycloalkyl (e.g., 3 to 8 membered, 3 to 6 membered, 4 to 6 membered, 4 to 5 membered, or 5 to 6 membered), $R^{25B}$-substituted or unsubstituted aryl (e.g., $C_6$-$C_{12}$, $C_6$-$C_{10}$, or phenyl), or $R^{25B}$-substituted or unsubstituted heteroaryl (e.g., 5 to 12 membered, 5 to 10 membered, 5 to 9 membered, or 5 to 6 membered). In embodiments, $R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24B}$ is independently —F, —Cl, —Br, or —I. In embodiments, $R^{24B}$ is independently unsubstituted methyl. In embodiments, $R^{24B}$ is independently unsubstituted ethyl.

$R^{25B}$ is independently oxo, halogen, —$CX^{25B}_3$, —$CHX^{25B}_2$, —$CH_2X^{25B}$, —$OCX^{25B}_3$, —$OCH_2X^{25B}$, —$OCHX^{25B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25B}$ is independently —F, —Cl, —Br, or —I. In embodiments, $R^{25B}$ is independently unsubstituted methyl. In embodiments, $R^{25B}$ is independently unsubstituted ethyl.

In embodiments, $R^{2AA}$ is independently hydrogen, halogen, —$CX^{2AA}_3$, —$CHX^{2AA}_2$, —$CH_2X^{2AA}$, —C(O)OH, —C(O)$NH_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{2AA}_3$, —$OCHX^{2AA}_2$, —$OCH_2X^{2AA}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{2AA}$ is independently —Cl, —Br, —I, or —F.

In embodiments, a substituted $R^{2AA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2AA}$ is substituted with a plurality of groups selected from substituent groups, size-limited substituent groups, and lower substituent groups; each substituent group, size-limited substituent group, and/or lower substituent group may optionally be different. In embodiments, when $R^{2AA}$ is substituted, it is substituted with at least one substituent group. In embodiments, when $R^{2AA}$ is substituted, it is substituted with at least one size-limited substituent group. In embodiments, when $R^{2AA}$ is substituted, it is substituted with at least one lower substituent group.

In embodiments, $R^{2A}$ is independently hydrogen, halogen, —$CX^{2AB}_3$, —$CHX^{2AB}_2$, —$CH_2X^{2AB}$, —C(O)OH, —C(O)$NH_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{2A}_3$, —$OCHX^{2AB}_2$, —$OCH_2X^{2AB}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{2A}$ is independently —Cl, —Br, —I, or —F.

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^{2A}$ is substituted, it is substituted with at least one lower substituent group.

In embodiments, $R^{2AA}$ and $R^{2A}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12 membered, 5 to 10 membered, 5 to 9 membered, or 5 to 6 membered). In embodiments, a substituted heterocycloalkyl or substituted heteroaryl formed by the joining of $R^{2AA}$ and $R^{2A}$ substituents bonded to the same nitrogen atom is substituted with at least one substituent group, size-limited substituent group, or lower substituent group; wherein if the substituted heterocycloalkyl or substituted heteroaryl is substituted with a plurality of groups selected from substituent groups, size-limited substituent groups, and lower substituent groups; each substituent group, size-limited substituent group, and/or lower substituent group may optionally be different. In embodiments, when a heterocycloalkyl formed by the joining of $R^{2AA}$ and $R^{2A}$ substituents bonded to the same nitrogen atom is substituted, it is substituted with at least one substituent group. In embodiments, when a heterocycloalkyl formed by the joining of $R^{2AA}$ and $R^{2A}$ substituents bonded to the same nitrogen atom is substituted, it is substituted with at least one size-limited substituent group. In embodiments, when a heterocycloalkyl formed by the joining of $R^{2AA}$ and $R^{2A}$ substituents bonded to the same nitrogen atom is substituted, it is substituted with at least one lower substituent group. In embodiments, when a heteroaryl formed by the joining of $R^{2AA}$ and $R^{2A}$ substituents bonded to the same nitrogen atom is substituted, it is substituted with at least one substituent group. In embodiments, when a heteroaryl formed by the joining of $R^{2AA}$ and $R^{2A}$ substituents bonded to the same nitrogen atom is substituted, it is substituted with at least one size-limited substituent group. In embodiments, when a heteroaryl formed by the joining of $R^{2AA}$ and $R^{2AB}$ substituents bonded to the same nitrogen atom is substituted, it is substituted with at least one lower substituent group.

In embodiments, $R^{2BA}$ is independently hydrogen, halogen, $-CX^{2BA}_3$, $-CHX^{2BA}_2$, $-CH_2X^{2BA}$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{2BA}_3$, $-OCHX^{2BA}_2$, $-OCH_2X^{2BA}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{2BA}$ is independently $-Cl$, $-Br$, $-I$, or $-F$.

In embodiments, a substituted $R^{2BA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2BA}$ is substituted with a plurality of groups selected from substituent groups, size-limited substituent groups, and lower substituent groups; each substituent group, size-limited substituent group, and/or lower substituent group may optionally be different. In embodiments, when $R^{2BA}$ is substituted, it is substituted with at least one substituent group. In embodiments, when $R^{2BA}$ is substituted, it is substituted with at least one size-limited substituent group. In embodiments, when $R^{2BA}$ is substituted, it is substituted with at least one lower substituent group.

In embodiments, $R^{2BB}$ is independently hydrogen, halogen, $-CX^{2BB}_3$, $-CHX^{2BB}_2$, $-CH_2X^{2BB}$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{2BB}_3$, $-OCHX^{2BB}_2$, $-OCH_2X^{2BB}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{2BB}$ is independently $-Cl$, $-Br$, $-I$, or $-F$.

In embodiments, a substituted $R^{2BB}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2BB}$ is substituted with a plurality of groups selected from substituent groups, size-limited substituent groups, and lower substituent groups; each substituent group, size-limited substituent group, and/or lower substituent group may optionally be different. In embodiments, when $R^{2BB}$ is substituted, it is substituted with at least one substituent group. In embodiments, when $R^{2BB}$ is substituted, it is substituted with at least one size-limited substituent group. In embodiments, when $R^{2BB}$ is substituted, it is substituted with at least one lower substituent group.

In embodiments, $R^{2BA}$ and $R^{2BB}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12 membered, 5 to 10 membered, 5 to 9 membered, or 5 to 6 membered). In embodiments, a substituted heterocycloalkyl or substituted heteroaryl formed by the joining of $R^{2BA}$ and $R^{2BB}$ substituents bonded to the same nitrogen atom is substituted with at least one substituent group, size-limited substituent group, or lower substituent group; wherein if the substituted heterocycloalkyl or substituted heteroaryl is substituted with a plurality of groups selected from substituent groups, size-limited substituent groups, and lower substituent groups; each substituent group, size-limited substituent group, and/or lower substituent group may optionally be different. In embodiments, when a heterocycloalkyl formed by the joining of $R^{2BA}$ and $R^{2BB}$ substituents bonded to the same nitrogen atom is substituted, it is substituted with at least one substituent group. In embodiments, when a heterocycloalkyl formed by the joining of $R^{2BA}$ and $R^{2BB}$ substituents bonded to the same nitrogen atom is substituted, it is substituted with at least one size-limited substituent group. In embodiments, when a heterocycloalkyl formed by the joining of $R^{2BA}$ and $R^{2BB}$ substituents bonded to the same nitrogen atom is substituted, it is substituted with at least one lower substituent group. In embodiments, when a heteroaryl formed by the joining of $R^{2BA}$ and $R^{2BB}$ substituents bonded to the same nitrogen atom is substituted, it is substituted with at least one substituent group. In embodiments, when a heteroaryl formed by the joining of $R^{2BA}$ and $R^{2BB}$ substituents bonded to the same nitrogen atom is substituted, it is substituted with at least one size-limited substituent group. In embodiments, when a heteroaryl formed by the joining of $R^{2BA}$ and $R^{2BB}$ substituents bonded to the same nitrogen atom is substituted, it is substituted with at least one lower substituent group.

In embodiments, $R^3$ is independently hydrogen, halogen, —$CX^3_3$, —$CHX^3_2$, —$CH_2X^3$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^3{}_3$, —OCHX$^3{}_2$, —OCH$_2$X$^3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), or substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^3$ is independently —Cl, —Br, —I, or —F.

In embodiments, $R^3$ is independently hydrogen. In embodiments, $R^3$ is independently unsubstituted methyl. In embodiments, $R^3$ is independently —CH$_2$OH. In embodiments, $R^3$ is independently unsubstituted phenyl.

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^{3A}$ is independently hydrogen, halogen, —$CX^{3A}_3$, —$CHX^{3A}_2$, —$CH_2X^{3A}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{3A}{}_3$, —OCHX$^{3A}{}_2$, —OCH$_2$X$^{3A}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), or substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{3A}$ is independently —Cl, —Br, —I, or —F.

In embodiments, a substituted $R^{3A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, $R^{3B}$ is independently hydrogen, halogen, —$CX^{3B}_3$, —$CHX^{3B}_2$, —$CH_2X^{3B}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{3B}{}_3$, —OCHX$^{3B}{}_2$, —OCH$_2$X$^{3B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{3B}$ is independently —Cl, —Br, —I, or —F.

In embodiments, a substituted $R^{3B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, $R^4$ is independently hydrogen, halogen, —$CX^4_3$, —$CHX^4_2$, —$CH_2X^4$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^4{}_3$, —OCHX$^4$$_2$, —OCH$_2$X$^4$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^4$ is independently hydrogen. In embodiments, R$^4$ is independently —OH. X$^4$ is independently —Cl, —Br, —I, or —F.

In embodiments, a substituted R$^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^4$ is substituted with a plurality of groups selected from substituent groups, size-limited substituent groups, and lower substituent groups; each substituent group, size-limited substituent group, and/or lower substituent group may optionally be different. In embodiments, when R$^4$ is substituted, it is substituted with at least one substituent group. In embodiments, when R$^4$ is substituted, it is substituted with at least one size-limited substituent group. In embodiments, when R$^4$ is substituted, it is substituted with at least one lower substituent group.

In embodiments, R$^{4A}$ is independently hydrogen, halogen, —CX$^{4A}$$_3$, —CHX$^{4A}$$_2$, —CH$_2$X$^{4A}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{4A}$$_3$, —OCHX$^{4A}$$_2$, —OCH$_2$X$^{4A}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{4A}$ is independently —Cl, —Br, —I or, —F.

In embodiments, a substituted R$^{4A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{4A}$ is substituted with a plurality of groups selected from substituent groups, size-limited substituent groups, and lower substituent groups; each substituent group, size-limited substituent group, and/or lower substituent group may optionally be different. In embodiments, when R$^{4A}$ is substituted, it is substituted with at least one substituent group. In embodiments, when R$^{4A}$ is substituted, it is substituted with at least one size-limited substituent group. In embodiments, when R$^{4A}$ is substituted, it is substituted with at least one lower substituent group.

In embodiments, R$^{4B}$ is independently hydrogen, halogen, —CX$^{4B}$$_3$, —CHX$^{4B}$$_2$, —CH$_2$X$^{4B}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{4B}$$_3$, —OCHX$^{4B}$$_2$, —OCH$_2$X$^{4B}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{4B}$ is independently —Cl, —Br, —I, or —F.

In embodiments, a substituted R$^{4B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{4B}$ is substituted with a plurality of groups selected from substituent groups, size-limited substituent groups, and lower substituent groups; each substituent group, size-limited substituent group, and/or lower substituent group may optionally be different. In embodiments, when R$^{4B}$ is substituted, it is substituted with at least one substituent group. In embodiments, when R$^{4B}$ is substituted, it is substituted with at least one size-limited substituent group. In embodiments, when R$^{4B}$ is substituted, it is substituted with at least one lower substituent group.

In embodiments, R$^5$ is independently hydrogen, halogen, —CX$^5$$_3$, —CHX$^5$$_2$, —CH$_2$X$^5$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^5$$_3$, —OCHX$^5$$_2$, —OCH$_2$X$^5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^5$ is independently hydrogen. In embodiments, R$^5$ is independently —OH. X$^5$ is independently —Cl, —Br, —I, or —F.

In embodiments, a substituted R$^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^5$ is substituted with a plurality of groups selected from substituent groups, size-limited substituent groups, and lower substituent groups; each substituent group, size-limited substituent group, and/or lower substituent group may optionally be different. In embodiments, when R$^5$ is substituted, it is substituted with at least one substituent group. In embodiments, when R$^5$ is substituted, it is substituted with at least one size-limited substituent group. In embodiments, when R$^5$ is substituted, it is substituted with at least one lower substituent group.

In embodiments, R$^{5A}$ is independently hydrogen, halogen, —CX$^{5A}$$_3$, —CHX$^{5A}$$_2$, —CH$_2$X$^{5A}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{5A}$$_3$, —OCHX$^{5A}$$_2$, —OCH$_2$X$^{5A}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{5A}$ is independently —Cl, —Br, —I, or —F.

In embodiments, a substituted R$^{5A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{5A}$ is substituted with a plurality of groups selected from substituent groups, size-limited substituent groups, and lower substituent groups; each substituent group, size-limited substituent group, and/or lower substituent group may optionally be different. In embodiments, when R$^{5A}$ is substituted, it is substituted with at least one substituent group. In embodiments, when R$^{5A}$ is substituted, it is substituted with at least one size-limited substituent group. In embodiments, when R$^{5A}$ is substituted, it is substituted with at least one lower substituent group.

In embodiments, R$^{5B}$ is independently hydrogen, halogen, —CX$^{5B}$$_3$, —CHX$^{5B}$$_2$, —CH$_2$X$^{5B}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{5B}$$_3$, —OCHX$^{5B}$$_2$, —OCH$_2$X$^{5B}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{5B}$ is independently —Cl, —Br, —I, or —F.

In embodiments, a substituted R$^{5B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{5B}$ is substituted with a plurality of groups selected from substituent groups, size-limited substituent groups, and lower substituent groups; each substituent group, size-limited substituent group, and/or lower substituent group may optionally be different. In embodiments, when R$^{5B}$ is substituted, it is substituted with at least one substituent group. In embodiments, when R$^{5B}$ is substituted, it is substituted with at least one size-limited substituent group. In embodiments, when R$^{5B}$ is substituted, it is substituted with at least one lower substituent group.

In embodiments, R$^6$ is independently hydrogen, halogen, —CX$^6$$_3$, —CHX$^6$$_2$, —CH$_2$X$^6$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^6$$_3$, —OCHX$^6$$_2$, —OCH$_2$X$^6$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^6$ is independently —Cl, —Br, —I, or —F.

In embodiments, a substituted R$^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^6$ is substituted with a plurality of groups selected from substituent groups, size-limited substituent groups, and lower substituent groups; each substituent group, size-limited substituent group, and/or lower substituent group may optionally be different. In embodiments, when R$^6$ is substituted, it is substituted with at least one substituent group. In embodiments, when R$^6$ is substituted, it is substituted with at least one size-limited substituent group. In embodiments, when R$^6$ is substituted, it is substituted with at least one lower substituent group.

In embodiments, R$^{6A}$ is independently hydrogen, halogen, —CX$^{6A}$ 3, —CHX$^{6A}$ 2, —CH$_2$X$^{6A}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{6A}$$_3$, —OCHX$^{6A}$$_2$, —OCH$_2$X$^{6A}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{6A}$ is independently —Cl, —Br, —I, or —F.

In embodiments, a substituted R$^{6A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{6A}$ is substituted with a plurality of groups selected from substituent groups, size-limited substituent groups, and lower substituent groups; each substituent group, size-limited substituent group, and/or lower substituent group may optionally be different. In embodiments, when R$^{6A}$ is substituted, it is substituted with at least one substituent group. In embodiments, when R$^{6A}$ is substituted, it is substituted with at least one size-limited substituent group. In embodiments, when R$^{6A}$ is substituted, it is substituted with at least one lower substituent group.

In embodiments, R$^{6B}$ is independently hydrogen, halogen, —CX$^{6B}$$_3$, —CHX$^{6B}$$_2$, —CH$_2$X$^{6B}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{6B}$$_3$, —OCHX$^{6B}_2$, —OCH$_2$X$^{6B}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{6B}$ is independently —Cl, —Br, —I, or —F.

In embodiments, a substituted R$^{6B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{6B}$ is substituted with a plurality of groups selected from substituent groups, size-limited substituent groups, and lower substituent groups; each substituent group, size-limited substituent group, and/or lower substituent group may optionally be different. In embodiments, when R$^{6B}$ is substituted, it is substituted with at least one substituent group. In embodiments, when R$^{6B}$ is substituted, it is substituted with at least one size-limited substituent group. In embodiments, when R$^{6B}$ is substituted, it is substituted with at least one lower substituent group.

In embodiments, R$^7$ is independently hydrogen, halogen, —CX$^7_3$, —CHX$^7_2$, —CH$_2$X$^7$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^7_3$, —OCHX$^7_2$, —OCH$_2$X$^7$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^7$ is independently —Cl, —Br, —I, or —F.

In embodiments, a substituted R$^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^7$ is substituted with a plurality of groups selected from substituent groups, size-limited substituent groups, and lower substituent groups; each substituent group, size-limited substituent group, and/or lower substituent group may optionally be different. In embodiments, when R$^7$ is substituted, it is substituted with at least one substituent group. In embodiments, when R$^7$ is substituted, it is substituted with at least one size-limited substituent group. In embodiments, when R$^7$ is substituted, it is substituted with at least one lower substituent group.

In embodiments, R$^{7A}$ is independently hydrogen, halogen, —CX$^{7A}_3$, —CHX$^{7A}_2$, —CH$_2$X$^{7A}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{7A}_3$, —OCHX$^{7A}_2$, —OCH$_2$X$^{7A}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{7A}$ is independently —Cl, —Br, —I, or —F.

In embodiments, a substituted R$^{7A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{7A}$ is substituted with a plurality of groups selected from substituent groups, size-limited substituent groups, and lower substituent groups; each substituent group, size-limited substituent group, and/or lower substituent group may optionally be different. In embodiments, when R$^{7A}$ is substituted, it is substituted with at least one substituent group. In embodiments, when R$^{7A}$ is substituted, it is substituted with at least one size-limited substituent group. In embodiments, when R$^{7A}$ is substituted, it is substituted with at least one lower substituent group.

In embodiments, R$^{7B}$ is independently hydrogen, halogen, —CX$^{7B}_3$, —CHX$^{7B}_2$, —CH$_2$X$^{7B}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{7B}_3$, —OCHX$^{7B}_2$, —OCH$_2$X$^{7B}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{7B}$ is independently —Cl, —Br, —I, or —F.

In embodiments, a substituted R$^{7B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{7B}$ is substituted with a plurality of groups selected from substituent groups, size-limited substituent groups, and lower substituent groups; each substituent group, size-limited substituent group, and/or lower substituent group may optionally be different. In embodiments, when R$^{7B}$ is substituted, it is substituted with at least one substituent group. In embodiments, when R$^{7B}$ is substituted, it is substituted with at least one size-limited substituent group. In embodiments, when R$^{7B}$ is substituted, it is substituted with at least one lower substituent group.

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —CN, —SO$_{n8}$R$^{8A}$, SO$_{v8}$NR$^{8A}$R$^{8B}$, —NHC(O)NR$^{8A}$R$^{8B}$, —N(O)$_{m8}$, —NR$^{8A}$R$^{8B}$, —NHNR$^{8A}$R$^{8B}$, —C(O)R$^{8A}$, —C(O)—OR$^{8A}$, —C(O)NR$^{8A}$R$^{8B}$, —C(O)NHNR$^{8A}$R$^{8B}$, —OR$^{8A}$, —NR$^{8A}$SO$_2$R$^{8B}$, —NR$^{8A}$C(O)R$^{8B}$, —NR$^{8A}$C(O)OR$^{8B}$, —NR$^{8A}$OR$^{8B}$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $R^8$ is independently hydrogen, halogen, —$CX^8_3$, —$CHX^8_2$, —$CH_2X^8$, —$OCX^8_3$, —$OCH_2X^8$, —$OCHX^8_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 8 membered, 3 to 6 membered, 4 to 6 membered, 4 to 5 membered, or 5 to 6 membered), $R^{41}$-substituted or unsubstituted aryl (e.g., $C_6$-$C_{12}$, $C_6$—$C_{10}$, or phenyl), or $R^{41}$-substituted or unsubstituted heteroaryl (e.g., 5 to 12 membered, 5 to 10 membered, 5 to 9 membered, or 5 to 6 membered). In embodiments, $R^8$ is independently hydrogen, halogen, —$CX^8_3$, —$CHX^8_2$, —$CH_2X^8$, —$OCX^8_3$, —$OCH_2X^8$, —$OCHX^8_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^8$ is independently —F, —Cl, —Br, or —I.

In embodiments, $R^8$ is independently hydrogen. In embodiments, $R^8$ is independently unsubstituted methyl. In embodiments, $R^8$ is independently —$OCH_3$. In embodiments, $R^8$ is independently —CN. In embodiments, $R^8$ is independently —OPh. In embodiments, $R^8$ is independently an $R^{41}$-substituted or unsubstituted phenyl. In embodiments, $R^8$ is independently an $R^{41}$-substituted phenyl. In embodiments, $R^8$ is independently an unsubstituted phenyl. In embodiments, $R^{41}$ is independently —F, —Cl, —CN, —$CH_3$, —$OCH_3$, or —$OCH_2CH_3$.

In embodiments, $R^8$ and $R^9$ substituents may optionally be joined to form a $R^{41}$-substituted or unsubstituted heterocycloalkyl (e.g., 3 to 8 membered, 3 to 6 membered, 4 to 6 membered, 4 to 5 membered, or 5 to 6 membered), or $R^{41}$-substituted or unsubstituted heteroaryl (e.g., 5 to 12 membered, 5 to 10 membered, 5 to 9 membered, or 5 to 6 membered). In embodiments, $R^8$ and $R^9$ substituents may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^8$ and $R^9$ substituents may optionally be joined to form a $R^{41}$-substituted or unsubstituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form an unsubstituted heterocycloalkyl (e.g., 3 to 8 membered, 3 to 6 membered, 4 to 6 membered, 4 to 5 membered, or 5 to 6 membered).

$R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, —NHPh, —OPh, $R^4_2$-substituted or unsubstituted alkyl (e.g., $C_1$-$C_8$, $C_1$-$C_6$, $C_1$-$C_4$, or $C_1$-$C_2$), $R^4_2$-substituted or unsubstituted heteroalkyl (e.g., 2 to 8 membered, 2 to 6 membered, 4 to 6 membered, 2 to 3 membered, or 4 to 5 membered), $R^4_2$-substituted or unsubstituted cycloalkyl (e.g., $C_3$-$C_8$, $C_3$-$C_6$, $C_4$-$C_6$, or $C_5$-$C_6$), $R^4_2$-substituted or unsubstituted heterocycloalkyl (e.g., 3 to 8 membered, 3 to 6 membered, 4 to 6 membered, 4 to 5 membered, or 5 to 6 membered), $R^4_2$-substituted or unsubstituted aryl (e.g., $C_6$-$C_{12}$, $C_6$-$C_{10}$, or phenyl), or $R^4_2$-substituted or unsubstituted heteroaryl (e.g., 5 to 12 membered, 5 to 10 membered, 5 to 9 membered, or 5 to 6 membered).

In embodiments, $R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^4_2$-substituted or unsubstituted alkyl (e.g., $C_1$-$C_8$, $C_1$-$C_6$, $C_1$-$C_4$, or $C_1$-$C_2$), $R^4_2$-substituted or unsubstituted heteroalkyl (e.g., 2 to 8 membered, 2 to 6 membered, 4 to 6 membered, 2 to 3 membered, or 4 to 5 membered), $R^4_2$-substituted or unsubstituted cycloalkyl (e.g., $C_3$-$C_8$, $C_3$-$C_6$, $C_4$-$C_6$, or $C_5$-$C_6$), $R^4_2$-substituted or unsubstituted heterocycloalkyl (e.g., 3 to 8 membered, 3 to 6 membered, 4 to 6 membered, 4 to 5 membered, or 5 to 6 membered), $R^4_2$-substituted or unsubstituted aryl (e.g., $C_6$-$C_{12}$, $C_6$-$C_{10}$, or phenyl), or $R^4_2$-substituted or unsubstituted heteroaryl (e.g., 5 to 12 membered, 5 to 10 membered, 5 to 9 membered, or 5 to 6 membered). In embodiments, $R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{41}$ is independently —F, —Cl, —Br, or —I. In embodiments, $R^{41}$ is independently unsubstituted methyl. In embodiments, $R^{41}$ is independently unsubstituted ethyl.

$R^4_2$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^4_3$- substituted or unsubstituted alkyl (e.g., $C_1$-$C_8$, $C_1$-$C_6$, $C_1$-$C_4$, or $C_1$-$C_2$), $R^4_3$-substituted or unsubstituted heteroalkyl (e.g., 2 to 8 membered, 2 to 6 membered, 4 to 6 membered, 2 to 3 membered, or 4 to 5 membered), $R^4_3$-substituted or unsubstituted cycloalkyl (e.g., $C_3$-$C_8$, $C_3$-$C_6$, $C_4$-$C_6$, or $C_5$-$C_6$), $R^4_3$-substituted or unsubstituted heterocycloalkyl (e.g., 3 to 8 membered, 3 to 6 membered, 4 to 6 membered, 4 to 5 membered, or 5 to 6 membered), $R^4_3$-substituted or unsubstituted aryl (e.g., $C_6$-$C_{12}$, $C_6$-$C_{10}$, or phenyl), or $R^4_3$-substituted or unsubstituted heteroaryl (e.g., 5 to 12 membered, 5 to 10 membered, 5 to 9 membered, or 5 to 6 membered). In embodiments, $R^4_2$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^4_2$ is independently —F, —Cl, —Br, or —I. In embodiments, $R^4_2$ is independently unsubstituted methyl. In embodiments, $R^4_2$ is independently unsubstituted ethyl.

$R^{43}$ is independently oxo, halogen, —$CX^{43}_3$, —$CHX^{43}_2$, —$CH_2X^{43}$, —$OCX^{43}_3$, —$OCH_2X^{43}$, —$OCHX^{43}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^4_3$ is independently —F, —Cl, —Br, or —I. In embodiments, $R^4_3$ is independently unsubstituted methyl. In embodiments, $R^4_3$ is independently unsubstituted ethyl.

$R^{8A}$ is hydrogen, halogen, —$CX^{8A}_3$, —$CHX^{8A}_2$, —$CH_2X^{8A}$, —$OCX^{8A}_3$, —$OCH_2X^{8A}$, —$OCHX^{8A}2$, —CN, —$SO_{n8A}R^{8AA}$, —$SO_{v8A}NR^{8AA}R^{8AB}$, —NHC(O)$NR^{8AA}R^{8AB}$, —$N(O)^{m8A}$, —$NR^{8AA}R^{8AB}$, —$NHNR^{8AA}R^{8AB}$, —C(O)$R^{8AA}$, C(O)—$OR^{8AA}$, —C(O)$NR^{8AA}R^{8AB}$, —$OR^{8AA}$, —$NR^{8AA}SO_2R^{8AB}$, —$NR^{8AA}C(O)R^{8AB}$, —$NR^{8AA}C(O)OR^{8AB}$, —$NR^{8AA}OR^{8AB}$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $R^{8A}$ is independently hydrogen, —$CX^{8A}_3$, —$CHX^{8A}_2$, —$CH_2X^{8A}$, —CN, —COOH, —$CONH_2$, $R^{41A}$-substituted or unsubstituted alkyl (e.g., $C_1$-$C_8$, $C_1$-$C_6$, $C_1$-$C_4$, or $C_1$-$C_2$), $R^{41A}$-substituted or unsubstituted heteroalkyl (e.g., 2 to 8 membered, 2 to 6 membered, 4 to 6 membered, 2 to 3 membered, or 4 to 5 membered), $R^{41A}$-substituted or unsubstituted cycloalkyl (e.g., $C_3$-$C_8$, $C_3$-$C_6$, $C_4$-$C_6$, or $C_5$-$C_6$), $R^{41A}$-substituted or unsubstituted heterocycloalkyl (e.g., 3 to 8 membered, 3 to 6 membered, 4 to 6 membered, 4 to 5 membered, or 5 to 6 membered), $R^{41A}$-substituted or unsubstituted aryl (e.g., $C_6$-$C_{12}$, $C_6$-$C_{10}$, or phenyl), or $R^{41A}$-substituted or unsubstituted heteroaryl (e.g., 5 to 12 membered, 5 to 10 membered, 5 to 9 membered, or 5 to 6 membered). In embodiments, $R^{8A}$ is independently hydrogen, —$CX^{8A}_3$, —$CHX^{8A}_2$, —$CH_2X^{8A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{8A}$ is independently —F, —Cl, —Br, or —I. In embodiments, $R^{8A}$ is independently hydrogen. In embodiments, $R^{8A}$ is independently unsubstituted methyl. In embodiments, $R^{8A}$ is independently unsubstituted ethyl.

In embodiments, $R^{8A}$ and $R^{8B}$ substituents bonded to the same nitrogen atom may optionally be joined to form a $R^{41A}$-substituted or unsubstituted heterocycloalkyl (e.g., 3 to 8 membered, 3 to 6 membered, 4 to 6 membered, 4 to 5 membered, or 5 to 6 membered) or $R^{41A}$-substituted or unsubstituted heteroaryl (e.g., 5 to 12 membered, 5 to 10 membered, 5 to 9 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{8A}$ and $R^{8B}$ substituents bonded to the same nitrogen atom may optionally be joined to form a $R^{41A}$-substituted or unsubstituted heterocycloalkyl (e.g., 3 to 8 membered, 3 to 6 membered, 4 to 6 membered, 4 to 5 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^8$ and $R^9$ substituents may optionally be joined to form a $R^{41}$-substituted or unsubstituted heterocycloalkyl (e.g., 3 to 8 membered, 3 to 6 membered, 4 to 6 membered, 4 to 5 membered, or 5 to 6 membered), or $R^{41}$-substituted or unsubstituted heteroaryl (e.g., 5 to 12 membered, 5 to 10 membered, 5 to 9 membered, or 5 to 6 membered). In embodiments, $R^8$ and $R^9$ substituents may optionally be joined to form a $R^{41}$-substituted or unsubstituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form a $R^{41}$-substituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form an unsubstituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form a $R^{41}$-substituted or unsubstituted heteroaryl (e.g., 5 to 12 membered, 5 to 10 membered, 5 to 9 membered, or 5 to 6 membered). In embodiments, $R^8$ and $R^9$ substituents may optionally be joined to form a $R^{41}$-substituted heteroaryl (e.g., 5 to 12 membered, 5 to 10 membered, 5 to 9 membered, or 5 to 6 membered). In embodiments, $R^8$ and $R^9$ substituents may optionally be joined to form an unsubstituted heteroaryl (e.g., 5 to 12 membered, 5 to 10 membered, 5 to 9 membered, or 5 to 6 membered).

$R^{41A}$ is independently oxo, halogen, $-CX^{41A}_3$, $-CHX^{41A}_2$, $-CH_2X^{41A}$, $-OCX^{41A}_3$, $-OCH_2X^{41A}$, $-OCHX^{41A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{42A}$-substituted or unsubstituted alkyl (e.g., $C_1$-$C_8$, $C_1$-$C_6$, $C_1$-$C_4$, or $C_1$-$C_2$), $R^{42A}$-substituted or unsubstituted heteroalkyl (e.g., 2 to 8 membered, 2 to 6 membered, 4 to 6 membered, 2 to 3 membered, or 4 to 5 membered), $R^{42A}$-substituted or unsubstituted cycloalkyl (e.g., $C_3$-$C_8$, $C_3$-$C_6$, $C_4$-$C_6$, or $C_5$-$C_6$), $R^{42A}$-substituted or unsubstituted heterocycloalkyl (e.g., 3 to 8 membered, 3 to 6 membered, 4 to 6 membered, 4 to 5 membered, or 5 to 6 membered), $R^{42A}$-substituted or unsubstituted aryl (e.g., $C_6$-$C_{12}$, $C_6$-$C_{10}$, or phenyl), or $R^{42A}$-substituted or unsubstituted heteroaryl (e.g., 5 to 12 membered, 5 to 10 membered, 5 to 9 membered, or 5 to 6 membered). In embodiments, $R^{41A}$ is independently oxo, halogen, $-CX^{41A}_3$, $-CHX^{41A}_2$, $-CH_2X^{41A}$, $-OCX^{41A}_3$, $-OCH_2X^{41A}$, $-OCHX^{41A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{41A}$ is independently $-F$, $-Cl$, $-Br$, or $-I$. In embodiments, $R^{41A}$ is independently unsubstituted methyl. In embodiments, $R^{41A}$ is independently unsubstituted ethyl.

$R^{42A}$ is independently oxo, halogen, $-CX^{42A}_3$, $-CHX^{42A}_2$, $-CH_2X^{42A}$, $-OCX^{42A}_3$, $-OCH_2X^{42A}$, $-OCHX^{42A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{43A}$-substituted or unsubstituted alkyl (e.g., $C_1$-$C_8$, $C_1$-$C_6$, $C_1$-$C_4$, or $C_1$-$C_2$), $R^{43A}$-substituted or unsubstituted heteroalkyl (e.g., 2 to 8 membered, 2 to 6 membered, 4 to 6 membered, 2 to 3 membered, or 4 to 5 membered), $R^{43A}$-substituted or unsubstituted cycloalkyl (e.g., $C_3$-$C_8$, $C_3$-$C_6$, $C_4$-$C_6$, or $C_5$-$C_6$), $R^{43A}$-substituted or unsubstituted heterocycloalkyl (e.g., 3 to 8 membered, 3 to 6 membered, 4 to 6 membered, 4 to 5 membered, or 5 to 6 membered), $R^{43A}$-substituted or unsubstituted aryl (e.g., $C_6$-$C_{12}$, $C_6$-$C_{10}$, or phenyl), or $R^{43A}$-substituted or unsubstituted heteroaryl (e.g., 5 to 12 membered, 5 to 10 membered, 5 to 9 membered, or 5 to 6 membered). In embodiments, $R^{42A}$ is independently oxo, halogen, $-CX^{42A}_3$, $-CHX^{42A}_2$, $-CH_2X^{42A}$, $-OCX^{42A}_3$, $-OCH_2X^{42A}$, $-OCHX^{42A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{42A}$ is independently $-F$, $-Cl$, $-Br$, or $-I$. In embodiments, $R^{42A}$ is independently unsubstituted methyl. In embodiments, $R^{42A}$ is independently unsubstituted ethyl.

$R^{43A}$ is independently oxo, halogen, $-CX^{43A}_3$, $-CHX^{43A}_2$, $-CH_2X^{43A}$, $-OCX^{43A}_3$, $-OCH_2X^{43A}$, $-OCHX^{43A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{43A}$ is independently $-F$, $-Cl$, $-Br$, or $-I$. In embodiments, $R^{43A}$ is independently unsubstituted methyl. In embodiments, $R^{43A}$ is independently unsubstituted ethyl.

$R^{8B}$ is hydrogen, halogen, $-CX^{8B}_3$, $-CHX^{8B}_2$, $-CH_2X^{8B}$, $-OCX^{8B}_3$, $-OCH_2X^{8B}$, $-OCHX^{8B}2$, $-CN$, $-SO_{n8B}R^{8BA}$, $-SO_{v8B}NR^{8BA}R^{8BB}$, $-NHC(O)NR^{8BA}R^{8BB}$, $-N(O)_{m8B}$, $-NR^{8BA}R^{8BB}$, $-NHNR^{8BA}R^{8BB}$, $-C(O)R^{8BA}$, $-C(O)-OR^{8BA}$, $-C(O)NR^{8BA}R^{8BB}$, $-OR^{8BA}$, $-NR^{8BA}SO_2R^{8BB}$, $-NR^{8BA}C(O)R^{8BB}$, $-NR^{8BA}C(O)OR^{8BB}$, $-NR^{8BA}OR^{8BB}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $R^{8B}$ is independently hydrogen, $-CX^{8B}_3$, $-CHX^{8B}_2$, $-CH_2X^{8B}$, $-CN$, $-COOH$, $-CONH_2$, $R^{41B}$-substituted or unsubstituted alkyl (e.g., $C_1$-$C_8$, $C_1$-$C_6$, $C_1$-$C_4$, or $C_1$-$C_2$), $R^{41B}$-substituted or unsubstituted heteroalkyl (e.g., 2 to 8 membered, 2 to 6 membered, 4 to 6 membered, 2 to 3 membered, or 4 to 5 membered), $R^{41B}$-substituted or unsubstituted cycloalkyl (e.g., $C_3$-$C_8$, $C_3$-$C_6$, $C_4$-$C_6$, or $C_5$-$C_6$), $R^{41B}$-substituted or unsubstituted heterocycloalkyl (e.g., 3 to 8 membered, 3 to 6 membered, 4 to 6 membered, 4 to 5 membered, or 5 to 6 membered), $R^{41B}$-substituted or unsubstituted aryl (e.g., $C_6$-$C_{12}$, $C_6$-$C_{10}$, or phenyl), or $R^{41B}$-substituted or unsubstituted heteroaryl (e.g., 5 to 12 membered, 5 to 10 membered, 5 to 9 membered, or 5 to 6 membered). In embodiments, $R^{8B}$ is independently hydrogen, $-CX^{8B}_3$, $-CHX^{8B}_2$, $-CH_2X^{8B}$, $-CN$, $-COOH$, $-CONH_2$, unsubstituted alkyl (e.g., $C_1-C_8$, $C_1-C_6$, $C_1-C_4$, or $C_1-C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3-C_8$, $C_3-C_6$, $C_4-C_6$, or $C_5-C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6-C_{12}$, $C_6-C_{10}$, or phenyl), or unsubstituted heteroaryl (e.g., 5 to 12 membered, 5 to 10 membered, 5 to 9 membered, or 5 to 6 membered). $X^{8B}$ is independently $-F$, $-Cl$, $-Br$, or $-I$. In embodiments, $R^{8B}$ is independently hydrogen. In embodiments, $R^{8B}$ is independently unsubstituted methyl. In embodiments, $R^{8B}$ is independently unsubstituted ethyl.

In embodiments, $R^{8A}$ and $R^{8B}$ substituents bonded to the same nitrogen atom may optionally be joined to form a $R^{41B}$-substituted or unsubstituted heterocycloalkyl (e.g., 3 to 8 membered, 3 to 6 membered, 4 to 6 membered, 4 to 5 membered, or 5 to 6 membered) or $R^{41B}$-substituted or unsubstituted heteroaryl (e.g., 5 to 12 membered, 5 to 10 membered, 5 to 9 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{8A}$ and $R^{8B}$ substituents bonded to the same nitrogen atom may optionally be joined to form a $R^{41B}$-substituted or unsubstituted heterocycloalkyl (e.g., 3 to 8 membered, 3 to 6 membered, 4 to 6 membered, 4 to 5 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{41B}$ is independently oxo, halogen, $-CX^{41B}_3$, $-CHX^{41B}_2$, $-CH_2X^{41B}$, $-OCX^{41B}_3$, $-OCH_2X^{41B}$, $-OCHX^{41B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{42B}$-substituted or unsubstituted alkyl (e.g., $C_1-C_8$, $C_1-C_6$, $C_1-C_4$, or $C_1-C_2$), $R^{42B}$-substituted or unsubstituted heteroalkyl (e.g., 2 to 8 membered, 2 to 6 membered, 4 to 6 membered, 2 to 3 membered, or 4 to 5 membered), $R^{42B}$-substituted or unsubstituted cycloalkyl (e.g., $C_3-C_8$, $C_3-C_6$, $C_4-C_6$, or $C_5-C_6$), $R^{42B}$-substituted or unsubstituted heterocycloalkyl (e.g., 3 to 8 membered, 3 to 6 membered, 4 to 6 membered, 4 to 5 membered, or 5 to 6 membered), $R^{42B}$-substituted or unsubstituted aryl (e.g., $C_6-C_{12}$, $C_6-C_{10}$, or phenyl), or $R^{42B}$-substituted or unsubstituted heteroaryl (e.g., 5 to 12 membered, 5 to 10 membered, 5 to 9 membered, or 5 to 6 membered). In embodiments, $R^{41B}$ is independently oxo, halogen, $-CX^{41B}_3$, $-CHX^{41B}_2$, $-CH_2X^{41B}$, $-OCX^{41B}_3$, $-OCH_2X^{41B}$, $-OCHX^{41B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1-C_8$, $C_1-C_6$, $C_1-C_4$, or $C_1-C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3-C_8$, $C_3-C_6$, $C_4-C_6$, or $C_5-C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6-C_{12}$, $C_6-C_{10}$, or phenyl), or unsubstituted heteroaryl (e.g., 5 to 12 membered, 5 to 10 membered, 5 to 9 membered, or 5 to 6 membered). $X^{41B}$ is independently $-F$, $-Cl$, $-Br$, or $-I$. In embodiments, $R^{41B}$ is independently unsubstituted methyl. In embodiments, $R^{41B}$ is independently unsubstituted ethyl.

$R^{42B}$ is independently oxo, halogen, $-CX^{42B}_3$, $-CHX^{42B}_2$, $-CH_2X^{42B}$, $-OCX^{42B}_3$, $-OCH_2X^{42B}$, $-OCHX^{42B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{43B}$-substituted or unsubstituted alkyl (e.g., $C_1-C_8$, $C_1-C_6$, $C_1-C_4$, or $C_1-C_2$), $R^{43B}$-substituted or unsubstituted heteroalkyl (e.g., 2 to 8 membered, 2 to 6 membered, 4 to 6 membered, 2 to 3 membered, or 4 to 5 membered), $R^{43B}$-substituted or unsubstituted cycloalkyl (e.g., $C_3-C_8$, $C_3-C_6$, $C_4-C_6$, or $C_5-C_6$), $R^{43B}$-substituted or unsubstituted heterocycloalkyl (e.g., 3 to 8 membered, 3 to 6 membered, 4 to 6 membered, 4 to 5 membered, or 5 to 6 membered), $R^{43B}$-substituted or unsubstituted aryl (e.g., $C_6-C_{12}$, $C_6-C_{10}$, or phenyl), or $R^{43B}$-substituted or unsubstituted heteroaryl (e.g., 5 to 12 membered, 5 to 10 membered, 5 to 9 membered, or 5 to 6 membered). In embodiments, $R^{42B}$ is independently oxo, halogen, $-CX^{42B}_3$, $-CHX^{42B}_2$, $-CH_2X^{42B}$, $-OCX^{42B}_3$, $-OCH_2X^{42B}$, $-OCHX^{42B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1-C_8$, $C_1-C_6$, $C_1-C_4$, or $C_1-C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3-C_8$, $C_3-C_6$, $C_4-C_6$, or $C_5-C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6-C_{12}$, $C_6-C_{10}$, or phenyl), or unsubstituted heteroaryl (e.g., 5 to 12 membered, 5 to 10 membered, 5 to 9 membered, or 5 to 6 membered). $X^{42B}$ is independently $-F$, $-Cl$, $-Br$, or $-I$. In embodiments, $R^{42B}$ is independently unsubstituted methyl. In embodiments, $R^{42B}$ is independently unsubstituted ethyl.

$R^{43B}$ is independently oxo, halogen, $-CX^{43B}_3$, $-CHX^{43B}_2$, $-CH_2X^{43B}$, $-OCX^{43B}_3$, $-OCH_2X^{43B}$, $-OCHX^{43B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1-C_8$, $C_1-C_6$, $C_1-C_4$, or $C_1-C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3-C_8$, $C_3-C_6$, $C_4-C_6$, or $C_5-C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6-C_{12}$, $C_6-C_{10}$, or phenyl), or unsubstituted heteroaryl (e.g., 5 to 12 membered, 5 to 10 membered, 5 to 9 membered, or 5 to 6 membered). $X^{43B}$ is independently $-F$, $-Cl$, $-Br$, or $-I$. In embodiments, $R^{43B}$ is independently unsubstituted methyl. In embodiments, $R^{43B}$ is independently unsubstituted ethyl.

$R^{8AA}$ is independently hydrogen, halogen, —$CX^{8AA}_3$, —$CHX^{8AA}_2$, —$CH_2X^{8AA}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8AA}_3$, —OCHX$^{8AA}_2$, —OCH$_2$X$^{8AA}$, substituted or unsubstituted alkyl, substituted or unsubstituted heteroalkyl, substituted or unsubstituted cycloalkyl), substituted or unsubstituted heterocycloalkyl, substituted or unsubstituted aryl, or substituted or unsubstituted heteroaryl. $X^{8AA}$ is independently —Cl, —Br, —I, or —F.

In embodiments, $R^{8AA}$ is independently hydrogen, halogen, —$CX^{8AA}_3$, —$CHX^{8AA}_2$-$CH_2X^{8AA}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8AA}_3$, —OCHX$^{8AA}_2$, —OCH$_2$X$^{8AA}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{8AA}$ is independently —Cl, —Br, —I, or —F.

In embodiments, a substituted $R^{8AA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8AA}$ is substituted with a plurality of groups selected from substituent groups, size-limited substituent groups, and lower substituent groups; each substituent group, size-limited substituent group, and/or lower substituent group may optionally be different. In embodiments, when $R^{8AA}$ is substituted, it is substituted with at least one substituent group. In embodiments, when $R^{8AA}$ is substituted, it is substituted with at least one size-limited substituent group. In embodiments, when $R^{8AA}$ is substituted, it is substituted with at least one lower substituent group.

$R^{8AB}$ is independently hydrogen, halogen, —$CX^{8AB}_3$, —$CHX^{8AB}_2$, —$CH_2X^{8AB}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8'AB}_3$, —OCHX$^{8'AB}_2$, —OCH$_2$X$^{8AB}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{8A}$ is independently —Cl, —Br, —I, or —F.

In embodiments, $R^{8A}$ is independently hydrogen, halogen, —$CX^{8AB}_3$, —$CHX^{8AB}_2$, —$CH_2X^{8AB}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8'AB}_3$, —OCHX$^{8'AB}_2$, —OCH$_2$X$^{8AB}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{8A}$ is independently —Cl, —Br, —I, or —F.

In embodiments, a substituted $R^{8A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8A}$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

$R^{8BA}$ is independently hydrogen, halogen, —$CX^{8BA}_3$, —$CHX^{8BA}_2$, —$CH_2X^{8BA}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8BA}_3$, —OCHX$^{8BA}_2$, —OCH$_2$X$^{8BA}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{8BA}$ is independently —Cl, —Br, —I, or —F.

In embodiments, $R^{8BA}$ is independently hydrogen, halogen, —$CX^{8BA}_3$, —$CHX^{8BA}_2$, —$CH_2X^{8BA}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8BA}_3$, —OCHX$^{8BA}_2$, —OCH$_2$X$^{8BA}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{8BA}$ is independently —Cl, —Br, —I, or —F.

In embodiments, a substituted $R^{8BA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8BA}$ is substituted with a plurality of groups selected from substituent groups, size-limited substituent groups, and lower substituent groups; each substituent group, size-limited substituent group, and/or lower substituent group may optionally be different. In embodiments, when $R^{8BA}$ is substituted, it is substituted with at least one substituent group. In embodiments, when $R^{8BA}$ is substituted, it is substituted with at least one size-limited substituent group. In embodiments, when $R^{8BA}$ is substituted, it is substituted with at least one lower substituent group.

$R^{8BB}$ is independently hydrogen, halogen, —$CX^{8BB}_3$, —$CHX^{8BB}_2$, —$CH_2X^{8BB}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8BB}_3$, —OCHX$^{8BB}_2$, —OCH$_2$X$^{8BB}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{8BB}$ is independently —Cl, —Br, —I, or —F.

In embodiments, $R^{8BB}$ is independently hydrogen, halogen, —$CX^{8BB}_3$, —$CHX^{8BB}_2$, —$CH_2X^{8BB}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{8BB}_3$, —OCHX$^{8BB}_2$, —OCH$_2$X$^{8BB}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{8BB}$ is independently —Cl, —Br, —I, or —F.

In embodiments, a substituted $R^{8BB}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8BB}$ is substituted with a plurality of groups selected from substituent groups, size-limited substituent groups, and lower substituent groups; each substituent group, size-limited substituent group, and/or lower substituent group may optionally be different. In embodiments, when $R^{8BB}$ is substituted, it is substituted with at least one substituent group. In embodiments, when $R^{8BB}$ is substituted, it is substituted with at least one size-limited substituent group. In embodiments, when $R^{8BB}$ is substituted, it is substituted with at least one lower substituent group.

$R^9$ is hydrogen, halogen, —$CX^9_3$, —$CHX^9_2$, —$CH_2X^9$, —$OCX^9_3$, —$OCH_2X^9$, —$OCHX^9_2$, —CN, —SO$_{n9}$R$^{9A}$, —SO$_{v9}$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)—OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{44}$-substituted or unsubstituted alkyl (e.g., $C_1$-$C_8$, $C_1$-$C_6$, $C_1$-$C_4$, or $C_1$-$C_2$), $R^{44}$-substituted or unsubstituted heteroalkyl (e.g., 2 to 8 membered, 2 to 6 membered, 4 to 6 membered, 2 to 3 membered, or 4 to 5 membered), $R^{44}$-substituted or unsubstituted cycloalkyl (e.g., $C_3$-$C_8$, $C_3$-$C_6$, $C_4$-$C_6$, or $C_5$-$C_6$), $R^{44}$-substituted or unsubstituted heterocycloalkyl (e.g., 3 to 8 membered, 3 to 6 membered, 4 to 6 membered, 4 to 5 membered, or 5 to 6 membered), $R^{44}$-substituted or unsubstituted aryl (e.g., $C_6$-$C_{12}$, $C_6$-$C_{10}$, or phenyl), or $R^{44}$-substituted or unsubstituted heteroaryl (e.g., 5 to 12 membered, 5 to 10 membered, 5 to 9 membered, or 5 to 6 membered). In embodiments, $R^9$ is independently hydrogen, halogen, —$CX^9_3$, —$CHX^9_2$, —$CH_2X^9$, —$OCX^9_3$, —$OCH_2X^9$, —$OCHX^9_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^9$ is independently —F, —Cl, —Br, or —I.

In embodiments, $R^8$ and $R^9$ substituents may optionally be joined to form a $R^{44}$-substituted or unsubstituted heterocycloalkyl (e.g., 3 to 8 membered, 3 to 6 membered, 4 to 6 membered, 4 to 5 membered, or 5 to 6 membered), or $R^{44}$-substituted or unsubstituted heteroaryl (e.g., 5 to 12 membered, 5 to 10 membered, 5 to 9 membered, or 5 to 6 membered). In embodiments, $R^8$ and $R^9$ substituents may optionally be joined to form a $R^{44}$-substituted or unsubstituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form a $R^{44}$-substituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form an unsubstituted heterocycloalkyl (e.g., 3 to 8 membered, 3 to 6 membered, 4 to 6 membered, 4 to 5 membered, or 5 to 6 membered). In embodiments, $R^8$ and $R^9$ substituents may optionally be joined to form a $R^{44}$-substituted or unsubstituted heteroaryl (e.g., 5 to 12 membered, 5 to 10 membered, 5 to 9 membered, or 5 to 6 membered). In embodiments, $R^8$ and $R^9$ substituents may optionally be joined to form a $R^{44}$-substituted heteroaryl (e.g., 5 to 12 membered, 5 to 10 membered, 5 to 9 membered, or 5 to 6 membered). In embodiments, $R^8$ and $R^9$ substituents may optionally be joined to form an unsubstituted heteroaryl (e.g., 5 to 12 membered, 5 to 10 membered, 5 to 9 membered, or 5 to 6 membered).

$R^{44}$ is independently oxo, halogen, —$CX^{44}_3$, —$CHX^{44}_2$, —$CH_2X^{44}$, —$OCX^{44}_3$, —$OCH_2X^{44}$, —$OCHX^{44}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, —NHPh, —OPh, R$^{45}$-substituted or unsubstituted alkyl (e.g., C$_1$-C$_8$, C$_1$-C$_6$, C$_1$-C$_4$, or C$_1$-C$_2$), R$^{45}$-substituted or unsubstituted heteroalkyl (e.g., 2 to 8 membered, 2 to 6 membered, 4 to 6 membered, 2 to 3 membered, or 4 to 5 membered), R$^{45}$-substituted or unsubstituted cycloalkyl (e.g., C$_3$-C$_8$, C$_3$-C$_6$, C$_4$-C$_6$, or C$_5$-C$_6$), R$^{45}$-substituted or unsubstituted heterocycloalkyl (e.g., 3 to 8 membered, 3 to 6 membered, 4 to 6 membered, 4 to 5 membered, or 5 to 6 membered), R$^{45}$-substituted or unsubstituted aryl (e.g., C$_6$-C$_{12}$, C$_6$-C$_{10}$, or phenyl), or R$^{45}$-substituted or unsubstituted heteroaryl (e.g., 5 to 12 membered, 5 to 10 membered, 5 to 9 membered, or 5 to 6 membered).

In embodiments, R$^{44}$ is independently oxo, halogen, —CX$^{44}_3$, —CHX$^{44}_2$, —CH$_2$X$^{44}$, —OCX$^{44}_3$, —OCH$_2$X$^{44}$, —OCHX$^{44}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{45}$-substituted or unsubstituted alkyl (e.g., C$_1$-C$_8$, C$_1$-C$_6$, C$_1$-C$_4$, or C$_1$-C$_2$), R$^{45}$-substituted or unsubstituted heteroalkyl (e.g., 2 to 8 membered, 2 to 6 membered, 4 to 6 membered, 2 to 3 membered, or 4 to 5 membered), R$^{45}$-substituted or unsubstituted cycloalkyl (e.g., C$_3$-C$_8$, C$_3$-C$_6$, C$_4$-C$_6$, or C$_5$-C$_6$), R$^{45}$-substituted or unsubstituted heterocycloalkyl (e.g., 3 to 8 membered, 3 to 6 membered, 4 to 6 membered, 4 to 5 membered, or 5 to 6 membered), R$^{45}$-substituted or unsubstituted aryl (e.g., C$_6$-C$_{12}$, C$_6$-C$_{10}$, or phenyl), or R$^{45}$-substituted or unsubstituted heteroaryl (e.g., 5 to 12 membered, 5 to 10 membered, 5 to 9 membered, or 5 to 6 membered). In embodiments, R$^{44}$ is independently oxo, halogen, —CX$^{44}_3$, —CHX$^{44}_2$, —CH$_2$X$^{44}$, —OCX$^{44}_3$, —OCH$_2$X$^{44}$, —OCHX$^{44}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{44}$ is independently —F, —Cl, —Br, or —I. In embodiments, R$^{44}$ is independently unsubstituted methyl. In embodiments, R$^{44}$ is independently unsubstituted ethyl.

R$^{45}$ is independently oxo, halogen, —CX$^{45}_3$, —CHX$^{45}_2$, —CH$_2$X$^{45}$, —OCX$^{45}_3$, —OCH$_2$X$^{45}$, —OCHX$^{45}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{46}$-substituted or unsubstituted alkyl (e.g., C$_1$-C$_8$, C$_1$-C$_6$, C$_1$-C$_4$, or C$_1$-C$_2$), R$^{46}$-substituted or unsubstituted heteroalkyl (e.g., 2 to 8 membered, 2 to 6 membered, 4 to 6 membered, 2 to 3 membered, or 4 to 5 membered), R$^{46}$-substituted or unsubstituted cycloalkyl (e.g., C$_3$-C$_8$, C$_3$-C$_6$, C$_4$-C$_6$, or C$_5$-C$_6$), R$^{46}$-substituted or unsubstituted heterocycloalkyl (e.g., 3 to 8 membered, 3 to 6 membered, 4 to 6 membered, 4 to 5 membered, or 5 to 6 membered), R$^{46}$-substituted or unsubstituted aryl (e.g., C$_6$-C$_{12}$, C$_6$-C$_{10}$, or phenyl), or R$^{46}$-substituted or unsubstituted heteroaryl (e.g., 5 to 12 membered, 5 to 10 membered, 5 to 9 membered, or 5 to 6 membered). In embodiments, R$^{45}$ is independently oxo, halogen, —CX$^{45}_3$, —CHX$^{45}_2$, —CH$_2$X$^{45}$, —OCX$^{45}_3$, —OCH$_2$X$^{45}$, —OCHX$^{45}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{45}$ is independently —F, —Cl, —Br, or —I. In embodiments, R$^{45}$ is independently unsubstituted methyl. In embodiments, R$^{45}$ is independently unsubstituted ethyl.

R$^{46}$ is independently oxo, halogen, —CX$^{46}_6$, —CHX$^{46}_2$, —CH$_2$X$^{46}$, —OCX$^{46}_3$, —OCH$_2$X$^{46}$, —OCHX$^4$62, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{46}$ is independently —F, —Cl, —Br, or —I. In embodiments, R$^{46}$ is independently unsubstituted methyl. In embodiments, R$^{46}$ is independently unsubstituted ethyl.

In embodiments, R$^9$ is independently an R$^{44}$-substituted or unsubstituted C$_1$-C$_4$ alkyl. In embodiments, R$^9$ is independently an unsubstituted C$_1$-C$_4$ alkyl. In embodiments, R$^9$ is independently an R$^{44}$-substituted or unsubstituted C$_4$-C$_6$ cycloalkyl. In embodiments, R$^9$ is independently an unsubstituted C$_4$-C$_6$ cycloalkyl. In embodiments, R$^9$ is independently R$^{44}$-substituted or unsubstituted 5 to 6 membered heterocycloalkyl. In embodiments, R$^9$ is independently an unsubstituted 5 to 6 membered heterocycloalkyl. In embodiments, R$^9$ is independently R$^{44}$-substituted or unsubstituted phenyl. In embodiments, R$^9$ is independently an unsubstituted phenyl. In embodiments, R$^9$ is independently an R$^{44}$-substituted or unsubstituted naphthyl. In embodiments, R$^9$ is independently an unsubstituted naphthyl. In embodiments, R$^9$ is independently an R$^{44}$-substituted or unsubstituted pyridyl. In embodiments, R$^9$ is independently an unsubstituted pyridyl. In embodiments, R$^9$ is independently an R$^{44}$-substituted or unsubstituted 10 membered heteroaryl. In embodiments, R$^9$ is independently an unsubstituted 10 membered heteroaryl. In embodiments, R$^{44}$ is independently —F, —Cl, —Br, or —I. In embodiments, R$^{44}$ is independently —CN. In embodiments, R$^{44}$ is independently —O—(C$_1$-C$_4$ alkyl). In embodiments, R$^{44}$ is independently —OCH$_3$. In embodiments, R$^{44}$ is independently —OCH$_2$CH$_3$. In embodiments, R$^{44}$ is independently —OCF$_3$. In embodiments, R$^{44}$ is independently an R$^{45}$-substituted or unsubstituted C$_1$-C$_4$ alkyl. In embodiments, R$^{44}$ is an unsubstituted methyl. In embodiments, R$^{44}$ is independently an $R^{45}$-substituted or unsubstituted 2 to 5 membered heteroalkyl. In embodiments, $R^{44}$ is independently —CH$_2$OH. In embodiments, $R^{44}$ is independently —CH$_2$CH$_2$OH. In embodiments, $R^{44}$ is independently an $R^{45}$-substituted or unsubstituted phenyl. In embodiments, $R^{44}$ is independently an unsubstituted phenyl. In embodiments, $R^{45}$ is independently oxo. In embodiments, $R^{45}$ is independently an unsubstituted 5 to 6 membered heterocycloalkyl. In embodiments, $R^{45}$ is independently

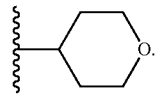

$R^{9A}$ is hydrogen, halogen, —CX$^{9A}_3$, —CHX$^{9A}_2$, —CH$_2$X$^{9A}$, —OCX$^{9A}_3$, —OCH$_2$X$^{9A}$, —OCHX$^{9A}$2, —CN, —SO$_{n9A}$R$^{9AA}$, —SO$_{v9A}$NR$^{9AA}$R$^{9AB}$, —NHC(O)NR$^{9AA}$R$^{9AB}$, —N(O)$_{m9A}$, —NR$^{9AA}$R$^{9AB}$, —NHNR$^{9AA}$R$^{9AB}$, —C(O)R$^{9AA}$, C(O)—OR$^{9AA}$, —C(O)NR$^{9AA}$R$^{9AB}$, —OR$^{9AA}$, —NR$^{9AA}$SO$_2$R$^{9AB}$, —NR$^{9AA}$C(O)R$^{9AB}$, —NR$^{9AA}$C(O)OR$^{9AB}$, —NR$^{9AA}$OR$^{9AB}$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered).

In embodiments, $R^{9A}$ is independently hydrogen, —CX$^{9A}_3$, —CHX$^{9A}_2$, —CH$_2$X$^{9A}$, —CN, —COOH, —CONH$_2$, $R^{44A}$-substituted or unsubstituted alkyl (e.g., C$_1$-C$_8$, C$_1$-C$_6$, C$_1$-C$_4$, or C$_1$-C$_2$), $R^{44A}$-substituted or unsubstituted heteroalkyl (e.g., 2 to 8 membered, 2 to 6 membered, 4 to 6 membered, 2 to 3 membered, or 4 to 5 membered), $R^{44A}$-substituted or unsubstituted cycloalkyl (e.g., C$_3$-C$_8$, C$_3$-C$_6$, C$_4$-C$_6$, or C$_5$-C$_6$), $R^{44A}$-substituted or unsubstituted heterocycloalkyl (e.g., 3 to 8 membered, 3 to 6 membered, 4 to 6 membered, 4 to 5 membered, or 5 to 6 membered), $R^{44A}$-substituted or unsubstituted aryl (e.g., C$_6$-C$_{12}$, C$_6$-C$_{10}$, or phenyl), or $R^{44A}$-substituted or unsubstituted heteroaryl (e.g., 5 to 12 membered, 5 to 10 membered, 5 to 9 membered, or 5 to 6 membered). In embodiments, $R^{9A}$ is independently hydrogen, —CX$^{9A}_3$, —CHX$^{9A}_2$, —CH$_2$X$^{9A}$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). $X^{9A}$ is independently —F, —Cl, —Br, or —I. In embodiments, $R^{9A}$ is independently hydrogen. In embodiments, $R^{9A}$ is independently unsubstituted methyl. In embodiments, $R^{9A}$ is independently unsubstituted ethyl.

In embodiments, $R^{9A}$ and $R^{9B}$ substituents bonded to the same nitrogen atom may optionally be joined to form a $R^{44A}$-substituted or unsubstituted heterocycloalkyl (e.g., 3 to 8 membered, 3 to 6 membered, 4 to 6 membered, 4 to 5 membered, or 5 to 6 membered) or $R^{44A}$-substituted or unsubstituted heteroaryl (e.g., 5 to 12 membered, 5 to 10 membered, 5 to 9 membered, or 5 to 6 membered). In embodiments, $R^{9A}$ and $R^{9B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{9A}$ and $R^{9B}$ substituents bonded to the same nitrogen atom may optionally be joined to form a $R^{44A}$-substituted or unsubstituted heterocycloalkyl (e.g., 3 to 8 membered, 3 to 6 membered, 4 to 6 membered, 4 to 5 membered, or 5 to 6 membered). In embodiments, $R^{9A}$ and $R^{9B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{44A}$ is independently oxo, halogen, —CX$^{44A}_3$, —CHX$^{44A}_2$, —CH$_2$X$^{44A}$, —OCX$^{44A}_3$-OCH$_2$X$^{44A}$, —OCHX$^{44A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{45A}$-substituted or unsubstituted alkyl (e.g., C$_1$-C$_8$, C$_1$-C$_6$, C$_1$-C$_4$, or C$_1$-C$_2$), $R^{45A}$-substituted or unsubstituted heteroalkyl (e.g., 2 to 8 membered, 2 to 6 membered, 4 to 6 membered, 2 to 3 membered, or 4 to 5 membered), $R^{45A}$-substituted or unsubstituted cycloalkyl (e.g., C$_3$-C$_8$, C$_3$-C$_6$, C$_4$-C$_6$, or C$_5$-C$_6$), $R^{45A}$-substituted or unsubstituted heterocycloalkyl (e.g., 3 to 8 membered, 3 to 6 membered, 4 to 6 membered, 4 to 5 membered, or 5 to 6 membered), $R^{45A}$-substituted or unsubstituted aryl (e.g., C$_6$-C$_{12}$, C$_6$-C$_{10}$, or phenyl), or $R^{45A}$-substituted or unsubstituted heteroaryl (e.g., 5 to 12 membered, 5 to 10 membered, 5 to 9 membered, or 5 to 6 membered). In embodiments, $R^{44A}$ is independently oxo, halogen, —CX$^{44A}_3$, —CHX$^{44A}_2$, —CH$_2$X$^{44A}$, —OCX$^{44A}_3$, —OCH$_2$X$^{44A}$-OCHX$^{44A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). $X^{44A}$ is independently —F, —Cl, —Br, or —I. In embodiments, $R^{44A}$ is independently unsubstituted methyl. In embodiments, $R^{44A}$ is independently unsubstituted ethyl.

$R^{45A}$ is independently oxo, halogen, —CX$^{45A}_3$, —CHX$^{45A}_2$, —CH$_2$X$^{45A}$, —OCX$^{45A}_3$, —OCH$_2$X$^{45A}$, —OCHX$^{45A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{46A}$-substituted or unsubstituted alkyl (e.g., C$_1$-C$_8$, C$_1$-C$_6$, C$_1$-C$_4$, or C$_1$-C$_2$), $R^{46A}$-substituted or unsubstituted heteroalkyl (e.g., 2 to 8 membered, 2 to 6 membered, 4 to 6 membered, 2 to 3 membered, or 4 to 5 membered), $R^{46A}$-substituted or unsubstituted cycloalkyl (e.g., C$_3$-C$_8$, C$_3$-C$_6$, C$_4$-C$_6$, or C$_5$-C$_6$), $R^{46A}$-substituted or unsubstituted heterocycloalkyl (e.g., 3 to 8 membered, 3 to 6 membered, 4 to 6 membered, 4 to 5 membered, or 5 to 6 membered), $R^{46A}$-substituted or unsubstituted aryl (e.g., $C_6$-$C_{12}$, $C_6$-$C_{10}$, or phenyl), or $R^{46A}$-substituted or unsubstituted heteroaryl (e.g., 5 to 12 membered, 5 to 10 membered, 5 to 9 membered, or 5 to 6 membered). In embodiments, $R^{45A}$ is independently oxo, halogen, —$CX^{45A}_3$, —$CHX^{45A}_2$, —$CH_2X^{45A}$, —$OCX^{45A}_3$, —$OCH_2X^{45A}$, —$OCHX^{45A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{45A}$ is independently —F, —Cl, —Br, or —I. In embodiments, $R^{45A}$ is independently unsubstituted methyl. In embodiments, $R^{45A}$ is independently unsubstituted ethyl.

$R^{46A}$ is independently oxo, halogen, —$CX^{46A}_3$, —$CHX^{46A}_2$, —$CH_2X^{46A}$, —$OCX^{46A}_3$-$OCH_2X^{46A}$, —$OCHX^{46A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{46A}$ is independently —F, —Cl, —Br, or —I. In embodiments, $R^{46A}$ is independently unsubstituted methyl. In embodiments, $R^{46A}$ is independently unsubstituted ethyl.

$R^{9B}$ is hydrogen, halogen, —$CX^{9B}_3$, —$CHX^{9B}_2$, —$CH_2X^{9B}$, —$OCX^{9B}_3$, —$OCH_2X^{9B}$, —$OCHX^{9B}2$, —CN, —$SO_{n9B}R^{9BA}$, —$SO_{v9B}NR^{9BA}R^{9BB}$, —NHC(O)$NR^{9BA}R^{9BB}$, —$N(O)_{m9B}$, —$NR^{9BA}R^{9BB}$, —$NHNR^{9BA}R^{9BB}$, —$C(O)R^{9BA}$, —C(O)—$OR^{9BA}$, —$C(O)NR^{9BA}R^{9BB}$, —$OR^{9BA}$, —$NR^{9BA}SO_2R^{9BB}$, —$NR^{9BA}C(O)R^{9BB}$, —$NR^{9BA}C(O)OR^{9BB}$, —$NR^{9BA}OR^{9BB}$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered).

In embodiments, $R^{9B}$ is independently hydrogen, —$CX^{9B}_3$, —$CHX^{9B}_2$, —$CH_2X^{9B}$, —CN, —COOH, —$CONH_2$, $R^{44B}$-substituted or unsubstituted alkyl (e.g., $C_1$-$C_8$, $C_1$-$C_6$, $C_1$-$C_4$, or $C_1$-$C_2$), $R^{44B}$-substituted or unsubstituted heteroalkyl (e.g., 2 to 8 membered, 2 to 6 membered, 4 to 6 membered, 2 to 3 membered, or 4 to 5 membered), $R^{44B}$-substituted or unsubstituted cycloalkyl (e.g., $C_3$-$C_8$, $C_3$-$C_6$, $C_4$-$C_6$, or $C_5$-$C_6$), $R^{44B}$-substituted or unsubstituted heterocycloalkyl (e.g., 3 to 8 membered, 3 to 6 membered, 4 to 6 membered, 4 to 5 membered, or 5 to 6 membered), $R^{44B}$-substituted or unsubstituted aryl (e.g., $C_6$-$C_{12}$, $C_6$-$C_{10}$, or phenyl), or $R^{44B}$-substituted or unsubstituted heteroaryl (e.g., 5 to 12 membered, 5 to 10 membered, 5 to 9 membered, or 5 to 6 membered). In embodiments, $R^{9B}$ is independently hydrogen, —$CX^{9B}_3$, —$CHX^{9B}_2$, —$CH_2X^{9B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{9B}$ is independently —F, —Cl, —Br, or —I. In embodiments, $R^{9B}$ is independently hydrogen. In embodiments, $R^{9B}$ is independently unsubstituted methyl. In embodiments, $R^{9B}$ is independently unsubstituted ethyl.

In embodiments, $R^{9A}$ and $R^{9B}$ substituents bonded to the same nitrogen atom may optionally be joined to form a $R^{44B}$-substituted or unsubstituted heterocycloalkyl (e.g., 3 to 8 membered, 3 to 6 membered, 4 to 6 membered, 4 to 5 membered, or 5 to 6 membered) or $R^{44B}$-substituted or unsubstituted heteroaryl (e.g., 5 to 12 membered, 5 to 10 membered, 5 to 9 membered, or 5 to 6 membered). In embodiments, $R^{9A}$ and $R^{9B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{9A}$ and $R^{9B}$ substituents bonded to the same nitrogen atom may optionally be joined to form a $R^{44B}$-substituted or unsubstituted heterocycloalkyl (e.g., 3 to 8 membered, 3 to 6 membered, 4 to 6 membered, 4 to 5 membered, or 5 to 6 membered). In embodiments, $R^{9A}$ and $R^{9B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{44B}$ is independently oxo, halogen, —$CX^{44B}_3$, —$CHX^{44B}_2$, —$CH_2X^{44B}$, —$OCX^{44B}_3$, —$OCH_2X^{44B}$, —$OCHX^{44B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$N_3$, $R^{45B}$-substituted or unsubstituted alkyl (e.g., $C_1$-$C_8$, $C_1$-$C_6$, $C_1$-$C_4$, or $C_1$-$C_2$), $R^{45B}$-substituted or unsubstituted heteroalkyl (e.g., 2 to 8 membered, 2 to 6 membered, 4 to 6 membered, 2 to 3 membered, or 4 to 5 membered), $R^{45B}$-substituted or unsubstituted cycloalkyl (e.g., $C_3$-$C_8$, $C_3$-$C_6$, $C_4$-$C_6$, or $C_5$-$C_6$), $R^{45B}$-substituted or unsubstituted heterocycloalkyl (e.g., 3 to 8 membered, 3 to 6 membered, 4 to 6 membered, 4 to 5 membered, or 5 to 6 membered), $R^{45B}$-substituted or unsubstituted aryl (e.g., $C_6$-$C_{12}$, $C_6$-$C_{10}$, or phenyl), or $R^{45B}$-substituted or unsubstituted heteroaryl (e.g., 5 to 12 membered, 5 to 10 membered, 5 to 9 membered, or 5 to 6 membered). In embodiments, $R^{44B}$ is independently oxo, halogen, —$CX^{44B}_3$, —$CHX^{44B}_2$, —$CH_2X^{44B}$, —$OCX^{44B}_3$, —$OCH_2X^{44B}$—$OCHX^{44B}_2$, —CN, —OH, —$NH_2$, —COOH, —$CONH_2$, —$NO_2$, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{44B}$ is independently —F, —Cl, —Br, or —I. In embodiments, $R^{44B}$ is independently unsubstituted methyl. In embodiments, $R^{44B}$ is independently unsubstituted ethyl.

$R^{45B}$ is independently oxo, halogen, —$CX^{45B}_3$, —$CHX^{45B}_2$, —$CH_2X^{45B}$, —$OCX^{45B}_3$, —$OCH_2X^{45B}$, —$OCHX^{45B}_2$, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, $R^{46B}$-substituted or unsubstituted alkyl (e.g., $C_1$-$C_8$, $C_1$-$C_6$, $C_1$-$C_4$, or $C_1$-$C_2$), $R^{46B}$-substituted or unsubstituted heteroalkyl (e.g., 2 to 8 membered, 2 to 6 membered, 4 to 6 membered, 2 to 3 membered, or 4 to 5 membered), $R^{46B}$-substituted or unsubstituted cycloalkyl (e.g., $C_3$-$C_8$, $C_3$-$C_6$, $C_4$-$C_6$, or $C_5$-$C_6$), $R^{46B}$-substituted or unsubstituted heterocycloalkyl (e.g., 3 to 8 membered, 3 to 6 membered, 4 to 6 membered, 4 to 5 membered, or 5 to 6 membered), $R^{46B}$-substituted or unsubstituted aryl (e.g., $C_6$-$C_{12}$, $C_6$-$C_{10}$, or phenyl), or $R^{46B}$-substituted or unsubstituted heteroaryl (e.g., 5 to 12 membered, 5 to 10 membered, 5 to 9 membered, or 5 to 6 membered). In embodiments, $R^{45B}$ is independently oxo, halogen, —$CX^{45B}_3$, —$CHX^{45B}_2$, —$CH_2X^{45B}$, —$OCX^{45B}_3$, —$OCH_2X^{45B}$, —$OCHX^{45B}_2$, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{45B}$ is independently —F, —Cl, —Br, or —I. In embodiments, $R^{45B}$ is independently unsubstituted methyl. In embodiments, $R^{45B}$ is independently unsubstituted ethyl.

$R^{46B}$ is independently oxo, halogen, —$CX^{46B}_3$, —$CHX^{46B}_2$, —$CH_2X^{46B}$, —$OCX^{46B}_3$, —$OCH_2X^{46B}$, —$OCHX^{46B}_2$, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{46B}$ is independently —F, —Cl, —Br, or —I. In embodiments, $R^{46B}$ is independently unsubstituted methyl. In embodiments, $R^{46B}$ is independently unsubstituted ethyl.

$R^{9AA}$ is independently hydrogen, halogen, —$CX^{9AA}_3$, —$CHX^{9AA}_2$, —$CH_2X^{9AA}$, —C(O)OH, —C(O)NH₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —$OCX^{9AA}_3$, —$OCHX^{9AA}_2$, —$OCH_2X^{9AA}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{9AA}$ is independently —Cl, —Br, —I, or —F.

In embodiments, $R^{9AA}$ is independently hydrogen, halogen, —$CX^{9AA}_3$, —$CHX^{9AA}_2$-$CH_2X^{9AA}$, —C(O)OH, —C(O)NH₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —$OCX^{9AA}_3$, —$OCHX^{9AA}_2$, —$OCH_2X^{9AA}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 9 membered, or 5 to 6 membered). $X^{9AA}$ is independently —Cl, —Br, —I, or —F.

In embodiments, a substituted $R^{9AA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9AA}$ is substituted with a plurality of groups selected from substituent groups, size-limited substituent groups, and lower substituent groups; each substituent group, size-limited substituent group, and/or lower substituent group may optionally be different. In embodiments, when $R^{9AA}$ is substituted, it is substituted with at least one substituent group. In embodiments, when $R^{9AA}$ is substituted, it is substituted with at least one size-limited substituent group. In embodiments, when $R^{9AA}$ is substituted, it is substituted with at least one lower substituent group.

$R^{9AB}$ is independently hydrogen, halogen, —$CX^{9AB}_3$, —$CHX^{9AB}_2$, —$CH_2X^{9AB}$, —C(O)OH, —C(O)NH₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —$OCX^{9AB}_3$, —$OCHX^{9AB}_2$, —$OCH_2X^{9AB}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^{9AB}$ is independently —Cl, —Br, —I, or —F.

In embodiments, $R^{9AB}$ is independently hydrogen, halogen, —$CX^{9AB}_3$, —$CHX^{9AB}_2$, —$CH_2X^{9AB}$, —C(O)OH, —C(O)NH₂, —CN, —OH, —NH₂, —COOH, —CONH₂, —NO₂, —SH, —SO₃H, —SO₄H, —SO₂NH₂, —NHNH₂, —ONH$_2$, —NHC═(O)NHNH$_2$, —NHC═(O)NH$_2$, —NHSO$_2$H, —NHC═(O)H, —NHC(O)OH, —NHOH, —OCX$^{9AB}_3$, —OCHX$^{9AB}_2$, —OCH$_2$X$^{9AB}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{9AB}$ is independently —Cl, —Br, —I, or —F.

In embodiments, a substituted R$^{9AB}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{9AB}$ is substituted with a plurality of groups selected from substituent groups, size-limited substituent groups, and lower substituent groups; each substituent group, size-limited substituent group, and/or lower substituent group may optionally be different. In embodiments, when R$^{9AB}$ is substituted, it is substituted with at least one substituent group. In embodiments, when R$^{9AB}$ is substituted, it is substituted with at least one size-limited substituent group. In embodiments, when R$^{9AB}$ is substituted, it is substituted with at least one lower substituent group.

R$^{9BA}$ is independently hydrogen, halogen, —CX$^{9BA}_3$, —CHX$^{9BA}_2$, —CH$_2$X$^{9BA}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$^{9BA}_3$, —OCHX$^{9BA}_2$, —OCH$_2$X$^{9BA}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^{9BA}$ is independently —Cl, —Br, —I, or —F.

In embodiments, R$^{9BA}$ is independently hydrogen, halogen, —CX$^{9BA}_3$, —CHX$^{9BA}_2$, —CH$_2$X$^{9BA}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$^{9BA}_3$, —OCHX$^{9BA}_2$, —OCH$_2$X$^{9BA}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{9BA}$ is independently —Cl, —Br, —I, or —F.

In embodiments, a substituted R$^{9BA}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{9BA}$ is substituted with a plurality of groups selected from substituent groups, size-limited substituent groups, and lower substituent groups; each substituent group, size-limited substituent group, and/or lower substituent group may optionally be different. In embodiments, when R$^{9BA}$ is substituted, it is substituted with at least one substituent group. In embodiments, when R$^{9BA}$ is substituted, it is substituted with at least one size-limited substituent group. In embodiments, when R$^{9BA}$ is substituted, it is substituted with at least one lower substituent group.

R$^{9BB}$ is independently hydrogen, halogen, —CX$^{9BB}_3$, —CHX$^{9BB}_2$, —CH$_2$X$^{9BB}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$^{9BB}_3$, —OCHX$^{9BB}_2$, —OCH$_2$X$^{9BB}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^{9BB}$ is independently —Cl, —Br, —I, or —F.

In embodiments, R$^{9BB}$ is independently hydrogen, halogen, —CX$^{9BB}_3$, —CHX$^{9BB}_2$, —CH$_2$X$^{9BB}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$^{9BB}_3$, —OCHX$^{9BB}_2$, —OCH$_2$X$^{9BB}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{9BB}$ is independently —Cl, —Br, —I, or —F.

In embodiments, a substituted R$^{9BB}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{9BB}$ is substituted with a plurality of groups selected from substituent groups, size-limited substituent groups, and lower substituent groups; each substituent group, size-limited substituent group, and/or lower substituent group may optionally be different. In embodiments, when R$^{9BB}$ is substituted, it is substituted with at least one substituent group. In embodiments, when R$^{9BB}$ is substituted, it is substituted with at least one size-limited substituent group. In embodiments, when R$^{9BB}$ is substituted, it is substituted with at least one lower substituent group.

m8A, m8B, m9A, and m9B are independently 1 or 2.
v8A, v8B, v9A, and v9B are independently 1 or 2.
n8A, n8B, n9A, and n9B are independently an integer from 0 to 4.
X$^{8A}$, X$^{8B}$, X$^{9A}$, and X$^{9B}$ are independently —Cl, —Br, —I or —F.

In embodiments, R$^{10}$ is independently hydrogen, halogen, —CX$^{10}_3$, —CHX$^{10}$, —CH$_2$X$^{10}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{10}$$_3$, —OCHX$^{10}$$_2$, —OCH$_2$X$^{10}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). In embodiments, R$^{10}$ is independently hydrogen or unsubstituted methyl. X$^{10}$ is independently —Cl, —Br, —I, or —F.

In embodiments, a substituted R$^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{10}$ is substituted with a plurality of groups selected from substituent groups, size-limited substituent groups, and lower substituent groups; each substituent group, size-limited substituent group, and/or lower substituent group may optionally be different. In embodiments, when R$^{10}$ is substituted, it is substituted with at least one substituent group. In embodiments, when R$^{10}$ is substituted, it is substituted with at least one size-limited substituent group. In embodiments, when R$^{10}$ is substituted, it is substituted with at least one lower substituent group.

In embodiments, R$^{10A}$ is independently hydrogen, halogen, —CX$^{10A}$$_3$, —CHX$^{10A}$$_2$, —CH$_2$X$^{10A}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{10A}$$_3$, —OCHX$^{10A}$$_2$, —OCH$_2$X$^{10A}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{10A}$ is independently —Cl, —Br, —I, or —F.

In embodiments, a substituted R$^{10A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{10A}$ is substituted with a plurality of groups selected from substituent groups, size-limited substituent groups, and lower substituent groups; each substituent group, size-limited substituent group, and/or lower substituent group may optionally be different. In embodiments, when R$^{10A}$ is substituted, it is substituted with at least one substituent group. In embodiments, when R$^{10A}$ is substituted, it is substituted with at least one size-limited substituent group. In embodiments, when R$^{10A}$ is substituted, it is substituted with at least one lower substituent group.

In embodiments, R$^{10B}$ is independently hydrogen, halogen, —CX$^{10B}$$_3$, —CHX$^{10B}$$_2$, —CH$_2$X$^{10B}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{10B}$$_3$, —OCHX$^{10B}$$_2$, —OCH$_2$X$^{10B}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12 membered, 5 to 10 membered, 5 to 9 membered, or 5 to 6 membered). X$^{10B}$ is independently —Cl, —Br, —I, or —F.

In embodiments, a substituted R$^{10B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{10B}$ is substituted with a plurality of groups selected from substituent groups, size-limited substituent groups, and lower substituent groups; each substituent group, size-limited substituent group, and/or lower substituent group may optionally be different. In embodiments, when R$^{10B}$ is substituted, it is substituted with at least one substituent group. In embodiments, when R$^{10B}$ is substituted, it is substituted with at least one size-limited substituent group. In embodiments, when R$^{10B}$ is substituted, it is substituted with at least one lower substituent group.

In embodiments, a substituted L$^1$, L$^2$, L$^3$, L$^6$, L$^8$, and/or L$^9$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted L$^1$, L$^2$, L$^3$, L$^6$, L$^8$, and/or L$^9$ is substituted with a plurality of groups selected from substituent groups, size-limited substituent groups, and lower substituent groups; each substituent group, size-limited substituent group, and/or lower substituent group may optionally be different. In embodiments, when L$^1$, L$^2$, L$^3$, L$^6$, L$^8$, and/or L$^9$ is substituted, it is substituted with at least one substituent group. In embodiments, when L$^1$, L$^2$, L$^3$, L$^6$, L$^8$, and/or L$^9$ is substituted, it is substituted with at least one size-limited substituent group. In embodiments, when L$^1$, L$^2$, L$^3$, L$^6$, L$^8$, and/or L$^9$ is substituted, it is substituted with at least one lower substituent group.

In embodiments, L$^9$ is independently a bond. In embodiments, L$^9$ is independently —CH$_2$—. In embodiments, L$^9$ is independently

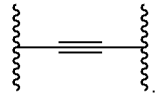

In embodiments, L$^9$ is independently unsubstituted C$_2$-C$_4$ alkyl. In embodiments, L$^9$ is independently a substituted or unsubstituted phenylene. In embodiments, L$^9$ is independently a substituted phenylene. In embodiments, $L^9$ is independently an unsubstituted phenylene.

In embodiments, $R^9$ is an $R^{44}$-substituted or unsubstituted $C_1$-$C_4$ alkyl. In embodiments, $R^9$ is an $R^{44}$-substituted $C_1$-$C_4$ alkyl. In embodiments, $R^9$ is an unsubstituted $C_1$-$C_4$ alkyl.

In embodiments, $R^{44}$ is an $R^{45}$-substituted or unsubstituted heterocycloalkyl. In embodiments, $R^{44}$ is an $R^{45}$-substituted heterocycloalkyl. In embodiments, $R^{44}$ is an unsubstituted heterocycloalkyl. In embodiments, $R^{44}$ is an unsubstituted morpholinyl.

In embodiments, $L^9$-$R^9$ is

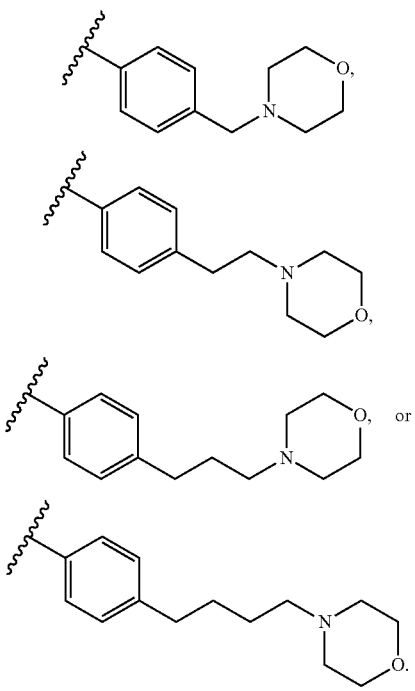

In embodiments, $L^9$-$R^9$ is

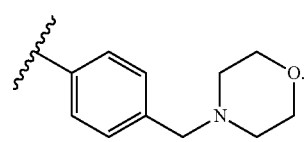 [SMILES: *c1ccc(CN2CCOCC2)cc1]

In embodiments, $L^9$-$R^9$ is

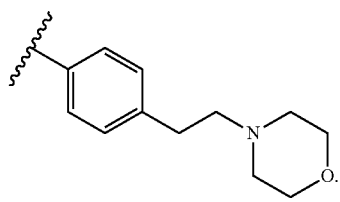 [SMILES: *c1ccc(CCN2CCOCC2)cc1]

In embodiments, $L^9$-$R^9$ is

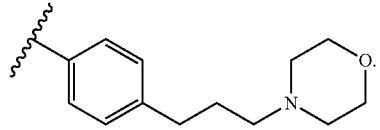 [SMILES: *c1ccc(CCCN2CCOCC2)cc1]

In embodiments, $L^9$-$R^9$ is

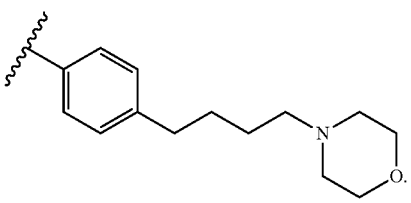 [SMILES: *c1ccc(CCCCN2CCOCC2)cc1]

In embodiments, the compound has the formula:

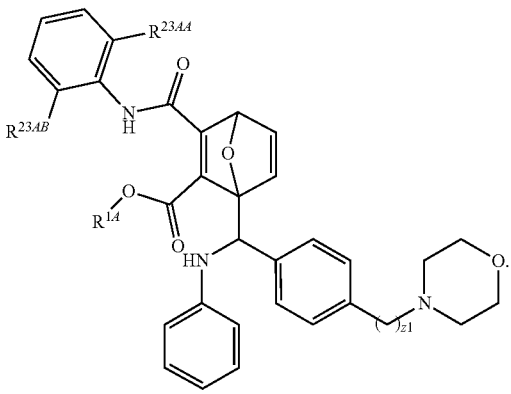

(IIIe)

$R^{1A}$ is as described herein, including in embodiments. The symbol z1 is an integer from 0 to 4.

$R^{23AA}$ is independently hydrogen, oxo, halogen, —$CX^{23AA}_3$, —$CHX^{23AA}_2$, —$CH_2X^{23AA}$, —$OCX^{23AA}_3$, —$OCH_2X^{23AA}$, —$OCHX^{23AA}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —N$_3$, —OPh, $R^{24AA}$-substituted or unsubstituted alkyl (e.g., $C_1$-$C_8$, $C_1$-$C_6$, $C_1$-$C_4$, or $C_1$-$C_2$), $R^{24AA}$-substituted or unsubstituted heteroalkyl (e.g., 2 to 8 membered, 2 to 6 membered, 4 to 6 membered, 2 to 3 membered, or 4 to 5 membered), $R^{24AA}$-substituted or unsubstituted cycloalkyl (e.g., $C_3$-$C_8$, $C_3$-$C_6$, $C_4$-$C_6$, or $C_5$-$C_6$), $R^{24AA}$-substituted or unsubstituted heterocycloalkyl (e.g., 3 to 8 membered, 3 to 6 membered, 4 to 6 membered, 4 to 5 membered, or 5 to 6 membered), $R^{24AA}$-substituted or unsubstituted aryl (e.g., $C_6$-$C_{12}$, $C_6$-$C_{10}$, or phenyl), or $R^{24AA}$-substituted or unsubstituted heteroaryl (e.g., 5 to 12 membered, 5 to 10 membered, 5 to 9 membered, or 5 to 6 membered). In embodiments, $R^{23AA}$ is independently hydrogen, oxo, halogen, —$CX^{23AA}_3$, —$CHX^{23AA}_2$, —$CH_2X^{23A}$A, —$OCX^{23AA}_3$, —$OCH_2X^{23A}$A, —$OCHX^{23AA}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{23AA}$ is independently —F, —Cl, —Br, or —I. In embodiments, R$^{23AA}$ is independently hydrogen. In embodiments, R$^{23AA}$ is independently unsubstituted methyl. In embodiments, R$^{23AA}$ is independently unsubstituted ethyl. In embodiments, R$^{23AA}$ is independently unsubstituted propyl. In embodiments, R$^{23AA}$ is independently unsubstituted butyl. In embodiments, R$^{23AA}$ is independently unsubstituted tert-butyl. In embodiments, two adjacent R$^{23AA}$ substituents may optionally be joined to form an R$^{24A}$A-substituted or unsubstituted cycloalkyl, R$^{24AA}$-substituted or unsubstituted heterocycloalkyl, R$^{24A}$A-substituted or unsubstituted aryl, or R$^{24AA}$-substituted or unsubstituted heteroaryl.

R$^{23AB}$ is independently hydrogen, oxo, halogen, —CX$^{23AB}{}_3$, —CHX$^{23AB}{}_2$, —CH$_2$X$^{23AB}$, —OCX$^{23AB}{}_3$, —OCH$_2$X$^{23A}$B, —OCHX$^{23AB}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, —OPh, R$^{24A}$B-substituted or unsubstituted alkyl (e.g., C$_1$-C$_8$, C$_1$-C$_6$, C$_1$-C$_4$, or C$_1$-C$_2$), R$^{24A}$B-substituted or unsubstituted heteroalkyl (e.g., 2 to 8 membered, 2 to 6 membered, 4 to 6 membered, 2 to 3 membered, or 4 to 5 membered), R$^{24A}$B-substituted or unsubstituted cycloalkyl (e.g., C$_3$-C$_8$, C$_3$-C$_6$, C$_4$-C$_6$, or C$_5$-C$_6$), R$^{24A}$B-substituted or unsubstituted heterocycloalkyl (e.g., 3 to 8 membered, 3 to 6 membered, 4 to 6 membered, 4 to 5 membered, or 5 to 6 membered), R$^{24A}$-substituted or unsubstituted aryl (e.g., C$_6$-C$_{12}$, C$_6$-C$_{10}$, or phenyl), or R$^{24A}$B-substituted or unsubstituted heteroaryl (e.g., 5 to 12 membered, 5 to 10 membered, 5 to 9 membered, or 5 to 6 membered). In embodiments, R$^{23A}$ is independently hydrogen, oxo, halogen, —CX$^{23AB}{}_3$, —CHX$^{23AB}{}_2$, —CH$_2$X$^{23A}$B, —OCX$^{23AB}{}_3$, —OCH$_2$X$^{23A}$B, —OCHX$^{23AB}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{23B}$ is independently —F, —Cl, —Br, or —I. In embodiments, R$^{23A}$ is independently hydrogen. In embodiments, R$^{23A}$ is independently unsubstituted methyl. In embodiments, R$^{23AB}$ is independently unsubstituted ethyl. In embodiments, R$^{23A}$ is independently unsubstituted propyl. In embodiments, R$^{23A}$ is independently unsubstituted butyl. In embodiments, R$^{23A}$ is independently unsubstituted tert-butyl. In embodiments, two adjacent R$^{23A}$ substituents may optionally be joined to form an R$^{24A}$B-substituted or unsubstituted cycloalkyl, R$^{24AB}$-substituted or unsubstituted heterocycloalkyl, R$^{24A}$-substituted or unsubstituted aryl, or R$^{24A}$-substituted or unsubstituted heteroaryl.

R$^{24AA}$ is independently oxo, halogen, —CX$^{24AA}{}_3$, —CHX$^{24AA}{}_2$, —CH$_2$X$^{24A}$A, —OCX$^{24A}$3, —OCH$_2$X$^{24A}$A, —OCHX$^{24AA}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{25AA}$-substituted or unsubstituted alkyl (e.g., C$_1$-C$_8$, C$_1$-C$_6$, C$_1$-C$_4$, or C$_1$-C$_2$), R$^{25AA}$-substituted or unsubstituted heteroalkyl (e.g., 2 to 8 membered, 2 to 6 membered, 4 to 6 membered, 2 to 3 membered, or 4 to 5 membered), R$^{25AA}$-substituted or unsubstituted cycloalkyl (e.g., C$_3$-C$_8$, C$_3$-C$_6$, C$_4$-C$_6$, or C$_5$-C$_6$), R$^{25A}$A-substituted or unsubstituted heterocycloalkyl (e.g., 3 to 8 membered, 3 to 6 membered, 4 to 6 membered, 4 to 5 membered, or 5 to 6 membered), R$^{25AA}$-substituted or unsubstituted aryl (e.g., C$_6$-C$_{12}$, C$_6$-C$_{10}$, or phenyl), or R$^{25AA}$-substituted or unsubstituted heteroaryl (e.g., 5 to 12 membered, 5 to 10 membered, 5 to 9 membered, or 5 to 6 membered). In embodiments, R$^{24AA}$ is independently oxo, halogen, —CX$^{24AA}{}_3$, —CHX$^{24AA}{}_2$, —CH$_2$X$^{24AA}$, —OCX$^{24AA}{}_3$, —OCH$_2$X$^{24A}$A, —OCHX$^{24AA}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{24AA}$ is independently —F, —Cl, —Br, or —I. In embodiments, R$^{24AA}$ is independently unsubstituted methyl. In embodiments, R$^{24AA}$ is independently unsubstituted ethyl.

R$^{25AA}$ is independently oxo, halogen, —CX$^{25AA}{}_3$, —CHX$^{25AA}{}_2$, —CH$_2$X$^{25A}$A, —OCX$^{25A}{}_3$, —OCH$_2$X$^{25A}$A, —OCHX$^{25AA}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{25AA}$ is independently —F, —Cl, —Br, or —I. In embodiments, R$^{25AA}$ is independently unsubstituted methyl. In embodiments, $R^{25AA}$ is independently unsubstituted ethyl.

$R^{24AB}$ is independently oxo, halogen, —$CX^{24A}_3$, —$CHX^{24AB}_2$, —$CH_2X^{24A}B$, —$OCX^{24A}_3$, —$OCH_2X^{24A}B$, —$OCHX^{24AB}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{25A}$B-substituted or unsubstituted alkyl (e.g., $C_1$-$C_8$, $C_1$-$C_6$, $C_1$-$C_4$, or $C_1$-$C_2$), $R^{25A}$B-substituted or unsubstituted heteroalkyl (e.g., 2 to 8 membered, 2 to 6 membered, 4 to 6 membered, 2 to 3 membered, or 4 to 5 membered), $R^{25A}$-substituted or unsubstituted cycloalkyl (e.g., $C_3$-$C_8$, $C_3$-$C_6$, $C_4$-$C_6$, or $C_5$-$C_6$), $R^{25A}$B-substituted or unsubstituted heterocycloalkyl (e.g., 3 to 8 membered, 3 to 6 membered, 4 to 6 membered, 4 to 5 membered, or 5 to 6 membered), $R^{25A}$B-substituted or unsubstituted aryl (e.g., $C_6$-$C_{12}$, $C_6$-$C_{10}$, or phenyl), or $R^{25A}$-substituted or unsubstituted heteroaryl (e.g., 5 to 12 membered, 5 to 10 membered, 5 to 9 membered, or 5 to 6 membered). In embodiments, $R^{24A}$ is independently oxo, halogen, —$CX^{24A}_3$, —$CHX^{24AB}_2$, —$CH_2X^{24A}B$, —$OCX^{24A}_3$, —$OCH_2X^{24AB}$, —$OCHX^{24AB}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24A}$ is independently —F, —Cl, —Br, or —I. In embodiments, $R^{24AB}$ is independently unsubstituted methyl. In embodiments, $R^{24AB}$ is independently unsubstituted ethyl.

$R^{25AB}$ is independently oxo, halogen, —$CX^{25A}_3$, —$CHX^{25A}_2$, —$CH_2X^{25A}B$, —$OCX^{25A}B_3$, —$OCH_2X^{25A}B$, —$OCHX^{25A}B_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25A}$ is independently —F, —Cl, —Br, or —I. In embodiments, $R^{25AB}$ is independently unsubstituted methyl. In embodiments, $R^{25AB}$ is independently unsubstituted ethyl.

In embodiments, z1 is 0. In embodiments, z1 is 1. In embodiments, z1 is 2. In embodiments, z1 is 3. In embodiments, z1 is 4.

In embodiments, the compound has the formula:

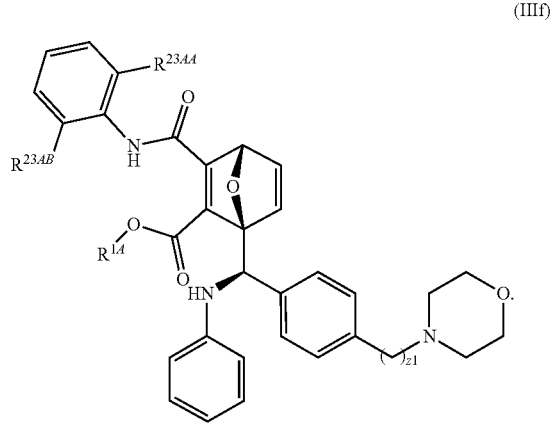

(IIIf)

$R^{1A}$, $R^{23AA}$, $R^{23AB}$, and z1 are as described herein, including in embodiments.

In embodiments, the compound has the formula:

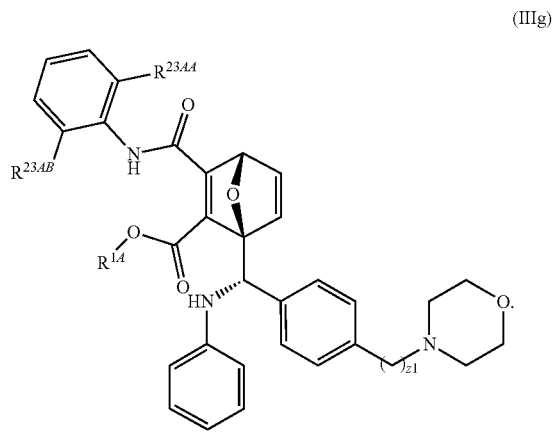

(IIIg)

$R^{1A}$, $R^{23AA}$, $R^{23AB}$, and z1 are as described herein, including in embodiments.

In embodiments, the compound has the formula:

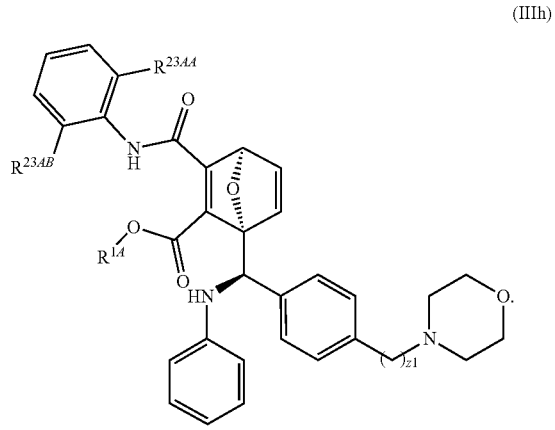

(IIIh)

$R^{1A}$, $R^{23AA}$, $R^{23AB}$, and z1 are as described herein, including in embodiments.

In embodiments, the compound has the formula:

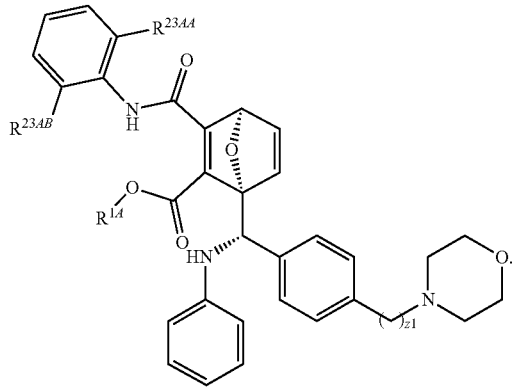

(IIIi)

$R^{1A}$, $R^{23AA}$, $R^{23AB}$, and z1 are as described herein, including in embodiments.

In embodiments, the compound has the formula:

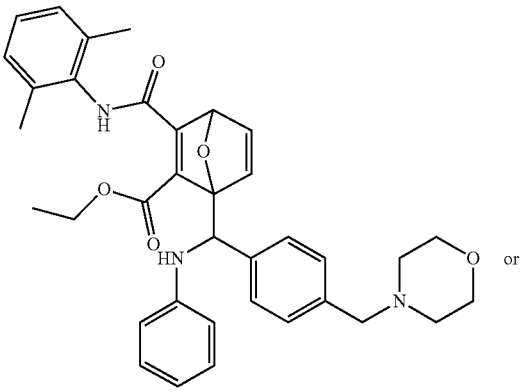

or

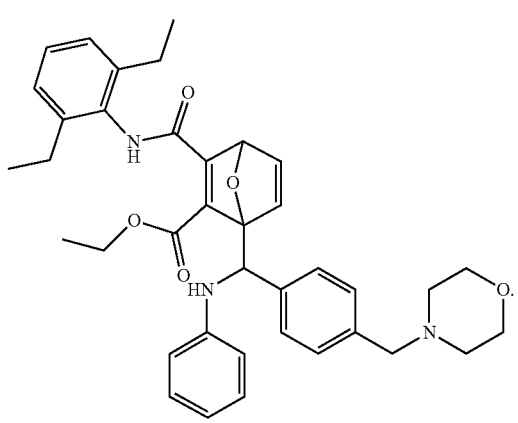

In embodiments, the compound has the formula

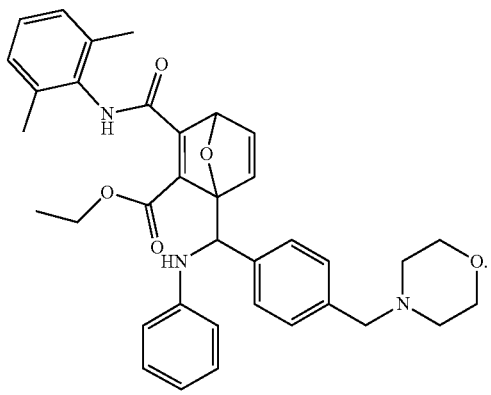 [SMILES: CCOC(=O)C1=C(C(=O)Nc2c(C)cccc2C)C2C=CC1(C(Nc1ccccc1)c1ccc(CN3CCOCC3)cc1)O2]

In embodiments, the compound has the formula

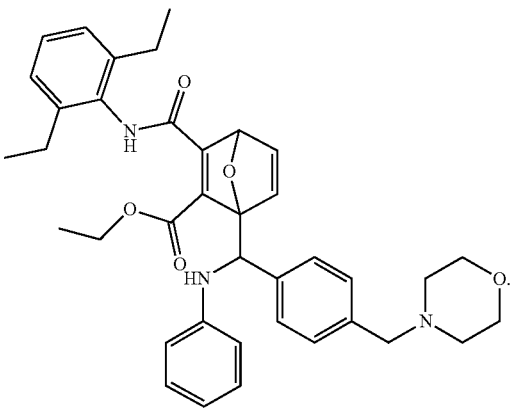 [SMILES: CCOC(=O)C1=C(C(=O)Nc2c(CC)cccc2CC)C2C=CC1(C(Nc1ccccc1)c1ccc(CN3CCOCC3)cc1)O2]

In embodiments, the compound has the formula:

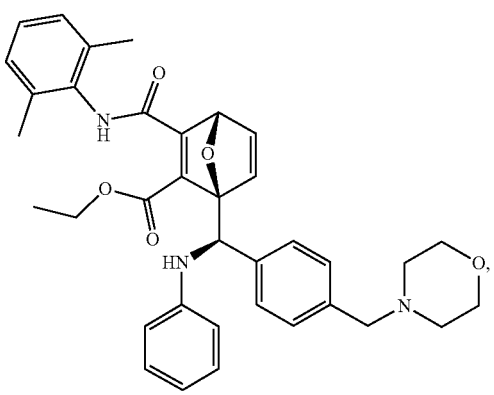

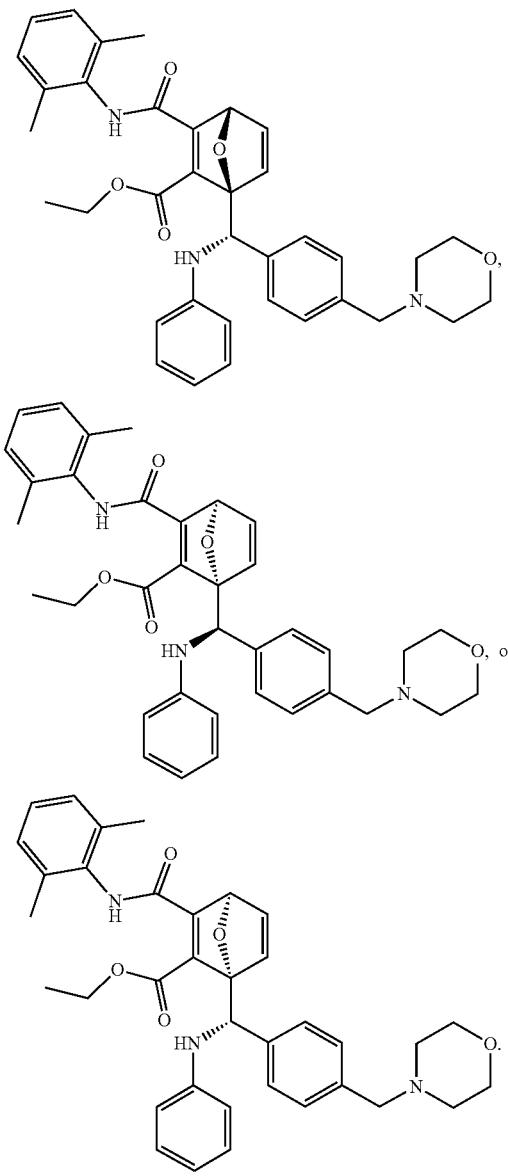
or
In embodiments, the compound has the formula
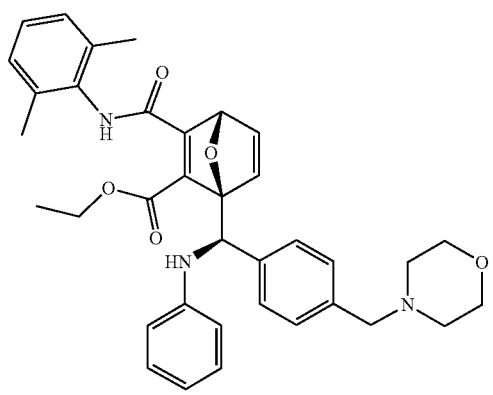 [SMILES: CCOC(=O)C1=C(C(=O)Nc2c(C)cccc2C)[C@@H]2C=C[C@@]1([C@H](Nc1ccccc1)c1ccc(CN3CCOCC3)cc1)O2]
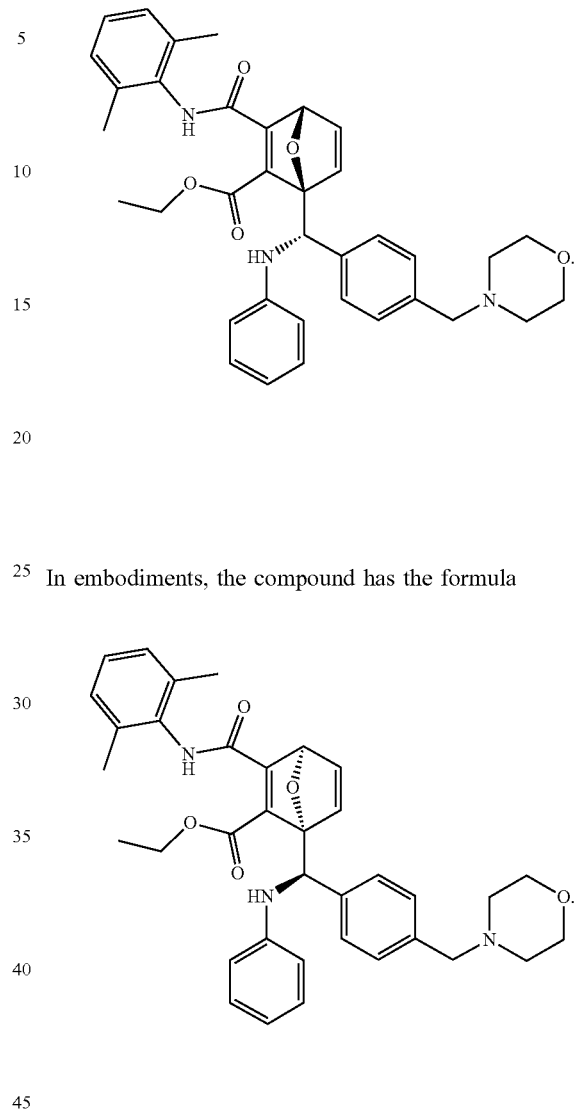
In embodiments, the compound has the formula
In embodiments, the compound has the formula
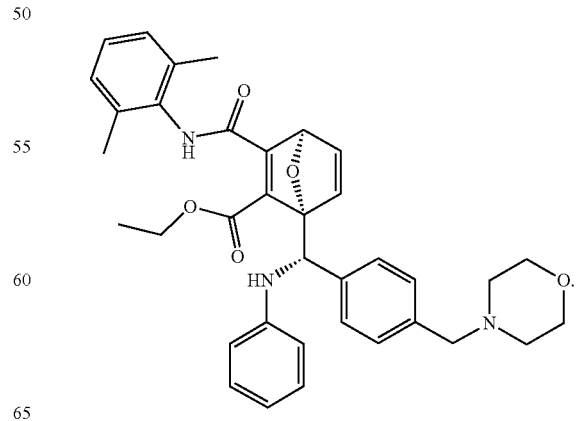

In embodiments, the compound has the formula:
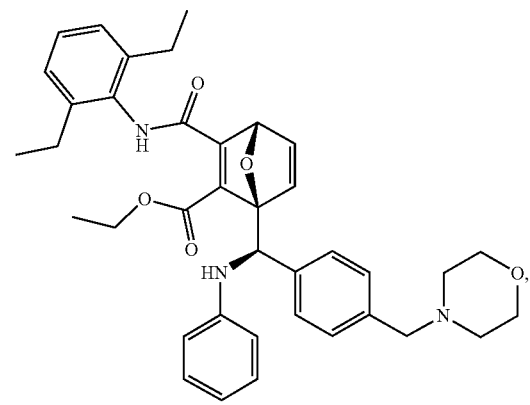 [SMILES: CCOC(=O)C1=C(C(=O)Nc2c(CC)cccc2CC)[C@@H]2C=C[C@@]1([C@H](Nc1ccccc1)c1ccc(CN3CCOCC3)cc1)O2]
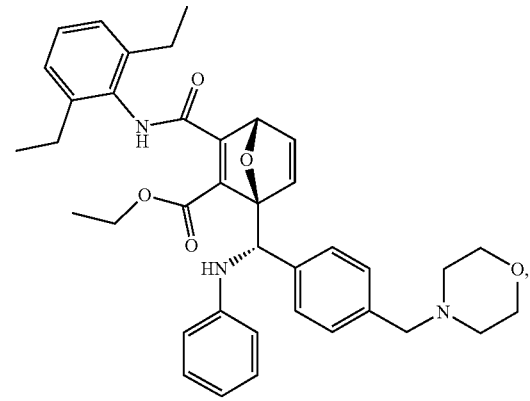 [SMILES: CCOC(=O)C1=C(C(=O)Nc2c(CC)cccc2CC)[C@@H]2C=C[C@@]1([C@@H](Nc1ccccc1)c1ccc(CN3CCOCC3)cc1)O2]
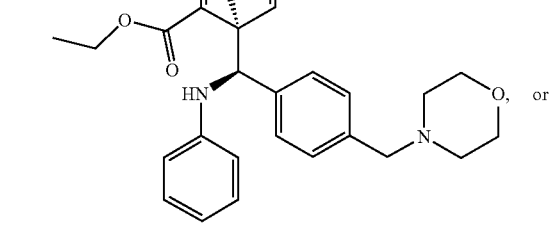, or
In embodiments, the compound has the formula
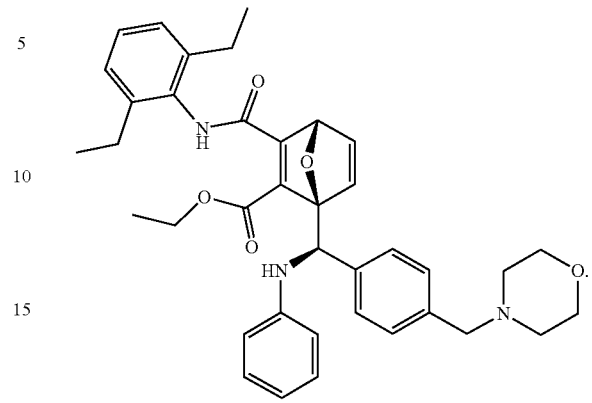
In embodiments, the compound has the formula
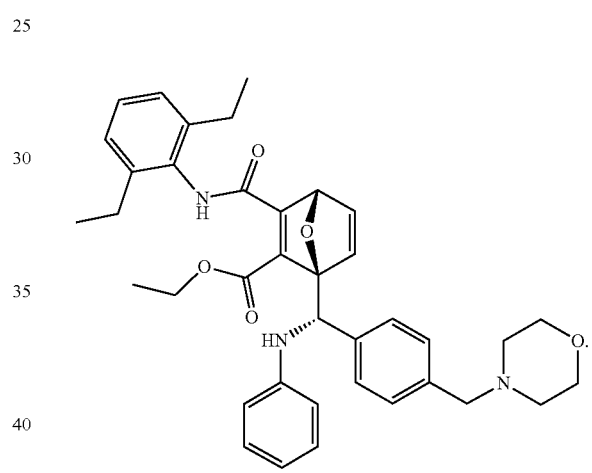
In embodiments, the compound has the formula
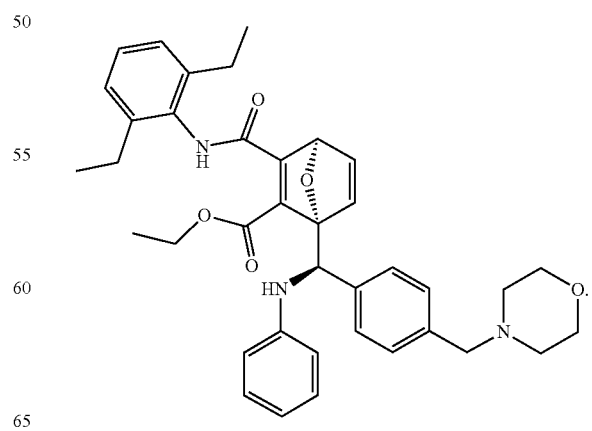

In embodiments, the compound has the formula

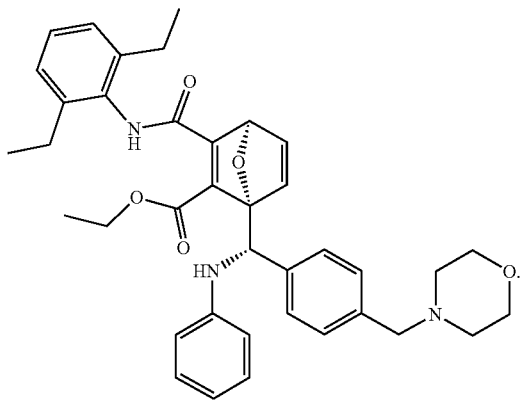 [SMILES: CCOC(=O)C1=C(C(=O)Nc2c(CC)cccc2CC)[C@H]2C=C[C@]1([C@@H](Nc1ccccc1)c1ccc(CN3CCOCC3)cc1)O2]

In embodiments, the compound is covalently attached to an E1 cysteine amino acid corresponding to Cys30 of Uba2 subunit 2. In embodiments, at least one of $R^1$ or $R^2$ includes an electron-withdrawing moiety. In embodiments, at least one of $R^1$ or $R^2$ are sufficiently electron withdrawing to allow the compound to covalently bind to an E1 cysteine amino acid corresponding to Cys30 of Uba2 subunit 2, wherein the E1 cysteine amino acid is bound to ring carbon $C_2$ attached to $R^2$ or ring carbon $C_1$ attached to $R^1$. In embodiments, the compound covalently binds to an E1 cysteine amino acid corresponding to Cys30 of Uba2 subunit 2; and forms a complex of formula:

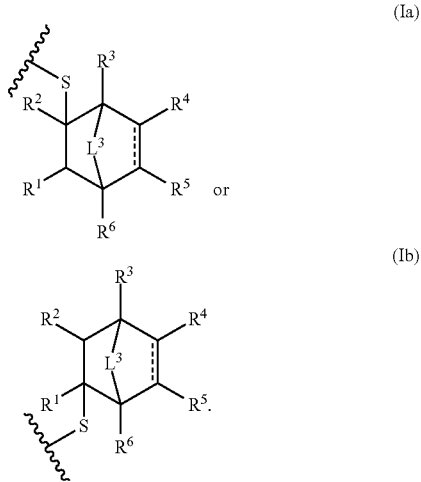

$R^1$, $R^2$, $R^3$, $R^4$, $R^5$, $R^6$, and $L^3$ are as described herein, including in embodiments. In embodiments, $R^4$ is hydrogen. In embodiments, $R^5$ is hydrogen. In embodiments, $R^8$ is substituted or unsubstituted cycloalkyl, substituted or unsubstituted heterocycloalkyl, substituted or unsubstituted aryl, or substituted or unsubstituted heteroaryl. In embodiments, $R^8$ is substituted or unsubstituted aryl or substituted or unsubstituted heteroaryl. In embodiments, $R^8$ is substituted or unsubstituted phenyl or substituted or unsubstituted 5 to 6 membered heteroaryl. In embodiments, $R^8$ is substituted or unsubstituted phenyl. In embodiments, $R^{41}$ is independently halogen or OPh. In embodiments, z41 is 2. In embodiments, z41 is 1. In embodiments, z41 is 0. In embodiments, $L^9$ is a bond or substituted or unsubstituted alkylene. In embodiments, $L^9$ is a bond or unsubstituted $C_1$-$C_3$ alkylene. In embodiments, $L^9$ is an unsubstituted methylene. In embodiments, $L^9$ is a bond. In embodiments, $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^9$ is unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^9$ is unsubstituted propyl, unsubstituted butyl, unsubstituted pentyl, unsubstituted propenyl, unsubstituted butenyl, unsubstituted pentenyl, unsubstituted propynyl, unsubstituted butynyl, unsubstituted pentynyl, unsubstituted cyclobutyl, unsubstituted cyclopentyl, unsubstituted tetrahydropyranyl, unsubstituted morpholinyl, or unsubstituted phenyl. In embodiments, $R^9$ is unsubstituted phenyl. In embodiments, $R^{2A}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{2A}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_3$-$C_6$ aryl, or substituted or unsubstituted 5 to 10 membered heteroaryl. In embodiments, $R^{2A}$ is hydrogen. In embodiments, $R^{2B}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{2B}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_3$-$C_6$ aryl, or substituted or unsubstituted 5 to 10 membered heteroaryl. In embodiments, $R^{2B}$ is hydrogen. In embodiments, $R^{2A}$ and $R^{2B}$ are joined to form a substituted or unsubstituted heterocycloalkyl or substituted or unsubstituted heteroaryl. In embodiments, $R^{2A}$ and $R^{2B}$ are joined to form a substituted or unsubstituted heterocycloalkyl. In embodiments, $R^{2A}$ and $R^{2B}$ are joined to form a substituted or unsubstituted 4 to 6 membered heterocycloalkyl. In embodiments, $R^{14}$ is hydrogen, —$CX^{14}_3$, —$CHX^{14}_2$, —$CH_2X^{14}$, —$OCX^{14}_3$, —$OCH_2X^{14}$—$OCHX^{14}_2$, —$C(O)R^{14A}$, —$C(O)OR^{14A}$, —$C(O)NR^{14A}R^{14B}$, —$OR^{14A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{14}$ is hydrogen, —$CX^{14}_3$, —$CHX^{14}_2$, —$CH_2X^{14}$ unsubstituted $C_1$-$C_3$ alkyl. In embodiments, $R^{14}$ is unsubstituted $C_1$-$C_3$ alkyl. In embodiments, $R^{14}$ is hydrogen. In embodiments, $R^3$ is hydrogen, —$CX^3_3$, —$CHX^3_2$, —$CH_2X^3$, substituted or unsubstituted alkyl. In embodiments, $R^3$ is —$CH_2OH$ or —$CH_3$. In embodiments, $R^3$ is hydrogen. In embodiments, $R^3$ is substituted or unsubstituted phenyl. In embodiments, $R^3$ is unsubstituted phenyl.

In some embodiments, a compound as described herein may include multiple instances of $R^1$ and/or other variables. In such embodiments, each variable may optional be different and be appropriately labeled to distinguish each group for greater clarity. For example, where each $R^1$ is different, they may be referred to, for example, as $R^{1.1}$, $R^{1.2}$, $R^{1.3}$, $R^{1.4}$, $R^{1.5}$, respectively, wherein the definition of $R^1$ is assumed by $R^{1.1}$, $R^{1.2}$, $R^{1.3}$, $R^{1.4}$, $R^{1.5}$. The variables used within a definition of $R^1$ and/or other variables that appear at multiple instances and are different may similarly be appropriately labeled to distinguish each group for greater clarity.

In some embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, $R^{2.4}$, $R^{2.5}$, respectively, wherein the definition of $R^2$ is assumed by $R^{2.1}$, $R^{2.2}$, $R^{2.3}$, $R^{2.4}$, $R^{2.5}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, figure, table, scheme, or claim).

In embodiments, the compound is a compound described herein (e.g., in an aspect, embodiment, example, claim, table, scheme, drawing, or figure). In embodiments, a moiety of a compound is a moiety described in a compound of Table I in the Example section below.

In embodiments, the moieties of a compound are moieties described in one or a plurality of compounds of Table I in the Example section below.

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g., therapeutic agent). In embodiments of the pharmaceutical compositions, the pharmaceutical composition includes a second agent (e.g., therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic. In embodiments, the administering does not include administration of any active agent other than the recited active agent (e.g., a compound described herein).

IV. Methods of Treatment

In an aspect is provided a method of treating cancer, the method including administering to a subject in need thereof an effective amount of a compound described herein. In embodiments, the compound is included in a therapeutically effective amount. In embodiments, the compound is administered at a rate approximately equal to the half-life of an E1 enzyme.

In embodiments, the half-life of an E1 enzyme is about 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is greater than 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is less than 1, 2, 4, 6, 8, 10, 12, 14, 16, 18, 20, 21, 22, 23, 24, 25, 26, 27, 28, 29, 30, 32, 34, or 36 hours.

In an aspect is provided a method of treating a proliferative disease, the method including administering to a subject in need thereof an effective amount of a compound described herein. In embodiments, the compound is included in a therapeutically effective amount. In embodiments, the compound is administered at a rate approximately equal to the half-life of an E1 enzyme.

In embodiments, the half-life of an E1 enzyme is about 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is greater than 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is less than 1, 2, 4, 6, 8, 10, 12, 14, 16, 18, 20, 21, 22, 23, 24, 25, 26, 27, 28, 29, 30, 32, 34, or 36 hours.

In an aspect is provided a method of treating cancer in a subject in need thereof, said method including administering to the subject a pharmaceutically acceptable excipient and a therapeutically effective amount of a compound of formula:

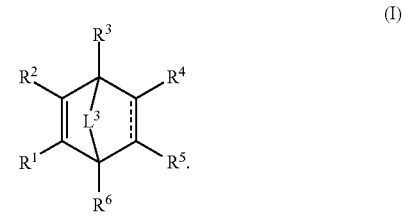

(I)

$R^1$, $R^2$, $R^3$, $R^4$, $R^5$, $R^6$, and $L^3$ are as described herein, including in embodiments.

===  is a single bond or double bond.

$L^3$ is —O—, —S—, —N—, —S(O)—, —S(O)$_2$—, —C(O)—, —N(R$^7$)—, substituted or unsubstituted alkylene, or substituted or unsubstituted heteroalkylene.

$R^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, -L$^1$-E$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2A}$, $-SO_{v2}NR^{2A}R^{2B}$, $-NHC(O)NR^{2A}R^{2B}$, $-N(O)_{m2}$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, $-L^2-E^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3A}$, $SO_{v3}NR^{3A}R^{3B}$, $-NHC(O)NR^{3A}R^{3B}$, $-N(O)_{m3}$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4A}$, $-SO_{v4}NR^{4A}R^{4B}$, $-NHC(O)NR^{4A}R^{4B}$, $-N(O)_{m4}$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5A}$, $SO_{v5}NR^{5A}R^{5B}$, $-NHC(O)NR^{5A}R^{5B}$, $-N(O)_{m5}$, $-NR^{5A}R^{5B}$, $-NHNR^{5A}R^{5B}$, $-C(O)R^{5A}$, $-C(O)-OR^{5A}$, $-C(O)NR^{5A}R^{5B}$, $-C(O)NHNR^{5A}R^{5B}$, $-OR^{5A}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6A}$, $-SO_{v6}NR^{6A}R^{6B}$, $-NHC(O)NR^{6A}R^{6B}$, $-N(O)_{m6}$, $-NR^{6A}R^{6B}$, $-NHNR^{6A}R^{6B}$, $-C(O)R^{6A}$, $-C(O)-OR^{6A}$, $-C(O)NR^{6A}R^{6B}$, $-C(O)NHNR^{6A}R^{6B}$, $-OR^{6A}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7A}$, $SO_{v7}NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)-OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted aryl, or substituted or unsubstituted heteroaryl.

$E^1$ and $E^2$ are independently an electron-withdrawing moiety.

Each $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, $R^{7A}$, and $R^{7B}$ is independently hydrogen, $-CX_3$, $-CHX_2$, $-CH_2X$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl.

m1, m2, m3, m4, m5, m6, and m7 are independently 1 or 2.

v1, v2, v3, v4, v5, v6, and v7 are independently 1 or 2.

n1, n2, n3, n4, n5, n6, and n7, are independently an integer from 0 to 4.

$X, X^1, X^2, X^3, X^4, X^5, X^6,$ and $X^7$ are independently $-Cl$, $-Br$, $-I$ or $-F$.

$L^1$ and $L^2$ are independently a bond, $-O-$, $-S-$, $-S(O)-$, $-S(O)_2-$, $-NH-$, $-C(O)-$, $-C(O)O-$, $-C(O)NH-$, $-OC(O)-$, $-NHC(O)-$, $-NH-C(O)-NH-$, $-OC(O)NH-$, $-NHC(O)O-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ and $R^2$ may optionally be joined to form a substituted or unsubstituted cycloalkyl, substituted or unsubstituted heterocycloalkyl, substituted or unsubstituted aryl, or substituted or unsubstituted heteroaryl.

$R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl.

Wherein the compound is administered at a rate approximately equal to the half-life of an E1 enzyme.

In embodiments, the half-life of an E1 enzyme is about 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is greater than 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is less than 1, 2, 4, 6, 8, 10, 12, 14, 16, 18, 20, 21, 22, 23, 24, 25, 26, 27, 28, 29, 30, 32, 34, or 36 hours.

In embodiments, the cancer is a human cancer, carcinoma, sarcoma, adenocarcinoma, lymphoma, or leukemia. In embodiments, the cancer is a solid cancer, lymphoid cancer, kidney, breast, lung, bladder, colon, ovarian, prostate, pancreas, stomach, brain, head and neck, skin, uterine, testicular, glioma, esophagus, or liver cancer. In embodiments, the cancer is hepatocarcinoma or lymphoma. In embodiments, the lymphoma is B-acute lymphoblastic lymphoma, non-Hodgkin's lymphoma (e.g., Burkitt's, Small Cell, and Large Cell lymphomas), Hodgkin's lymphoma, leukemia (e.g., AML, ALL, and CML), or multiple myeloma.

In embodiments, the compound is covalently attached to an E1 cysteine amino acid corresponding to Cys30 of Uba2 subunit 2. In embodiments, at least one of $R^1$ or $R^2$ includes an electron-withdrawing moiety. In embodiments, at least one of $R^1$ or $R^2$ are sufficiently electron withdrawing to allow the compound to covalently bind to an E1 cysteine amino acid corresponding to Cys30 of Uba2 subunit 2, wherein the E1 cysteine amino acid is bound to ring carbon $C_2$ attached to $R^2$ or ring carbon $C_1$ attached to R'. In embodiments, the compound covalently binds to an E1 cysteine amino acid corresponding to Cys30 of Uba2 subunit 2; and forms a complex of formula:

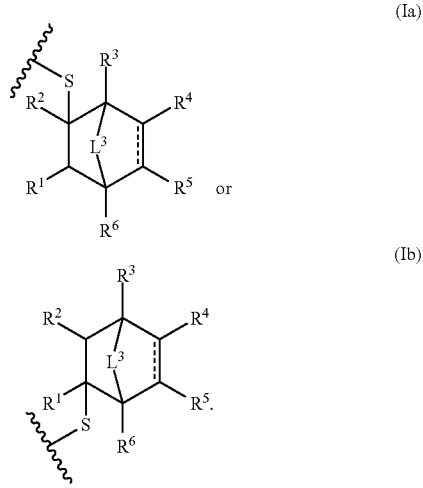

(Ia)

(Ib)

$R^1$, $R^2$, $R^3$, $R^4$, $R^5$, $R^6$, and $L^3$ are as described herein, including in embodiments.

In embodiments, the method includes allowing the compound to covalently bind an E1 enzyme. In embodiments, the method includes allowing the compound to covalently bind an E1 cysteine amino acid corresponding to Cys30 of Uba2 subunit 2. In embodiments, the method includes allowing the E1 cysteine amino acid to bind to carbon $C_2$ attached to $R^{2A}$ and $R^{2B}$ or to ring carbon $C_1$ attached to $R^{1A}$. In embodiments, the method includes allowing the E1 cysteine amino acid to bind (e.g., covalently bind) to carbon $C_2$ attached to $R^{2A}$ and $R^{2B}$ or to carbon $C_1$ attached to $R^{1A}$.

It will be understood that the carbon $C_1$ is adjacent (e.g., bonded) to an $R^1$ or $R^{1A}$ group as appropriate for the specified embodiment. It will be understood that the carbon $C_2$ is adjacent (e.g., bonded) to an $R^2$ or $R^{2A}$ or $R^{2B}$ group as appropriate for the specified embodiment.

V. Methods of Inhibition

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In embodiments, the half-life of an E1 enzyme is about 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is greater than 1, 2, 4, 6, 8, 10, 12, 14, 16, 18, 20, 21, 22, 23, 24, 25, 26, 27, 28, 29, 30, 32, 34, or 36 hours. In embodiments, the half-life of an E1 enzyme is less than 1, 2, 4, 6, 8, 10, 12, 14, 16, 18, 20, 21, 22, 23, 24, 25, 26, 27, 28, 29, 30, 32, 34, or 36 hours.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2. In embodiments, the method includes allowing the E1 cysteine amino acid to bind to carbon $C_2$ attached to $R^{2A}$ and $R^{2B}$ or to ring carbon $C_1$ attached to $R^{1A}$. In embodiments, the method includes allowing the E1 cysteine amino acid to bind (e.g., covalently bind) to carbon $C_2$ attached to $R^{2A}$ and $R^{2B}$ or to carbon $C_1$ attached to $R^{1A}$.

VI. Methods of Screening

Also provided are methods of identifying ligands (e.g., therapeutic target proteins, druggable hotspots) capable of covalently binding a compound provided herein including embodiments thereof. The methods include combining a ligand and a compound provided herein in a reaction vessel, allowing the ligand and the compound to form a covalent ligand-compound complex, and detecting the covalent ligand-compound complex thereby identifying the ligand as target protein or druggable hotspot. A "reaction vessel" as provided herein refers to a vial, tube, flask, bottle, syringe or other container means, into which the ligand and the compound are combined to allow the formation of a covalent ligand-compound complex. Optionally, one or more of the ligands or compounds are labeled. Optionally, the label is a fluorescent label. Optionally, the compound includes a fluorescent label.

Provided herein are methods of detecting a ligand capable of covalently binding a compound provided herein including embodiments thereof. The method includes contacting a ligand with a compound provided herein and allowing the compound to covalently bind to the ligand, thereby forming a covalent compound-ligand complex; and detecting the covalent compound-ligand complex by nuclear magnetic resonance (NMR). The ligand may be a protein, for example, any cellular or extracellular protein including without limitation, an enzyme, a structural protein, a cytoplasmic protein and a nuclear protein.

In one aspect, a method of detecting covalent binding of a ligand to a compound provided herein is provided. The method includes: (i) contacting a ligand with a compound provided herein; (ii) allowing the compound to covalently bind to the ligand, thereby forming a covalent ligand-compound complex; and (iii) detecting the covalent ligand-compound complex using nuclear magnetic resonance, thereby detecting covalent binding of the ligand to the compound. In embodiments, the contacting is performed in a reaction vessel. In embodiments, the ligand is a cysteine bearing polypeptide. In embodiments, the detecting includes determining a chemical shift for an amino acid in the ligand. In embodiments, the detecting includes producing an NMR spectra of the covalent ligand-compound complex and identifying a change in the NMR spectra relative to the absence of the compound. In embodiments, a cysteine residue of the ligand is covalently bound to the compound. A sulfhydryl functional group of a cysteine amino acid of the ligand may form a covalent bond with a compound provided herein including embodiments thereof. Thus, in embodiments, the covalent bond between the ligand and the compound may be formed by a cysteine of the ligand and an electrophilic moiety (e.g., $E^1$ or $E^2$) of the compound. In embodiments, the covalent bond between the ligand and the compound may be formed by a cysteine of the ligand and an atom adjacent to an electrophilic moiety (e.g., $E^1$ or $E^2$) of the compound. In embodiments, the covalent bond between the ligand and the compound may be formed by a cysteine of the ligand and an atom adjacent to L' or $L^2$ of the compound. In embodiments, the ligand is a Uba2 enzyme and the amino acid corresponds to Cys30 of Uba2 subunit 2.

Provided herein are methods of detecting a ligand capable of covalently binding a compound provided herein including embodiments thereof. The method includes contacting a ligand with a compound provided herein and allowing the compound to covalently bind to the ligand, thereby forming a covalent compound-ligand complex; and detecting the covalent compound-ligand complex by quantitative mass spectrometry. The ligand may be a protein, for example, any cellular or extracellular protein including without limitation, an enzyme, a structural protein, a cytoplasmic protein and a nuclear protein.

In another aspect, a method of detecting covalent binding of a ligand to a compound provided herein is provided. The method includes: (i) contacting a ligand with a compound provided herein; (ii) allowing the compound to covalently bind to the ligand, thereby forming a covalent ligand-compound complex; and (iii) detecting the covalent ligand-compound complex using quantitative mass spectrometry, thereby detecting covalent binding of the ligand to the compound. In embodiments, the contacting is performed in a reaction vessel. In embodiments, the ligand is a cysteine bearing polypeptide. In embodiments, the detecting includes determining a molecular weight for the covalent ligand-compound complex. In embodiments, the detecting includes producing a quantitative mass spectrometry spectrum of the covalent ligand-compound complex and identifying a change in the quantitative mass spectrometry spectrum relative to the absence of the compound. In embodiments, a cysteine residue of the ligand is covalently bound to the compound. A sulfhydryl functional group of a cysteine amino acid of the ligand may form a covalent bond with a compound provided herein including embodiments thereof. Thus, in embodiments, the covalent bond between the ligand and the compound may be formed by a cysteine of the ligand and an electrophilic moiety (e.g., $E^1$ or $E^2$) of the compound. In embodiments, the covalent bond between the ligand and the compound may be formed by a cysteine of the ligand and an atom adjacent to an electrophilic moiety (e.g., $E^1$ or $E^2$) of the compound. In embodiments, the covalent bond between the ligand and the compound may be formed by a cysteine of the ligand and an atom adjacent to $L^1$ or $L^2$ of the compound. In embodiments, the ligand is a Uba2 enzyme and the amino acid corresponds to Cys30 of Uba2 subunit 2.

VII. Embodiments

Embodiment P1. A method of treating cancer in a subject in need thereof, said method comprising administering to said subject a pharmaceutically acceptable excipient and a therapeutically effective amount of a compound of formula:

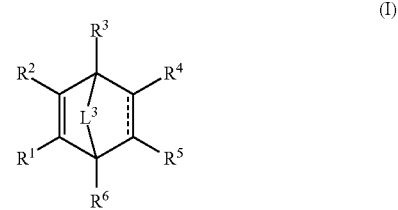

(I)

wherein:
≈≈≈ is a single bond or double bond;
$L^3$ is —O—, —S—, —N—, —S(O)—, —S(O)$_2$—, —C(O)—, —N(R$^7$)—, substituted or unsubstituted alkylene, or substituted or unsubstituted heteroalkylene;
$R^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, -L$^1$-E$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2A}$, —SO$_{v2}$NR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, -L$^2$-E$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4A}$, —SO$_{v4}$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5A}$, —SO$_{v5}$NR$^{5A}$R$^{5B}$, —NHC(O)NR$^{5A}$R$^{5B}$, —N(O)$_{m5}$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{n6}$R$^{6A}$, —SO$_{v6}$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7A}$, SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E$^1$ and E$^2$ are independently an electron-withdrawing moiety;

Each R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$, R$^{7A}$, and R$^{7B}$ is independently hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl;

m1, m2, m3, m4, m5, m6, and m7 are independently 1 or 2;

v1, v2, v3, v4, v5, v6, and v7 are independently 1 or 2;

n1, n2, n3, n4, n5, n6, and n7, are independently an integer from 0 to 4;

X, X$^1$, X$^2$, X$^3$, X$^4$, X$^5$, X$^6$, and X$^7$ are independently —Cl, —Br, —I or —F;

L$^1$ and L$^2$ are independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^1$ and R$^2$ may optionally be joined to form a substituted or unsubstituted cycloalkyl, substituted or unsubstituted heterocycloalkyl, substituted or unsubstituted aryl, or substituted or unsubstituted heteroaryl;

R$^4$ and R$^5$ may optionally be joined to form a substituted or unsubstituted cycloalkyl, substituted or unsubstituted heterocycloalkyl, substituted or unsubstituted aryl, or substituted or unsubstituted heteroaryl; and wherein said compound is administered at a rate approximately equal to the half-life of an E1 enzyme.

Embodiment P2. The method of embodiment P1, wherein said compound is covalently attached to an E1 cysteine amino acid corresponding to Cys30 of Uba2 subunit 2.

Embodiment P3. The method of one of embodiments P1 to P2, wherein at least one of R$^1$ or R$^2$ comprises an electron-withdrawing moiety.

Embodiment P4. The method of one of embodiments P1 to P3, wherein at least one of R$^1$ or R$^2$ are sufficiently electron withdrawing to allow said compound to covalently bind to an E1 cysteine amino acid corresponding to Cys30 of Uba2 subunit 2, wherein said E1 cysteine amino acid is bound to ring carbon C$_2$ attached to R$^2$ or ring carbon C$_1$ attached to R$^1$.

Embodiment P5. The method of one of embodiments P1 to P3, wherein said compound covalently binds to an E1 cysteine amino acid corresponding to Cys30 of Uba2 subunit 2; and forms a complex of formula:

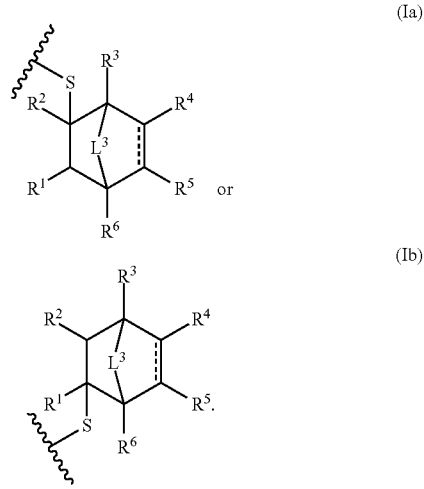

Embodiment P6. A compound of Formula:

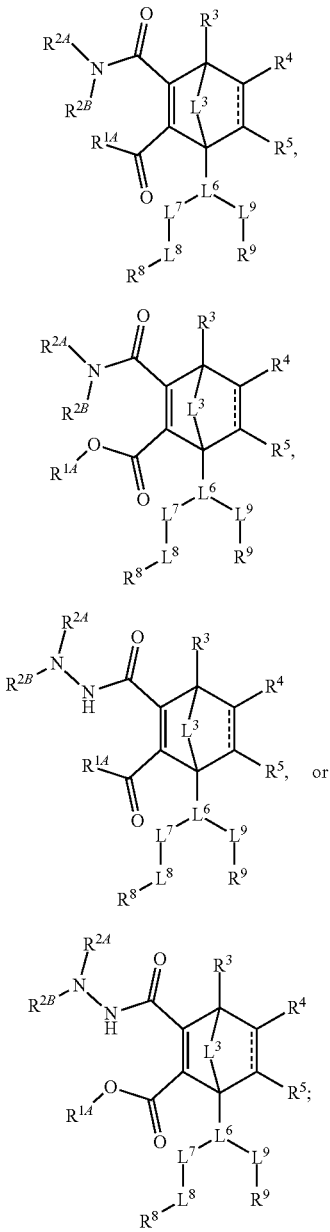

(II)

(III)

(IV)

(V)

wherein:
$L^3$ is —O—, —S—, or —N($R^7$)—;
$L^7$ is —O— or —N($R^{10}$)—;
$R^{1A}$ is hydrogen, halogen, —$CX^{1A}_3$, —$CHX^{1A}_2$, —$CH_2X^{1A}$, —$OCX^{1A}_3$, —$OCH_2X^{1A}$, —$OCHX^{1A}_2$, —CN, —$SO_{n1A}R^{1AA}$, —$SO_{v1A}NR^{1AA}R^{1AB}$, —NHC(O)$NR^{1AA}R^{1AB}$, —N(O)$_{m1A}$, —$NR^{1AA}R^{1AB}$, —$NHNR^{1AA}R^{1AB}$, —C(O)$R^{1AA}$, —C(O)—$OR^{1AA}$, —C(O)$NR^{1AA}R^{1AB}$, —$OR^{1AA}$, —$NR^{1AA}SO_2R^{1AB}$, —$NR^{1AA}C(O)R^{1AB}$, —$NR^{1AA}C(O)OR^{1AB}$, —$NR^{1AA}OR^{AB}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2A}$ is hydrogen, halogen, —$CX^{2A}_3$, —$CHX^{2A}_2$, —$CH_2X^{2A}$, —$OCX^{2A}_3$, —$OCH_2X^{2A}$, —$OCHX^{2A}_2$, —CN, —$SO_{n2}^AR^{2AA}$, —$SO_{v2A}NR^{2AA}R^{2AB}$, —NHC(O)$NR^{2AA}R^{2AB}$, —N(O)$_{m2A}$, —$NR^{2AA}R^{2AB}$, —$NHNR^{2AA}R^{2AB}$, —C(O)$R^{2AA}$, —C(O)—$OR^{2AA}$, —C(O)$NR^{2AA}R^{2AB}$, —$OR^{2AA}$, —$NR^{2AA}SO_2R^{2AB}$, —$NR^{2AA}C(O)R^{2AB}$, —$NR^{2AA}C(O)OR^{2AB}$, —$NR^{2AA}O^{2AB}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2B}$ is hydrogen, halogen, —$CX^{2B}_3$, —$CHX^{2B}_2$, —$CH_2X^{2B}$, —$OCX^{2B}_3$, —$OCH_2X^{2B}$, —$OCHX^{2B}_2$, —CN, —$SO_{n2B}R^{2BA}$, —$SO_{v2B}NR^{2BA}R^{2BB}$, —NHC(O)$NR^{2BA}R^{2BB}$, —N(O)$_{m2B}$, —$NR^{2BA}R^{2BB}$, —$NHNR^{2BA}R^{2BB}$, —C(O)$R^{2BA}$, —C(O)—$OR^{2BA}$, —C(O)$NR^{2BA}R^{2BB}$, —$OR^{2BA}$, —$NR^{2BA}SO_2R^{2BB}$, —$NR^{2BA}C(O)R^{2BB}$, —$NR^{2BA}C(O)OR^{2BB}$, —$NR^{2BA}OR^{2BB}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3A}$, $SO_{v3}NR^{3A}R^{3B}$, —NHC(O)$NR^{3A}R^{3B}$, —N(O)$_{m3}$, —$NR^{3A}R^{3B}$, —$NHNR^{3A}R^{3B}$, —C(O)$R^{3A}$, —C(O)—$OR^{3A}$, —C(O)$NR^{3A}R^{3B}$, —$OR^{3A}$, —$NR^{3A}SO_2R^{3B}$, —$NR^{3A}C(O)R^{3B}$, —$NR^{3A}C(O)OR^{3B}$, —$NR^{3A}OR^{3B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_nR^{4A}$, $SO_{v4}NR^{4A}R^{4B}$, —NHC(O)$NR^{4A}R^{4B}$, —N(O)$_{m4}$, —$NR^{4A}R^{4B}$, —$NHNR^{4A}R^{4B}$, —C(O)$R^{4A}$, —C(O)—$OR^{4A}$, —C(O)$NR^{4A}R^{4B}$, —C(O)$NHNR^{4A}R^{4B}$, —$OR^{4A}$, —$NR^{4A}SO_2R^{4B}$, —$N^{4A}C(O)R^{4B}$, —$NR^{4A}C(O)OR^{4B}$, —$NR^{4A}OR^{4B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5A}$, $SO_{v5}NR^{5A}R^{5B}$, —NHC(O)$NR^{5A}R^{5B}$, —N(O)$_{m5}$, —$NR^{5A}R^{5B}$, —$NHNR^{5A}R^{5B}$, —C(O)$R^{5A}$, —C(O)—$OR^{5A}$, —C(O)$NR^{5A}R^{5B}$, —C(O)$NHNR^{5A}R^{5B}$, —$OR^{5A}$, —$NR^{5A}SO_2R^{5B}$, —$NR^{5A}C(O)R^{5B}$, —$NR^{5A}C(O)OR^{5B}$, —$NR^{5A}OR^{5B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n5}R^{7A}$, —$SO_{v5}NR^{7A}R^{7B}$, —NHC(O)$NR^{7A}R^{7B}$, —N(O)$_{m5}$, —$NR^{7A}R^{7B}$, —$NHNR^{7A}R^{7B}$, —C(O)$R^{7A}$, —C(O)—$OR^{7A}$, —C(O)$NR^{7A}R^{7B}$, —C(O)$NHNR^{7A}R^{7B}$, —$OR^{7A}$, —$NR^{7A}SO_2R^{7B}$, —$NR^{7A}C(O)R^{7B}$, —$NR^{7A}C(O)OR^{7B}$, —$NR^{7A}OR^{7B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^8$ is hydrogen, halogen, —$CX^8_3$, —$CHX^8_2$, —$CH_2X^8$, —$OCX^8_3$, —$OCH_2X^8$, —$OCHX^8_2$, —CN, —$SO_{n5}R^{8A}$, —$SO_{v5}NR^{8A}R^{8B}$, —NHC(O)$NR^{8A}R^{8B}$, —N(O)$_{m5}$, —$NR^{8A}R^{8B}$, —$NHNR^{8A}R^{8B}$, —C(O)$R^{8A}$, —C(O)—$OR^{8A}$, —C(O)NR$^{8A}$R$^{8B}$, —C(O)NHNR$^{8A}$R$^{8B}$, —OR$^{8A}$, —NR$^{8A}$SO$_2$R$^{8B}$, —NR$^{8A}$C(O)R$^{8B}$, —NR$^{8A}$C(O)OR$^{8B}$, —NR$^{8A}$OR$^{8B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —CN, —SO$_{n5}$R$^{9A}$, —SO$_{v5}$NR$^{9A}$R$^{9B}$, —NHC(O)NR$^{9A}$R$^{9B}$, —N(O)$_{m5}$, —NR$^{9A}$R$^{9B}$, —NHNR$^{9A}$R$^{9B}$, —C(O)R$^{9A}$, —C(O)—OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1AA}$, R$^{1AB}$, R$^{2AA}$, R$^{2AB}$, R$^{2BA}$, R$^{2BB}$, R$^{3A}$, R$^{3B}$, R$^{4A}$, R$^{4B}$, R$^{5A}$, R$^{5B}$, R$^{7A}$, R$^{7B}$, R$^{8A}$, R$^{8B}$, R$^{9A}$, R$^{9B}$, R$^{10A}$, and R$^{10B}$ is independently hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1AA}$ and R$^{1AB}$ substituents bonded to the same nitrogen atom may optionally be joined to form a substituted or unsubstituted heterocycloalkyl or substituted or unsubstituted heteroaryl; R$^{2AA}$ and R$^{2A}$ substituents bonded to the same nitrogen atom may optionally be joined to form a substituted or unsubstituted heterocycloalkyl or substituted or unsubstituted heteroaryl; R$^{2BA}$ and R$^{2BB}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{8A}$ and R$^{8B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl;

m1A, m2A, m2B, m3, m4, m5, m7, m8, m9, and m10 are independently 1 or 2;

v1A, v2A, v2B, v3, v4, v5, v7, v8, v9, and v10 are independently 1 or 2;

n1A, n2A, n2B, n3, n4, n5, n7, n8, n9, and n10 are independently an integer from 0 to 4;

X, X$^{1A}$, X$^{2A}$, X$^{2B}$, X$^3$, X$^4$, X$^5$, X$^7$, X$^8$, X$^9$, and X$^{10}$ are independently —Cl, —Br, —I or, —F;

L$^6$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

L$^8$ is a bond, —C(O)—, —C(O)NH—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

L$^9$ is a bond, —O—, —S—, —NH—, —C(O)—, —C(O)O—, —C(O)NH—, —OC(O)—, —NHC(O)—, —NHC(O)NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein R$^{2A}$ and R$^{2B}$ may optionally be joined to form a substituted or unsubstituted heterocycloalkyl or substituted or unsubstituted heteroaryl; and.

R$^4$ and R$^5$ may optionally be joined to form a substituted or unsubstituted cycloalkyl, substituted or unsubstituted heterocycloalkyl, substituted or unsubstituted aryl, or substituted or unsubstituted heteroaryl.

Embodiment P7. The compound of embodiment P6, having the formula:

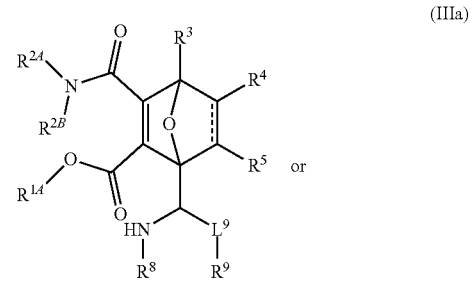

(IIIa)

or

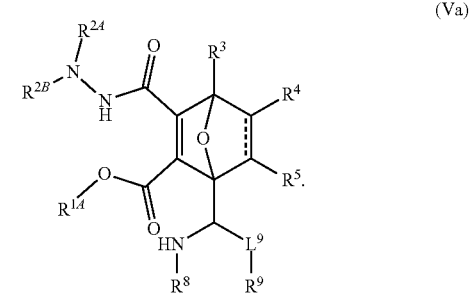

(Va)

Embodiment P8. The compound of one of embodiments P6 to P7, wherein $R^4$ is hydrogen.

Embodiment P9. The compound of one of embodiments P6 to P7, wherein $R^5$ is hydrogen.

Embodiment P10. The compound of one of embodiments P6 to P7, having the formula:

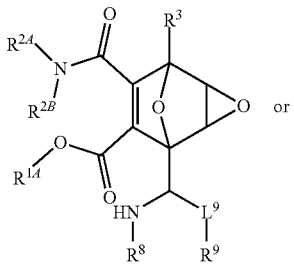

(IIIb)

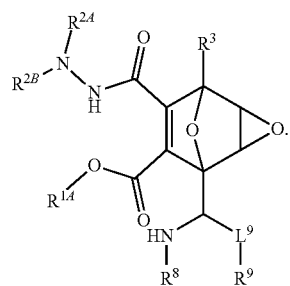

(Vb)

Embodiment P11. The compound of one of embodiments P6 to P10, wherein $R^8$ is substituted or unsubstituted cycloalkyl, substituted or unsubstituted heterocycloalkyl, substituted or unsubstituted aryl, or substituted or unsubstituted heteroaryl.

Embodiment P12. The compound of one of embodiments P6 to P10, wherein $R^8$ is substituted or unsubstituted aryl or substituted or unsubstituted heteroaryl.

Embodiment P13. The compound of one of embodiments P6 to P10, wherein $R^8$ is substituted or unsubstituted phenyl or substituted or unsubstituted 5 to 6 membered heteroaryl.

Embodiment P14. The compound of one of embodiments P6 to P10, wherein $R^8$ is substituted or unsubstituted phenyl.

Embodiment P15. The compound of one of embodiments P6 to P7, having the formula:

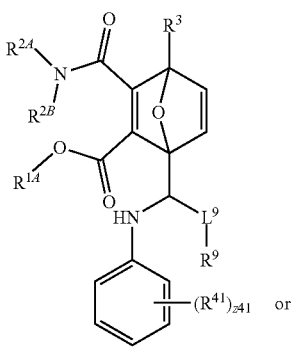

(IIIc)

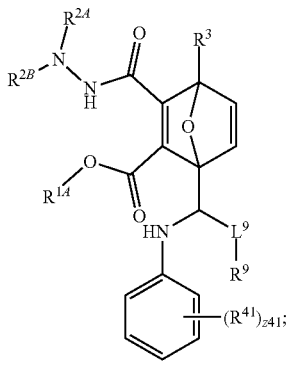

(Vc)

$R^{41}$ is independently halogen, $CX^{41}{}_3$, $-CHX^{41}{}_2$, $-CH_2X^{41}$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{41}{}_3$, $-OCHX^{41}{}_2$, $-OCH_2X^{41}$, $-OPh$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{41}$ substituents may optionally be joined to form a substituted or unsubstituted cycloalkyl, substituted or unsubstituted heterocycloalkyl, substituted or unsubstituted aryl, or substituted or unsubstituted heteroaryl;

z41 is an integer from 0 to 5;

$X^{41}$ is independently $-Cl$, $-Br$, $-I$ or, $-F$.

Embodiment P16. The compound of embodiment P15, wherein $R^{41}$ is independently halogen or OPh.

Embodiment P17. The compound of one of embodiments P15 to P16, wherein z41 is 2.

Embodiment P18. The compound of one of embodiments P15 to P16, wherein z41 is 1.

Embodiment P19. The compound of one of embodiments P15 to P16, wherein z41 is 0.

Embodiment P20. The compound of one of embodiments P6 to P19, wherein $L^9$ is a bond or substituted or unsubstituted alkylene.

Embodiment P21. The compound of one of embodiments P6 to P19, wherein $L^9$ is a bond or unsubstituted $C_1$-$C_3$ alkylene.

Embodiment P22. The compound of one of embodiments P6 to P19, wherein $L^9$ is an unsubstituted methylene.

Embodiment P23. The compound of one of embodiments P6 to P19, wherein $L^9$ is a bond.

Embodiment P24. The compound of one of embodiments P6 to P23, wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P25. The compound of one of embodiments P6 to P23, wherein $R^9$ is unsubstituted alkyl, unsubstituted heteroalkyl, unsubstituted cycloalkyl, unsubstituted heterocycloalkyl, unsubstituted aryl, or unsubstituted heteroaryl.

Embodiment P26. The compound of one of embodiments P6 to P23, wherein $R^9$ is unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment P27. The compound of one of embodiments P6 to P23, wherein $R^9$ is unsubstituted propyl, unsubstituted butyl, unsubstituted pentyl, unsubstituted propenyl, unsubstituted butenyl, unsubstituted pentenyl, unsubstituted propynyl, unsubstituted butynyl, unsubstituted pentynyl, unsubstituted cyclobutyl, unsubstituted cyclopentyl, unsubstituted tetrahydropyranyl, unsubstituted morpholinyl, or unsubstituted phenyl.

Embodiment P28. The compound of one of embodiments P6 to P23, wherein $R^9$ is unsubstituted phenyl.

Embodiment P29. The compound of one of embodiments P6 to P28, wherein $R^{2A}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P30. The compound of one of embodiments P6 to P28, wherein $R^{2A}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_3$-$C_6$ aryl, or substituted or unsubstituted 5 to 10 membered heteroaryl.

Embodiment P31. The compound of one of embodiments P6 to P28, wherein $R^{2A}$ is hydrogen.

Embodiment P32. The compound of one of embodiments P6 to P31, wherein $R^{2B}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P33. The compound of one of embodiments P6 to P31, wherein $R^{2B}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_3$-$C_6$ aryl, or substituted or unsubstituted 5 to 10 membered heteroaryl.

Embodiment P34. The compound of one of embodiments P6 to P31, wherein $R^{2B}$ is hydrogen.

Embodiment P35. The compound of one of embodiments P6 to P28, wherein $R^{2A}$ and $R^{2B}$ are joined to form a substituted or unsubstituted heterocycloalkyl or substituted or unsubstituted heteroaryl.

Embodiment P36. The compound of one of embodiments P6 to P28, wherein $R^{2A}$ and $R^{2B}$ are joined to form a substituted or unsubstituted heterocycloalkyl.

Embodiment P37. The compound of one of embodiments P6 to P28, wherein $R^{2A}$ and $R^{2B}$ are joined to form a substituted or unsubstituted 4 to 6 membered heterocycloalkyl.

Embodiment P38. The compound of one of embodiments P6 to P37, wherein $R^{1A}$ is hydrogen, $-CX^{1A}_3$, $-CHX^{1A}_2$, $-CH_2X^{1A}$, $-OCX^{1A}_3$, $-OCH_2X^{1A}$, $-OCHX^{1A}_2$, $-C(O)R^{1AA}$, $-C(O)OR^{1AA}$, $-C(O)NR^{1AA}R^{1AB}$, $-OR^{1AA}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P39. The compound of one of embodiments P6 to P37, wherein $R^{1A}$ is hydrogen, $-CX^{1A}_3$, $-CHX^{1A}_2$, $-CH_2X^{1A}$, unsubstituted $C_1$-$C_3$ alkyl.

Embodiment P40. The compound of one of embodiments P6 to P37, wherein $R^{1A}$ is unsubstituted $C_1$-$C_3$ alkyl.

Embodiment P41. The compound of one of embodiments P6 to P37, wherein $R^{1A}$ is hydrogen.

Embodiment P42. The compound of one of embodiments P6 to P41, wherein $R^3$ is hydrogen, $-CX^3_3$, $-CHX^3_2$, $-CH_2X^3$, substituted or unsubstituted alkyl.

Embodiment P43. The compound of one of embodiments P6 to P41, wherein $R^3$ is $CH_2OH$ or $CH_3$.

Embodiment P44. The compound of one of embodiments P6 to P41, wherein $R^3$ is hydrogen.

Embodiment P45. A method of inhibiting an E1 enzyme, said method comprising contacting an E1 enzyme with a compound of one of embodiments P6 to P44, thereby inhibiting said E1 enzyme.

Embodiment P46. The method of embodiment P45, wherein said method comprises allowing said compound to covalently bind said E1 enzyme.

Embodiment P47. The method of embodiment P45 or P46, wherein said method comprises allowing said compound to covalently bind an E1 cysteine amino acid corresponding to Cys30 of Uba2 subunit 2.

Embodiment P48. The method of embodiment P47, wherein said method comprises allowing said E1 cysteine amino acid to bind to carbon $C_2$ attached to $R^{2A}$ and $R^{2B}$ or to ring carbon $C_1$ attached to $R^{1A}$.

Embodiment P49. A method of treating cancer in a subject in need thereof, said method comprising administering to said subject a compound of one of embodiments P6 to P44.

Embodiment P50. The method of embodiment P49, wherein said method comprises allowing said compound to covalently bind an E1 enzyme.

Embodiment P51. The method of embodiment P49 or P50, wherein said method comprises allowing said compound to covalently bind an E1 cysteine amino acid corresponding to Cys30 of Uba2 subunit 2.

Embodiment P52. The method of embodiment P51, wherein said method comprises allowing said E1 cysteine amino acid to bind to carbon $C_2$ attached to $R^{2A}$ and $R^{2B}$ or to ring carbon $C_1$ attached to $R^{1A}$.

VIII. Additional Embodiments

Embodiment 1. A method of treating cancer in a subject in need thereof, said method comprising administering to said subject a pharmaceutically acceptable excipient and a therapeutically effective amount of a compound of formula:

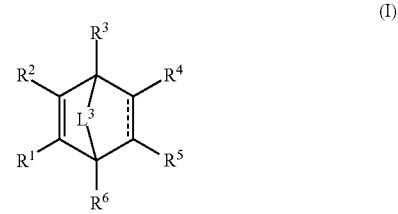

(I)

wherein

==== is a single bond or double bond;
$L^3$ is $-O-$, $-S-$, $-N-$, $-S(O)-$, $-S(O)_2-$, $-C(O)-$, $-N(R^7)-$, substituted or unsubstituted alkylene, or substituted or unsubstituted heteroalkylene;
$R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1A}$, $SO_{v1}NR^{1A}R^{1B}$, $-NHC(O)NR^{1A}R^{1B}$, $-N(O)_{m1}$, $-NR^{1A}R^{1B}$, $-NHNR^{1A}R^{1B}$, $-C(O)R^{1A}$, $-C(O)-OR^{1A}$, $-C(O)NR^{1A}R^{1B}$, $-C(O)NHNR^{1A}R^{1B}$, $-OR^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, -L$^1$-E$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is hydrogen, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2A}$, —SO$_{v2}$NR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, NR$^{2A}$C(O)R$^{2B}$, —NR$^{2A}$C(O)OR$^{2B}$, —NR$^{2A}$OR$^{2B}$, —N$_3$, -L$^2$-E$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4A}$, SO$_{v4}$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5A}$, SO$_{v5}$NR$^{5A}$R$^{5B}$, —NHC(O)NR$^{5A}$R$^{5B}$, —N(O)$_{m5}$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{n6}$R$^{6A}$, —SO$_{v6}$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7A}$, SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E$^1$ and E$^2$ are independently an electron-withdrawing moiety;

each R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$, R$^{7A}$, and R$^{7B}$ is independently hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O) NHNH$_2$, —NHC═(O)NH$_2$, —NHSO$_2$H, —NHC═(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl;

m1, m2, m3, m4, m5, m6, and m7 are independently 1 or 2;

v1, v2, v3, v4, v5, v6, and v7 are independently 1 or 2;

n1, n2, n3, n4, n5, n6, and n7 are independently an integer from 0 to 4;

X, X$^1$, X$^2$, X$^3$, X$^4$, X$^5$, X$^6$, and X$^7$ are independently —Cl, —Br, —I, or —F;

L$^1$ and L$^2$ are independently a bond, —O—, —S—, —NH—, —C(O)—, —C(O)O—, —C(O)NH—, —OC(O)—, —NHC(O)—, —NH—C(O)—NH—, —OC(O) NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^1$ and R$^2$ may optionally be joined to form a substituted or unsubstituted cycloalkyl, substituted or unsubstituted heterocycloalkyl, substituted or unsubstituted aryl, or substituted or unsubstituted heteroaryl;

R$^4$ and R$^5$ may optionally be joined to form a substituted or unsubstituted cycloalkyl, substituted or unsubstituted heterocycloalkyl, substituted or unsubstituted aryl, or substituted or unsubstituted heteroaryl; and wherein said compound is administered at a rate approximately equal to the half-life of an E1 enzyme.

Embodiment 2. The method of embodiment 1, wherein said compound is covalently attached to an E1 cysteine amino acid corresponding to Cys30 of Uba2 subunit 2.

Embodiment 3. The method of one of embodiments 1 to 2, wherein at least one of R$^1$ or R$^2$ comprises an electron-withdrawing moiety.

Embodiment 4. The method of one of embodiments 1 to 3, wherein at least one of $R^1$ or $R^2$ are sufficiently electron withdrawing to allow said compound to covalently bind to an E1 cysteine amino acid corresponding to Cys30 of Uba2 subunit 2, wherein said E1 cysteine amino acid is bound to ring carbon $C_2$ attached to $R^2$ or ring carbon $C_1$ attached to Embodiment 5. The method of one of embodiments 1 to 3, wherein said compound covalently binds to an E1 cysteine amino acid corresponding to Cys30 of Uba2 subunit 2; and forms a complex of formula:

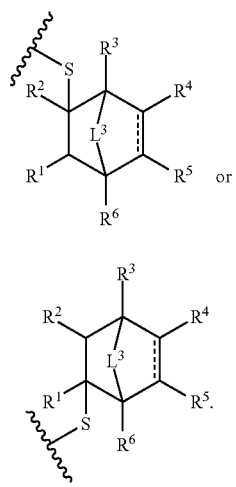

(Ia)

(Ib)

Embodiment 6. A compound of formula:

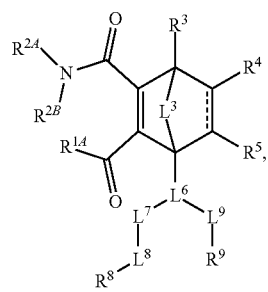

(II)

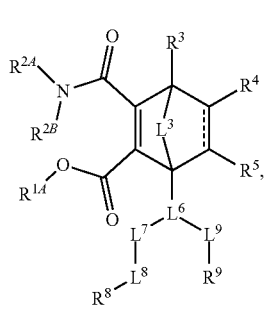

(III)

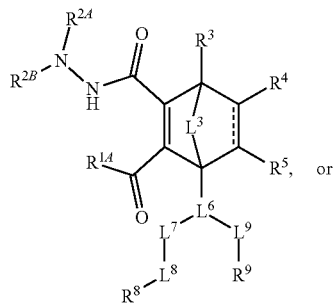

(IV)

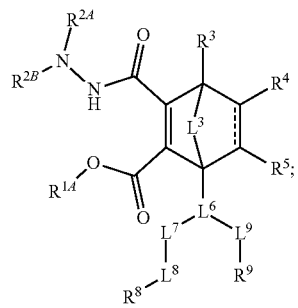

(V)

wherein
$L^3$ is —O—, —S—, or —N($R^7$)—;
$L^7$ is —O— or —N($R^{10}$)—;
$R^{1A}$ is hydrogen, halogen, —CX$^{1A}_3$, —CHX$^{1A}_2$, —CH$_2$X$^{1A}$, —OCX$^{1A}_3$, —OCH$_2$X$^{1A}$, —OCHX$^{1A}_2$, —CN, —SO$_{n1A}$R$^{1AA}$, —SO$_{v1A}$NR$^{1AA}$R$^{1AB}$, —NHC(O)NR$^{1AA}$R$^{1AB}$, —N(O)$_{m1A}$, —NR$^{1AA}$R$^{1AB}$, —NHNR$^{1AA}$R$^{1AB}$, —C(O)R$^{1AA}$, —C(O)—OR$^{1AA}$, —C(O)NR$^{1AA}$R$^{1AB}$, —OR$^{1AA}$, —NR$^{1AA}$SO$_2$R$^{1AB}$, —NR$^{1AA}$C(O)R$^{1AB}$, —NR$^{1AA}$C(O)OR$^{1AB}$, —NR$^{1AA}$OR$^{1AB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2A}$ is hydrogen, halogen, —CX$^{2A}_3$, —CHX$^{2A}_2$, —CH$_2$X$^{2A}$, —OCX$^{2A}_3$, —OCH$_2$X$^{2A}$, —OCHX$^{2A}_2$, —CN, —SO$_{n2A}$R$^{2AA}$, —SO$_{v2A}$NR$^{2AA}$R$^{2AB}$, —NHC(O)NR$^{2AA}$R$^{2AB}$, —N(O)$_{m2A}$, —NR$^{2AA}$R$^{2AB}$, —NHNR$^{2AA}$R$^{2AB}$, —C(O)R$^{2AA}$, —C(O)—OR$^{2AA}$, —C(O)NR$^{2AA}$R$^{2AB}$, —OR$^{2AA}$, —NR$^{2AA}$SO$_2$R$^{2AB}$, —NR$^{2AA}$C(O)R$^{2AB}$, —NR$^{2AA}$C(O)OR$^{2AB}$, —NR$^{2AA}$OR$^{2AB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2B}$ is hydrogen, halogen, —CX$^{2B}_3$, —CHX$^{2B}_2$, —CH$_2$X$^{2B}$, —OCX$^{2B}_3$, —OCH$_2$X$^{2B}$, —OCHX$^{2B}_2$, —CN, —SO$_{n2B}$R$^{2BA}$, —SO$_{v2B}$NR$^{2BA}$R$^{2BB}$, —NHC(O)NR$^{2BA}$R$^{2BB}$, —N(O)$_{m2B}$, —NR$^{2BA}$R$^{2BB}$, —NHNR$^{2BA}$R$^{2BB}$, —C(O)R$^{2BA}$, —C(O)—OR$^{2BA}$, —C(O)NR$^{2BA}$R$^{2BB}$, —OR$^{2BA}$, —NR$^{2BA}$SO$_2$R$^{2BB}$, —NR$^{2BA}$C(O)R$^{2BB}$, —NR$^{2BA}$C(O)OR$^{2BB}$, —NR$^{2BA}$OR$^{2BB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4A}$, SO$_{v4}$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5A}$, SO$_{v5}$NR$^{5A}$R$^{5B}$, —NHC(O)NR$^{5A}$R$^{5B}$, N(O)$_{m5}$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n5}$R$^{7A}$, —SO$_{v5}$NR$^{7A}$R$^{7B}$, —NHC(O)NR$^{7A}$R$^{7B}$, —N(O)$_{m5}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —CN, —SO$_{n5}$R$^{8A}$, —SO$_{v5}$NR$^{8A}$R$^{8B}$, —NHC(O)NR$^{8A}$R$^{8B}$, —N(O)$_{m5}$, —NR$^{8A}$R$^{8B}$, —NHNR$^{8A}$R$^{8B}$, —C(O)R$^{8A}$, —C(O)—OR$^{8A}$, —C(O)NR$^{8A}$R$^{8B}$, —C(O)NHNR$^{8A}$R$^{8B}$, —NR$^{8A}$SO$_2$R$^{8B}$, —NR$^{8A}$C(O)R$^{8B}$, —NR$^{8A}$C(O)OR$^{8B}$, —NR$^{8A}$OR$^{8B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —CN, —SO$_{n5}$R$^{9A}$, —SO$_{v5}$NR$^{9A}$R$^{9B}$, —NHC(O)NR$^{9A}$R$^{9B}$, —N(O)$_{m5}$, —NR$^{9A}$R$^{9B}$, —NHNR$^{9A}$R$^{9B}$, —C(O)R$^{9A}$, —C(O)—OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{1A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O)R$^{10A}$—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R$^{1AA}$, R$^{1AB}$, R$^{2AA}$, R$^{2AB}$, R$^{2BA}$, R$^{2BB}$, R$^{3A}$, R$^{3B}$, R$^{4A}$, R$^{4B}$, R$^{5A}$, R$^{5B}$, R$^{7A}$, R$^{7B}$, R$^{8A}$, R$^{8B}$, R$^{9A}$, R$^{9B}$, R$^{10A}$, and R$^{10B}$ is independently hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1AA}$ and R$^{1AB}$ substituents bonded to the same nitrogen atom may optionally be joined to form a substituted or unsubstituted heterocycloalkyl or substituted or unsubstituted heteroaryl; R$^{2AA}$ and R$^{2A}$ substituents bonded to the same nitrogen atom may optionally be joined to form a substituted or unsubstituted heterocycloalkyl or substituted or unsubstituted heteroaryl; R$^{2BA}$ and R$^{2BB}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{8A}$ and R$^{8B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl;

m1A, m2A, m2B, m3, m4, m5, m7, m8, m9, and m10 are independently 1 or 2;

v1A, v2A, v2B, v3, v4, v5, v7, v8, v9, and v10 are independently 1 or 2;

n1A, n2A, n2B, n3, n4, n5, n7, n8, n9, and n10 are independently an integer from 0 to 4;

X, X$^{1A}$, X$^{2A}$, X$^{2B}$, X$^3$, X$^4$, X$^5$, X$^7$, X$^8$, X$^9$, and X' are independently —Cl, —Br, —I, or —F;

L$^6$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

L$^8$ is a bond, —C(O)—, —C(O)NH—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

L⁹ is a bond, —O—, —S—, —NH—, —C(O)—, —C(O)O—, —C(O)NH—, —OC(O)—, —NHC(O)—, —NHC(O)NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein $R^{2A}$ and $R^{2B}$ may optionally be joined to form a substituted or unsubstituted heterocycloalkyl, or substituted or unsubstituted heteroaryl; and $R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl.

Embodiment 7. The compound of embodiment 6, having the formula:

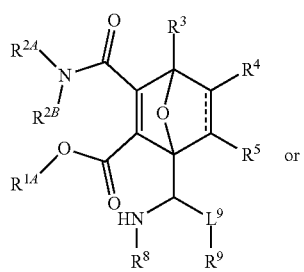
(IIIa)

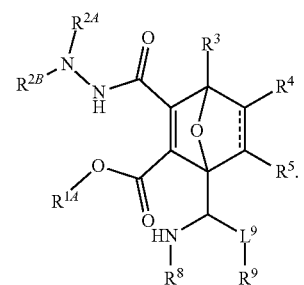
(Va)

Embodiment 8. The compound of one of embodiments 6 to 7, wherein $R^4$ is hydrogen.

Embodiment 9. The compound of one of embodiments 6 to 7, wherein $R^5$ is hydrogen.

Embodiment 10. The compound of one of embodiments 6 to 7, having the formula:

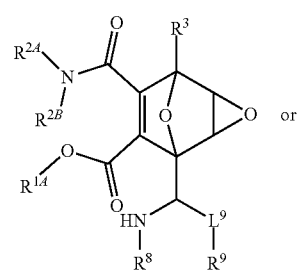
(IIIb)

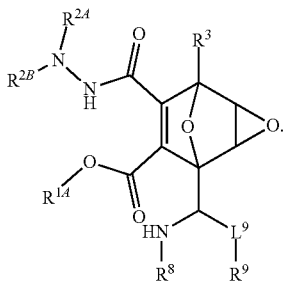
(Vb)

Embodiment 11. The compound of one of embodiments 6 to 10, wherein $R^8$ is substituted or unsubstituted cycloalkyl, substituted or unsubstituted heterocycloalkyl, substituted or unsubstituted aryl, or substituted or unsubstituted heteroaryl.

Embodiment 12. The compound of one of embodiments 6 to 10, wherein $R^8$ is substituted or unsubstituted aryl, or substituted or unsubstituted heteroaryl.

Embodiment 13. The compound of one of embodiments 6 to 10, wherein $R^8$ is substituted or unsubstituted phenyl, or substituted or unsubstituted 5 to 6 membered heteroaryl.

Embodiment 14. The compound of one of embodiments 6 to 10, wherein $R^8$ is substituted or unsubstituted phenyl.

Embodiment 15. The compound of one of embodiments 6 to 7, having the formula:

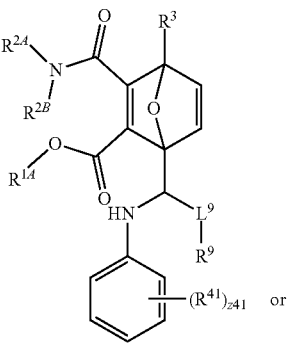
(IIIc)

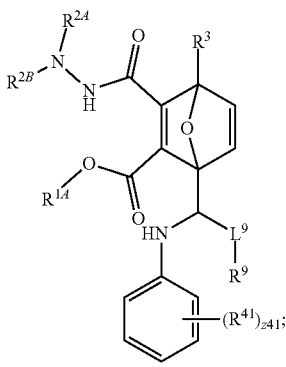
(Vc)

$R^{41}$ is independently halogen, $CX^{41}_3$, —$CHX^{41}_2$, —$CH_2X^{41}$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{41}_3$, —OCHX$^{41}_2$, —OCH$_2$X$^{41}$, —OPh, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{41}$ substituents may optionally be joined to form a substituted or unsubstituted cycloalkyl, substituted or unsubstituted heterocycloalkyl, substituted or unsubstituted aryl, or substituted or unsubstituted heteroaryl;

z41 is an integer from 0 to 5; and $X^{41}$ is independently —Cl, —Br, —I, or —F.

Embodiment 16. The compound of embodiment 15, wherein $R^{41}$ is independently halogen or —OPh.

Embodiment 17. The compound of one of embodiments 15 to 16, wherein z41 is 2.

Embodiment 18. The compound of one of embodiments 15 to 16, wherein z41 is 1.

Embodiment 19. The compound of one of embodiments 15 to 16, wherein z41 is 0.

Embodiment 20. The compound of one of embodiments 6 to 19, wherein $L^9$ is a bond, or substituted or unsubstituted alkylene.

Embodiment 21. The compound of one of embodiments 6 to 19, wherein $L^9$ is a bond or unsubstituted $C_1$-$C_3$ alkylene.

Embodiment 22. The compound of one of embodiments 6 to 19, wherein $L^9$ is an unsubstituted methylene.

Embodiment 23. The compound of one of embodiments 6 to 19, wherein $L^9$ is a bond.

Embodiment 24. The compound of one of embodiments 6 to 23, wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 25. The compound of one of embodiments 6 to 23, wherein $R^9$ is unsubstituted alkyl, unsubstituted heteroalkyl, unsubstituted cycloalkyl, unsubstituted heterocycloalkyl, unsubstituted aryl, or unsubstituted heteroaryl.

Embodiment 26. The compound of one of embodiments 6 to 23, wherein $R^9$ is unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 27. The compound of one of embodiments 6 to 23, wherein $R^9$ is unsubstituted propyl, unsubstituted butyl, unsubstituted pentyl, unsubstituted propenyl, unsubstituted butenyl, unsubstituted pentenyl, unsubstituted propynyl, unsubstituted butynyl, unsubstituted pentynyl, unsubstituted cyclobutyl, unsubstituted cyclopentyl, unsubstituted tetrahydropyranyl, unsubstituted morpholinyl, or unsubstituted phenyl.

Embodiment 28. The compound of one of embodiments 6 to 23, wherein $R^9$ is unsubstituted phenyl.

Embodiment 29. The compound of one of embodiments 6 to 28, wherein $R^{2A}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 30. The compound of one of embodiments 6 to 28, wherein $R^{2A}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_3$-$C_6$ aryl, or substituted or unsubstituted 5 to 10 membered heteroaryl.

Embodiment 31. The compound of one of embodiments 6 to 28, wherein $R^{2A}$ is hydrogen.

Embodiment 32. The compound of one of embodiments 6 to 31, wherein $R^{2B}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 33. The compound of one of embodiments 6 to 31, wherein $R^{2B}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_3$-$C_6$ aryl, or substituted or unsubstituted 5 to 10 membered heteroaryl.

Embodiment 34. The compound of one of embodiments 6 to 31, wherein $R^{2B}$ is hydrogen.

Embodiment 35. The compound of one of embodiments 6 to 28, wherein $R^{2A}$ and $R^{2B}$ are joined to form a substituted or unsubstituted heterocycloalkyl or substituted or unsubstituted heteroaryl.

Embodiment 36. The compound of one of embodiments 6 to 28, wherein $R^{2A}$ and $R^{2B}$ are joined to form a substituted or unsubstituted heterocycloalkyl.

Embodiment 37. The compound of one of embodiments 6 to 28, wherein $R^{2A}$ and $R^{2B}$ are joined to form a substituted or unsubstituted 4 to 6 membered heterocycloalkyl.

Embodiment 38. The compound of one of embodiments 6 to 37, wherein $R^{1A}$ is hydrogen, —$CX^{1A}_3$, —$CHX^{1A}_2$, —$CH_2X^{1A}$, —$OCX^{1A}_3$, —$OCH_2X^{1A}$, —$OCHX^{1A}_2$, —C(O)$R^{1AA}$, —C(O)O$R^{1AA}$, —C(O)NR$^{1AA}$R$^{1AB}$, —OR$^{1AA}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 39. The compound of one of embodiments 6 to 37, wherein $R^{1A}$ is hydrogen, —$CX^{1A}_3$, —$CHX^{1A}_2$, —$CH_2X^{1A}$, or unsubstituted $C_1$-$C_3$ alkyl.

Embodiment 40. The compound of one of embodiments 6 to 37, wherein $R^{1A}$ is unsubstituted $C_1$-$C_3$ alkyl.

Embodiment 41. The compound of one of embodiments 6 to 37, wherein $R^{1A}$ is hydrogen.

Embodiment 42. The compound of one of embodiments 6 to 41, wherein $R^3$ is hydrogen, —$CX^3_3$, —$CHX^3_2$, —$CH_2X^3$, or substituted or unsubstituted alkyl.

Embodiment 43. The compound of one of embodiments 6 to 41, wherein $R^3$ is —$CH_2OH$ or —$CH_3$.

Embodiment 44. The compound of one of embodiments 6 to 41, wherein $R^3$ is hydrogen.

Embodiment 45. A pharmaceutical composition comprising a compound, or a pharmaceutically acceptable salt thereof, of one of embodiments 6 to 44 and a pharmaceutically acceptable excipient.

Embodiment 46. A method of inhibiting an E1 enzyme, said method comprising contacting an E1 enzyme with a compound of one of embodiments 6 to 44, thereby inhibiting said E1 enzyme.

Embodiment 47. The method of embodiment 46, wherein said method comprises allowing said compound to covalently bind said E1 enzyme.

Embodiment 48. The method of embodiment 46 or 47, wherein said method comprises allowing said compound to covalently bind an E1 cysteine amino acid corresponding to Cys30 of Uba2 subunit 2.

Embodiment 49. The method of embodiment 48, wherein said method comprises allowing said E1 cysteine amino acid to bind to carbon $C_2$ attached to $R^{2A}$ and $R^{2B}$ or to ring carbon $C_1$ attached to $R^{1A}$.

Embodiment 50. A method of treating cancer in a subject in need thereof, said method comprising administering to said subject a compound of one of embodiments 6 to 44.

Embodiment 51. The method of embodiment 50, wherein said method comprises allowing said compound to covalently bind an E1 enzyme.

Embodiment 52. The method of embodiment 50 or 51, wherein said method comprises allowing said compound to covalently bind an E1 cysteine amino acid corresponding to Cys30 of Uba2 subunit 2.

Embodiment 53. The method of embodiment 52, wherein said method comprises allowing said E1 cysteine amino acid to bind to carbon $C_2$ attached to $R^{2A}$ and $R^{2B}$ or to carbon $C_1$ attached to $R^{1A}$.

EXAMPLES

A. Example 1. General Synthetic Procedures

The compounds of this invention can be synthesized according to the following Schemes.

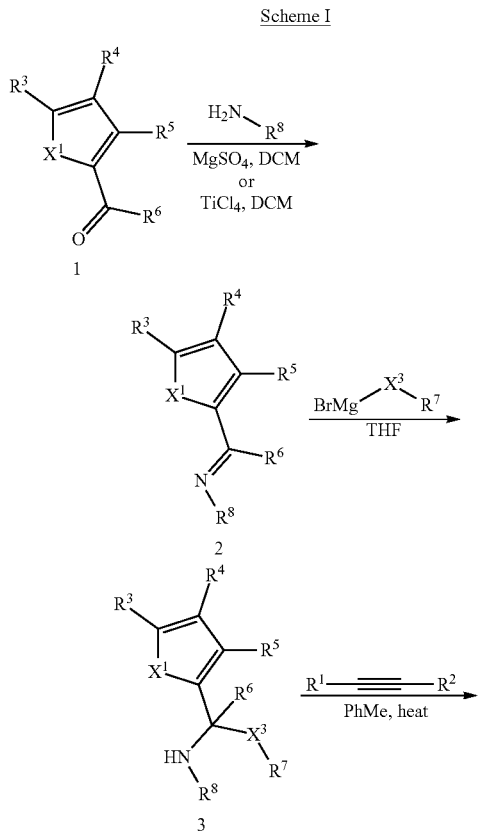

The compounds of Formula I can be synthesized according to Scheme I. In step 1, carbonyl compound 1 can react with an amine to form imine intermediate 2, which will further react with a Grignard reagent to give compound 3. Compound 3 will undergo Diels-Alder reaction with an alkyne dienophile (at least one of $R^1$ or $R^2$ is an electron withdrawing group) to yield compound 4 (Formula I, wherein $X^2$=NH).

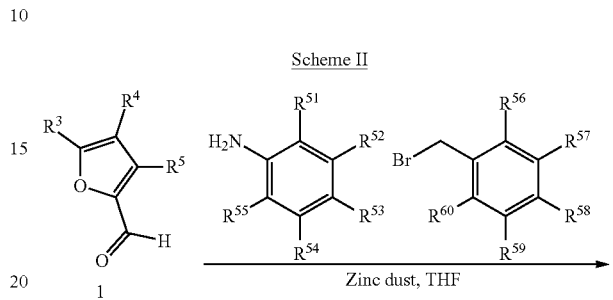

In certain cases, compound 3 can be synthesized directly by mixing 2-furaldehyde 1, aniline and benzyl bromide with Zinc dust in THF as shown in Scheme II, where in $R^{51}$, $R^{52}$, $R^{53}$, $R^{54}$, $R^{55}$, $R^{56}$, $R^{57}$, $R^{58}$, $R^{59}$, $R^{60}$, is independently hydrogen, deuterium, amino, nitro, cyano, hydroxyl, halo, alkyl, haloalkyl, haloalkyl, alkoxy, haloalkoxy, carboxyalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

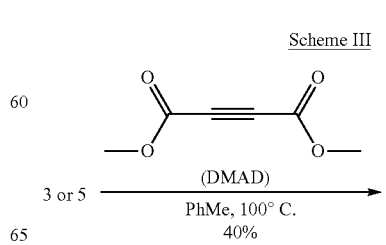

-continued

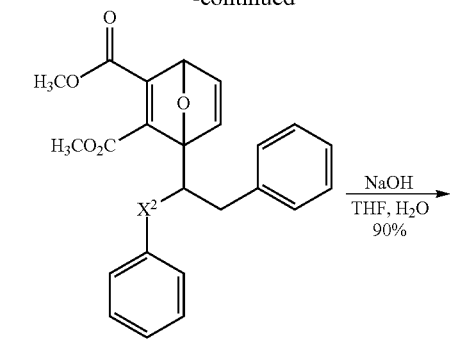

6A (X² = NH)
6B (X² = O)

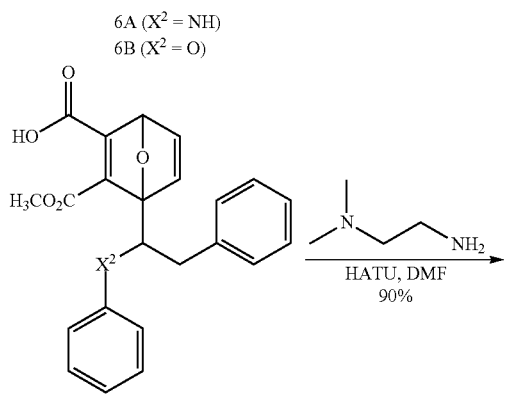

7A (X² = NH)
7B (X² = O)

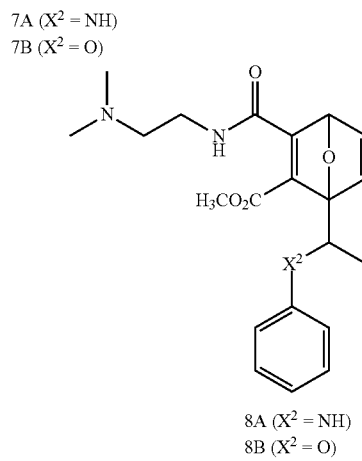

8A (X² = NH)
8B (X² = O)

Example I

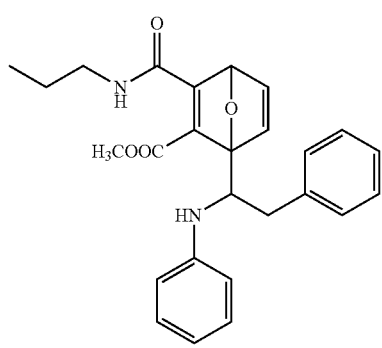

Step A (Scheme I)

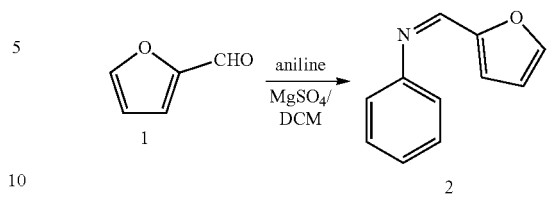

A mixture of aniline (50 g, 536 mmol), compound 1 (furfural, 47 g, 488 mmol) and MgSO₄ (118 g, 976 mmol) in anhydrous DCM (800 mL) was stirred at 45° C. for 18 hours. The mixture was filtered and the filtrate was concentrated, the residue was purified by silica gel column (Petroleum ether/EtOAc=50:1) to give compound 2 (50 g, 292 mmol, 60% yield) as a yellow oil. $^1$H NMR (CDCl₃): δ 8.37 (s, 1H), 7.66 (s, 1H), 7.45-7.41 (m, 2H), 7.30-7.26 (m, 3H), 7.01-7.00 (m, 1H), 6.61-6.60 (m, 1H).

Step B (Scheme I)

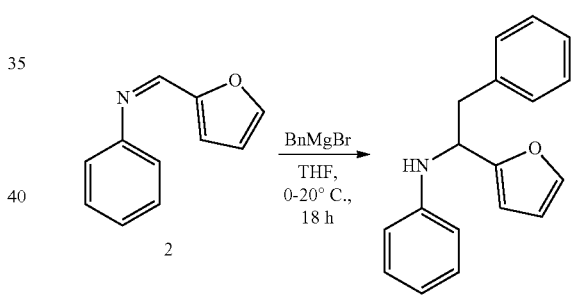

To a solution of compound 2 (100 g, 585 mmol) in THF (1 L) was added benzylmagnesium bromide (1 M, 1.05 L, 1.05 mol) dropwise with stirring at 0° C. Then the mixture was stirred at 20° C. for 18 hours. The reaction mixture was quenched by saturated NH₄Cl aqueous solution (1 L) and extracted with EtOAc (300 mL×3), the organic layer was washed with brine (300 mL×2), dried over Na₂SO₄ and concentrated. The crude product was purified by silica gel chromatography eluted with petroleum ether/ethyl acetate=30:1 to give compound 3 (20 g, 9.8% yield, 75% purity) as yellow oil. $^1$H NMR: (CDCl₃) δ 7.38 (s, 1H), 7.26-7.23 (m, 3H), 7.16-7.12 (m, 2H), 7.07-7.05 (m, 2H), 6.71-6.70 (m, 1H), 6.61-6.59 (m, 2H), 6.27-6.26 (m, 1H), 6.05-6.04 (m, 1H), 4.76 (t, J=6.4 Hz, 1H), 3.96 (s, H), 3.22-3.19 (m, 2H).

Step C (Scheme III)

Compound 3 (4.8 g, 18.25 mmol) in 100 mL anhydrous toluene was heated to 110° C., then dimethyl acetylenedicarboxylate (5.18 g, 36.5 mmol) was added and the mixture was refluxed overnight. TLC (hexanes/EtOAc=3:1) and LC-MS of a small pre-TLC indicated the formation of two adjacent spots with the same molecular weight. The solvents were evaporated in vacuo, and the crude product was sequentially recrystallized from methanol to give two portions: T and B. T. Bright yellow solid (2.75 g), less polar; LC/MS (M+1) 406.1; ¹H NMR (d6-DMSO): δ 7.05-7.30 (m, 6H), 6.90 (m, 3H), 6.40 (m, 3H), 5.80 (d, 1H), 5.55 (m, 1H), 4.50 (m, 1H), 3.67 (s, 3H), 3.20 (s, 3H), 2.85 (m, 1H), 2.75 (m, 1H). B. Pale yellow solid (2.16 g), more polar; LC/MS (M+1) 406.1; ¹H NMR (d6-DMSO): δ 7.25 (m, 1H), 7.21-7.12 (m, 5H), 7.10-7.05 (m, 1H), 6.97-6.90 (m, 2H), 6.50-6.42 (m, 2H), 6.40 (m, 1H), 5.80 (d, 1H), 5.68 (s, 1H), 4.50 (m, 1H), 3.65 (s, 3H), 3.55 (s, 3H), 2.85 (m, 1H), 2.75 (m, 1H).

Step D (Scheme III)

Compound 6A portion T (910 mg, 2.25 mmol) was dissolved in 22.5 mL THF and the mixture was cooled to 0° C., then 11.25 mL 0.2 M sodium hydroxide was added and the mixture was stirred at 0° C. for 1 hour. Then another portion of NaOH solution was added (11.25 mL, 0.2 M). After another hour, 20% HCl was added dropwise to neutralize the reaction mixture. The organic solvents were then evaporated in vacuo, and the remaining aqueous layer were acidified to pH 3 with 20% HCl then extracted with CHCl₃. The organic layer was dried over anhydrous MgSO₄ and then concentrated to give a crude oil. The crude product was purified by silica gel chromatography eluted with methanol/ethyl acetate=1:9 to give compound 7A (810 mg) as yellow solid. LC/MS (M+1): 392.1; (M−1): 390.1. ¹H NMR (d6-DMSO): δ 7.25 (m, 2H), 7.15 (m, 2H), 7.10 (m, 1H), 6.90 (m, 2H), 6.82 (m, 1H), 6.43 (m, 2H), 6.39 (m, 1H), 5.60 (m, 1H), 5.40 (m, 1H), 4.50 (m, 1H), 3.20 (s, 3H), 2.87 (m, 1H), 2.74 (m, 1H).

Compound 7A (190 mg, 0.486 mmol), EDCI (113 mg, 0.73 mmol) and HOBt (112 mg, 0.73 mmol) were mixed in 5 mL of anhydrous DMF at 0° C. in a ice water bath. Propylamine (28.6 mg, 0.485 mmol) was added to the cold mixture and stirred at 0° C. for 3 hours. The reaction was then allowed to warm up to ambient temperature and stirred overnight. Next morning, the reaction mixture was extracted between ethyl acetate and brine. The organic layer was dried over anhydrous MgSO$_4$ and then concentrated to give a crude oil. The crude product was purified by silica gel chromatography eluted with hexanes/ethyl acetate=(4:1 to 2:1) to give compound 150 (110 mg) as yellow gum. LC/MS (M+1): 433.1; (M−1): 431.1. $^1$H NMR (d6-DMSO): δ 8.08 (t, 1H), 7.26 (m, 2H), 7.18-7.13 (m, 3H), 7.11-7.07 (m, 1H), 6.90 (t, 2H), 6.75 (d, 1H), 6.47 (d, 2H), 6.41 (t, 1H), 5.68 (d, 1H), 5.42 (d, 1H), 4.70 (m, 1H), 3.31 (s, 3H), 2.06 (m, 2H), 2.88 (m, 1H), 2.76 (m, 1H), 1.40 (m, 2H), 0.81 (m, 3H).

Example II

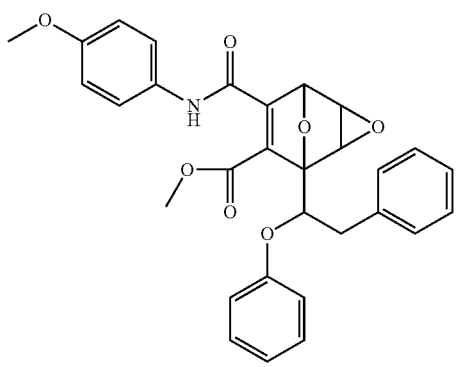 [SMILES: COC(=O)C1=C(C(=O)Nc2ccc(OC)cc2)C2OC1(C(Cc1ccccc1)Oc1ccccc1)C1OC21]

Step A:

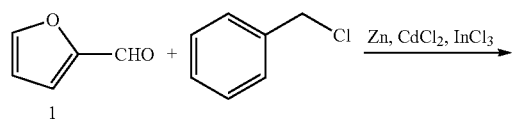

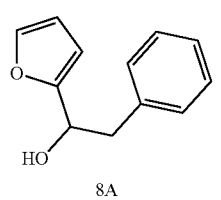

A mixture of 2-Furaldehyde 1 (19.2 g, 200 mmol), benzyl chloride (37.8 g, 300 mmol), zinc dust (19.5 g, 300 mmol), cadmium chloride (36.6 g, 200 mmol), indium chloride (2.2 g, 10 mmol) in distilled water (500 mL) was stirred at room temperature overnight. The mixture was filtered and the filtrate was concentrated, the residue was purified by silica gel column (Hexanes/EtOAc=8:1) to give compound 8A (15 g, 80 mmol, 40% yield) as a yellow oil.

Step B:

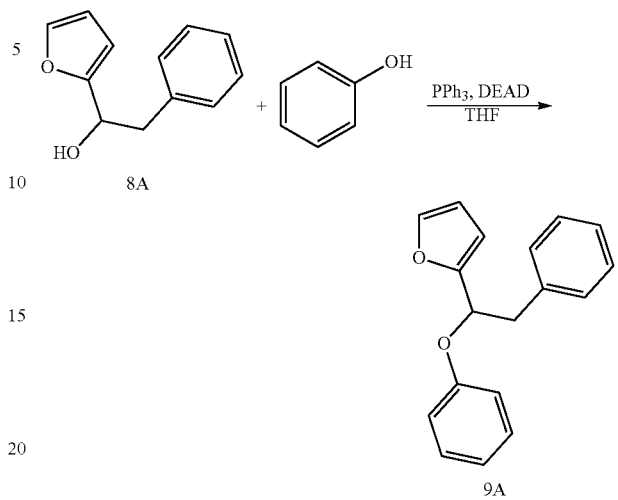

A solution of compound 8A (15 g, 80 mmol), phenol (7.5 g, 80 mmol), triphenylphosphine (23 g, 88 mmol) in anhydrous THF (300 mL) was cooled 0° C., then diethyl azodicarboxylate (16.7 g, 96 mmol) was added slowly to the mixture. The reaction mixture was stirred at room temperature overnight and then concentrated. The product was purified by silica gel chromatography eluted with hexanes/ethyl acetate=9:1 to 6:1 give compound 9A (15.5 g, 73% yield) as yellow oil.

Step C:

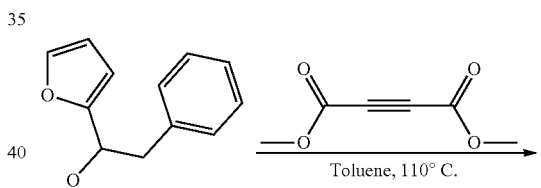

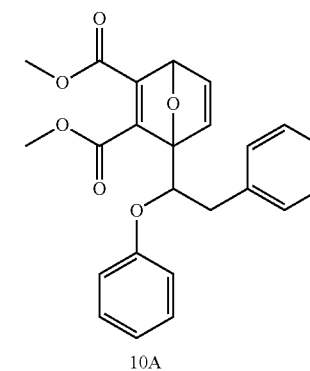

Compound 9A (15 g, 56.8 mmol) in 100 mL anhydrous toluene was heated to 110° C., then dimethyl acetylenedicarboxylate (12 g, 85.2 mmol) was added and the mixture was refluxed overnight. The solvents were evaporated in vacuo, and the crude product was purified by silica gel chromatography eluted with hexanes/ethyl acetate=5:1 to given a yellow oil, which was sequentially recrystallized from methanol to give 10A as a white solid (4.3 g, 19% yield). $^1$H NMR (d6-DMSO): δ 7.4-6.6 (m, 12H), 5.7 (m, 1H), 5.4 (m, 1H), 3.7 (s, 3H), 3.55 (s, 3H), 3.1 (m, 2H).

Step D:

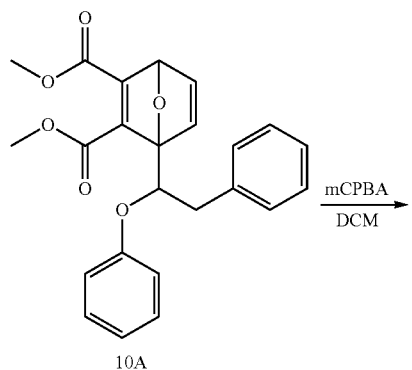

10A

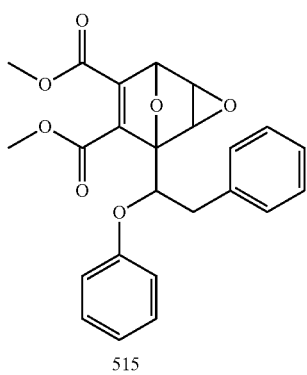

515

Compound 10A (4.3 g, 10.6 mmol) was dissolved in 100 mL anhydrous dichloromethane and the mixture was cooled to 0° C., then meta-Chloroperoxybenzoic acid (3.1 g) was added and the mixture was then stirred at room temperature overnight. The organic solvents were then evaporated in vacuo, and the remaining mixture was dissolved in ethyl acetate (50 mL) and then washed with saturated sodium bicarbonate (5×50 mL). The organic layer was dried over anhydrous MgSO$_4$ and then concentrated to give a crude oil. The crude product was purified by silica gel chromatography eluted with hexanes/ethyl acetate/triethylamine=5:1:0.01 to give compound 515 (1.9 g, 42% yield) as white solid. $^1$H NMR (CDCl$_3$): δ 7.4-6.7 (m, 10H), 5.3 (m, 1H), 5.2 (m, 1H), 3.80 (s, 3H), 3.75 (m, 1H), 3.65 (m, 1H), 3.55 (s, 3H), 3.2 (m, 2H).

Step E:

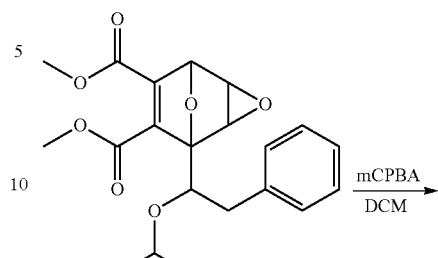

515

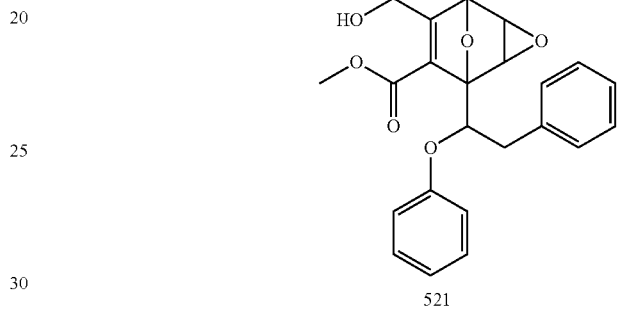

521

Compound 515 (1.9 g, 4.5 mmol) was dissolved in THF (50 mL) and cooled to 0° C., then NaOH (198 mg, 4.95 mmol) in distilled water (50 mL) was added. The reaction was then allowed to warm up to ambient temperature and stirred for 1 hour. The mixture was neutralized with 1 M HCl, and the THF was evaporated. The remaining aqueous layer was acidified to pH 4, then extracted with ethyl acetate (50 mL). The organic layer was washed with brine (50 mL), then dried over anhydrous MgSO$_4$ and then concentrated to give a crude oil. The crude product was purified by silica gel chromatography eluted with ethyl acetate/methanol/acetic acid=9:1:0.5 to give compound 521 (1.5 g, 82%) as orange solid. LC/MS (M−1): 407.2.

Step E:

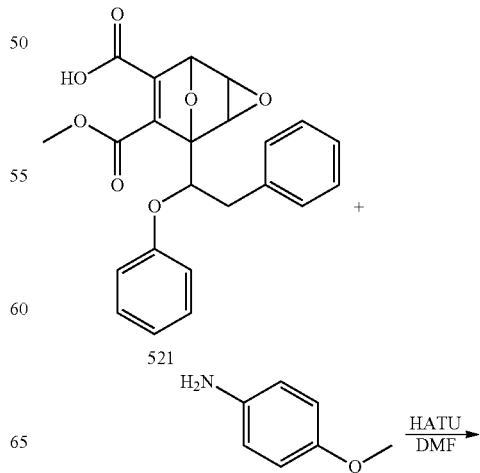

-continued

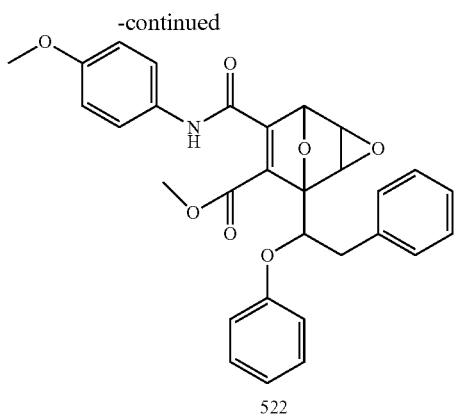

522

Compound 521 (23 mg, 0.056 mmol), HATU (28 mg, 0.073 mmol) and p-anisidine (8 mg, 0.062 mmol) were mixed at 0° C. in DMF (2 mL), then the mixture was stirred at room temperature for 1 hour. The mixture was extracted between ethyl acetate (20 mL) and brine (20 mL), the organic layer was dried over MgSO$_4$ and was then concentrated, the residue was purified by silica gel column (Hexanes/EtOAc=3:1) to give compound 8A (17 mg, 59% yield) as a yellow solid. LC/MS (M+1): 515.1. $^1$H NMR (d6-DMSO): δ 10.3 (s, 1H), 7.6-6.5 (m, 14H), 5.5 (m, 1H), 5.4 (s, 1H), 4.1 (m, 1H), 3.9 (m, 1H), 3.5 (s, 3H), 3.2 (s, 3H), 3.2-3.0 (m, 2H).

When incubating such compounds with the activating enzymes (E1) of ubiquitin, SUMO, Nedd8, Urm1, ISG15 or Atg7, it forms covalent adducts with the specific Cys residue (e.g., an E1 cysteine amino acid corresponding to Cys30 of Uba2 subunit 2, or an amino acid corresponding to the Cys residue highlighted and in bold in SEQ ID NO:2, SEQ ID NO:3, SEQ ID NO:4, SEQ ID NO:5, SEQ ID NO:6, or SEQ ID NO:7) as depicted herein.

For the compounds provided herein including embodiments thereof, a covalent adduct may be formed with a cysteine amino acid corresponding to a Cys residue highlighted and in bold from Uba1, Uba2, Uba3, Uba4, Uba7 or Atg7 as shown in the sequence alignment below.

```
Uba1 (ubiquitin)    LVGAGAICELLK   (SEQ ID NO: 2)
Uba2 (SUMO)         VVGAGGICELLK   (SEQ ID NO: 3)
Uba3 (Nedd8)        VIGAGGLCELLK   (SEQ ID NO: 4)
Uba4 (Urm1)         IVGCGGLCPLAQ   (SEQ ID NO: 5)
Uba7 (ISG15)        LVGAGAICELLK   (SEQ ID NO: 6)
Atg7 (Atg8, Atg12)  LLGAGTLCNVAR   (SEQ ID NO: 7)
```

B. Example 2. Compounds

TABLE I

| compounds synthesized and biological activities. | | | | | |
|---|---|---|---|---|---|
| Compound number Structure | SUMO | Nedd8 | Atg7 | Ubiquitin | c-Myc |
| 150 | ++ | | | | |
| 151 | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 152 | 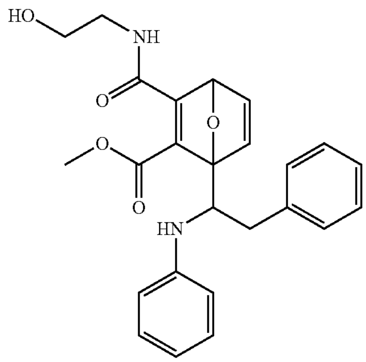 [SMILES: COC(=O)C1=C(C(=O)NCCO)C2C=CC1(C(Cc1ccccc1)Nc1ccccc1)O2] | | ++ | | | |
| 153 | 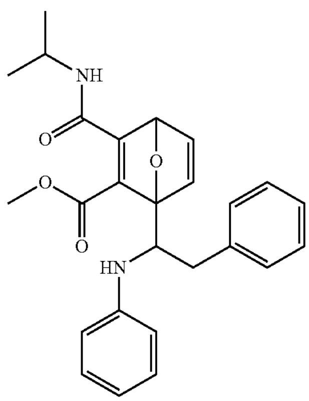 [SMILES: COC(=O)C1=C(C(=O)NC(C)C)C2C=CC1(C(Cc1ccccc1)Nc1ccccc1)O2] | | ++ | | | |
| 154 | 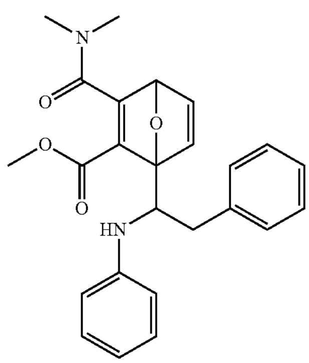 [SMILES: COC(=O)C1=C(C(=O)N(C)C)C2C=CC1(C(Cc1ccccc1)Nc1ccccc1)O2] | | + | | | |
| 155 | 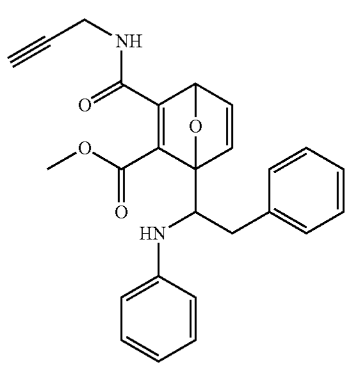 [SMILES: C#CCNC(=O)C1=C(C(=O)OC)C2(C(Cc3ccccc3)Nc3ccccc3)C=CC1O2] | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 156 | 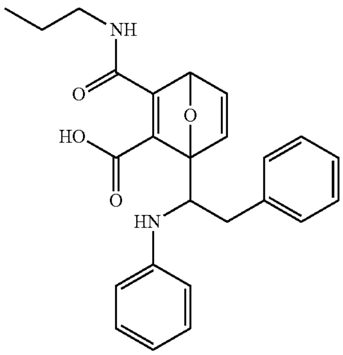 [SMILES: CCCNC(=O)C1=C(C(=O)O)C2(C(Cc3ccccc3)Nc3ccccc3)C=CC1O2] | | | | | |
| 157 | 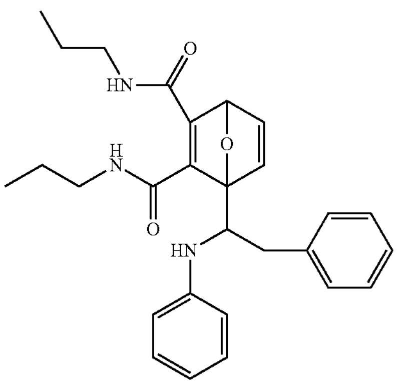 [SMILES: CCCNC(=O)C1=C(C(=O)NCCC)C2(C(Cc3ccccc3)Nc3ccccc3)C=CC1O2] | | + | | | |
| 159 | 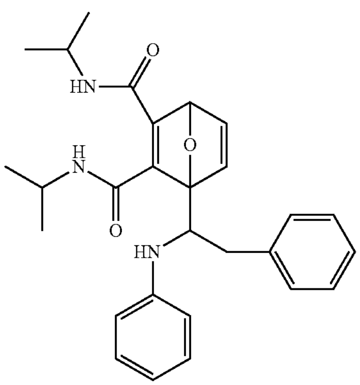 [SMILES: CC(C)NC(=O)C1=C(C(=O)NC(C)C)C2(C(Cc3ccccc3)Nc3ccccc3)C=CC1O2] | | + | | | |
| 160 | 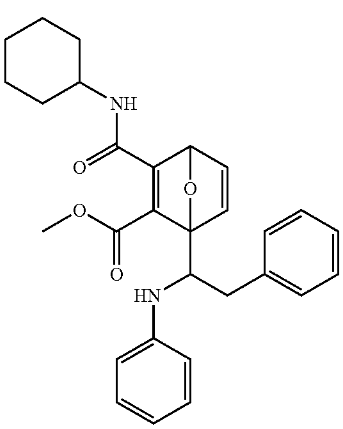 [SMILES: COC(=O)C1=C(C(=O)NC2CCCCC2)C2C=CC1(C(Cc1ccccc1)Nc1ccccc1)O2] | | + | | + | |

TABLE I-continued compounds synthesized and biological activities.

| Compound number | Structure | SUMO | Nedd8 | Atg7 | Ubiquitin | c-Myc |
|---|---|---|---|---|---|---|
| 161 | 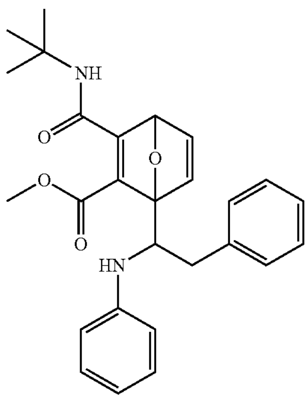 [SMILES: COC(=O)C1=C(C(=O)NC(C)(C)C)C2C=CC1(C(Cc1ccccc1)Nc1ccccc1)O2] | | + | | | + |
| 163 | 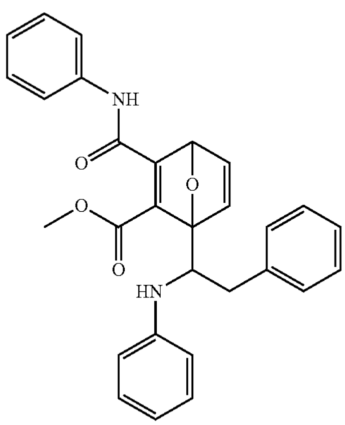 [SMILES: COC(=O)C1=C(C(=O)Nc2ccccc2)C2C=CC1(C(Cc1ccccc1)Nc1ccccc1)O2] | | ++ | | | + |
| 164 | 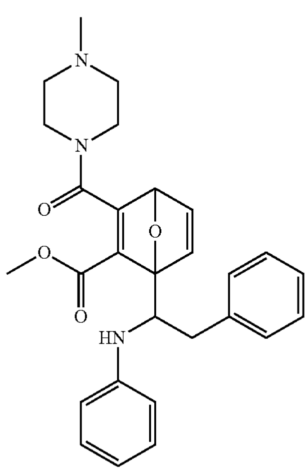 [SMILES: COC(=O)C1=C(C(=O)N2CCN(C)CC2)C2C=CC1(C(Cc1ccccc1)Nc1ccccc1)O2] | | + | | | |

TABLE I-continued compounds synthesized and biological activities.

| Compound number | Structure | SUMO | Nedd8 | Atg7 | Ubiquitin | c-Myc |
|---|---|---|---|---|---|---|
| 165 | 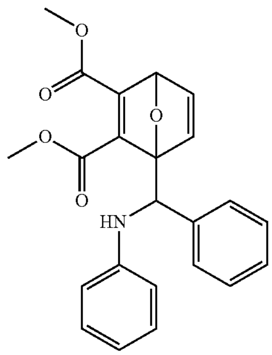 [SMILES: COC(=O)C1=C(C(=O)OC)C2(C(Nc3ccccc3)c3ccccc3)C=CC1O2] | ++ | | | | + |
| 166 | 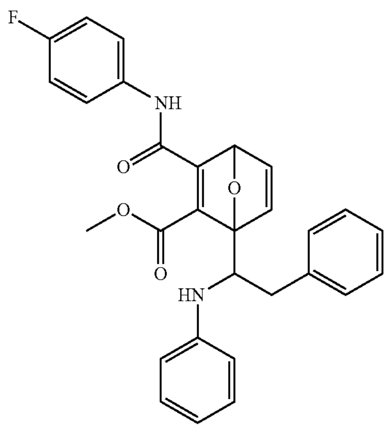 [SMILES: COC(=O)C1=C(C(=O)Nc2ccc(F)cc2)C2C=CC1(C(Cc1ccccc1)Nc1ccccc1)O2] | ++ | | | | + |
| 167 | 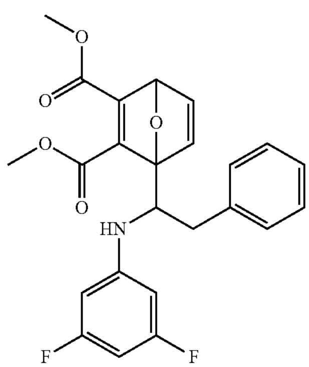 [SMILES: COC(=O)C1=C(C(=O)OC)C2(C(Cc3ccccc3)Nc3cc(F)cc(F)c3)C=CC1O2] | ++ | | | | + |
| 169 | 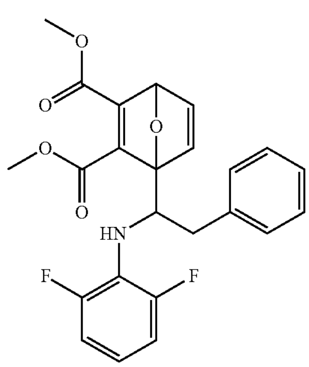 [SMILES: COC(=O)C1=C(C(=O)OC)C2(C(Cc3ccccc3)Nc3c(F)cccc3F)C=CC1O2] | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 171 | 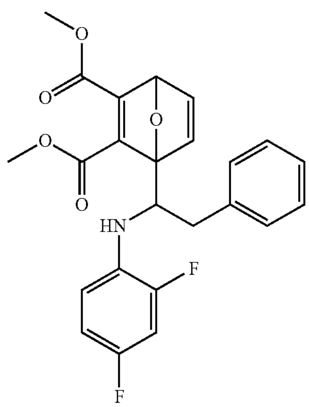 [SMILES: COC(=O)C1=C(C(=O)OC)C2(C(Cc3ccccc3)Nc3ccc(F)cc3F)C=CC1O2] | | ++ | | | ++ |
| 172 | 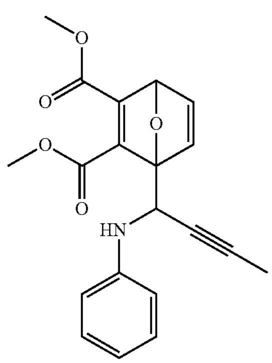 [SMILES: CC#CC(Nc1ccccc1)C12C=CC(O1)C(C(=O)OC)=C2C(=O)OC] | | ++ | | | ++ |
| 174 | 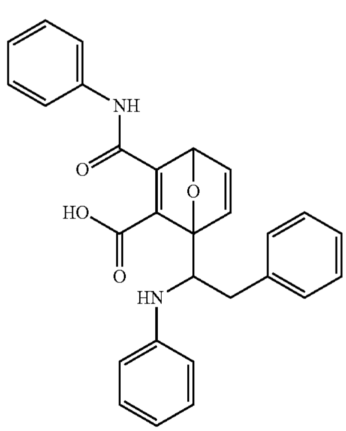 [SMILES: O=C(O)C1=C(C(=O)Nc2ccccc2)C2C=CC1(C(Cc1ccccc1)Nc1ccccc1)O2] | | | + | | |

TABLE I-continued compounds synthesized and biological activities.

| Compound number | Structure | SUMO | Nedd8 | Atg7 | Ubiquitin | c-Myc |
|---|---|---|---|---|---|---|
| 175 | 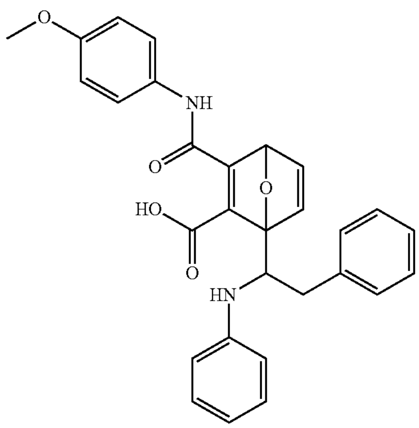 [SMILES: COc1ccc(NC(=O)C2=C(C(=O)O)C3(C(Cc4ccccc4)Nc4ccccc4)C=CC2O3)cc1] | | | + | | |
| 176 | 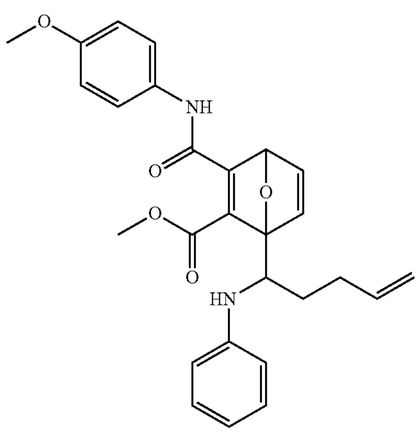 [SMILES: C=CCCC(Nc1ccccc1)C12C=CC(O1)C(C(=O)Nc1ccc(OC)cc1)=C2C(=O)OC] | | ++ | | | + |
| 177 | 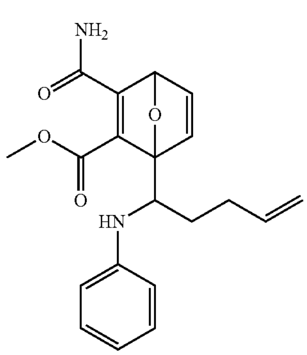 [SMILES: C=CCCC(Nc1ccccc1)C12C=CC(O1)C(C(N)=O)=C2C(=O)OC] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 178 | 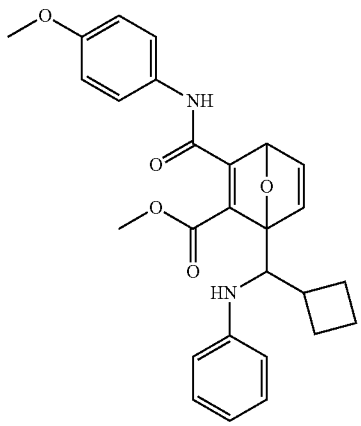 [SMILES: COC(=O)C1=C(C(=O)Nc2ccc(OC)cc2)C2C=CC1(C(Nc1ccccc1)C1CCC1)O2] | ++ | | | | + |
| 179 | 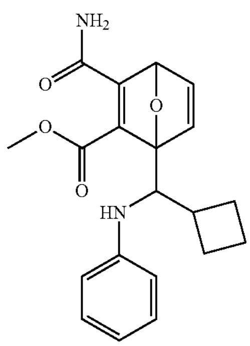 [SMILES: COC(=O)C1=C(C(N)=O)C2C=CC1(C(Nc1ccccc1)C1CCC1)O2] | + | | | | + |
| 180 | 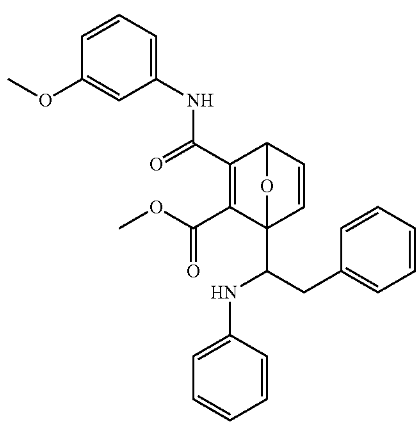 [SMILES: COC(=O)C1=C(C(=O)Nc2cccc(OC)c2)C2C=CC1(C(Cc1ccccc1)Nc1ccccc1)O2] | + | | | | + |
| 181 | 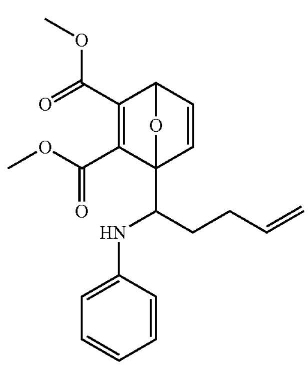 [SMILES: C=CCCC(Nc1ccccc1)C12C=CC(O1)C(C(=O)OC)=C2C(=O)OC] | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 184 | 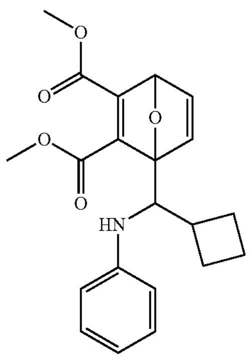 [SMILES: COC(=O)C1=C(C(=O)OC)C2(C(Nc3ccccc3)C3CCC3)C=CC1O2] | | ++ | | | + |
| 186 | 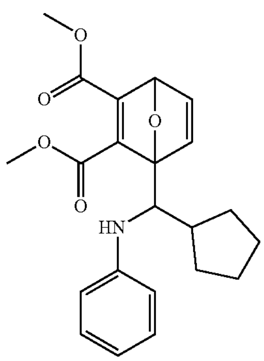 [SMILES: COC(=O)C1=C(C(=O)OC)C2(C(Nc3ccccc3)C3CCCC3)C=CC1O2] | | ++ | | | + |
| 188 | 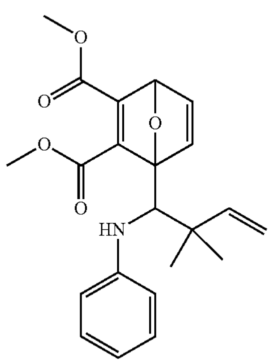 [SMILES: C=CC(C)(C)C(Nc1ccccc1)C12C=CC(O1)C(C(=O)OC)=C2C(=O)OC] | | ++ | | | |
| 191 | 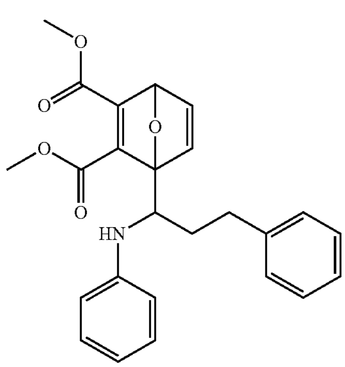 [SMILES: COC(=O)C1=C(C(=O)OC)C2(C(CCc3ccccc3)Nc3ccccc3)C=CC1O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 192 | 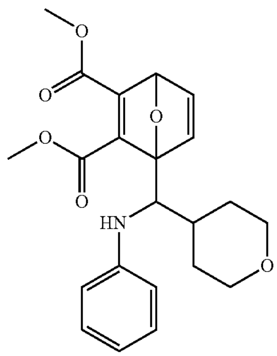 [SMILES: COC(=O)C1=C(C(=O)OC)C2(C(Nc3ccccc3)C3CCOCC3)C=CC1O2] | | | ++ | | |
| 193 | 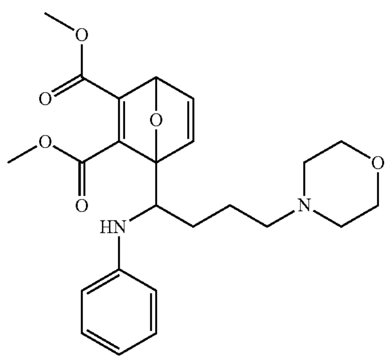 [SMILES: COC(=O)C1=C(C(=O)OC)C2(C(CCCN3CCOCC3)Nc3ccccc3)C=CC1O2] | | | + | | |
| 194 | 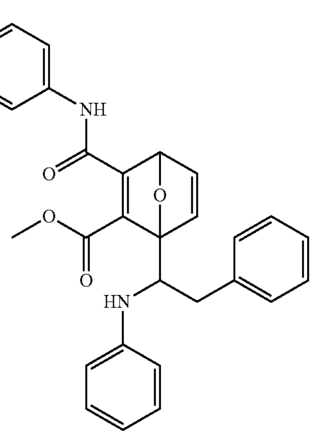 | | | ++ | | |

TABLE I-continued compounds synthesized and biological activities.

| Compound number | Structure | SUMO | Nedd8 | Atg7 | Ubiquitin | c-Myc |
|---|---|---|---|---|---|---|
| 195 | 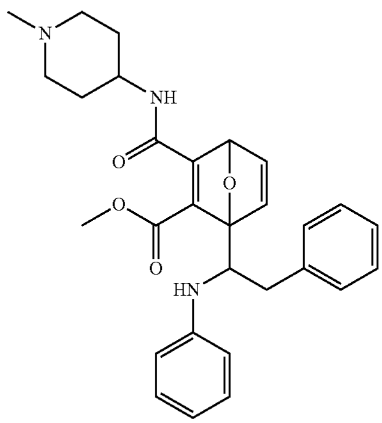 [SMILES: COC(=O)C1=C(C(=O)NC2CCN(C)CC2)C2C=CC1(C(Cc1ccccc1)Nc1ccccc1)O2] | | +++ | | | ++ |
| 196 | 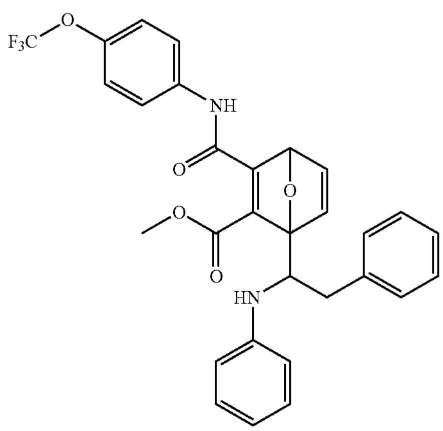 [SMILES: COC(=O)C1=C(C(=O)Nc2ccc(OC(F)(F)F)cc2)C2C=CC1(C(Cc1ccccc1)Nc1ccccc1)O2] | | + | | | |
| 197 | 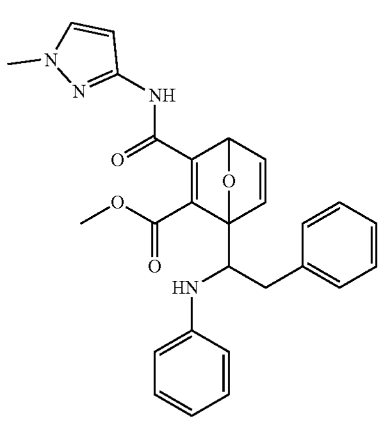 [SMILES: COC(=O)C1=C(C(=O)Nc2ccn(C)n2)C2C=CC1(C(Cc1ccccc1)Nc1ccccc1)O2] | | ++ | | | |

TABLE I-continued
compounds synthesized and biological activities.
| Compound number | Structure | SUMO | Nedd8 | Atg7 | Ubiquitin | c-Myc |
|---|---|---|---|---|---|---|
| 198 | 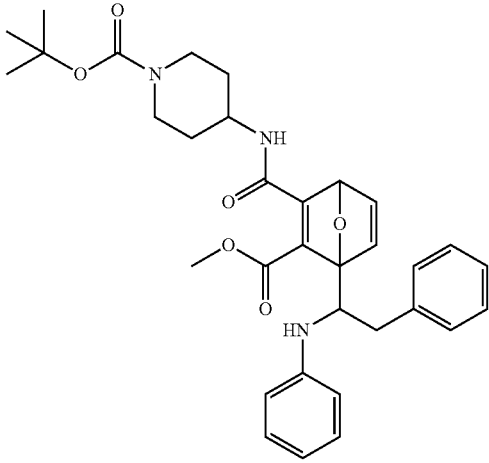 [SMILES: COC(=O)C1=C(C(=O)NC2CCN(C(=O)OC(C)(C)C)CC2)C2C=CC1(C(Cc1ccccc1)Nc1ccccc1)O2] | | + | | | |
| 199 | 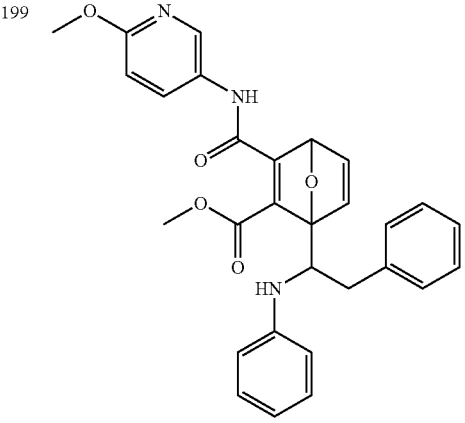 | | ++ | | | |
| 200 | 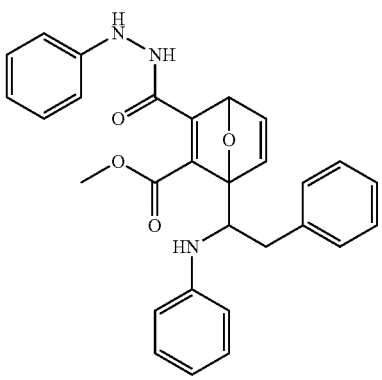 | | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 201 | 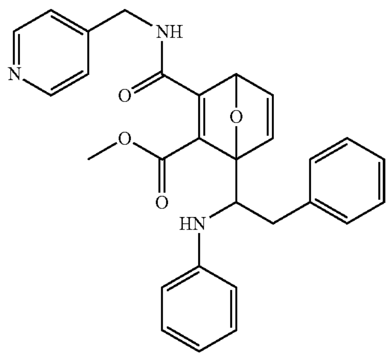 [SMILES: COC(=O)C1=C(C(=O)NCc2ccncc2)C2C=CC1(C(Cc1ccccc1)Nc1ccccc1)O2] | ++ | | | | + |
| 202 | 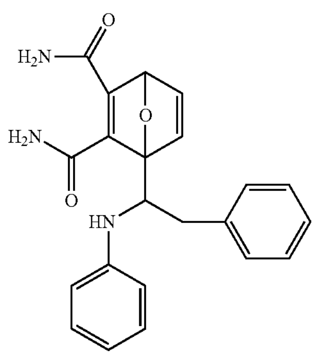 [SMILES: NC(=O)C1=C(C(N)=O)C2(C(Cc3ccccc3)Nc3ccccc3)C=CC1O2] | + | | | | |
| 203 | 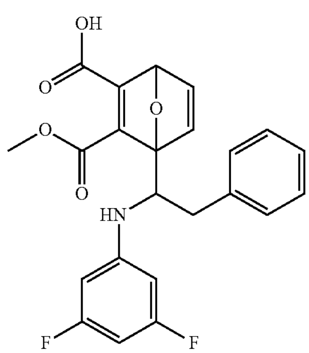 [SMILES: COC(=O)C1=C(C(=O)O)C2C=CC1(C(Cc1ccccc1)Nc1cc(F)cc(F)c1)O2] | ++ | | | | |
| 204 | 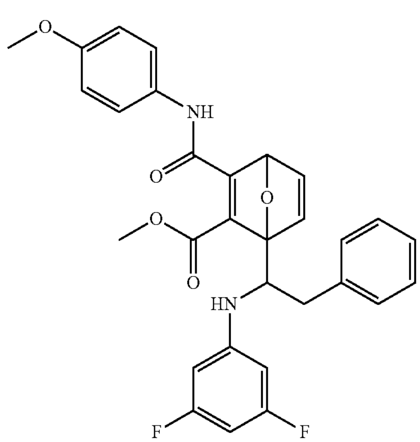 [SMILES: COC(=O)C1=C(C(=O)Nc2ccc(OC)cc2)C2C=CC1(C(Cc1ccccc1)Nc1cc(F)cc(F)c1)O2] | +++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 205 | 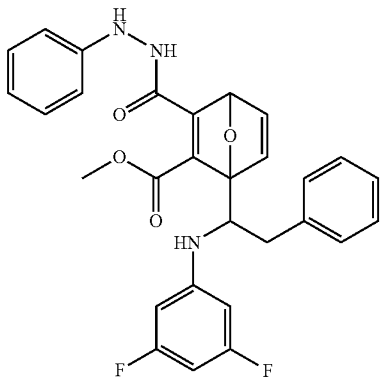 [SMILES: COC(=O)C1=C(C(=O)NNc2ccccc2)C2C=CC1(C(Cc1ccccc1)Nc1cc(F)cc(F)c1)O2] | ++ | | | | ++ |
| 206 | 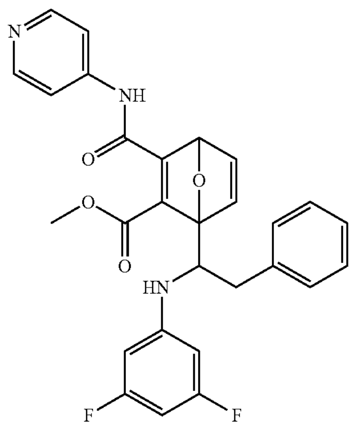 [SMILES: COC(=O)C1=C(C(=O)Nc2ccncc2)C2C=CC1(C(Cc1ccccc1)Nc1cc(F)cc(F)c1)O2] | | + | | | |
| 207 | 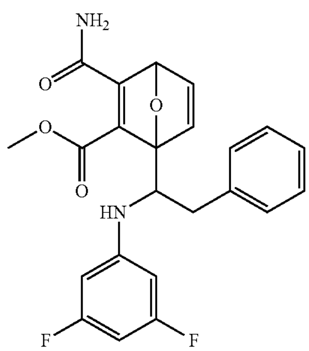 | | + | | | |
| 208 | 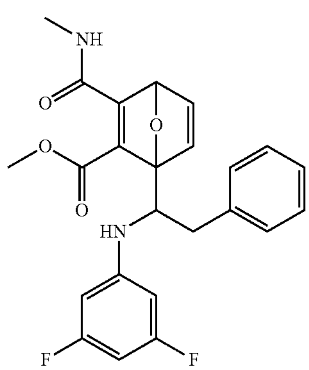 | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 209 | 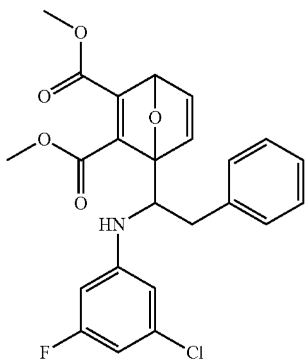 | | ++ | | | + |
| 210 | 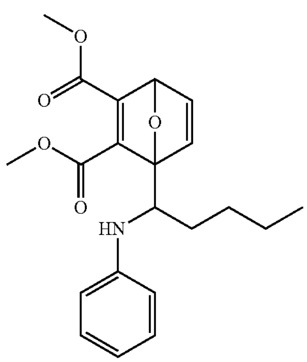 [SMILES: CCCCC(Nc1ccccc1)C12C=CC(O1)C(C(=O)OC)=C2C(=O)OC] | | +++ | | | |
| 212 | 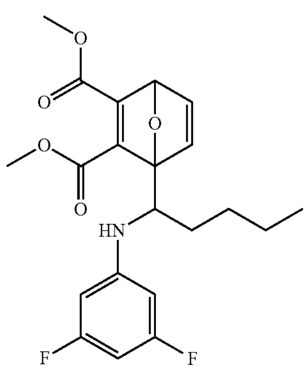 [SMILES: CCCCC(Nc1cc(F)cc(F)c1)C12C=CC(O1)C(C(=O)OC)=C2C(=O)OC] | | +++ | | | + |
| 214 | 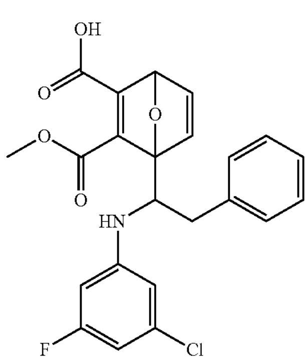 [SMILES: COC(=O)C1=C(C(=O)O)C2C=CC1(C(Cc1ccccc1)Nc1cc(F)cc(Cl)c1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 215 | 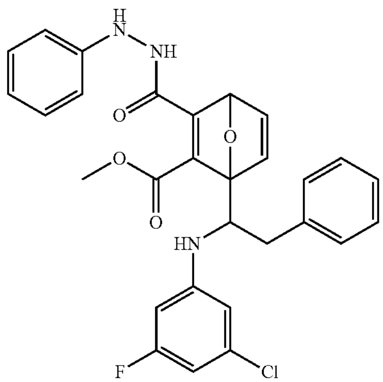 | | ++ | | | + |
| 216 | 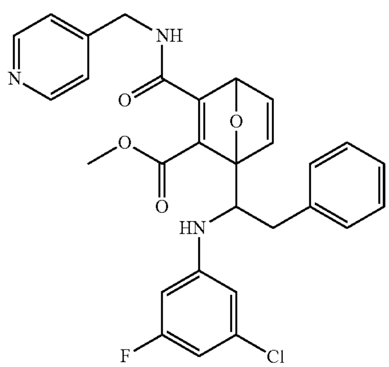 [SMILES: COC(=O)C1=C(C(=O)NCc2ccncc2)C2C=CC1(C(Cc1ccccc1)Nc1cc(F)cc(Cl)c1)O2] | | ++ | | | ++ |
| 217 | 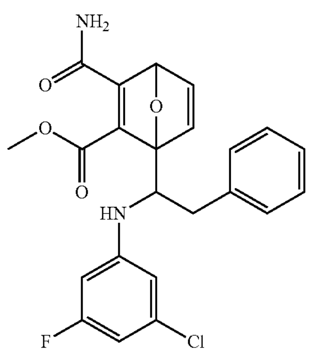 [SMILES: COC(=O)C1=C(C(N)=O)C2C=CC1(C(Cc1ccccc1)Nc1cc(F)cc(Cl)c1)O2] | | + | | | ++ |
| 218 | 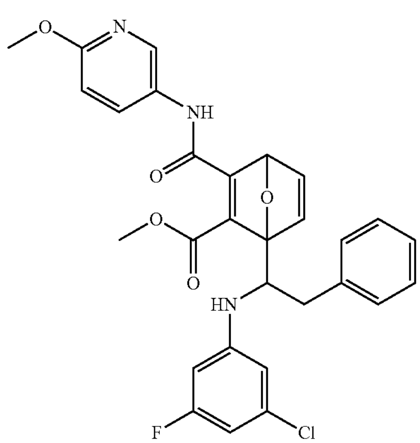 [SMILES: COC(=O)C1=C(C(=O)Nc2ccc(OC)nc2)C2C=CC1(C(Cc1ccccc1)Nc1cc(F)cc(Cl)c1)O2] | | +++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 219 | 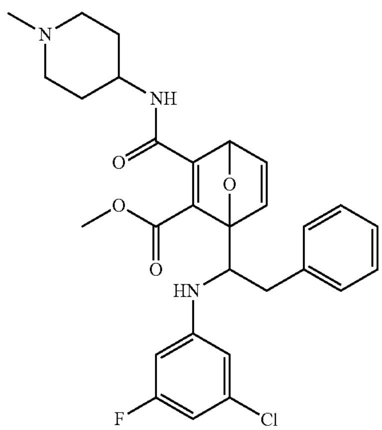 [SMILES: COC(=O)C1=C(C(=O)NC2CCN(C)CC2)C2C=CC1(C(Cc1ccccc1)Nc1cc(F)cc(Cl)c1)O2] | | ++ | | | ++ |
| 220 | 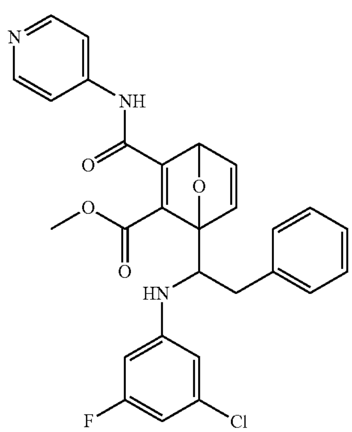 [SMILES: COC(=O)C1=C(C(=O)Nc2ccncc2)C2C=CC1(C(Cc1ccccc1)Nc1cc(F)cc(Cl)c1)O2] | | ++ | | | + |
| 221 | 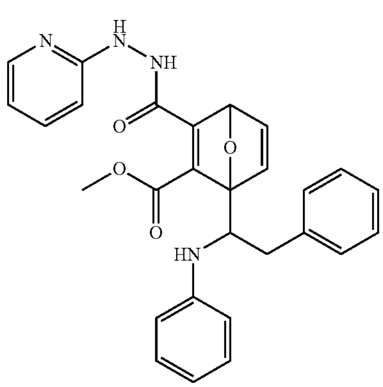 [SMILES: COC(=O)C1=C(C(=O)NNc2ccccn2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 222 | 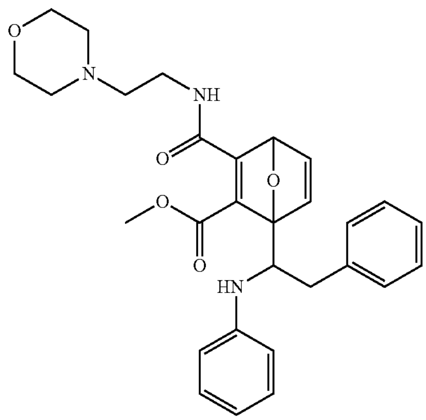 [SMILES: COC(=O)C1=C(C(=O)NCCN2CCOCC2)C2C=CC1(C(Cc1ccccc1)Nc1ccccc1)O2] | +++ | | | | |
| 223 | 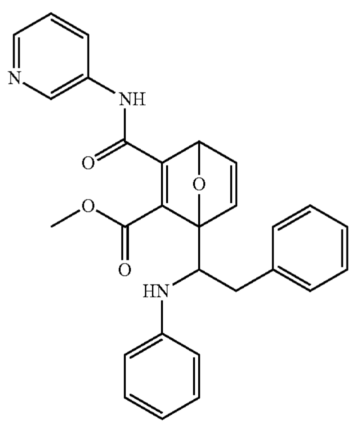 [SMILES: COC(=O)C1=C(C(=O)Nc2cccnc2)C2C=CC1(C(Cc1ccccc1)Nc1ccccc1)O2] | ++ | | | | + |
| 224 | 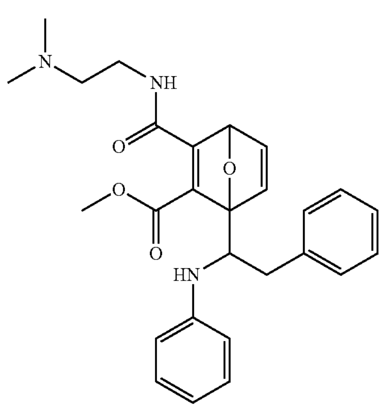 [SMILES: COC(=O)C1=C(C(=O)NCCN(C)C)C2C=CC1(C(Cc1ccccc1)Nc1ccccc1)O2] | +++ | | | | ++ |

TABLE I-continued
compounds synthesized and biological activities.
| Compound number | Structure | SUMO | Nedd8 | Atg7 | Ubiquitin | c-Myc |
|---|---|---|---|---|---|---|
| 225 | 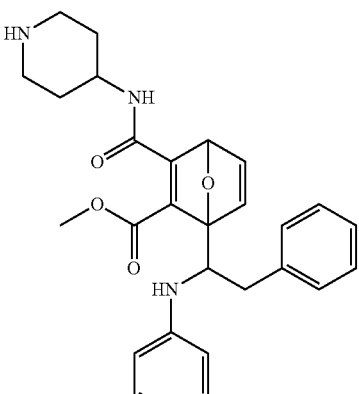 TsOH | +++ | | | | ++ |
| 226 | 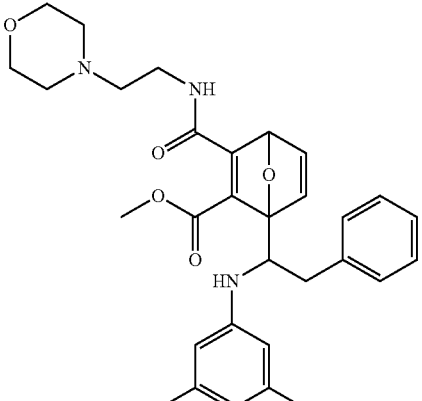 | +++ | | | | ++ |
| 227 | 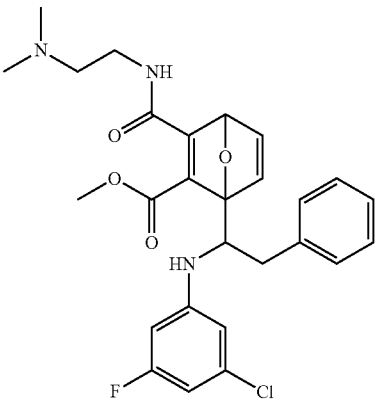 [SMILES: COC(=O)C1=C(C(=O)NCCN(C)C)C2C=CC1(C(Cc1ccccc1)Nc1cc(F)cc(Cl)c1)O2] | +++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 228 | 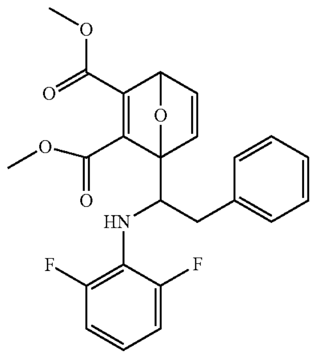 [SMILES: COC(=O)C1=C(C(=O)OC)C2(C(Cc3ccccc3)Nc3c(F)cccc3F)C=CC1O2] | | ++ | | | |
| 230 | 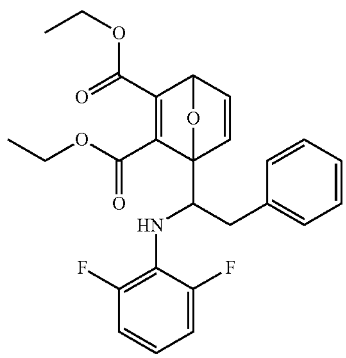 [SMILES: CCOC(=O)C1=C(C(=O)OCC)C2(C(Cc3ccccc3)Nc3c(F)cccc3F)C=CC1O2] | | ++ | | | |
| 232 | 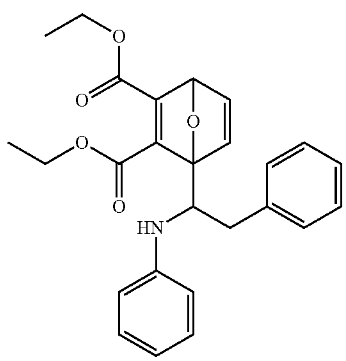 [SMILES: CCOC(=O)C1=C(C(=O)OCC)C2(C(Cc3ccccc3)Nc3ccccc3)C=CC1O2] | | +++ | | | |
| 234 | 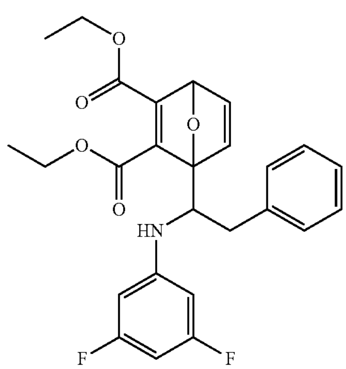 [SMILES: CCOC(=O)C1=C(C(=O)OCC)C2(C(Cc3ccccc3)Nc3cc(F)cc(F)c3)C=CC1O2] | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 236 | 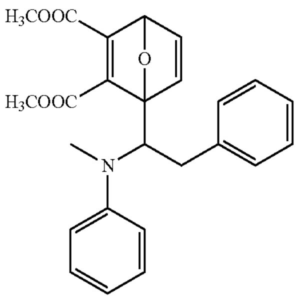 | ++ | | | | |
| 237 | 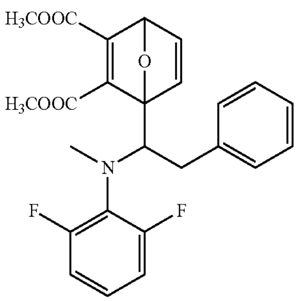 | + | | | | |
| 238 | 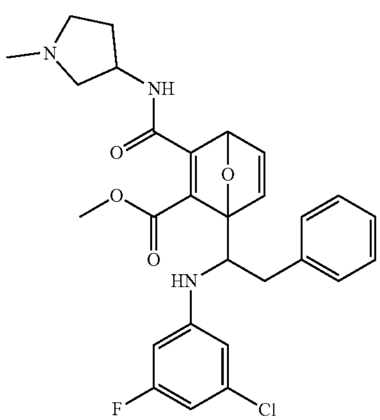 [SMILES: COC(=O)C1=C(C(=O)NC2CCN(C)C2)C2C=CC1(C(Cc1ccccc1)Nc1cc(F)cc(Cl)c1)O2] | +++ | | | | ++ |
| 239 | 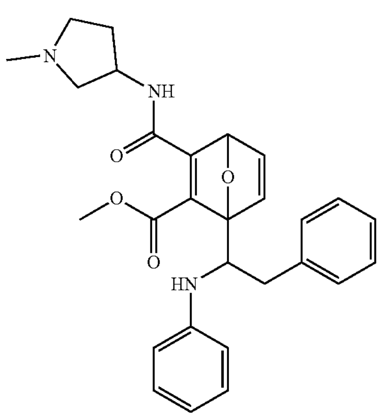 [SMILES: COC(=O)C1=C(C(=O)NC2CCN(C)C2)C2C=CC1(C(Cc1ccccc1)Nc1ccccc1)O2] | +++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 240 | 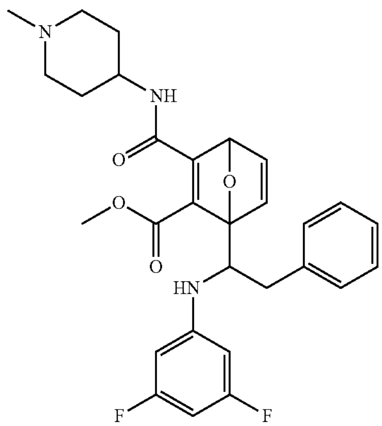 [SMILES: COC(=O)C1=C(C(=O)NC2CCN(C)CC2)C2C=CC1(C(Cc1ccccc1)Nc1cc(F)cc(F)c1)O2] | | ++ | | | + |
| 241 | 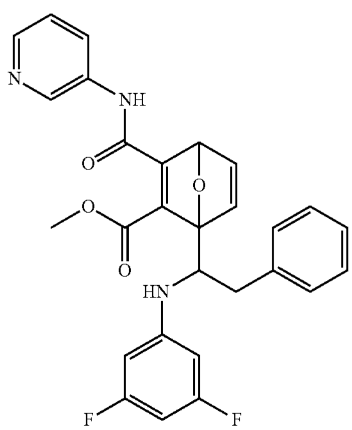 [SMILES: COC(=O)C1=C(C(=O)Nc2cccnc2)C2C=CC1(C(Cc1ccccc1)Nc1cc(F)cc(F)c1)O2] | | ++ | | | ++ |
| 242 | 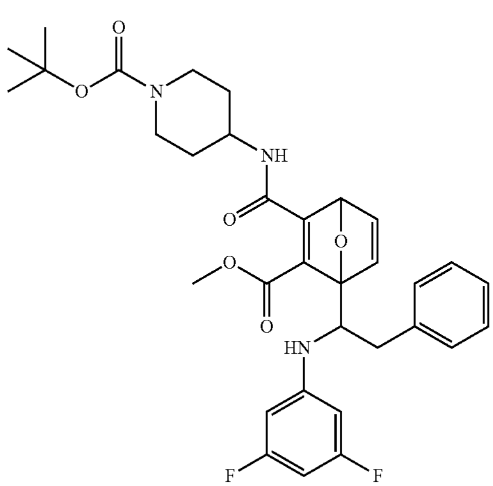 [SMILES: COC(=O)C1=C(C(=O)NC2CCN(C(=O)OC(C)(C)C)CC2)C2C=CC1(C(Cc1ccccc1)Nc1cc(F)cc(F)c1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 243 | 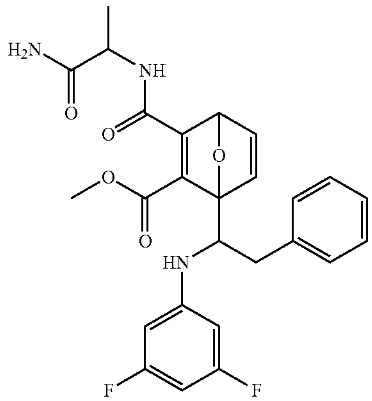 [SMILES: COC(=O)C1=C(C(=O)NC(C)C(N)=O)C2C=CC1(C(Cc1ccccc1)Nc1cc(F)cc(F)c1)O2] | ++ | | | | + |
| 244 | 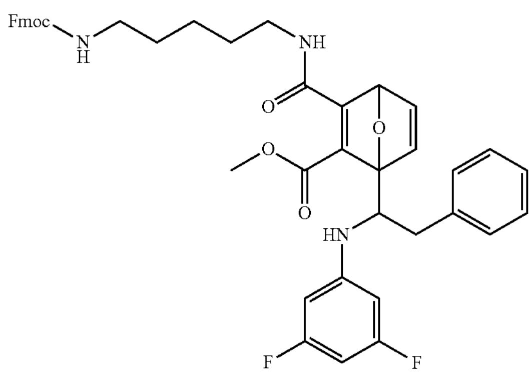 | + | | | | |
| 245 | 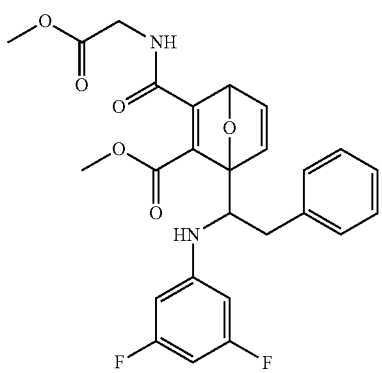 [SMILES: COC(=O)CNC(=O)C1=C(C(=O)OC)C2(C(Cc3ccccc3)Nc3cc(F)cc(F)c3)C=CC1O2] | +++ | | | | ++ |
| 246 | 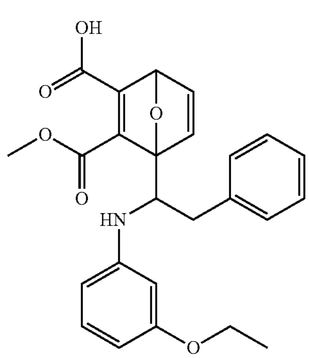 [SMILES: CCOc1cccc(NC(Cc2ccccc2)C23C=CC(O2)C(C(=O)O)=C3C(=O)OC)c1] | + | | | | |

TABLE I-continued compounds synthesized and biological activities.

| Compound number | Structure | SUMO | Nedd8 | Atg7 | Ubiquitin | c-Myc |
|---|---|---|---|---|---|---|
| 247 | 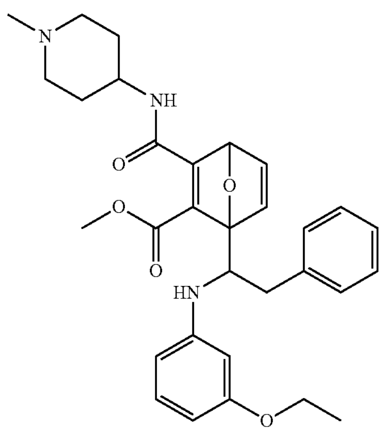 [SMILES: CCOc1cccc(NC(Cc2ccccc2)C23C=CC(O2)C(C(=O)NC2CCN(C)CC2)=C3C(=O)OC)c1] | | +++ | | | + |
| 248 | 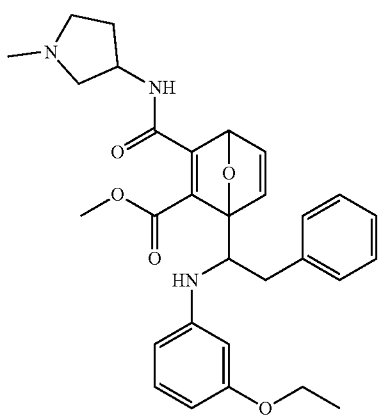 [SMILES: CCOc1cccc(NC(Cc2ccccc2)C23C=CC(O2)C(C(=O)NC2CCN(C)C2)=C3C(=O)OC)c1] | | +++ | | | ++ |
| 249 | 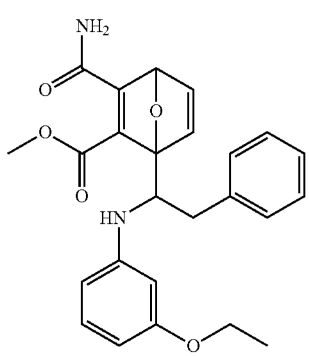 [SMILES: CCOc1cccc(NC(Cc2ccccc2)C23C=CC(O2)C(C(N)=O)=C3C(=O)OC)c1] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 250 | 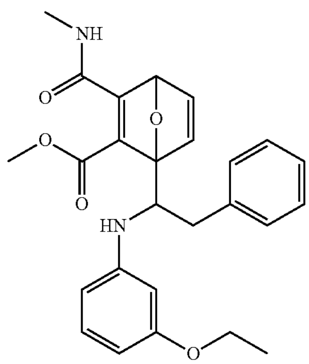 [SMILES: CCOc1cccc(NC(Cc2ccccc2)C23C=CC(O2)C(C(=O)NC)=C3C(=O)OC)c1] | | ++ | | | |
| 251 | 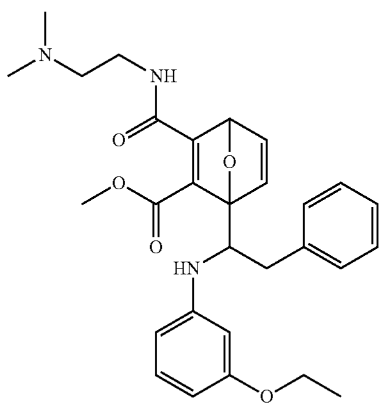 [SMILES: CCOc1cccc(NC(Cc2ccccc2)C23C=CC(O2)C(C(=O)NCCN(C)C)=C3C(=O)OC)c1] | | +++ | | | + |
| 252 | 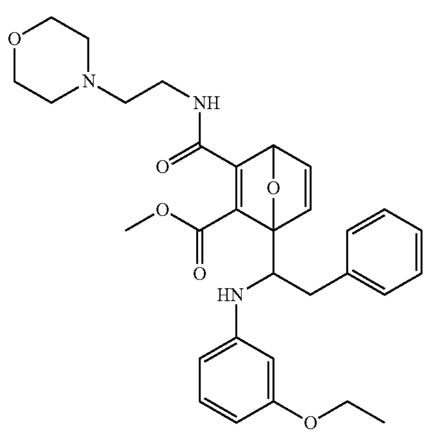 [SMILES: CCOc1cccc(NC(Cc2ccccc2)C23C=CC(O2)C(C(=O)NCCN2CCOCC2)=C3C(=O)OC)c1] | | +++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 253 | 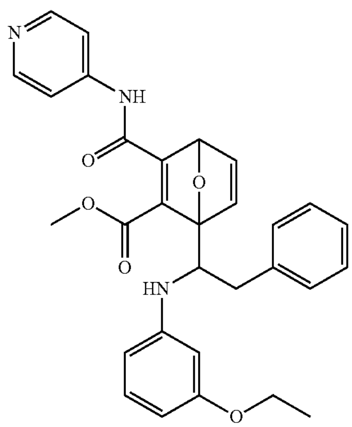 [SMILES: CCOc1cccc(NC(Cc2ccccc2)C23C=CC(O2)C(C(=O)Nc2ccncc2)=C3C(=O)OC)c1] | | ++ | | | + |
| 254 | 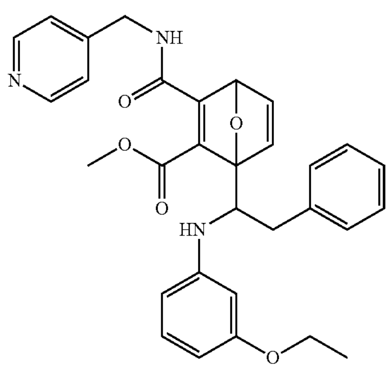 [SMILES: CCOc1cccc(NC(Cc2ccccc2)C23C=CC(O2)C(C(=O)NCc2ccncc2)=C3C(=O)OC)c1] | | ++ | | | + |
| 255 | 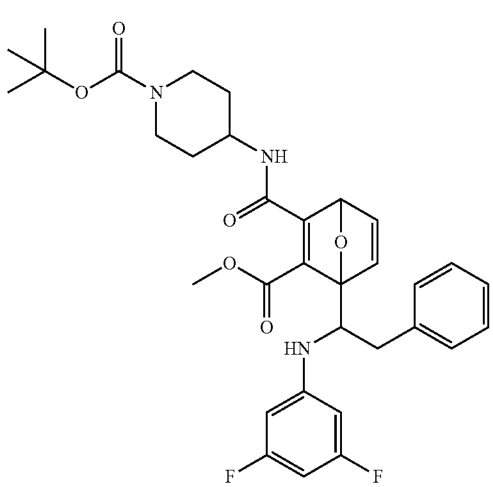 [SMILES: COC(=O)C1=C(C(=O)NC2CCN(C(=O)OC(C)(C)C)CC2)C2C=CC1(C(Cc1ccccc1)Nc1cc(F)cc(F)c1)O2] | | + | | | |

TABLE I-continued compounds synthesized and biological activities.

| Compound number | Structure | SUMO | Nedd8 | Atg7 | Ubiquitin | c-Myc |
|---|---|---|---|---|---|---|
| 256 | 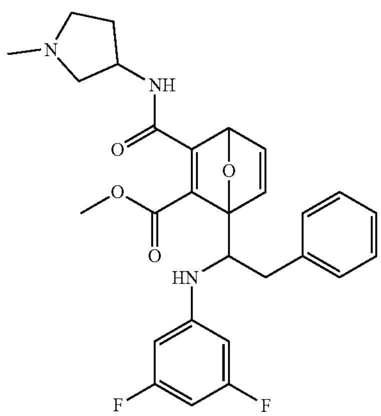 [SMILES: COC(=O)C1=C(C(=O)NC2CCN(C)C2)C2C=CC1(C(Cc1ccccc1)Nc1cc(F)cc(F)c1)O2] | | ++ | | | + |
| 258 | 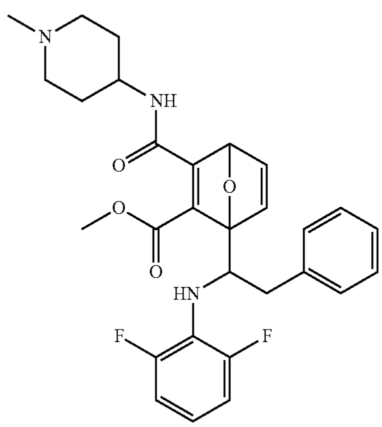 [SMILES: COC(=O)C1=C(C(=O)NC2CCN(C)CC2)C2C=CC1(C(Cc1ccccc1)Nc1c(F)cccc1F)O2] | | ++ | | | + |
| 259 | 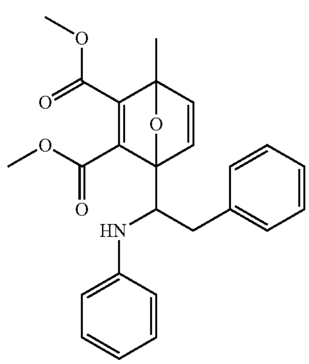 [SMILES: COC(=O)C1=C(C(=O)OC)C2(C(Cc3ccccc3)Nc3ccccc3)C=CC1(C)O2] | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 260 | 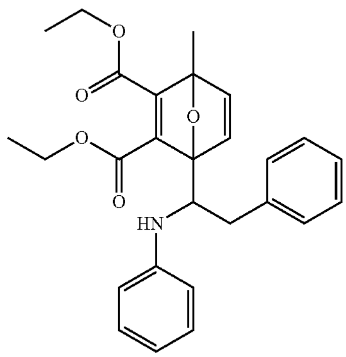 [SMILES: CCOC(=O)C1=C(C(=O)OCC)C2(C(Cc3ccccc3)Nc3ccccc3)C=CC1(C)O2] | | ++ | | | + |
| 262 | 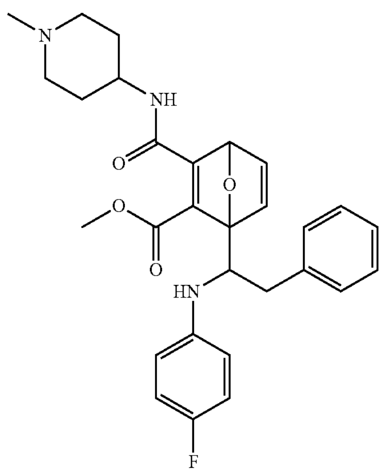 [SMILES: COC(=O)C1=C(C(=O)NC2CCN(C)CC2)C2C=CC1(C(Cc1ccccc1)Nc1ccc(F)cc1)O2] | | ++ | | | ++ |
| 263 | 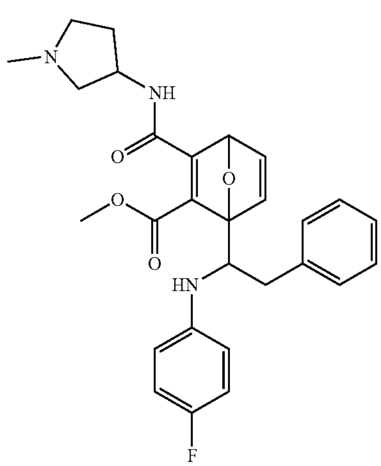 [SMILES: COC(=O)C1=C(C(=O)NC2CCN(C)C2)C2C=CC1(C(Cc1ccccc1)Nc1ccc(F)cc1)O2] | | +++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 264 | 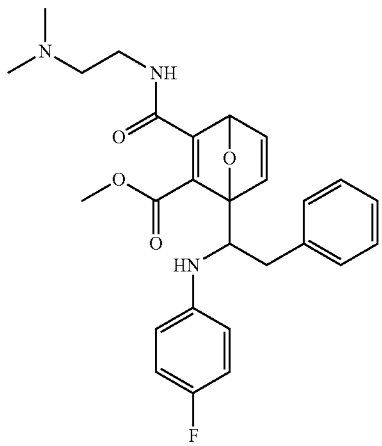 [SMILES: COC(=O)C1=C(C(=O)NCCN(C)C)C2C=CC1(C(Cc1ccccc1)Nc1ccc(F)cc1)O2] | +++ | | | | ++ |
| 265 | 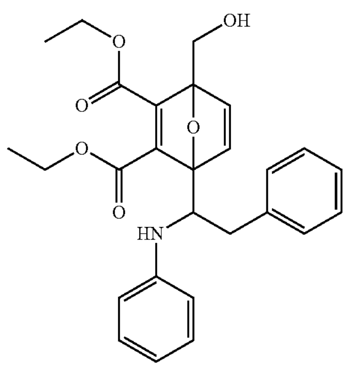 [SMILES: CCOC(=O)C1=C(C(=O)OCC)C2(C(Cc3ccccc3)Nc3ccccc3)C=CC1(CO)O2] | ++ | | | | |
| 266 | 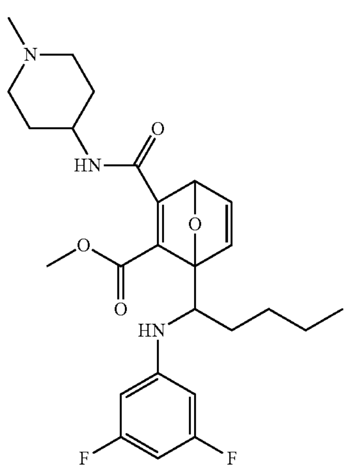 [SMILES: CCCCC(Nc1cc(F)cc(F)c1)C12C=CC(O1)C(C(=O)NC1CCN(C)CC1)=C2C(=O)OC] | +++ | | | | + |

TABLE I-continued
compounds synthesized and biological activities.
| Compound number | Structure | SUMO | Nedd8 | Atg7 | Ubiquitin | c-Myc |
|---|---|---|---|---|---|---|
| 267 | 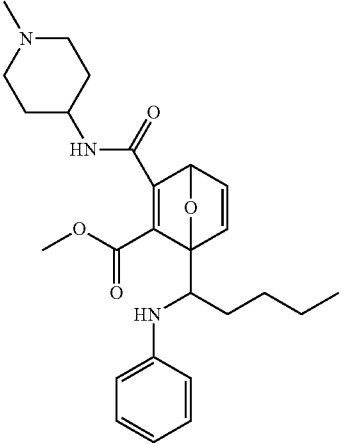 [SMILES: CCCCC(Nc1ccccc1)C12C=CC(O1)C(C(=O)NC1CCN(C)CC1)=C2C(=O)OC] | | ++ | | | ++ |
| 268 | 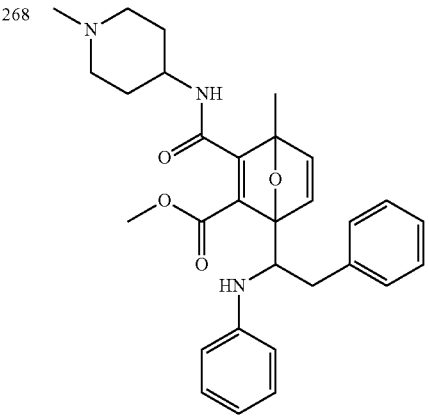 | | + | | | |
| 269 | 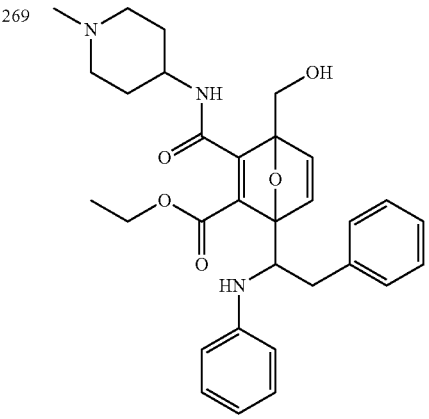 | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 270 | 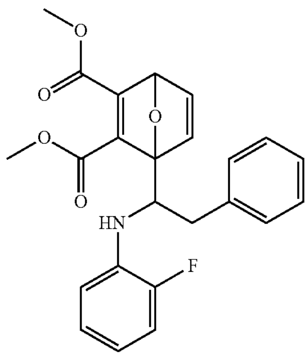 [SMILES: COC(=O)C1=C(C(=O)OC)C2(C(Cc3ccccc3)Nc3ccccc3F)C=CC1O2] | | ++ | | | |
| 271 | 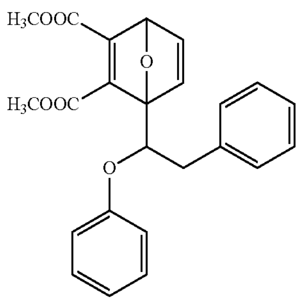 | | ++ | | | |
| 272 | 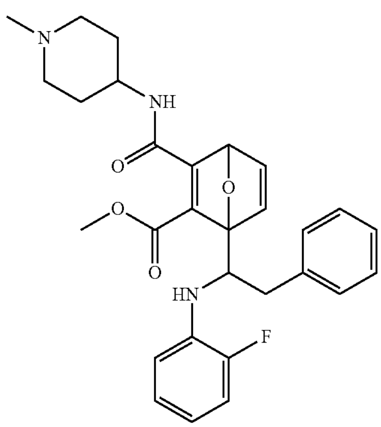 [SMILES: COC(=O)C1=C(C(=O)NC2CCN(C)CC2)C2C=CC1(C(Cc1ccccc1)Nc1ccccc1F)O2] | | ++ | | | + |
| 273 | 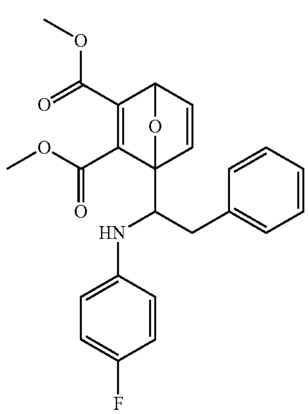 [SMILES: COC(=O)C1=C(C(=O)OC)C2(C(Cc3ccccc3)Nc3ccc(F)cc3)C=CC1O2] | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 274 | 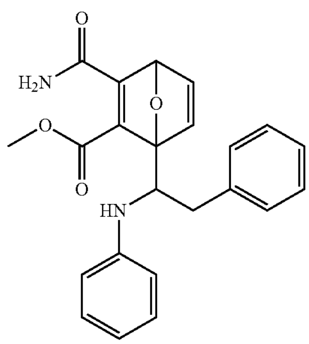 [SMILES: COC(=O)C1=C(C(N)=O)C2C=CC1(C(Cc1ccccc1)Nc1ccccc1)O2] | | +++ | | | ++ |
| 275 | 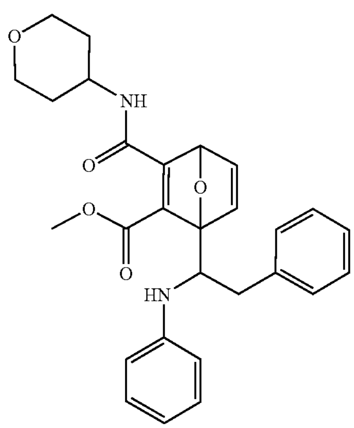 [SMILES: COC(=O)C1=C(C(=O)NC2CCOCC2)C2C=CC1(C(Cc1ccccc1)Nc1ccccc1)O2] | | +++ | | | |
| 276 | 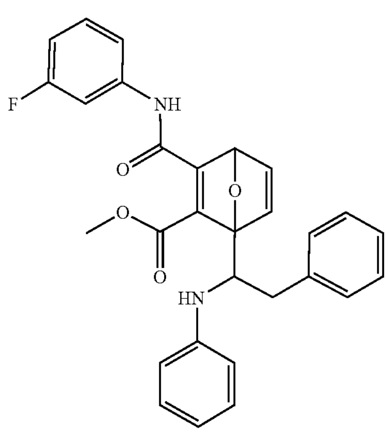 [SMILES: COC(=O)C1=C(C(=O)Nc2cccc(F)c2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 277 | 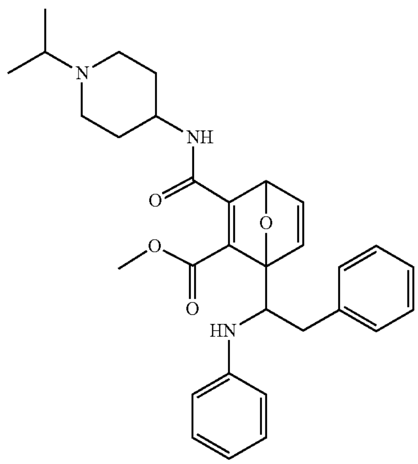 [SMILES: COC(=O)C1=C(C(=O)NC2CCN(C(C)C)CC2)C2C=CC1(C(Cc1ccccc1)Nc1ccccc1)O2] | +++ | | | | ++ |
| 278 | 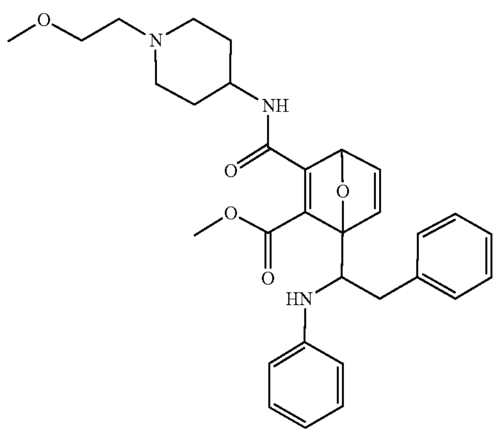 [SMILES: COCCN1CCC(NC(=O)C2=C(C(=O)OC)C3(C(Cc4ccccc4)Nc4ccccc4)C=CC2O3)CC1] | +++ | | | | ++ |
| 279 | 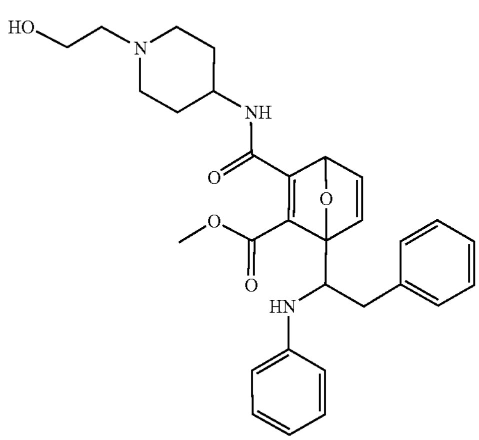 [SMILES: COC(=O)C1=C(C(=O)NC2CCN(CCO)CC2)C2C=CC1(C(Cc1ccccc1)Nc1ccccc1)O2] | +++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 284 | 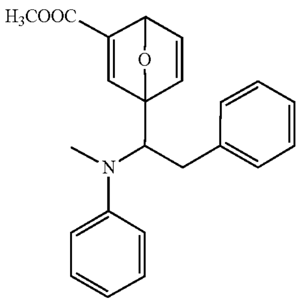 | ++ | | | | |
| 285 | 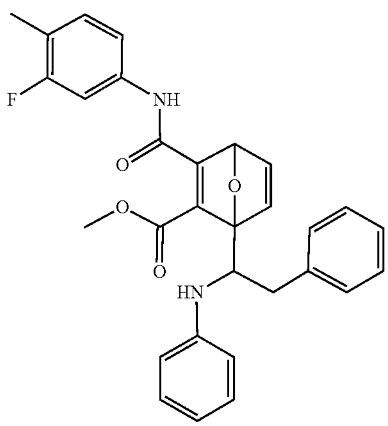 [SMILES: COC(=O)C1=C(C(=O)Nc2ccc(C)c(F)c2)C2C=CC1(C(Cc1ccccc1)Nc1ccccc1)O2] | ++ | | | | ++ |
| 286 | 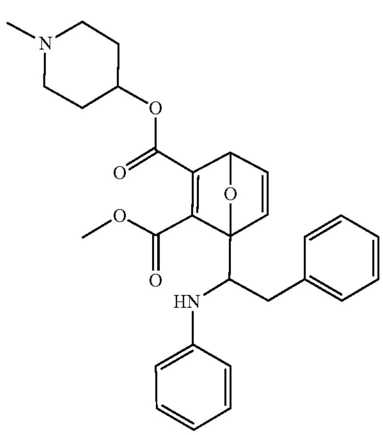 [SMILES: COC(=O)C1=C(C(=O)OC2CCN(C)CC2)C2C=CC1(C(Cc1ccccc1)Nc1ccccc1)O2] | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 287 | 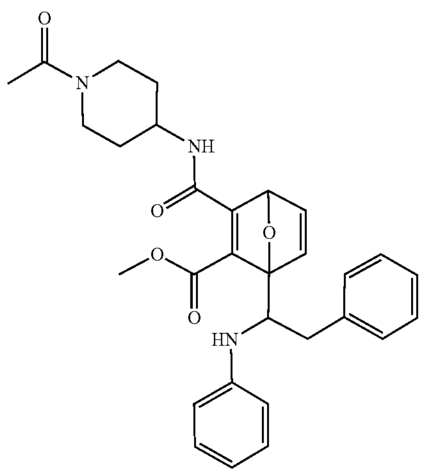 [SMILES: COC(=O)C1=C(C(=O)NC2CCN(C(C)=O)CC2)C2C=CC1(C(Cc1ccccc1)Nc1ccccc1)O2] | | ++ | | | ++ |
| 288 | 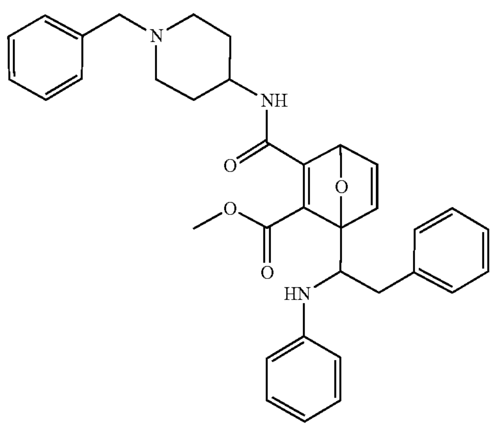 [SMILES: COC(=O)C1=C(C(=O)NC2CCN(Cc3ccccc3)CC2)C2C=CC1(C(Cc1ccccc1)Nc1ccccc1)O2] | | ++ | | | ++ |
| 289 | 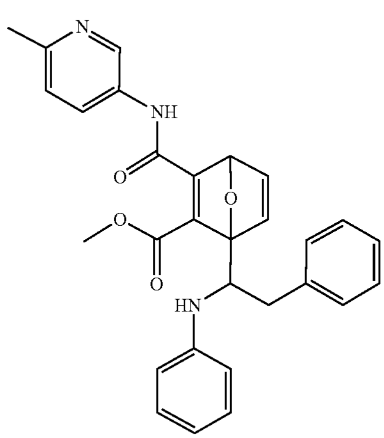 [SMILES: COC(=O)C1=C(C(=O)Nc2ccc(C)nc2)C2C=CC1(C(Cc1ccccc1)Nc1ccccc1)O2] | | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 290 | 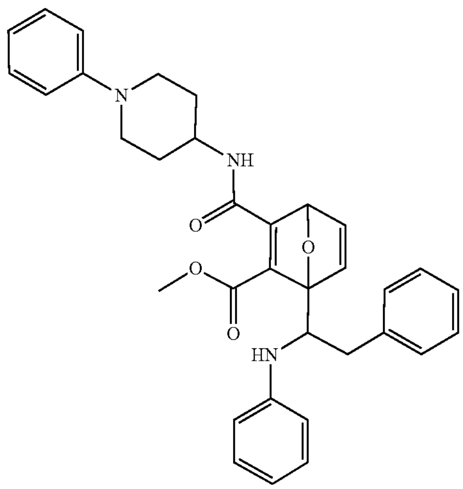 [SMILES: COC(=O)C1=C(C(=O)NC2CCN(c3ccccc3)CC2)C2C=CC1(C(Cc1ccccc1)Nc1ccccc1)O2] | | | + | | |
| 291 | 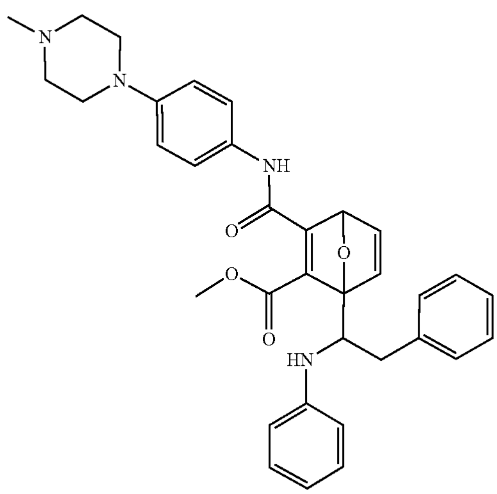 [SMILES: COC(=O)C1=C(C(=O)Nc2ccc(N3CCN(C)CC3)cc2)C2C=CC1(C(Cc1ccccc1)Nc1ccccc1)O2] | | | ++ | | |
| 292 | 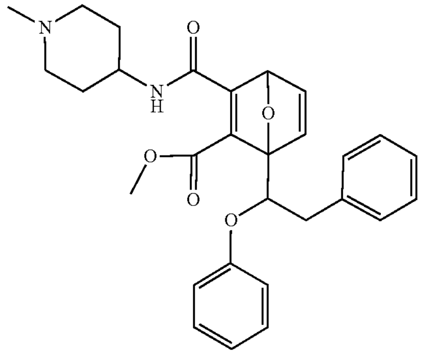 [SMILES: COC(=O)C1=C(C(=O)NC2CCN(C)CC2)C2C=CC1(C(Cc1ccccc1)Oc1ccccc1)O2] | | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 293 | 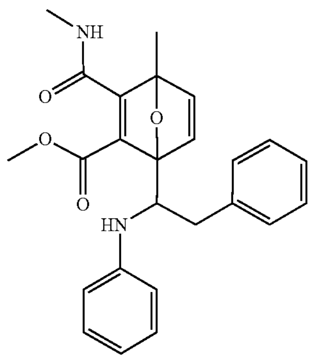 [SMILES: CNC(=O)C1=C(C(=O)OC)C2(C(Cc3ccccc3)Nc3ccccc3)C=CC1(C)O2] | | ++ | | | |
| 294 | 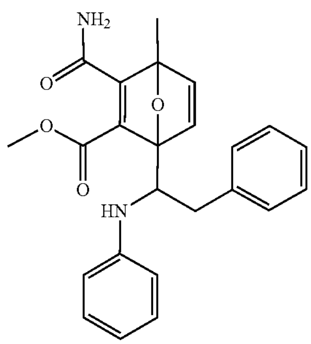 [SMILES: COC(=O)C1=C(C(N)=O)C2(C)C=CC1(C(Cc1ccccc1)Nc1ccccc1)O2] | | ++ | | | |
| 295 | 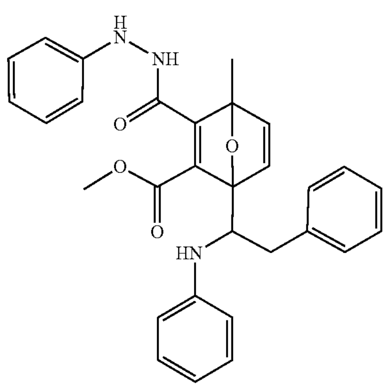 [SMILES: COC(=O)C1=C(C(=O)NNc2ccccc2)C2(C)C=CC1(C(Cc1ccccc1)Nc1ccccc1)O2] | | ++ | | | |
| 296 | 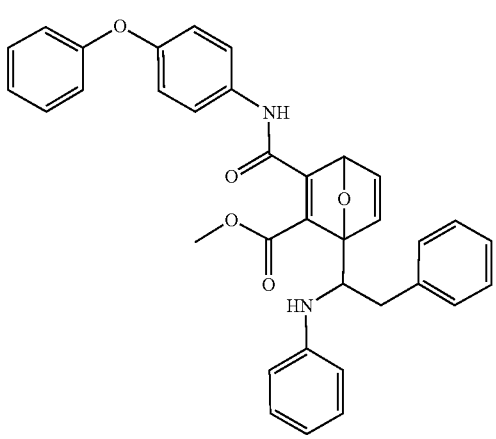 [SMILES: COC(=O)C1=C(C(=O)Nc2ccc(Oc3ccccc3)cc2)C2C=CC1(C(Cc1ccccc1)Nc1ccccc1)O2] | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 297 | 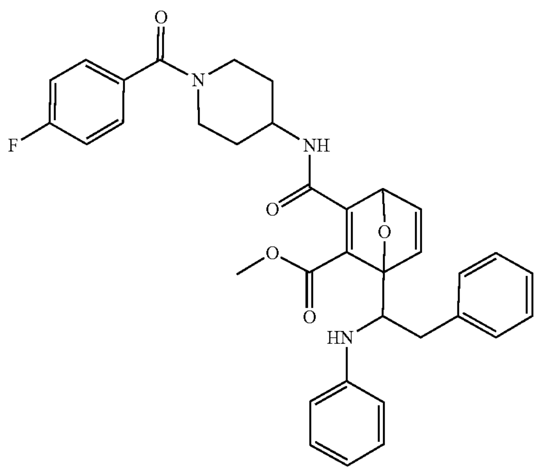 [SMILES: COC(=O)C1=C(C(=O)NC2CCN(C(=O)c3ccc(F)cc3)CC2)C2C=CC1(C(Cc1ccccc1)Nc1ccccc1)O2] | | ++ | | | ++ |
| 298 | 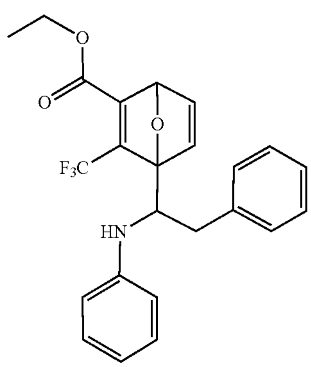 [SMILES: CCOC(=O)C1=C(C(F)(F)F)C2(C(Cc3ccccc3)Nc3ccccc3)C=CC1O2] | | ++ | | | + |
| 299 | 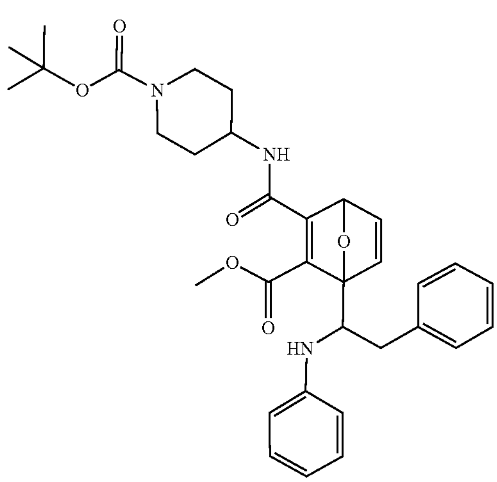 [SMILES: COC(=O)C1=C(C(=O)NC2CCN(C(=O)OC(C)(C)C)CC2)C2C=CC1(C(Cc1ccccc1)Nc1ccccc1)O2] | | | | | |

TABLE I-continued compounds synthesized and biological activities.

| Compound number | Structure | SUMO | Nedd8 | Atg7 | Ubiquitin | c-Myc |
|---|---|---|---|---|---|---|
| 300 | 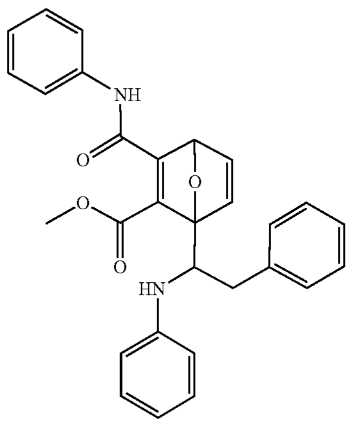 [SMILES: COC(=O)C1=C(C(=O)Nc2ccccc2)C2C=CC1(C(Cc1ccccc1)Nc1ccccc1)O2] | +++ | | | | + |
| 302 | 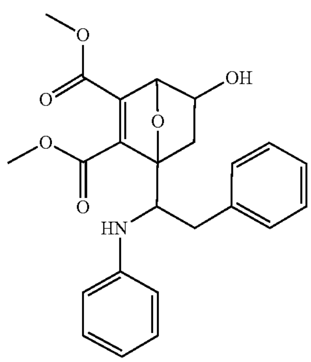 [SMILES: COC(=O)C1=C(C(=O)OC)C2(C(Cc3ccccc3)Nc3ccccc3)CC(O)C1O2] | ++ | | | | |
| 303 | 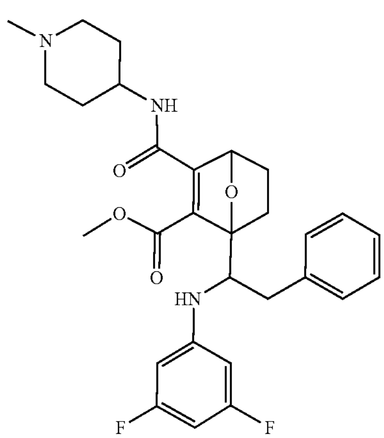 [SMILES: COC(=O)C1=C(C(=O)NC2CCN(C)CC2)C2CCC1(C(Cc1ccccc1)Nc1cc(F)cc(F)c1)O2] | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 304 | 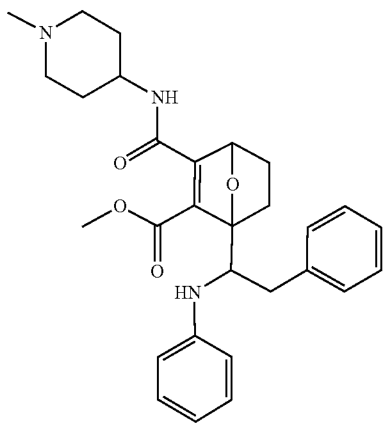 [SMILES: COC(=O)C1=C(C(=O)NC2CCN(C)CC2)C2CCC1(C(Cc1ccccc1)Nc1ccccc1)O2] | + | | | | + |
| 305 | 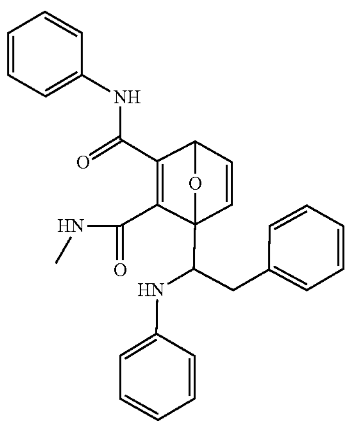 [SMILES: CNC(=O)C1=C(C(=O)Nc2ccccc2)C2C=CC1(C(Cc1ccccc1)Nc1ccccc1)O2] | + | | | | + |
| 307 | 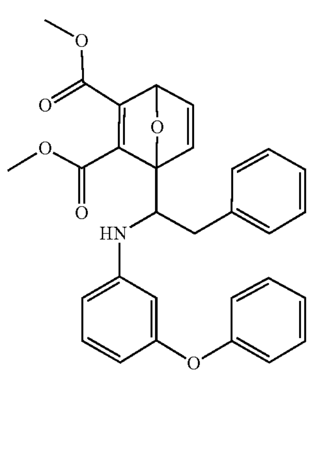 [SMILES: COC(=O)C1=C(C(=O)OC)C2(C(Cc3ccccc3)Nc3cccc(Oc4ccccc4)c3)C=CC1O2] | +++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 308 | 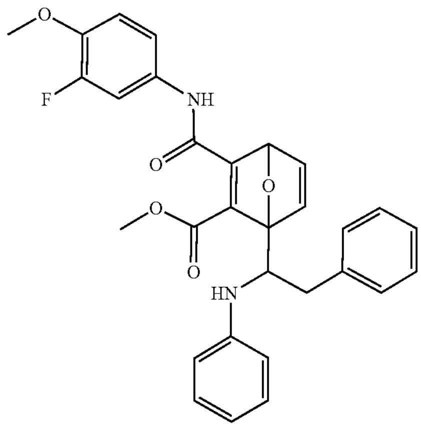 [SMILES: COC(=O)C1=C(C(=O)Nc2ccc(OC)c(F)c2)C2C=CC1(C(Cc1ccccc1)Nc1ccccc1)O2] | + | | | | + |
| 309 | 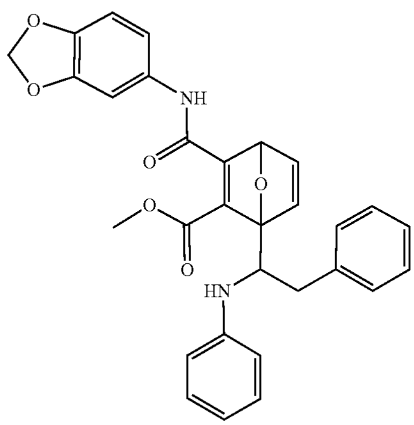 [SMILES: COC(=O)C1=C(C(=O)Nc2ccc3c(c2)OCO3)C2C=CC1(C(Cc1ccccc1)Nc1ccccc1)O2] | + | | | | + |
| 310 | 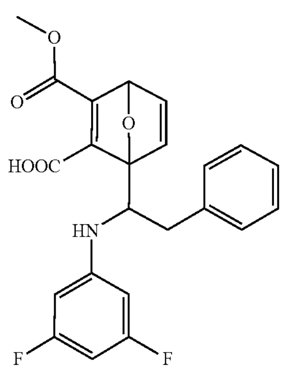 [SMILES: COC(=O)C1=C(C(=O)O)C2(C(Cc3ccccc3)Nc3cc(F)cc(F)c3)C=CC1O2] | + | | | | + |
| 311 | 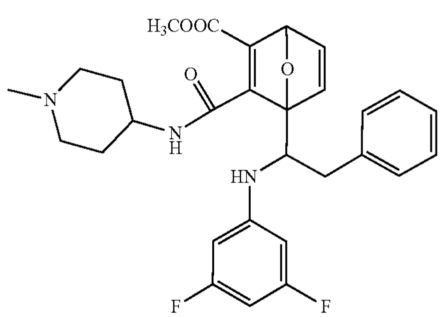 | ++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 312 | 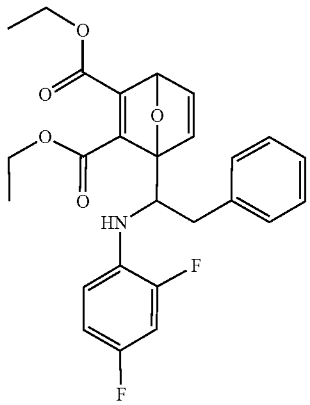 [SMILES: CCOC(=O)C1=C(C(=O)OCC)C2(C(Cc3ccccc3)Nc3ccc(F)cc3F)C=CC1O2] | | ++ | | | + |
| 313 | 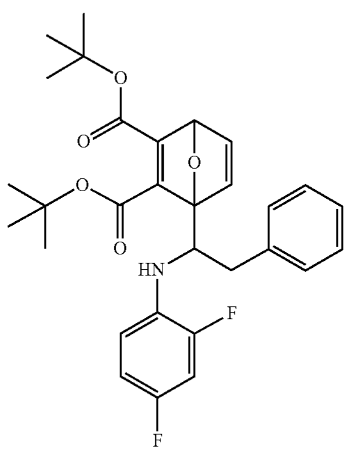 [SMILES: CC(C)(C)OC(=O)C1=C(C(=O)OC(C)(C)C)C2(C(Cc3ccccc3)Nc3ccc(F)cc3F)C=CC1O2] | | +++ | | | + |
| 314 | 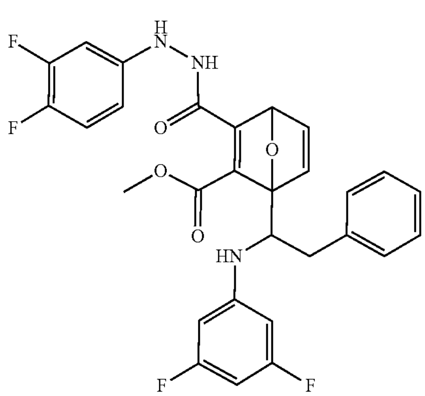 [SMILES: COC(=O)C1=C(C(=O)NNc2ccc(F)c(F)c2)C2C=CC1(C(Cc1ccccc1)Nc1cc(F)cc(F)c1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 315 | 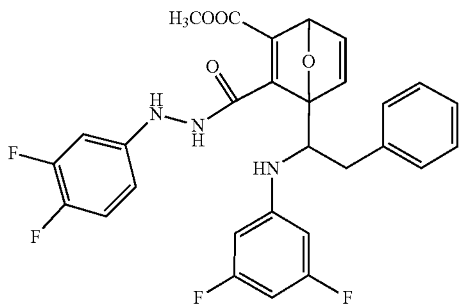 | ++ | | | | + |
| 316 | 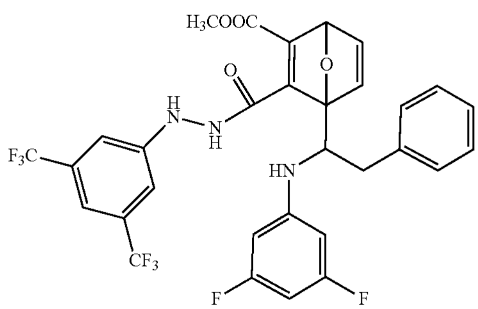 | ++ | | | | + |
| 317 | 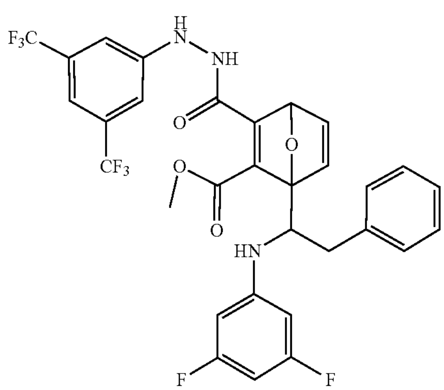 [SMILES: COC(=O)C1=C(C(=O)NNc2cc(C(F)(F)F)cc(C(F)(F)F)c2)C2C=CC1(C(Cc1ccccc1)Nc1cc(F)cc(F)c1)O2] | + | | | | + |
| 318 | 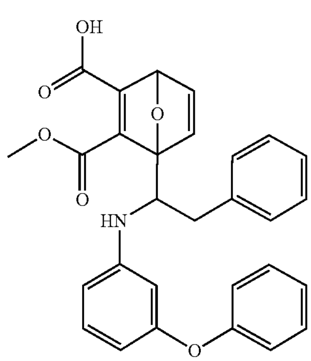 [SMILES: COC(=O)C1=C(C(=O)O)C2C=CC1(C(Cc1ccccc1)Nc1cccc(Oc3ccccc3)c1)O2] | | | | | |

TABLE I-continued compounds synthesized and biological activities.

| Compound number | Structure | SUMO | Nedd8 | Atg7 | Ubiquitin | c-Myc |
|---|---|---|---|---|---|---|
| 319 | 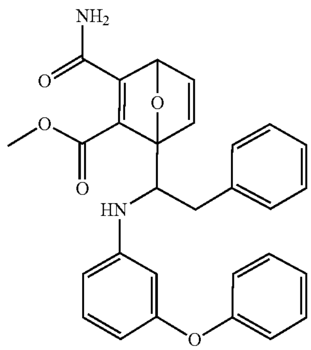 [SMILES: COC(=O)C1=C(C(N)=O)C2C=CC1(C(Cc1ccccc1)Nc1cccc(Oc3ccccc3)c1)O2] | +++ | | | | + |
| 320 | 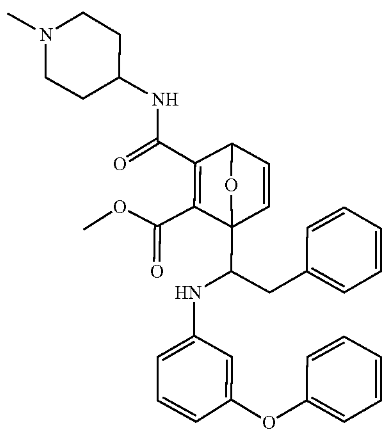 [SMILES: COC(=O)C1=C(C(=O)NC2CCN(C)CC2)C2C=CC1(C(Cc1ccccc1)Nc1cccc(Oc3ccccc3)c1)O2] | +++ | | | | ++ |
| 321 | 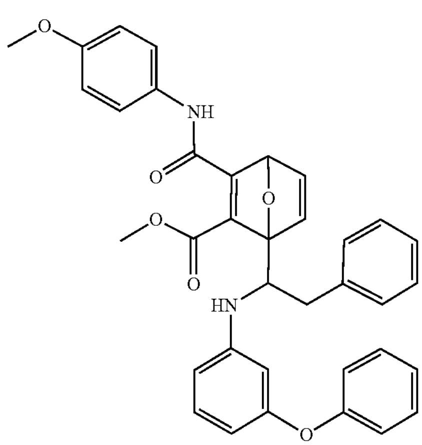 [SMILES: COC(=O)C1=C(C(=O)Nc2ccc(OC)cc2)C2C=CC1(C(Cc1ccccc1)Nc1cccc(Oc3ccccc3)c1)O2] | +++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 324 | 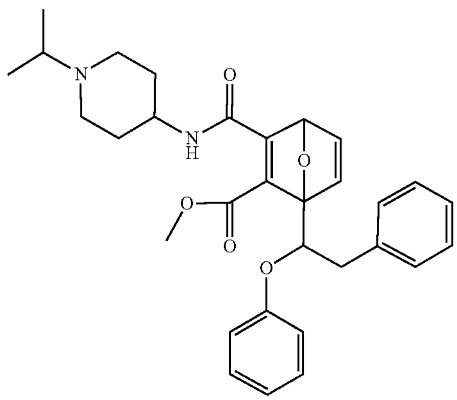 [SMILES: COC(=O)C1=C(C(=O)NC2CCN(C(C)C)CC2)C2C=CC1(C(Cc1ccccc1)Oc1ccccc1)O2] | | ++ | | | ++ |
| 325 | 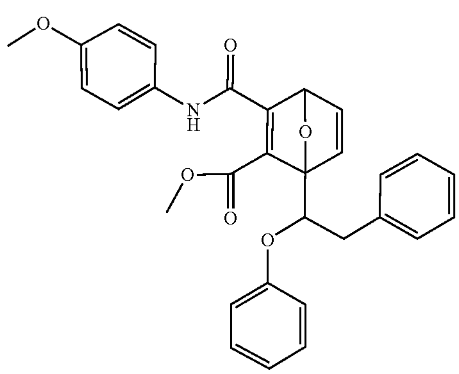 [SMILES: COC(=O)C1=C(C(=O)Nc2ccc(OC)cc2)C2C=CC1(C(Cc1ccccc1)Oc1ccccc1)O2] | | ++ | | | ++ |
| 326 | 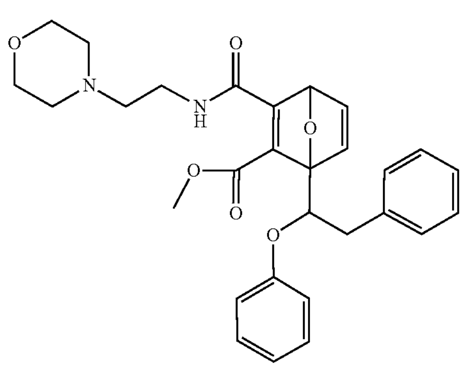 [SMILES: COC(=O)C1=C(C(=O)NCCN2CCOCC2)C2C=CC1(C(Cc1ccccc1)Oc1ccccc1)O2] | | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 329 | 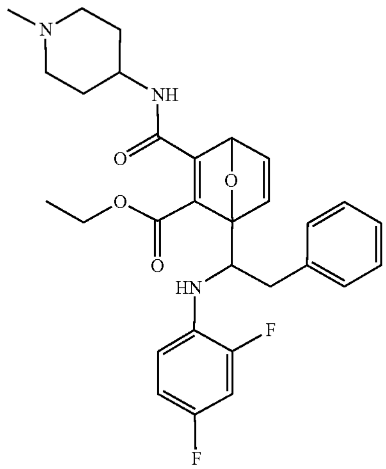 [SMILES: CCOC(=O)C1=C(C(=O)NC2CCN(C)CC2)C2C=CC1(C(Cc1ccccc1)Nc1ccc(F)cc1F)O2] | | +++ | | | ++ |
| 333 | 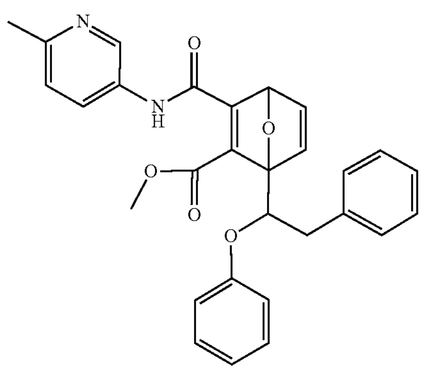 [SMILES: COC(=O)C1=C(C(=O)Nc2ccc(C)nc2)C2C=CC1(C(Cc1ccccc1)Oc1ccccc1)O2] | | + | | | + |
| 345 | 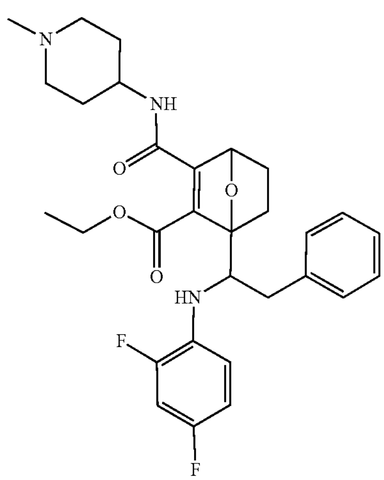 [SMILES: CCOC(=O)C1=C(C(=O)NC2CCN(C)CC2)C2CCC1(C(Cc1ccccc1)Nc1ccc(F)cc1F)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 346 | 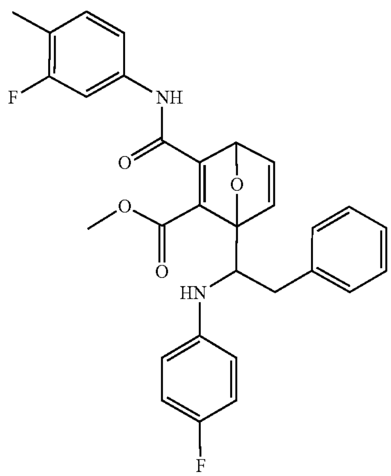 [SMILES: COC(=O)C1=C(C(=O)Nc2ccc(C)c(F)c2)C2C=CC1(C(Cc1ccccc1)Nc1ccc(F)cc1)O2] | | ++ | | | |
| 347 | 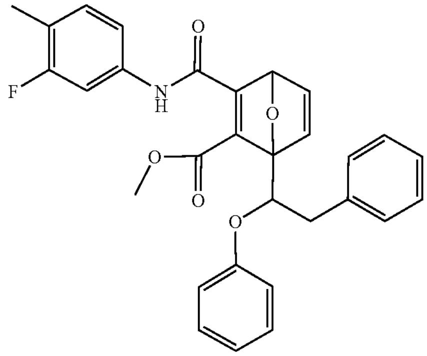 [SMILES: COC(=O)C1=C(C(=O)Nc2ccc(C)c(F)c2)C2C=CC1(C(Cc1ccccc1)Oc1ccccc1)O2] | | ++ | | | |
| 348 | 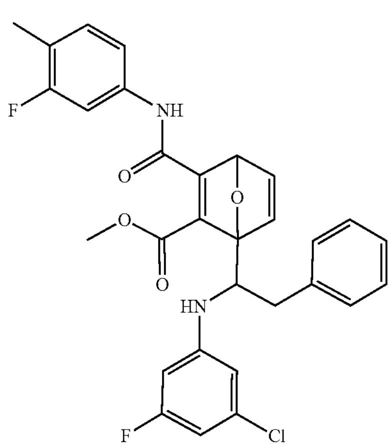 [SMILES: COC(=O)C1=C(C(=O)Nc2ccc(C)c(F)c2)C2C=CC1(C(Cc1ccccc1)Nc1cc(F)cc(Cl)c1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 349 | 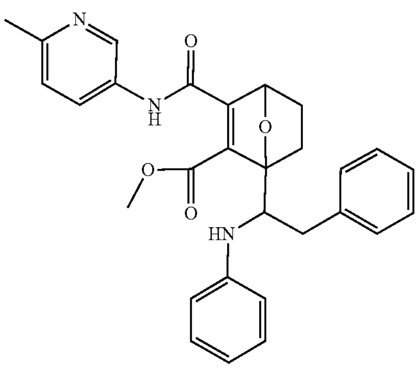 [SMILES: COC(=O)C1=C(C(=O)Nc2ccc(C)nc2)C2CCC1(C(Cc1ccccc1)Nc1ccccc1)O2] | | + | | | + |
| 350 | 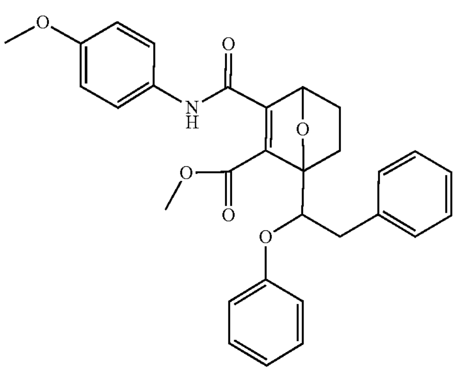 [SMILES: COC(=O)C1=C(C(=O)Nc2ccc(OC)cc2)C2CCC1(C(Cc1ccccc1)Oc1ccccc1)O2] | | + | | | + |
| 351 | 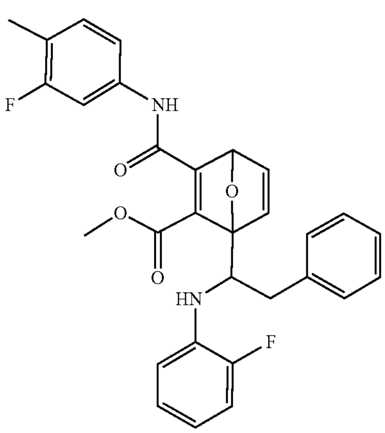 [SMILES: COC(=O)C1=C(C(=O)Nc2ccc(C)c(F)c2)C2C=CC1(C(Cc1ccccc1)Nc1ccccc1F)O2] | | +++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 352 | 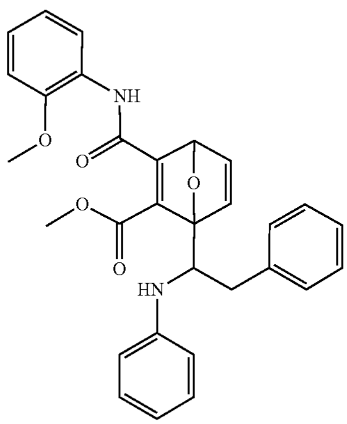 [SMILES: COC(=O)C1=C(C(=O)Nc2ccccc2OC)C2C=CC1(C(Cc1ccccc1)Nc1ccccc1)O2] | | ++ | | | + |
| 353 | 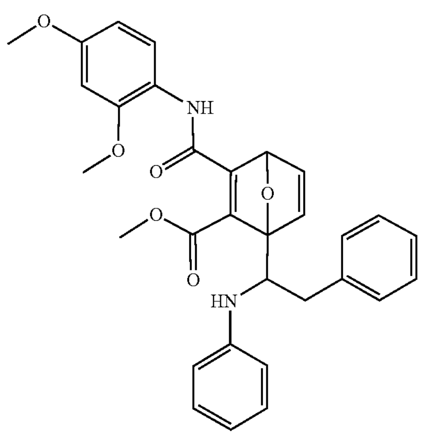 [SMILES: COC(=O)C1=C(C(=O)Nc2ccc(OC)cc2OC)C2C=CC1(C(Cc1ccccc1)Nc1ccccc1)O2] | | + | | | + |
| 354 | 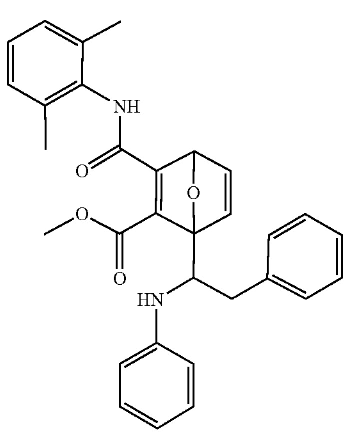 [SMILES: COC(=O)C1=C(C(=O)Nc2c(C)cccc2C)C2C=CC1(C(Cc1ccccc1)Nc1ccccc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 358 | 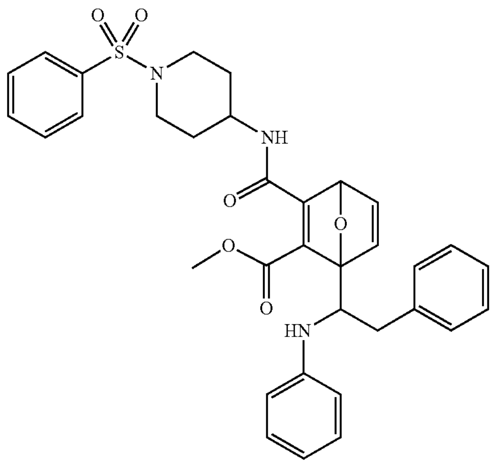 [SMILES: COC(=O)C1=C(C(=O)NC2CCN(S(=O)(=O)c3ccccc3)CC2)C2C=CC1(C(Cc1ccccc1)Nc1ccccc1)O2] | | + | | | + |
| 359 | 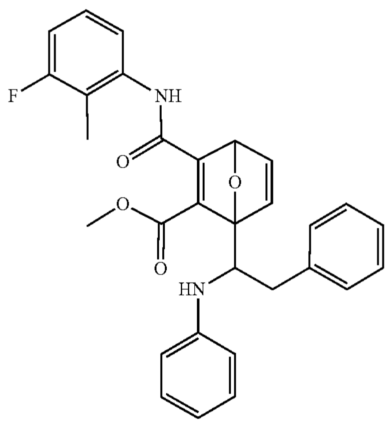 [SMILES: COC(=O)C1=C(C(=O)Nc2cccc(F)c2C)C2C=CC1(C(Cc1ccccc1)Nc1ccccc1)O2] | | ++ | | | + |
| 360 | 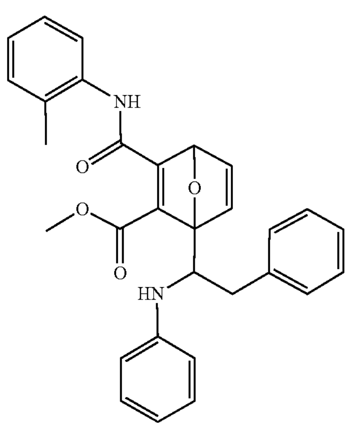 [SMILES: COC(=O)C1=C(C(=O)Nc2ccccc2C)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 361 | 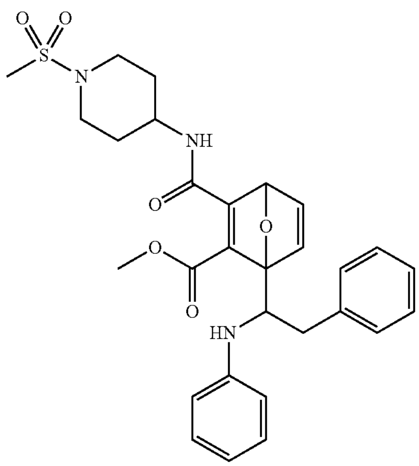 [SMILES: COC(=O)C1=C(C(=O)NC2CCN(S(C)(=O)=O)CC2)C2C=CC1(C(Cc1ccccc1)Nc1ccccc1)O2] | | ++ | | | + |
| 366 | 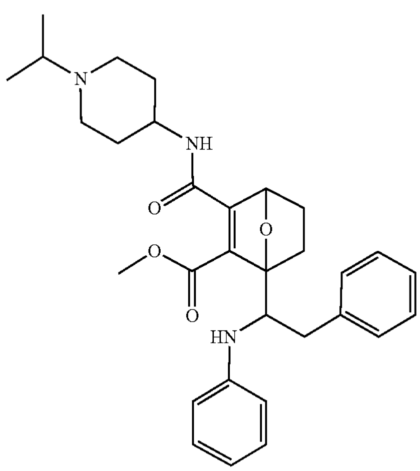 [SMILES: COC(=O)C1=C(C(=O)NC2CCN(C(C)C)CC2)C2CCC1(C(Cc1ccccc1)Nc1ccccc1)O2] | | + | | | + |
| 367 | 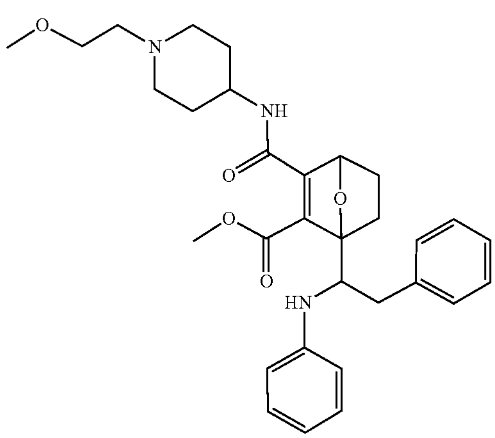 [SMILES: COCCN1CCC(NC(=O)C2=C(C(=O)OC)C3(C(Cc4ccccc4)Nc4ccccc4)CCC2O3)CC1] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 368 | 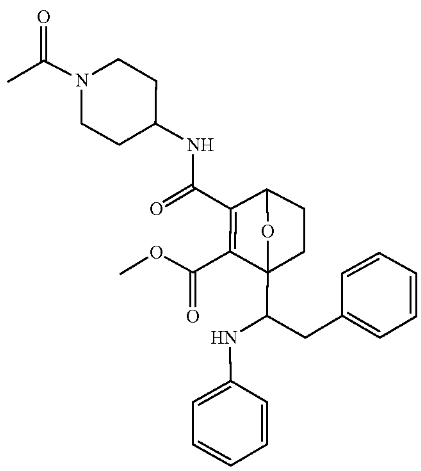 [SMILES: COC(=O)C1=C(C(=O)NC2CCN(C(C)=O)CC2)C2CCC1(C(Cc1ccccc1)Nc1ccccc1)O2] | | + | | | + |
| 369 | 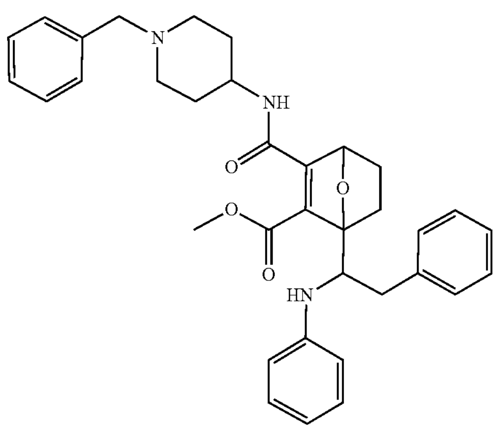 [SMILES: COC(=O)C1=C(C(=O)NC2CCN(Cc3ccccc3)CC2)C2CCC1(C(Cc1ccccc1)Nc1ccccc1)O2] | | + | | | + |
| 370 | 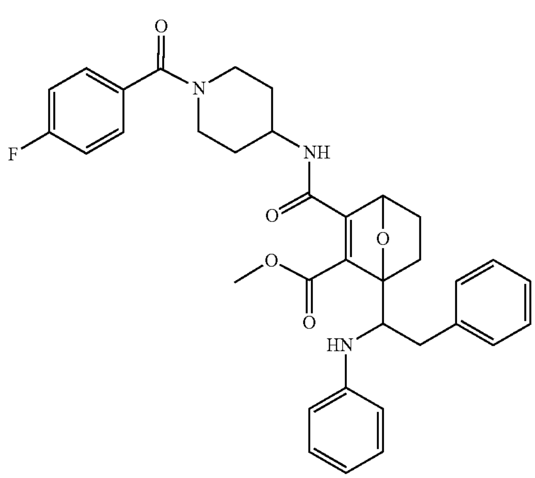 [SMILES: COC(=O)C1=C(C(=O)NC2CCN(C(=O)c3ccc(F)cc3)CC2)C2CCC1(C(Cc1ccccc1)Nc1ccccc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 371 | 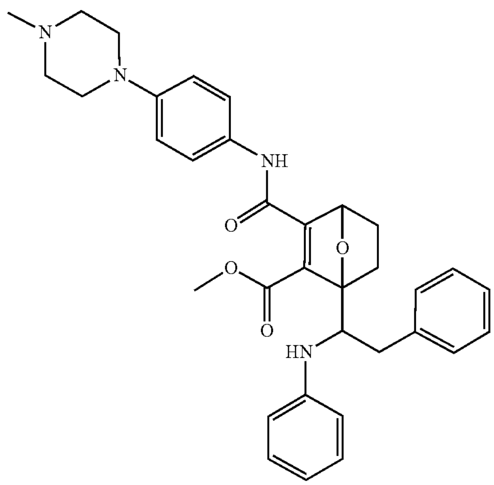 [SMILES: COC(=O)C1=C(C(=O)Nc2ccc(N3CCN(C)CC3)cc2)C2CCC1(C(Cc1ccccc1)Nc1ccccc1)O2] | + | | | | + |
| 375 | 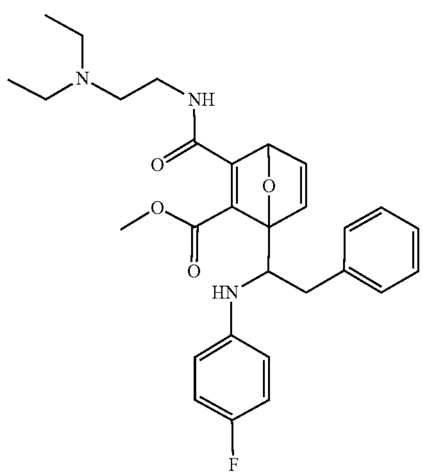 [SMILES: CCN(CC)CCNC(=O)C1=C(C(=O)OC)C2(C(Cc3ccccc3)Nc3ccc(F)cc3)C=CC1O2] | ++ | | | | + |
| 376 | 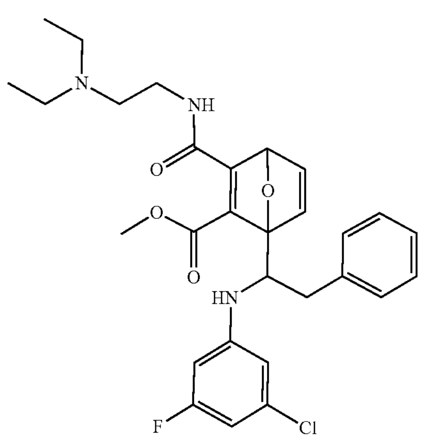 [SMILES: CCN(CC)CCNC(=O)C1=C(C(=O)OC)C2(C(Cc3ccccc3)Nc3cc(F)cc(Cl)c3)C=CC1O2] | +++ | | | | ++ |

TABLE I-continued
compounds synthesized and biological activities.
| Compound number | Structure | SUMO | Nedd8 | Atg7 | Ubiquitin | c-Myc |
|---|---|---|---|---|---|---|
| 377 | 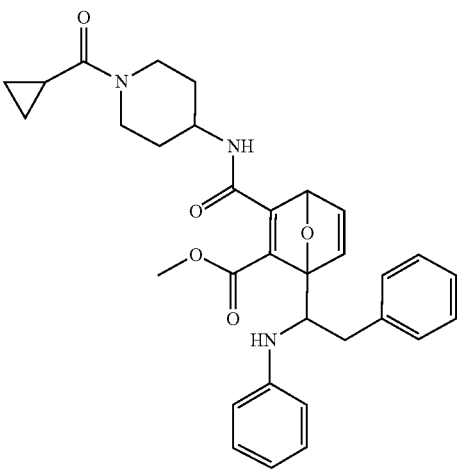 [SMILES: COC(=O)C1=C(C(=O)NC2CCN(C(=O)C3CC3)CC2)C2C=CC1(C(Cc1ccccc1)Nc1ccccc1)O2] | | ++ | | | + |
| 378 | 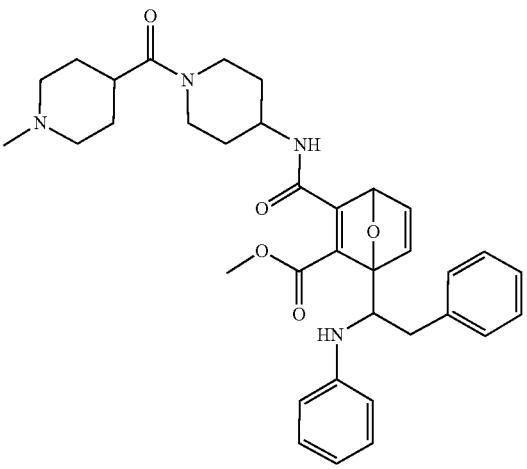 [SMILES: COC(=O)C1=C(C(=O)NC2CCN(C(=O)C3CCN(C)CC3)CC2)C2C=CC1(C(Cc1ccccc1)Nc1ccccc1)O2] | | ++ | | | + |
| 379 | 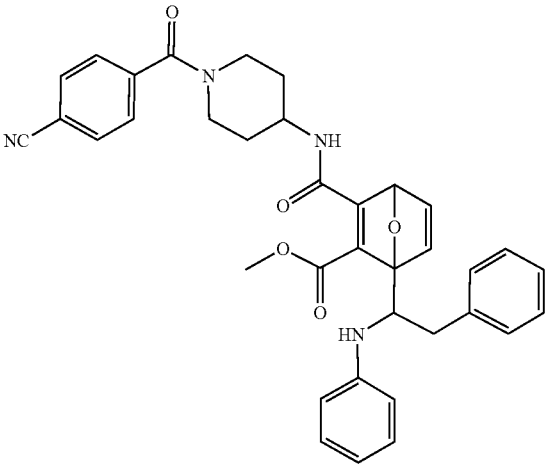 [SMILES: COC(=O)C1=C(C(=O)NC2CCN(C(=O)c3ccc(C#N)cc3)CC2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 380 | 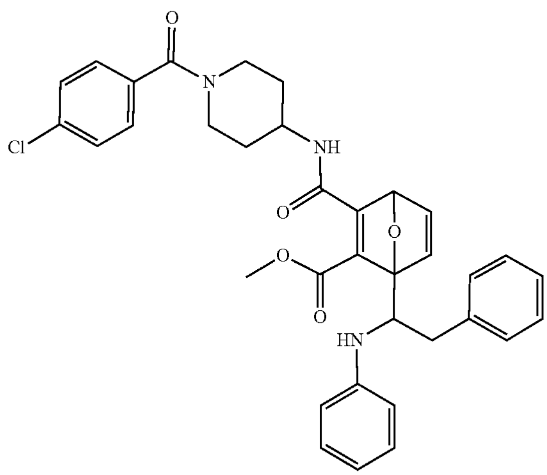 [SMILES: COC(=O)C1=C(C(=O)NC2CCN(C(=O)c3ccc(Cl)cc3)CC2)C2C=CC1(C(Cc1ccccc1)Nc1ccccc1)O2] | | ++ | | | + |
| 381 | 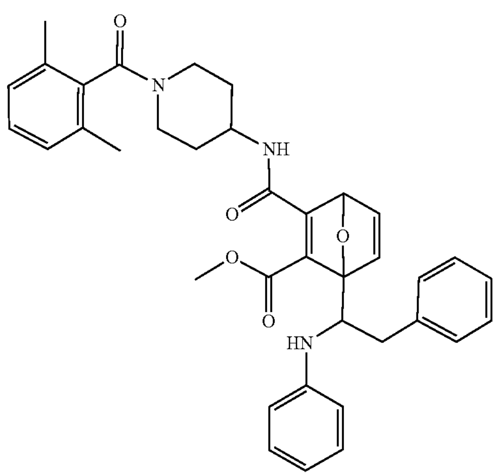 [SMILES: COC(=O)C1=C(C(=O)NC2CCN(C(=O)c3c(C)cccc3C)CC2)C2C=CC1(C(Cc1ccccc1)Nc1ccccc1)O2] | | ++ | | | + |
| 382 | 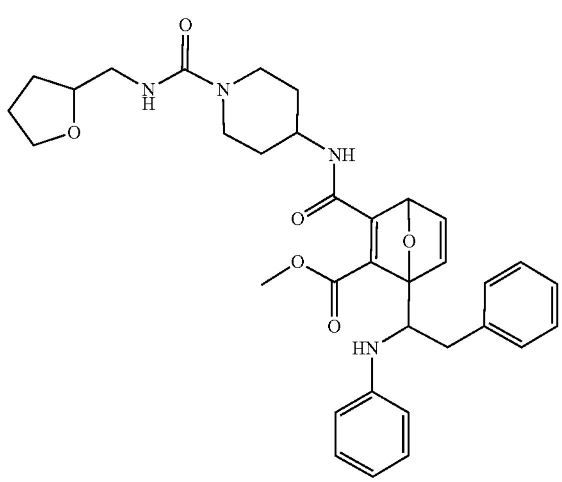 [SMILES: COC(=O)C1=C(C(=O)NC2CCN(C(=O)NCC3CCCO3)CC2)C2C=CC1(C(Cc1ccccc1)Nc1ccccc1)O2] | | ++ | | | + |

TABLE I-continued
compounds synthesized and biological activities.
| Compound number | Structure | SUMO | Nedd8 | Atg7 | Ubiquitin | c-Myc |
|---|---|---|---|---|---|---|
| 383 | 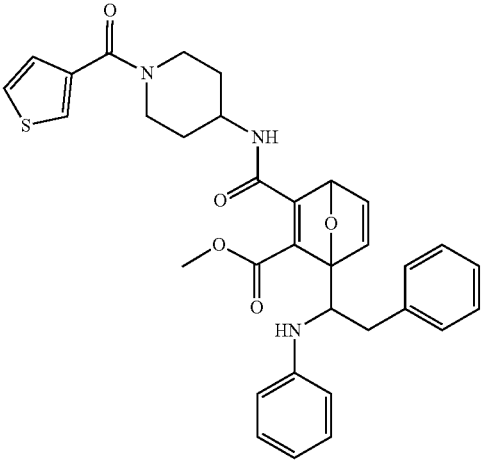 [SMILES: COC(=O)C1=C(C(=O)NC2CCN(C(=O)c3ccsc3)CC2)C2C=CC1(C(Cc1ccccc1)Nc1ccccc1)O2] | | ++ | | | + |
| 384 | 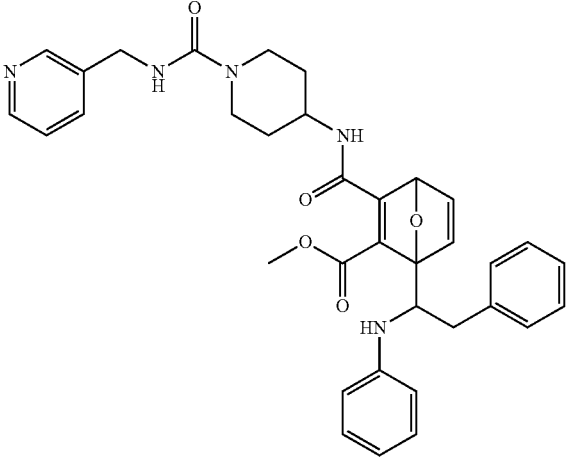 [SMILES: COC(=O)C1=C(C(=O)NC2CCN(C(=O)NCc3cccnc3)CC2)C2C=CC1(C(Cc1ccccc1)Nc1ccccc1)O2] | | ++ | | | + |
| 385 | 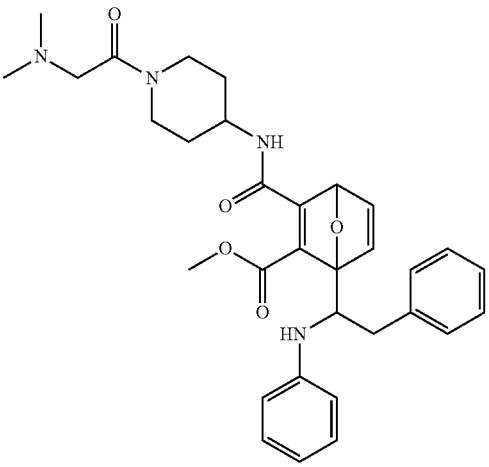 [SMILES: COC(=O)C1=C(C(=O)NC2CCN(C(=O)CN(C)C)CC2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 386 | 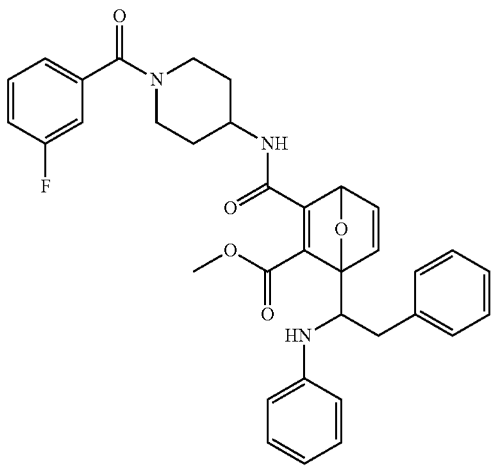 [SMILES: COC(=O)C1=C(C(=O)NC2CCN(C(=O)c3cccc(F)c3)CC2)C2C=CC1(C(Cc1ccccc1)Nc1ccccc1)O2] | | ++ | | | + |
| 387 | 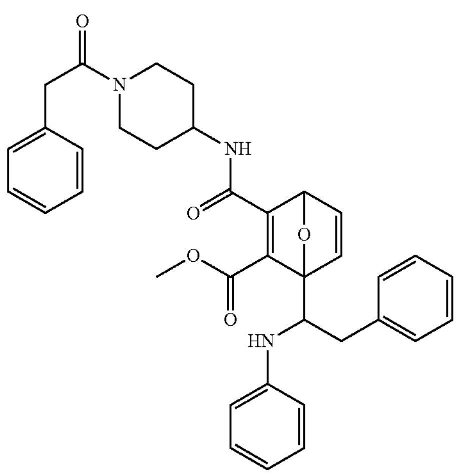 [SMILES: COC(=O)C1=C(C(=O)NC2CCN(C(=O)Cc3ccccc3)CC2)C2C=CC1(C(Cc1ccccc1)Nc1ccccc1)O2] | | ++ | | | + |
| 388 | 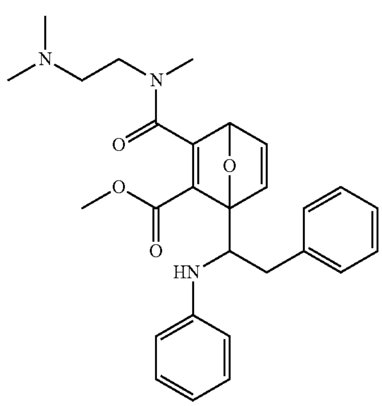 [SMILES: COC(=O)C1=C(C(=O)N(C)CCN(C)C)C2C=CC1(C(Cc1ccccc1)Nc1ccccc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 389 | 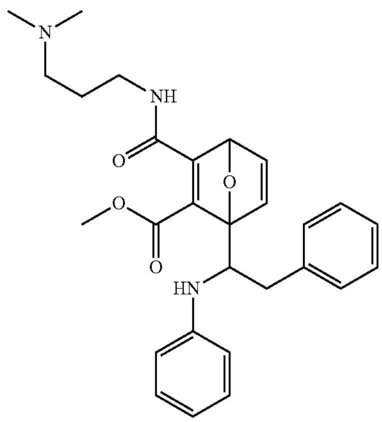 [SMILES: COC(=O)C1=C(C(=O)NCCCN(C)C)C2C=CC1(C(Cc1ccccc1)Nc1ccccc1)O2] | | ++ | | | + |
| 390 | 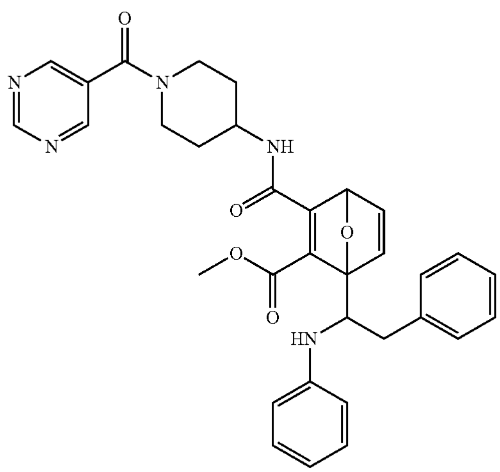 [SMILES: COC(=O)C1=C(C(=O)NC2CCN(C(=O)c3cncnc3)CC2)C2C=CC1(C(Cc1ccccc1)Nc1ccccc1)O2] | | ++ | | | + |
| 391 | 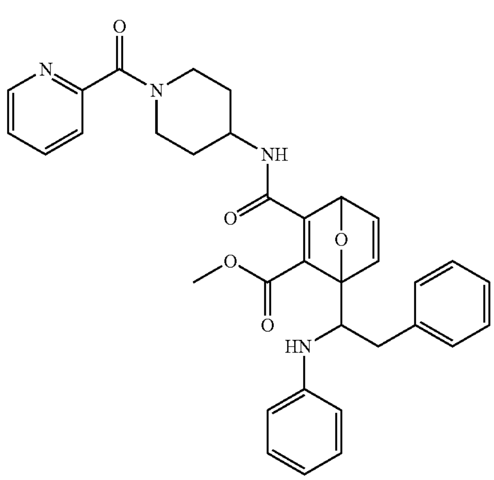 [SMILES: COC(=O)C1=C(C(=O)NC2CCN(C(=O)c3ccccn3)CC2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 392 | 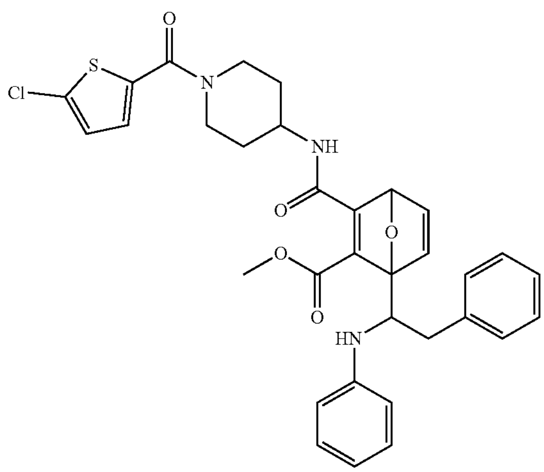 [SMILES: COC(=O)C1=C(C(=O)NC2CCN(C(=O)c3ccc(Cl)s3)CC2)C2C=CC1(C(Cc1ccccc1)Nc1ccccc1)O2] | | ++ | | | + |
| 394 | 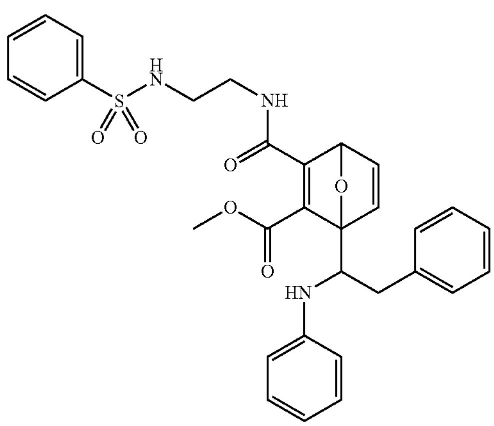 [SMILES: COC(=O)C1=C(C(=O)NCCNS(=O)(=O)c2ccccc2)C2C=CC1(C(Cc1ccccc1)Nc1ccccc1)O2] | | ++ | | | + |
| 395 | 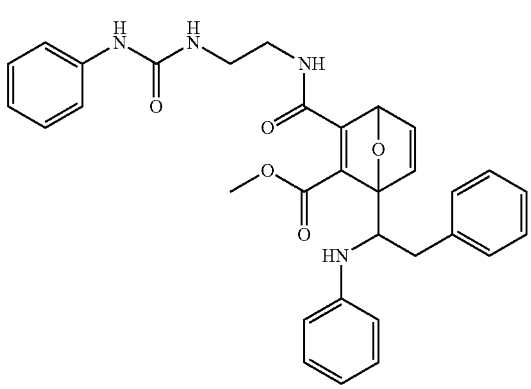 [SMILES: COC(=O)C1=C(C(=O)NCCNC(=O)Nc2ccccc2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 396 | 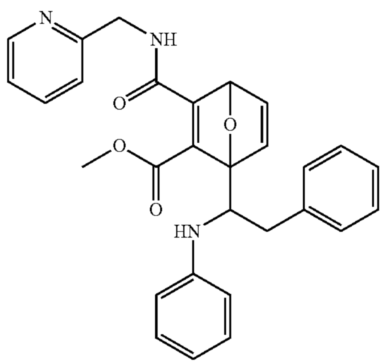 [SMILES: COC(=O)C1=C(C(=O)NCc2ccccn2)C2C=CC1(C(Cc1ccccc1)Nc1ccccc1)O2] | + | | | | ++ |
| 397 | 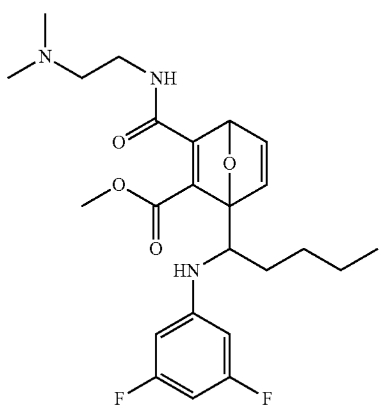 [SMILES: CCCCC(Nc1cc(F)cc(F)c1)C12C=CC(O1)C(C(=O)NCCN(C)C)=C2C(=O)OC] | + | | | | |
| 398 | 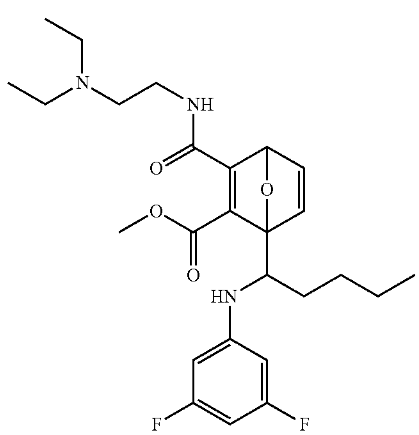 [SMILES: CCCCC(Nc1cc(F)cc(F)c1)C12C=CC(O1)C(C(=O)NCCN(CC)CC)=C2C(=O)OC] | + | | | | |

TABLE I-continued compounds synthesized and biological activities.

| Compound number | Structure | SUMO | Nedd8 | Atg7 | Ubiquitin | c-Myc |
|---|---|---|---|---|---|---|
| 399 | 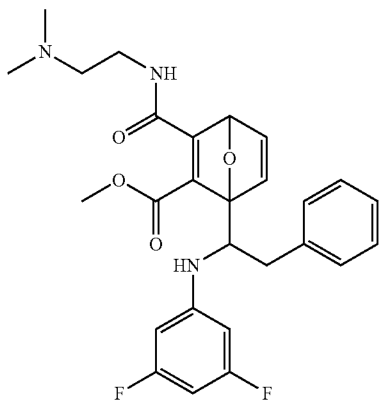 [SMILES: COC(=O)C1=C(C(=O)NCCN(C)C)C2C=CC1(C(Cc1ccccc1)Nc1cc(F)cc(F)c1)O2] | | ++ | | | + |
| 400 | 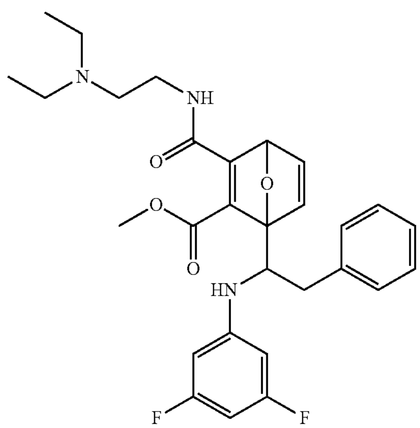 [SMILES: CCN(CC)CCNC(=O)C1=C(C(=O)OC)C2(C(Cc3ccccc3)Nc3cc(F)cc(F)c3)C=CC1O2] | | ++ | | | ++ |
| 401 | 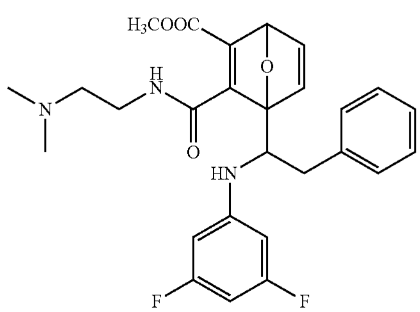 | | ++ | | | ++ |
| 402 | 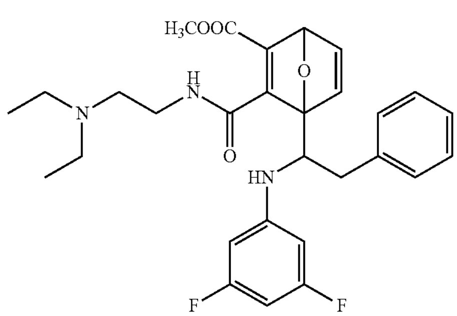 | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 403 | 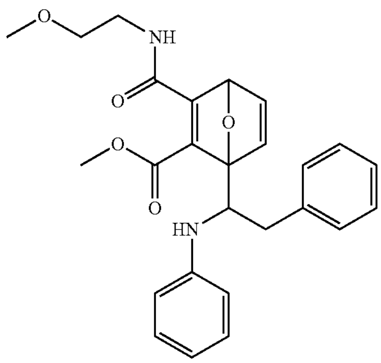 [SMILES: COCCNC(=O)C1=C(C(=O)OC)C2(C(Cc3ccccc3)Nc3ccccc3)C=CC1O2] | | ++ | | | + |
| 404 | 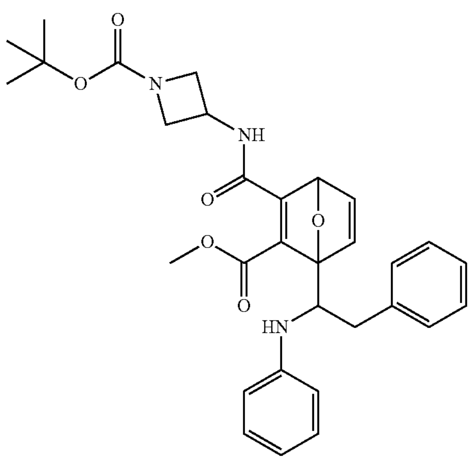 [SMILES: COC(=O)C1=C(C(=O)NC2CN(C(=O)OC(C)(C)C)C2)C2C=CC1(C(Cc1ccccc1)Nc1ccccc1)O2] | | ++ | | | + |
| 405 | 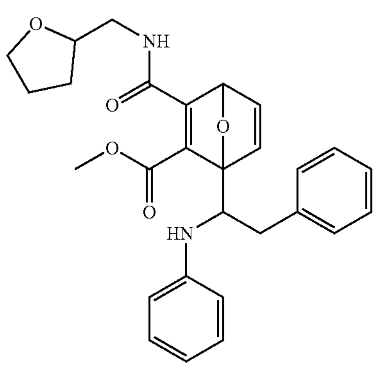 [SMILES: COC(=O)C1=C(C(=O)NCC2CCCO2)C2C=CC1(C(Cc1ccccc1)Nc1ccccc1)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 406 | 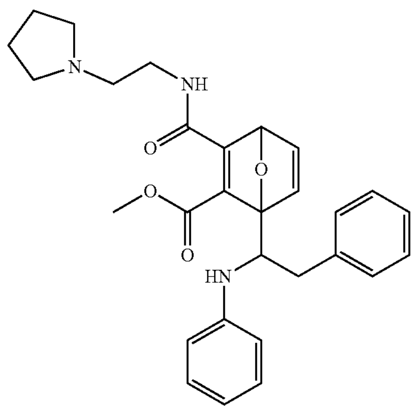 [SMILES: COC(=O)C1=C(C(=O)NCCN2CCCC2)C2C=CC1(C(Cc1ccccc1)Nc1ccccc1)O2] | | +++ | | | ++ |
| 407 | 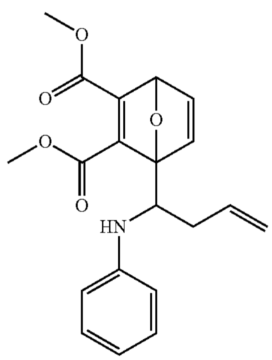 [SMILES: C=CCC(Nc1ccccc1)C12C=CC(O1)C(C(=O)OC)=C2C(=O)OC] | | ++ | | | |
| 409 | 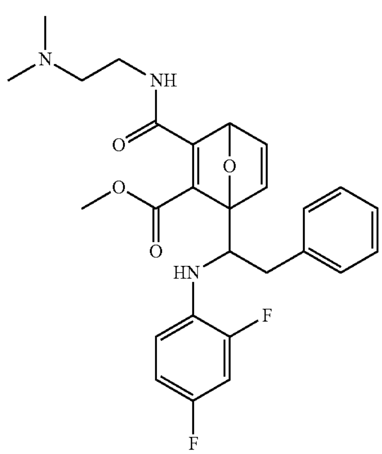 [SMILES: COC(=O)C1=C(C(=O)NCCN(C)C)C2C=CC1(C(Cc1ccccc1)Nc1ccc(F)cc1F)O2] | | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 410 | 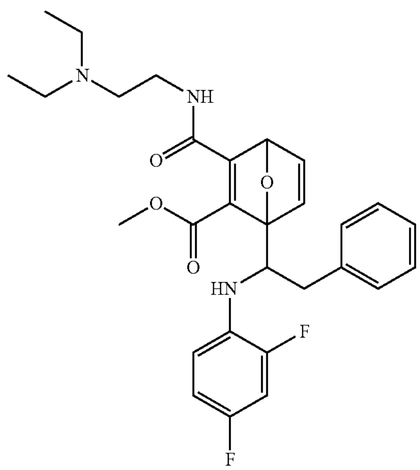 [SMILES: CCN(CC)CCNC(=O)C1=C(C(=O)OC)C2(C(Cc3ccccc3)Nc3ccc(F)cc3F)C=CC1O2] | | ++ | | | + |
| 411 | 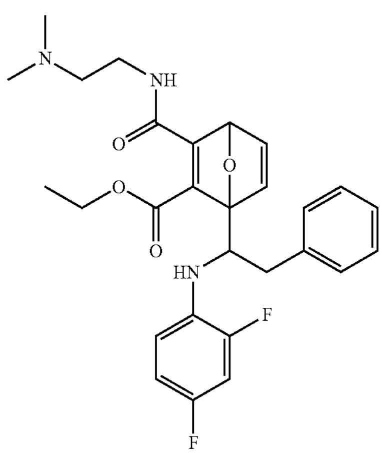 [SMILES: CCOC(=O)C1=C(C(=O)NCCN(C)C)C2C=CC1(C(Cc1ccccc1)Nc1ccc(F)cc1F)O2] | | ++ | | | + |
| 412 | 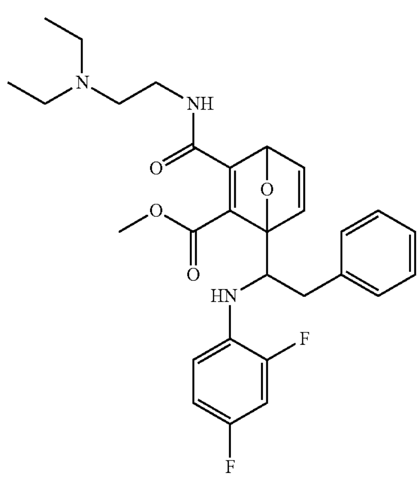 [SMILES: CCN(CC)CCNC(=O)C1=C(C(=O)OC)C2(C(Cc3ccccc3)Nc3ccc(F)cc3F)C=CC1O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 413 | 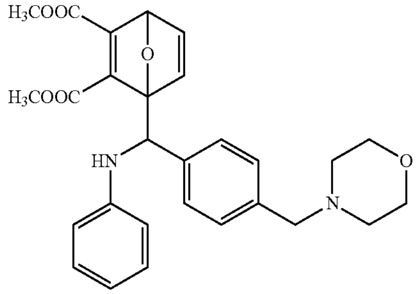 | + | | | | |
| 415 | 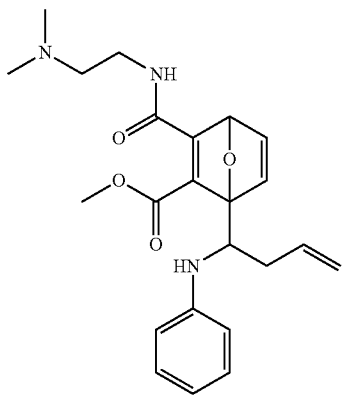 [SMILES: C=CCC(Nc1ccccc1)C12C=CC(O1)C(C(=O)NCCN(C)C)=C2C(=O)OC] | ++ | | | | + |
| 416 | 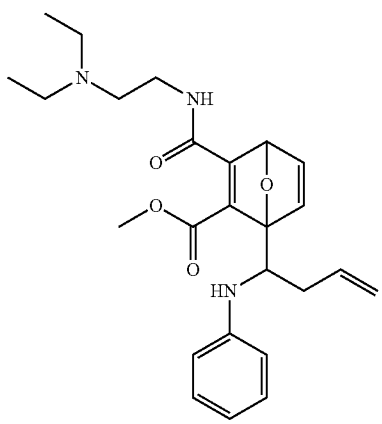 [SMILES: C=CCC(Nc1ccccc1)C12C=CC(O1)C(C(=O)NCCN(CC)CC)=C2C(=O)OC] | ++ | | | | + |
| 417 | 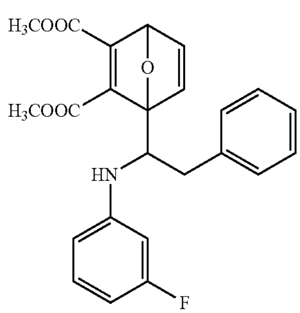 | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 418 | 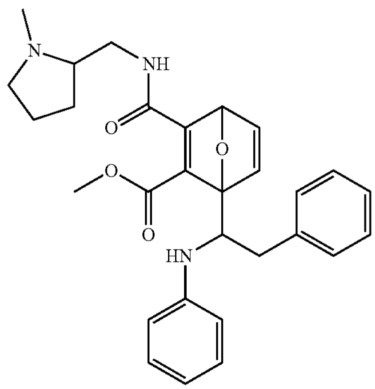 [SMILES: COC(=O)C1=C(C(=O)NCC2CCCN2C)C2C=CC1(C(Cc1ccccc1)Nc1ccccc1)O2] | | ++ | | | ++ |
| 419 | 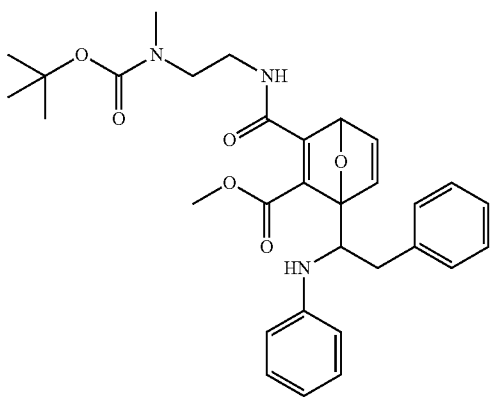 [SMILES: COC(=O)C1=C(C(=O)NCCN(C)C(=O)OC(C)(C)C)C2C=CC1(C(Cc1ccccc1)Nc1ccccc1)O2] | | ++ | | | + |
| 420 | 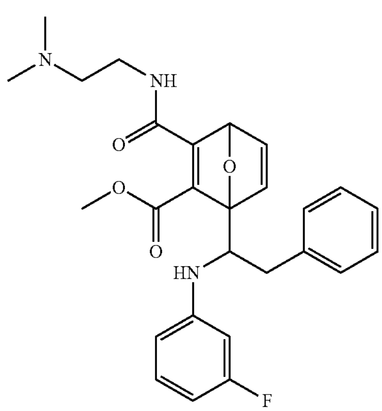 [SMILES: COC(=O)C1=C(C(=O)NCCN(C)C)C2C=CC1(C(Cc1ccccc1)Nc1cccc(F)c1)O2] | | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 421 | 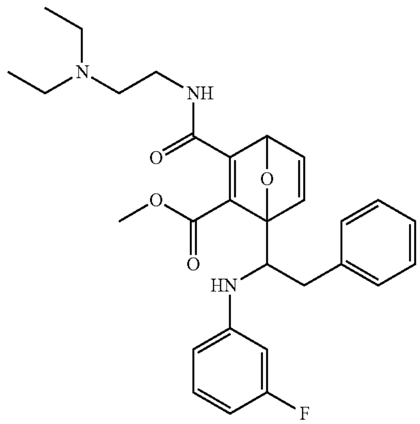 [SMILES: CCN(CC)CCNC(=O)C1=C(C(=O)OC)C2(C(Cc3ccccc3)Nc3cccc(F)c3)C=CC1O2] | ++ | | | | ++ |
| 422 | 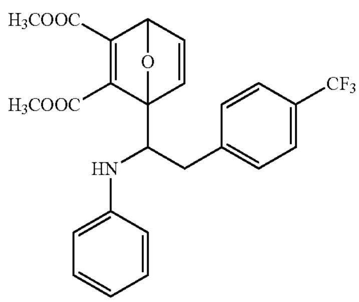 | ++ | | | | + |
| 423 | 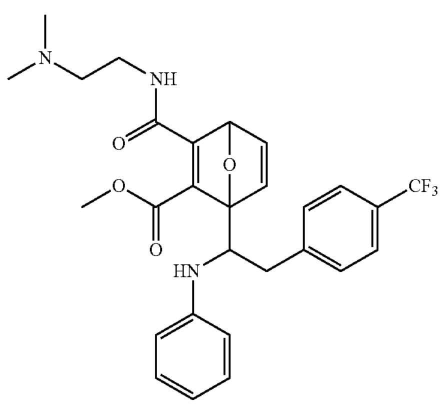 [SMILES: COC(=O)C1=C(C(=O)NCCN(C)C)C2C=CC1(C(Cc1ccc(C(F)(F)F)cc1)Nc1ccccc1)O2] | ++ | | | | ++ |
| 424 | 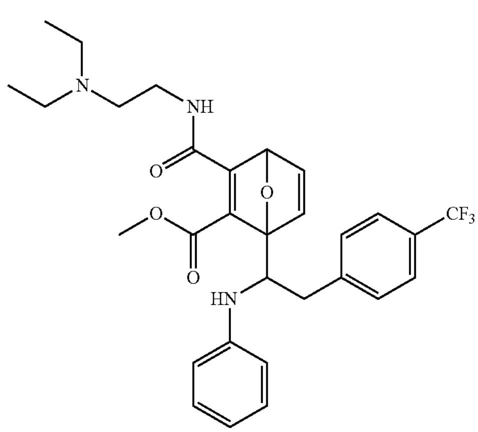 [SMILES: CCN(CC)CCNC(=O)C1=C(C(=O)OC)C2(C(Cc3ccc(C(F)(F)F)cc3)Nc3ccccc3)C=CC1O2] | ++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 425 | [structure] | | ++ | | | + |
| 426 | [structure] | | ++ | | | ++ |
| 427 | [structure] | | ++ | | | ++ |
| 428 | [structure] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 429 | 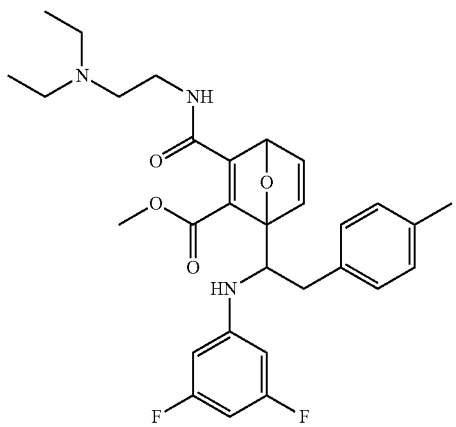 [SMILES: CCN(CC)CCNC(=O)C1=C(C(=O)OC)C2(C(Cc3ccc(C)cc3)Nc3cc(F)cc(F)c3)C=CC1O2] | | ++ | | | ++ |
| 430 | 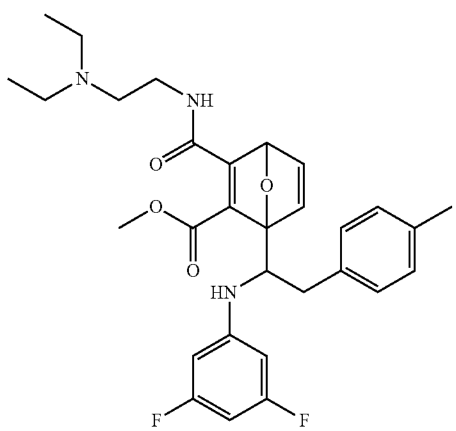 [SMILES: CCN(CC)CCNC(=O)C1=C(C(=O)OC)C2(C(Cc3ccc(C)cc3)Nc3cc(F)cc(F)c3)C=CC1O2] | | ++ | | | ++ |
| 431 | 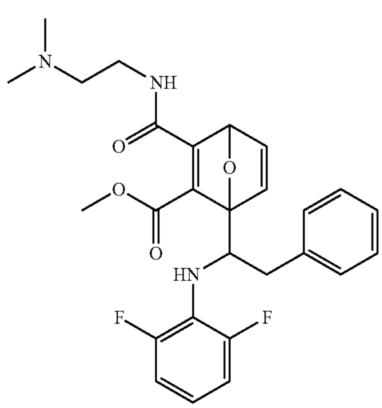 [SMILES: COC(=O)C1=C(C(=O)NCCN(C)C)C2C=CC1(C(Cc1ccccc1)Nc1c(F)cccc1F)O2] | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 432 | 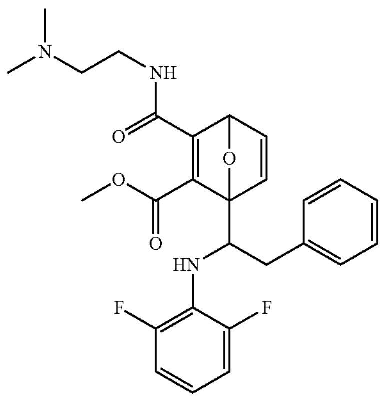 [SMILES: COC(=O)C1=C(C(=O)NCCN(C)C)C2C=CC1(C(Cc1ccccc1)Nc1c(F)cccc1F)O2] | | ++ | | | + |
| 433 | 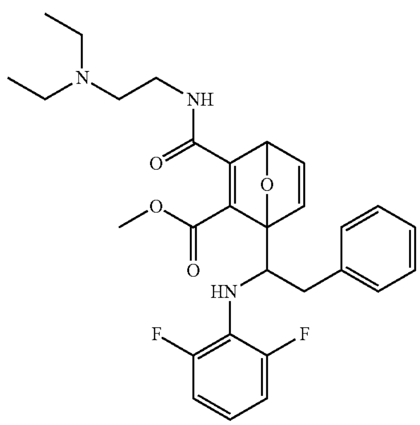 [SMILES: CCN(CC)CCNC(=O)C1=C(C(=O)OC)C2(C(Cc3ccccc3)Nc3c(F)cccc3F)C=CC1O2] | | ++ | | | + |
| 434 | 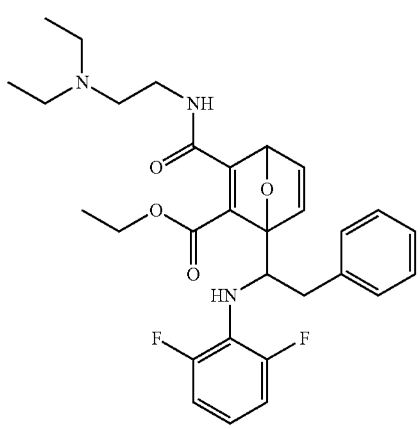 [SMILES: CCOC(=O)C1=C(C(=O)NCCN(CC)CC)C2C=CC1(C(Cc1ccccc1)Nc1c(F)cccc1F)O2] | | ++ | | | ++ |

TABLE I-continued
compounds synthesized and biological activities.
| Compound number | Structure | SUMO | Nedd8 | Atg7 | Ubiquitin | c-Myc |
|---|---|---|---|---|---|---|
| 435 | 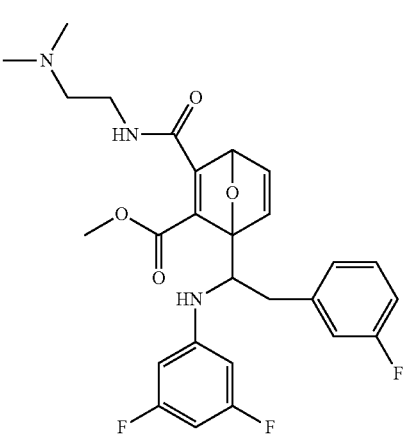 [SMILES: COC(=O)C1=C(C(=O)NCCN(C)C)C2C=CC1(C(Cc1cccc(F)c1)Nc1cc(F)cc(F)c1)O2] | +++ | | | | ++ |
| 436 | 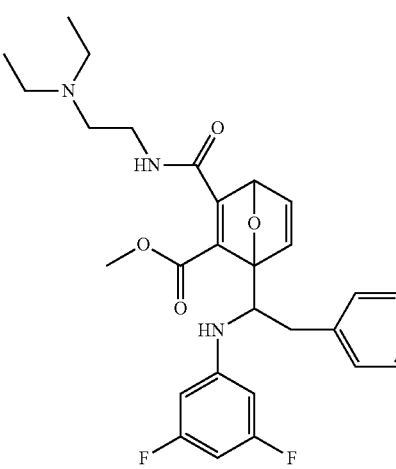 | +++ | | | | ++ |
| 437 | 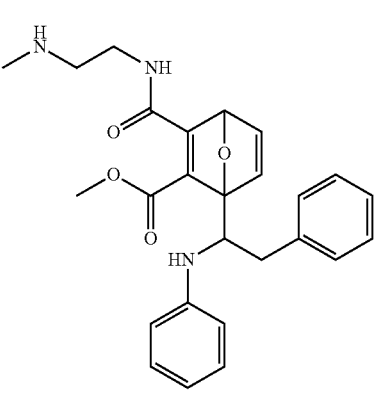 [SMILES: CNCCNC(=O)C1=C(C(=O)OC)C2(C(Cc3ccccc3)Nc3ccccc3)C=CC1O2] | + | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 438 | 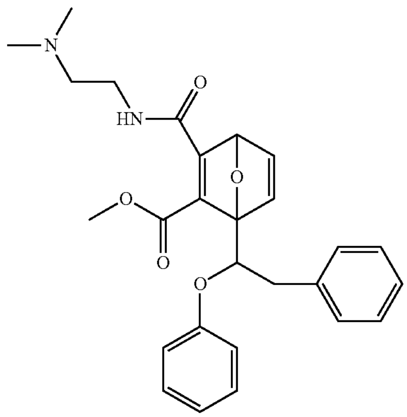 [SMILES: COC(=O)C1=C(C(=O)NCCN(C)C)C2C=CC1(C(Cc1ccccc1)Oc1ccccc1)O2] | ++ | | | | ++ |
| 439 | 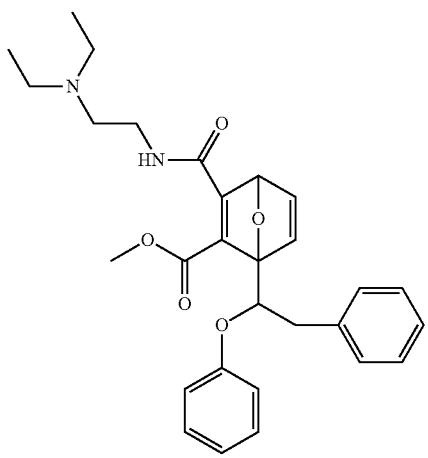 [SMILES: CCN(CC)CCNC(=O)C1=C(C(=O)OC)C2(C(Cc3ccccc3)Oc3ccccc3)C=CC1O2] | ++ | | | | ++ |
| 440 | 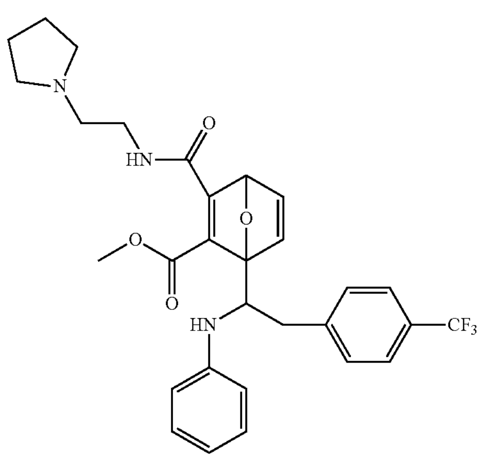 [SMILES: COC(=O)C1=C(C(=O)NCCN2CCCC2)C2C=CC1(C(Cc1ccc(C(F)(F)F)cc1)Nc1ccccc1)O2] | +++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 441 | 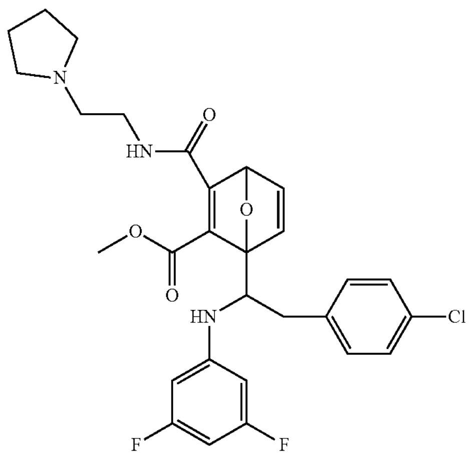 [SMILES: COC(=O)C1=C(C(=O)NCCN2CCCC2)C2C=CC1(C(Cc1ccc(Cl)cc1)Nc1cc(F)cc(F)c1)O2] | +++ | | | | ++ |
| 442 | 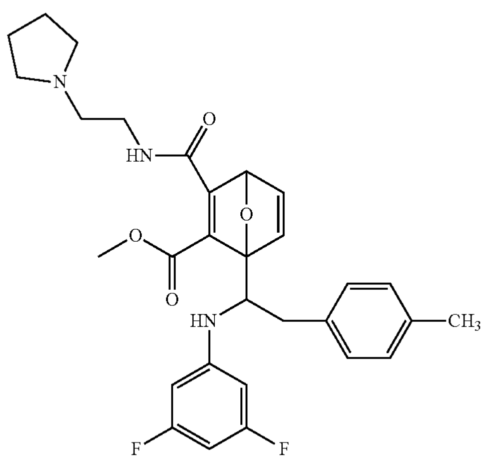 [SMILES: COC(=O)C1=C(C(=O)NCCN2CCCC2)C2C=CC1(C(Cc1ccc(C)cc1)Nc1cc(F)cc(F)c1)O2] | +++ | | | | ++ |
| 443 | 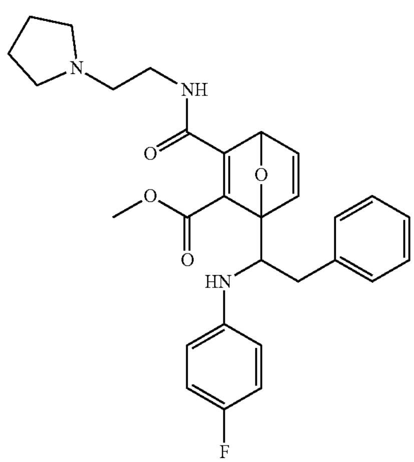 [SMILES: COC(=O)C1=C(C(=O)NCCN2CCCC2)C2C=CC1(C(Cc1ccccc1)Nc1ccc(F)cc1)O2] | +++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 444 | 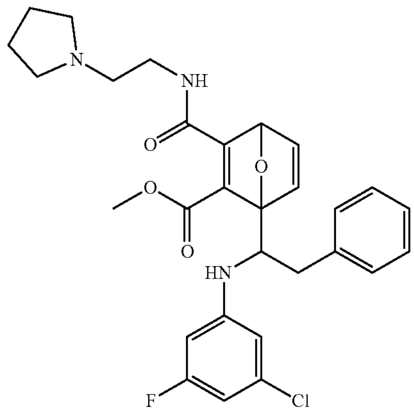 [SMILES: COC(=O)C1=C(C(=O)NCCN2CCCC2)C2C=CC1(C(Cc1ccccc1)Nc1cc(F)cc(Cl)c1)O2] | +++ | | | | ++ |
| 445 | 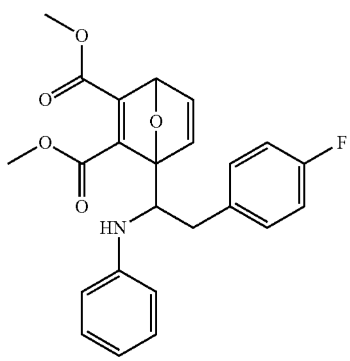 [SMILES: COC(=O)C1=C(C(=O)OC)C2(C(Cc3ccc(F)cc3)Nc3ccccc3)C=CC1O2] | ++ | | | | + |
| 446 | 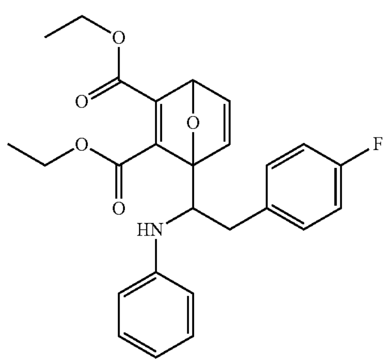 [SMILES: CCOC(=O)C1=C(C(=O)OCC)C2(C(Cc3ccc(F)cc3)Nc3ccccc3)C=CC1O2] | ++ | | | | + |
| 451 | 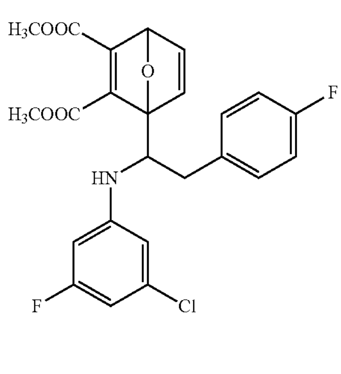 | +++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 452 | 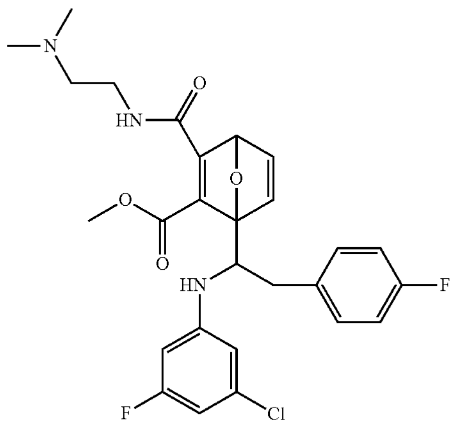 [SMILES: COC(=O)C1=C(C(=O)NCCN(C)C)C2C=CC1(C(Cc1ccc(F)cc1)Nc1cc(F)cc(Cl)c1)O2] | | ++ | | | + |
| 453 | 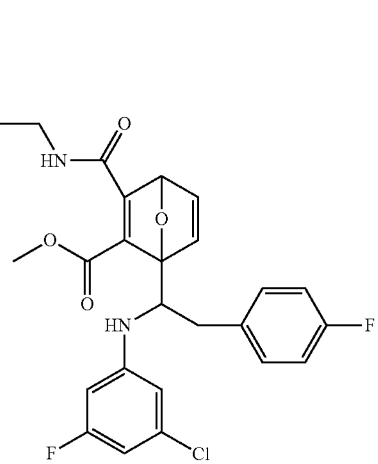 | | ++ | | | + |
| 454 | 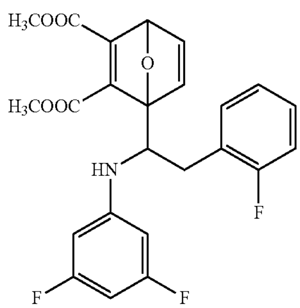 | | +++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 455 | 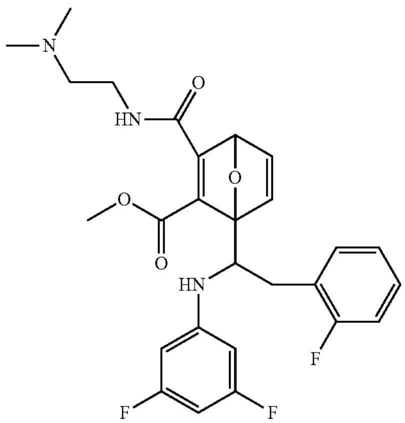 [SMILES: COC(=O)C1=C(C(=O)NCCN(C)C)C2C=CC1(C(Cc1ccccc1F)Nc1cc(F)cc(F)c1)O2] | ++ | | | | ++ |
| 456 | 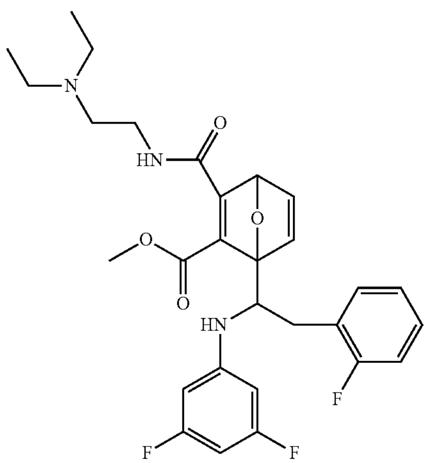 [SMILES: CCN(CC)CCNC(=O)C1=C(C(=O)OC)C2(C(Cc3ccccc3F)Nc3cc(F)cc(F)c3)C=CC1O2] | ++ | | | | ++ |
| 462 | 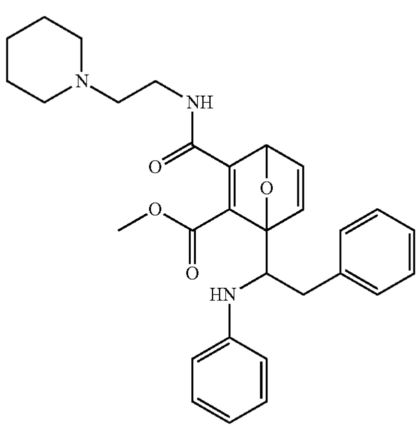 [SMILES: COC(=O)C1=C(C(=O)NCCN2CCCCC2)C2C=CC1(C(Cc1ccccc1)Nc1ccccc1)O2] | ++ | | ++ | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 463 | 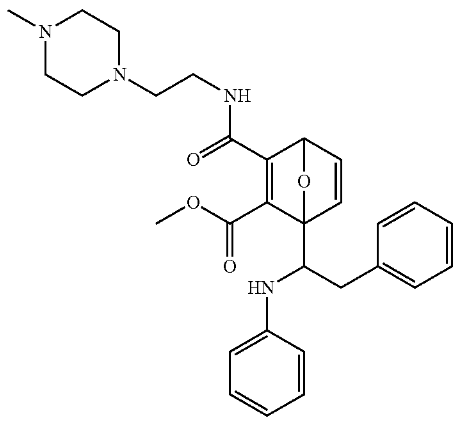 [SMILES: COC(=O)C1=C(C(=O)NCCN2CCN(C)CC2)C2C=CC1(C(Cc1ccccc1)Nc1ccccc1)O2] | | ++ | | ++ | ++ |
| 469 | 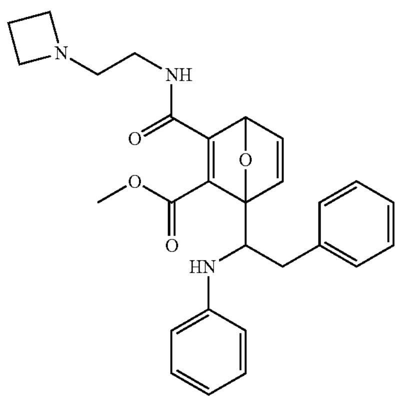 [SMILES: COC(=O)C1=C(C(=O)NCCN2CCC2)C2C=CC1(C(Cc1ccccc1)Nc1ccccc1)O2] | | ++ | | | + |
| 477 | 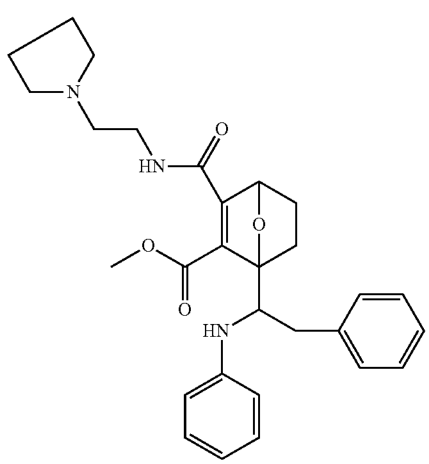 [SMILES: COC(=O)C1=C(C(=O)NCCN2CCCC2)C2CCC1(C(Cc1ccccc1)Nc1ccccc1)O2] | | | | | |

TABLE I-continued compounds synthesized and biological activities.

| Compound number | Structure | SUMO | Nedd8 | Atg7 | Ubiquitin | c-Myc |
|---|---|---|---|---|---|---|
| 478 | 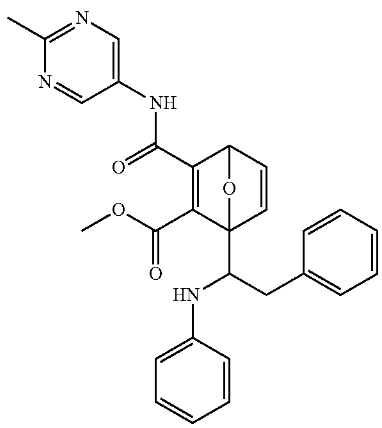 [SMILES: COC(=O)C1=C(C(=O)Nc2cnc(C)nc2)C2C=CC1(C(Cc1ccccc1)Nc1ccccc1)O2] | +++ | | | | + |
| 479 | 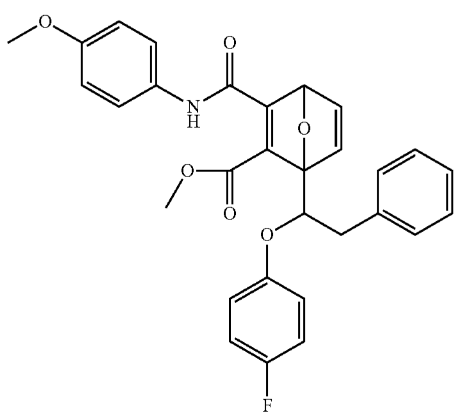 [SMILES: COC(=O)C1=C(C(=O)Nc2ccc(OC)cc2)C2C=CC1(C(Cc1ccccc1)Oc1ccc(F)cc1)O2] | ++ | | | | |
| 480 | 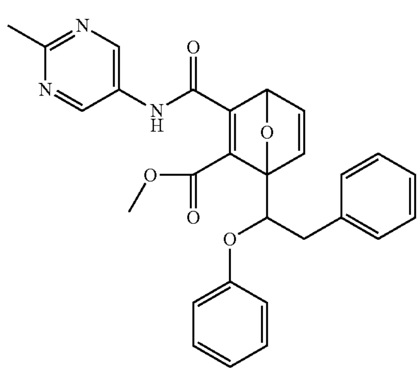 [SMILES: COC(=O)C1=C(C(=O)Nc2cnc(C)nc2)C2C=CC1(C(Cc1ccccc1)Oc1ccccc1)O2] | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 482 | 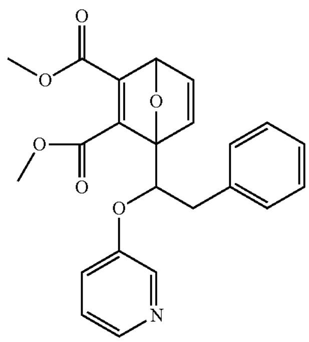 [SMILES: COC(=O)C1=C(C(=O)OC)C2(C(Cc3ccccc3)Oc3cccnc3)C=CC1O2] | | + | | | |
| 484 | 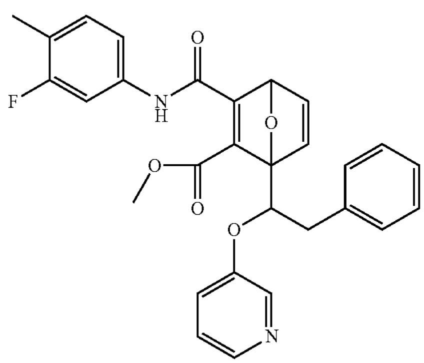 [SMILES: COC(=O)C1=C(C(=O)Nc2ccc(C)c(F)c2)C2C=CC1(C(Cc1ccccc1)Oc1cccnc1)O2] | | + | | | |
| 485 | 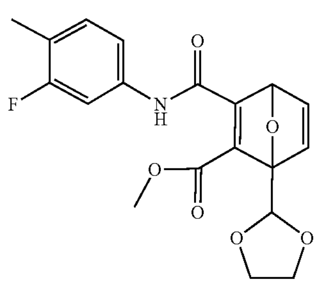 [SMILES: COC(=O)C1=C(C(=O)Nc2ccc(C)c(F)c2)C2C=CC1(C1OCCO1)O2] | | + | | | |
| 486 | 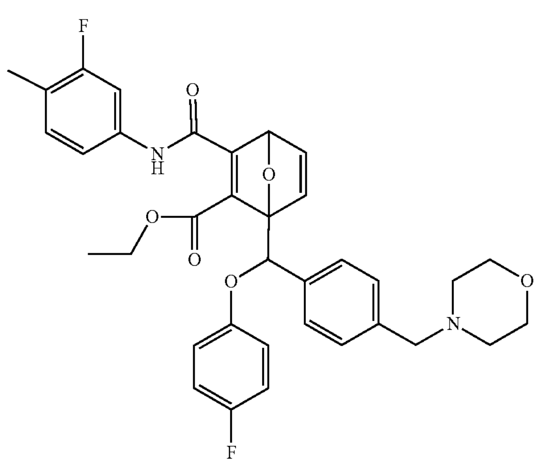 [SMILES: CCOC(=O)C1=C(C(=O)Nc2ccc(C)c(F)c2)C2C=CC1(C(Oc1ccc(F)cc1)c1ccc(CN3CCOCC3)cc1)O2] | | + | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 488 | 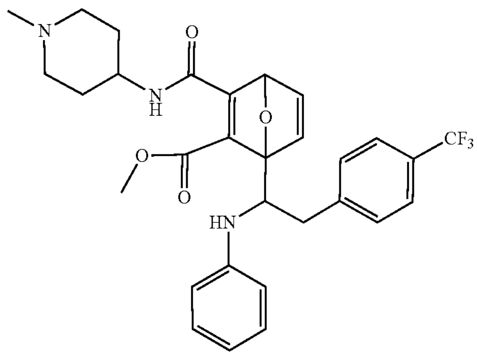 [SMILES: COC(=O)C1=C(C(=O)NC2CCN(C)CC2)C2C=CC1(C(Cc1ccc(C(F)(F)F)cc1)Nc1ccccc1)O2] | | ++ | | | ++ |
| 489 | 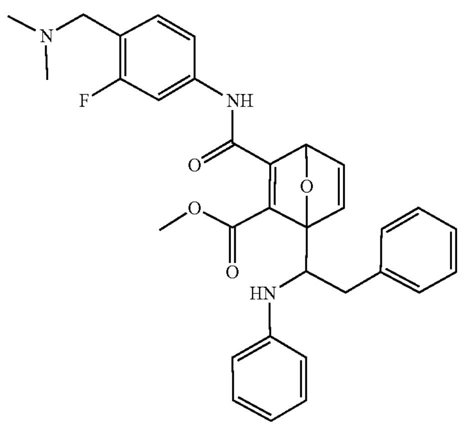 [SMILES: COC(=O)C1=C(C(=O)Nc2ccc(CN(C)C)c(F)c2)C2C=CC1(C(Cc1ccccc1)Nc1ccccc1)O2] | | ++ | | | + |
| 491 | 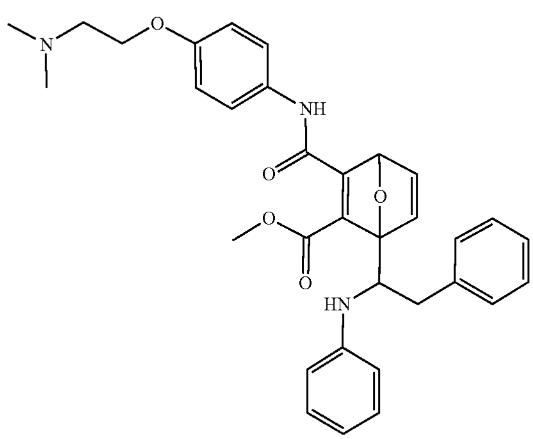 [SMILES: COC(=O)C1=C(C(=O)Nc2ccc(OCCN(C)C)cc2)C2C=CC1(C(Cc1ccccc1)Nc1ccccc1)O2] | | +++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 492 | 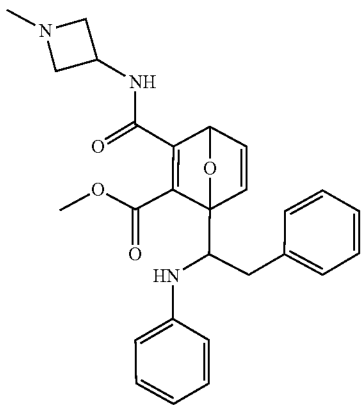 [SMILES: COC(=O)C1=C(C(=O)NC2CN(C)C2)C2C=CC1(C(Cc1ccccc1)Nc1ccccc1)O2] | +++ | | | | + |
| 494 | 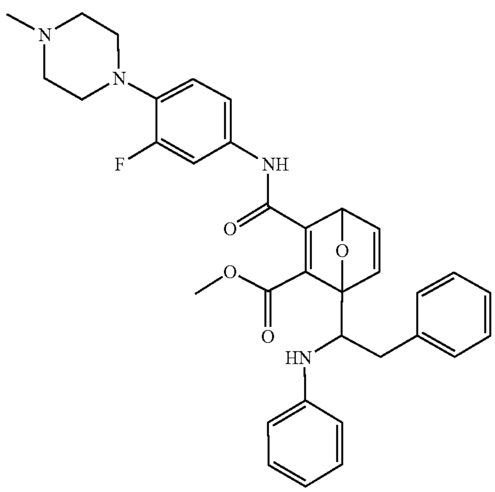 [SMILES: COC(=O)C1=C(C(=O)Nc2ccc(N3CCN(C)CC3)c(F)c2)C2C=CC1(C(Cc1ccccc1)Nc1ccccc1)O2] | + | | | | + |
| 495 | 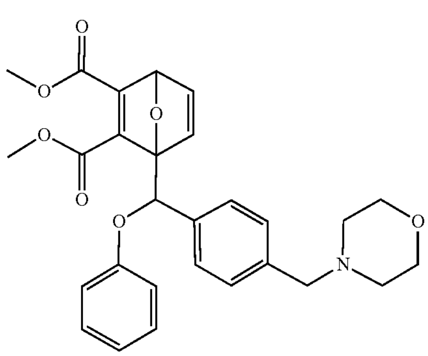 [SMILES: COC(=O)C1=C(C(=O)OC)C2(C(Oc3ccccc3)c3ccc(CN4CCOCC4)cc3)C=CC1O2] | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 496 | 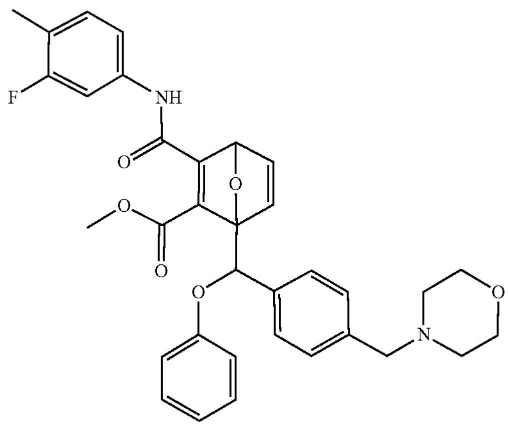 [SMILES: COC(=O)C1=C(C(=O)Nc2ccc(C)c(F)c2)C2C=CC1(C(Oc1ccccc1)c1ccc(CN3CCOCC3)cc1)O2] | + | | | | + |
| 500 | 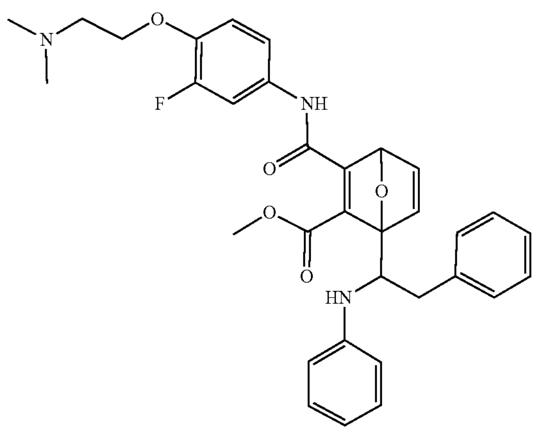 [SMILES: COC(=O)C1=C(C(=O)Nc2ccc(OCCN(C)C)c(F)c2)C2C=CC1(C(Cc1ccccc1)Nc1ccccc1)O2] | ++ | | | | + |
| 501 | 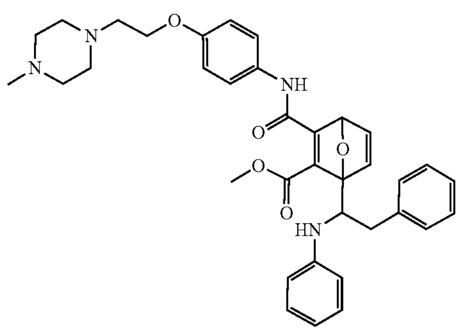 [SMILES: COC(=O)C1=C(C(=O)Nc2ccc(OCCN3CCN(C)CC3)cc2)C2C=CC1(C(Cc1ccccc1)Nc1ccccc1)O2] | +++ | | | | + |
| 502 | 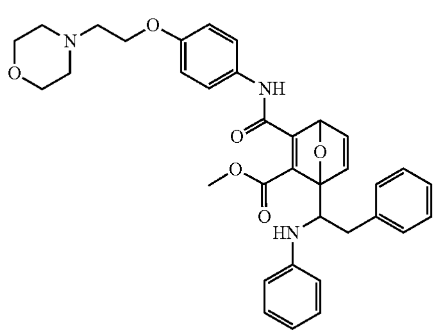 [SMILES: COC(=O)C1=C(C(=O)Nc2ccc(OCCN3CCOCC3)cc2)C2C=CC1(C(Cc1ccccc1)Nc1ccccc1)O2] | +++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 504 | 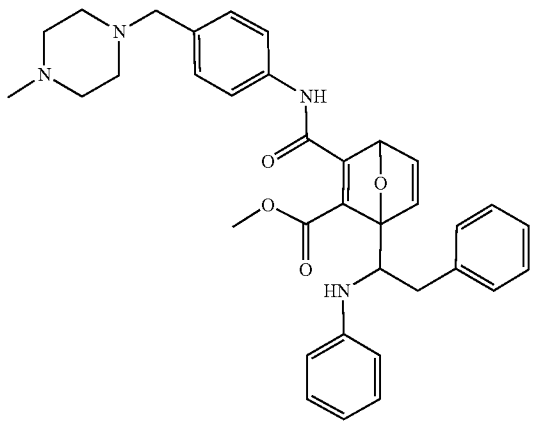 [SMILES: COC(=O)C1=C(C(=O)Nc2ccc(CN3CCN(C)CC3)cc2)C2C=CC1(C(Cc1ccccc1)Nc1ccccc1)O2] | ++ | | | | + |
| 505 | 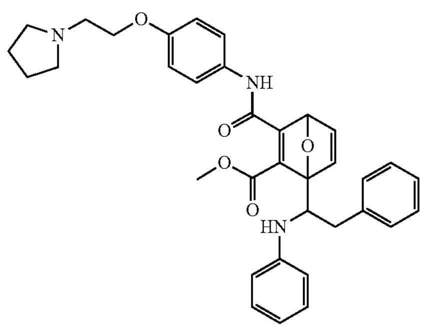 [SMILES: COC(=O)C1=C(C(=O)Nc2ccc(OCCN3CCCC3)cc2)C2C=CC1(C(Cc1ccccc1)Nc1ccccc1)O2] | ++ | | | | + |
| 506 | 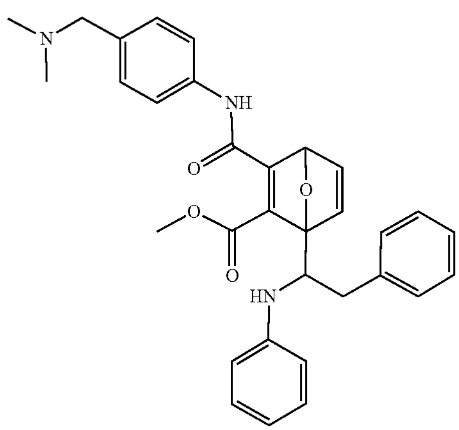 [SMILES: COC(=O)C1=C(C(=O)Nc2ccc(CN(C)C)cc2)C2C=CC1(C(Cc1ccccc1)Nc1ccccc1)O2] | ++ | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 507 | 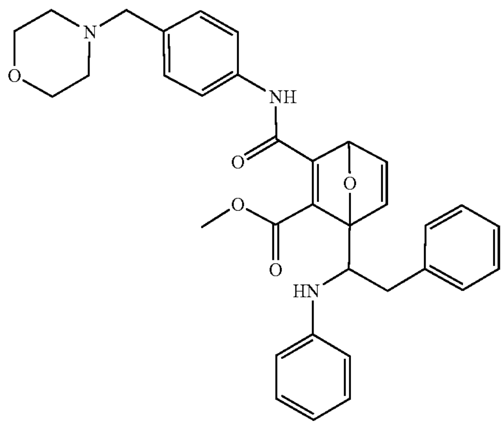 [SMILES: COC(=O)C1=C(C(=O)Nc2ccc(CN3CCOCC3)cc2)C2C=CC1(C(Cc1ccccc1)Nc1ccccc1)O2] | | ++ | | | + |
| 508 | 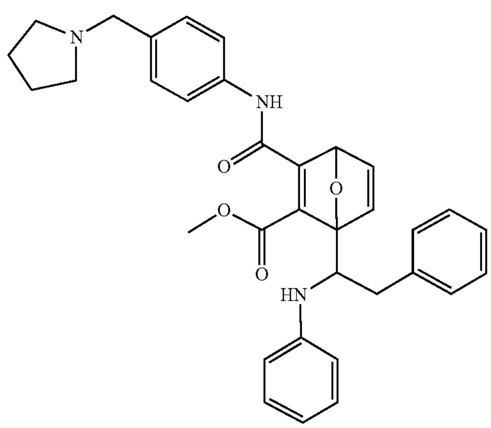 [SMILES: COC(=O)C1=C(C(=O)Nc2ccc(CN3CCCC3)cc2)C2C=CC1(C(Cc1ccccc1)Nc1ccccc1)O2] | | ++ | | | + |
| 513 | 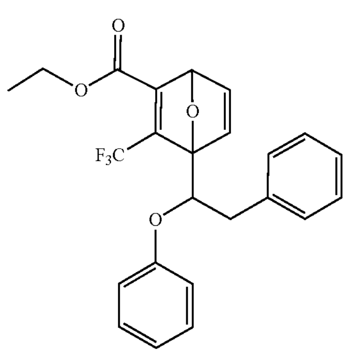 [SMILES: CCOC(=O)C1=C(C(F)(F)F)C2(C(Cc3ccccc3)Oc3ccccc3)C=CC1O2] | | ++ | | | ++ |
| 515 | 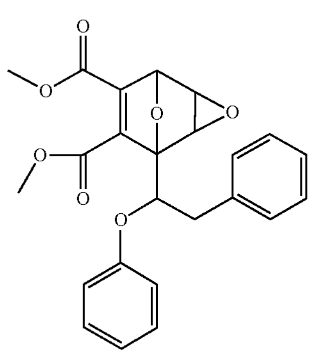 | | ++ | | | + |

TABLE I-continued compounds synthesized and biological activities.

| Compound number | Structure | SUMO | Nedd8 | Atg7 | Ubiquitin | c-Myc |
|---|---|---|---|---|---|---|
| 516 | 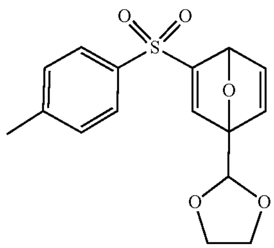 [SMILES: Cc1ccc(S(=O)(=O)C2=CC3(C4OCCO4)C=CC2O3)cc1] | | ++ | | | + |
| 518 | 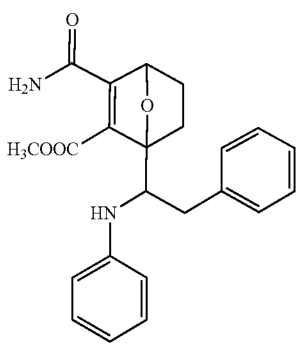 | | | | | |
| 519 | 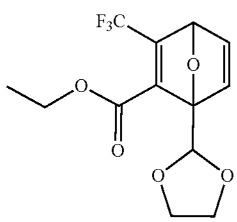 [SMILES: CCOC(=O)C1=C(C(F)(F)F)C2C=CC1(C1OCCO1)O2] | | ++ | | | + |
| 520 | 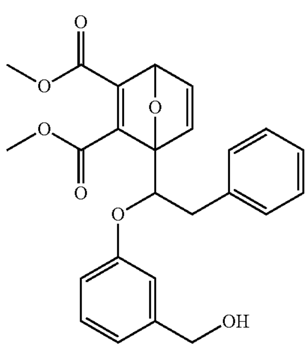 [SMILES: COC(=O)C1=C(C(=O)OC)C2(C(Cc3ccccc3)Oc3cccc(CO)c3)C=CC1O2] | | ++ | | | |
| 521 | 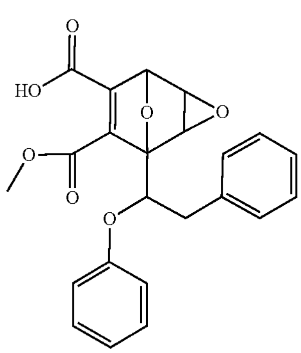 | | | | | |

TABLE I-continued compounds synthesized and biological activities.

| Compound number | Structure | SUMO | Nedd8 | Atg7 | Ubiquitin | c-Myc |
|---|---|---|---|---|---|---|
| 522 | 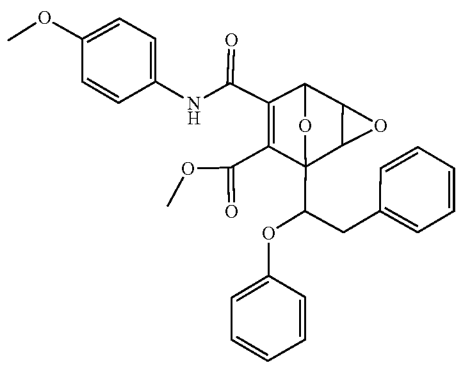 [SMILES: COC(=O)C1=C(C(=O)Nc2ccc(OC)cc2)C2OC1(C(Cc1ccccc1)Oc1ccccc1)C1OC21] | | + | | | + |
| 523 | 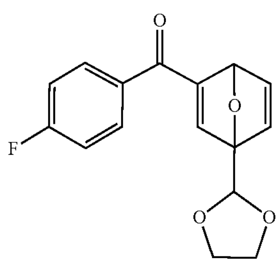 [SMILES: O=C(C1=CC2(C3OCCO3)C=CC1O2)c1ccc(F)cc1] | | ++ | | | + |
| 525 | 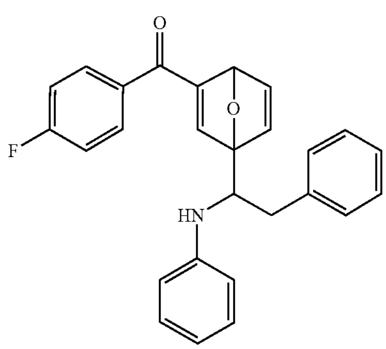 [SMILES: O=C(C1=CC2(C(Cc3ccccc3)Nc3ccccc3)C=CC1O2)c1ccc(F)cc1] | | + | | | + |
| 526 | 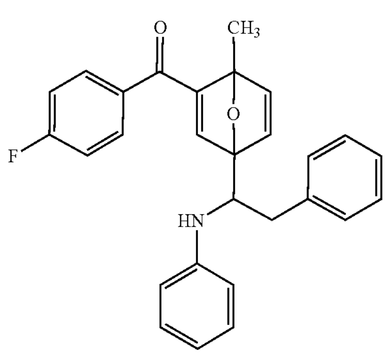 [SMILES: CC12C=CC(C(Cc3ccccc3)Nc3ccccc3)(C=C1C(=O)c1ccc(F)cc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 527 | 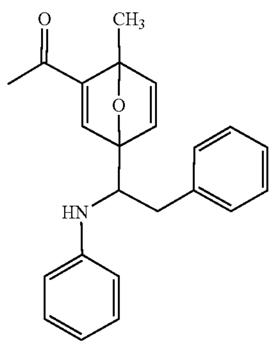 [SMILES: CC(=O)C1=CC2(C(Cc3ccccc3)Nc3ccccc3)C=CC1(C)O2] | | + | | | + |
| 528 | 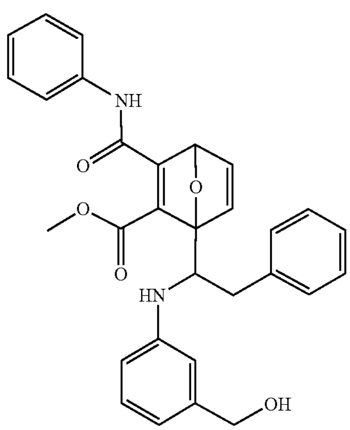 [SMILES: COC(=O)C1=C(C(=O)Nc2ccccc2)C2C=CC1(C(Cc1ccccc1)Nc1cccc(CO)c1)O2] | | ++ | | | ++ |
| 530 | 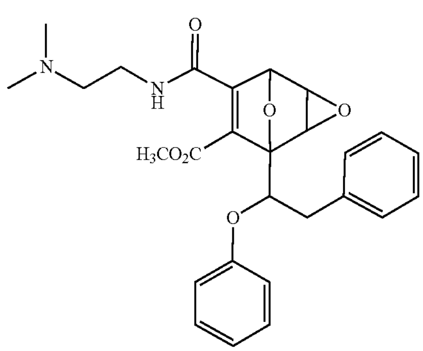 | + | ++ | | | ++ |
| 531 | 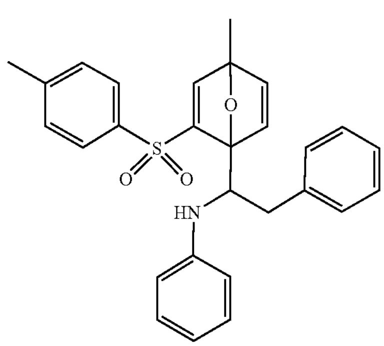 [SMILES: Cc1ccc(S(=O)(=O)C2=CC3(C)C=CC2(C(Cc2ccccc2)Nc2ccccc2)O3)cc1] | + | ++ | | | |

TABLE I-continued
compounds synthesized and biological activities.
| Compound number | Structure | SUMO | Nedd8 | Atg7 | Ubiquitin | c-Myc |
|---|---|---|---|---|---|---|
| 532 | 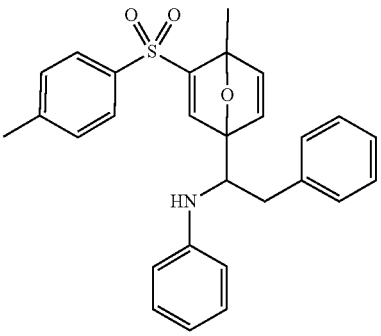 [SMILES: Cc1ccc(S(=O)(=O)C2=CC3(C(Cc4ccccc4)Nc4ccccc4)C=CC2(C)O3)cc1] | + | | | | |
| 534 | 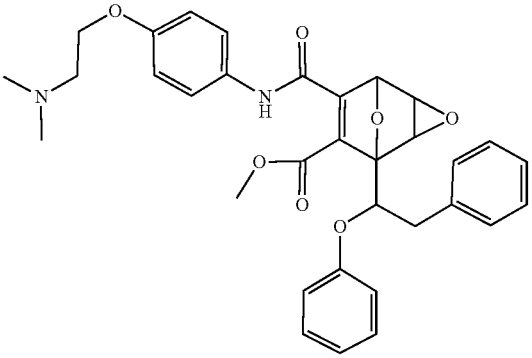 [SMILES: COC(=O)C1=C(C(=O)Nc2ccc(OCCN(C)C)cc2)C2OC1(C(Cc1ccccc1)Oc1ccccc1)C1OC21] | + | ++ | | + | ++ |
| 535 | 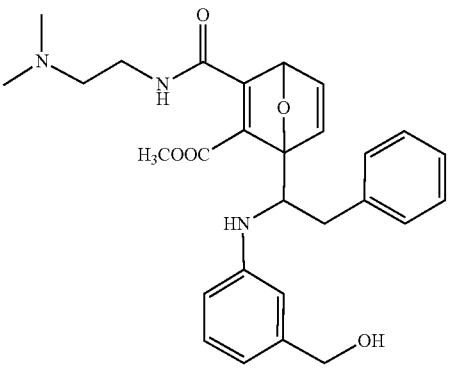 | +++ | ++ | | + | ++ |
| 536 | 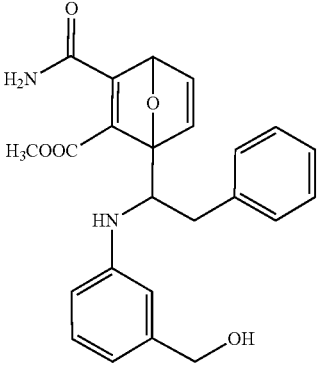 | ++ | ++ | | + | |

TABLE I-continued
compounds synthesized and biological activities.
| Compound number | Structure | SUMO | Nedd8 | Atg7 | Ubiquitin | c-Myc |
|---|---|---|---|---|---|---|
| 537 | 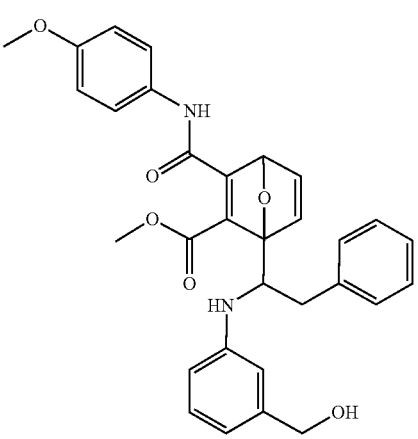 [SMILES: COC(=O)C1=C(C(=O)Nc2ccc(OC)cc2)C2C=CC1(C(Cc1ccccc1)Nc1cccc(CO)c1)O2] | ++ | ++ | | | + |
| 539 | 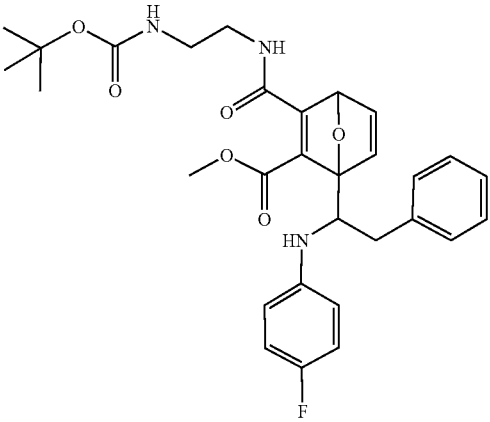 [SMILES: COC(=O)C1=C(C(=O)NCCNC(=O)OC(C)(C)C)C2C=CC1(C(Cc1ccccc1)Nc1ccc(F)cc1)O2] | ++ | | | | |
| 540 | 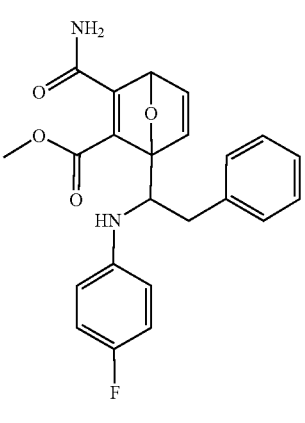 [SMILES: COC(=O)C1=C(C(N)=O)C2C=CC1(C(Cc1ccccc1)Nc1ccc(F)cc1)O2] | ++ | ++ | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 541 | 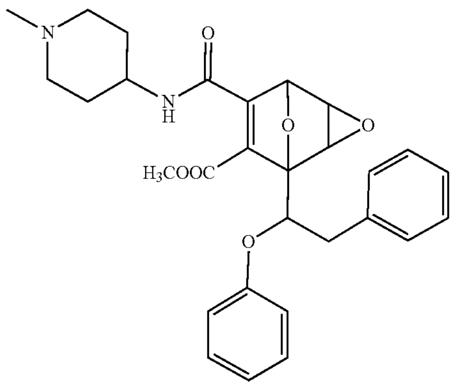 | ++ | ++ | | | ++ |
| 542 | 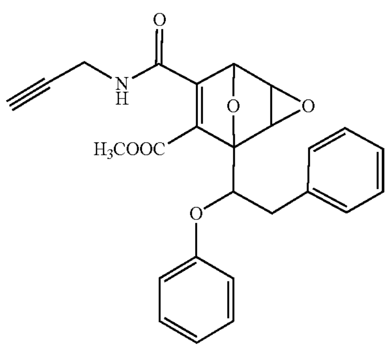 | | + | | + | + |
| 543 | 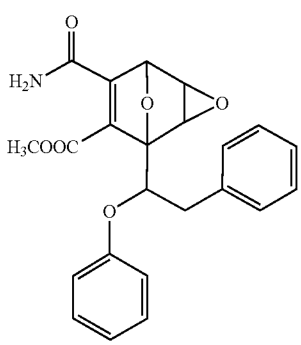 | | + | + | | ++ |
| 544 | 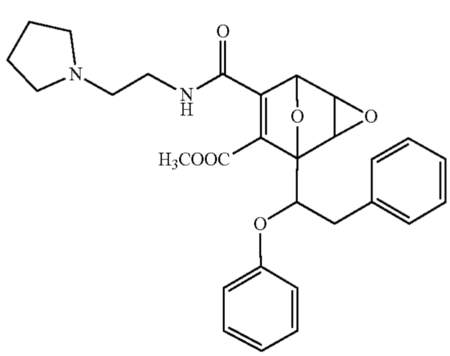 | | + | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 545 | 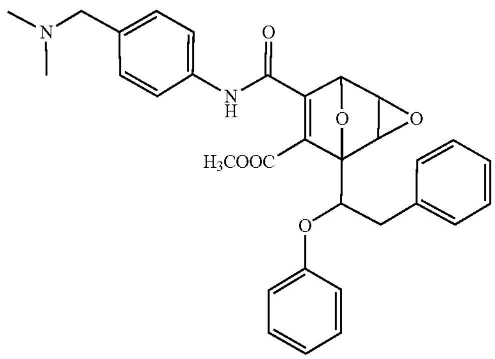 | ++ | | | + | ++ |
| 546 | 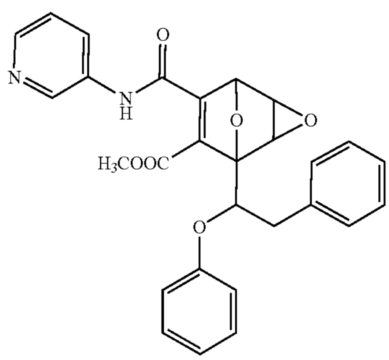 | ++ | | | | + |
| 547 | 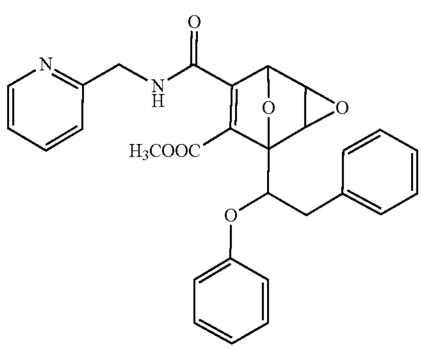 | ++ | | | | ++ |
| 548 | 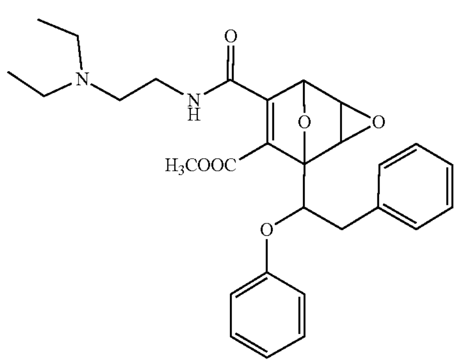 | + | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 549 | 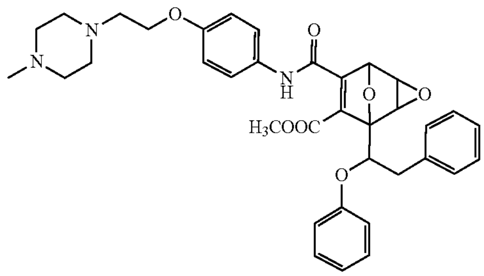 | ++ | | | | ++ |
| 550 | 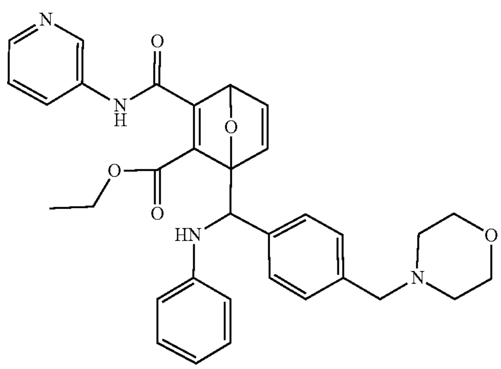 [SMILES: CCOC(=O)C1=C(C(=O)Nc2cccnc2)C2C=CC1(C(Nc1ccccc1)c1ccc(CN3CCOCC3)cc1)O2] | +++ | | | | + |
| 552 | 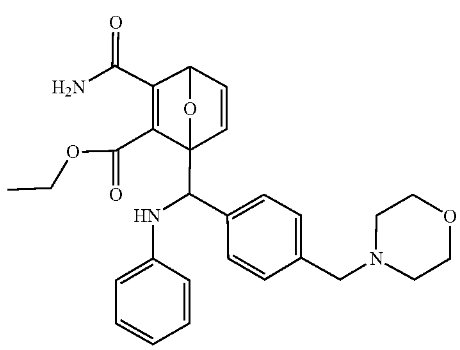 [SMILES: CCOC(=O)C1=C(C(N)=O)C2C=CC1(C(Nc1ccccc1)c1ccc(CN3CCOCC3)cc1)O2] | ++ | | | | + |
| 554 | 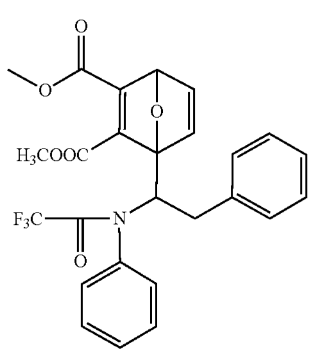 | ++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 555 | 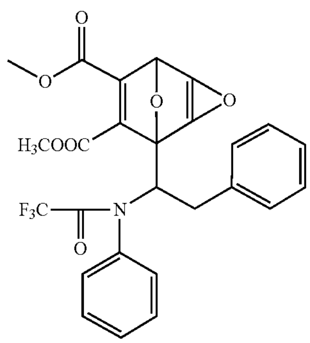 | | + | | | + |
| 556 | 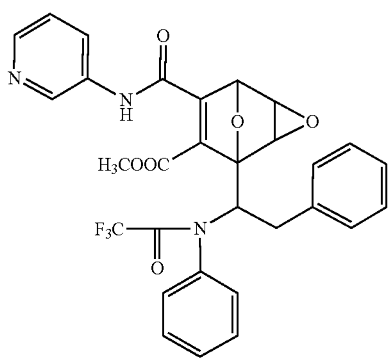 | | ++ | | | + |
| 557 | 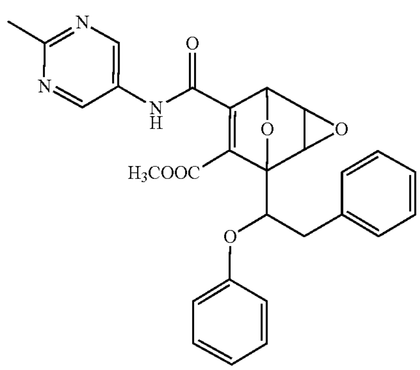 | | ++ | | | ++ |
| 558 | 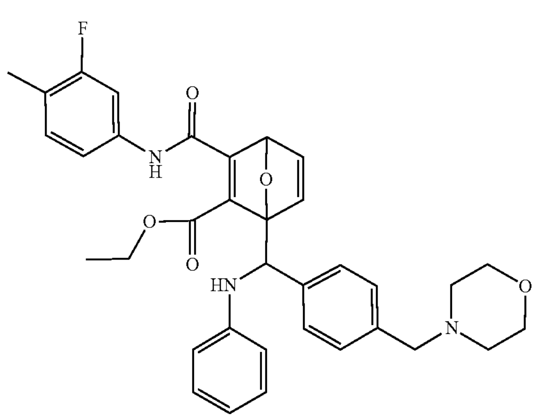 [SMILES: CCOC(=O)C1=C(C(=O)Nc2ccc(C)c(F)c2)C2C=CC1(C(Nc1ccccc1)c1ccc(CN3CCOCC3)cc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 564 | 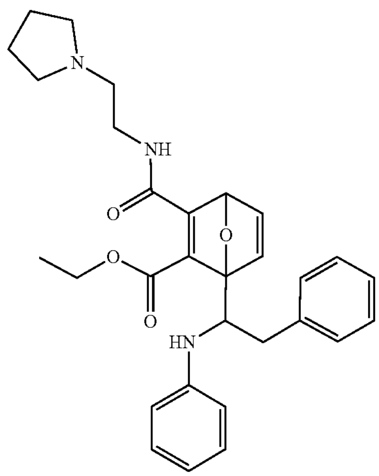 [SMILES: CCOC(=O)C1=C(C(=O)NCCN2CCCC2)C2C=CC1(C(Cc1ccccc1)Nc1ccccc1)O2] | | ++ | | | + |
| 565 | 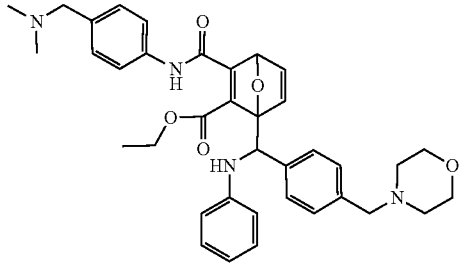 [SMILES: CCOC(=O)C1=C(C(=O)Nc2ccc(CN(C)C)cc2)C2C=CC1(C(Nc1ccccc1)c1ccc(CN3CCOCC3)cc1)O2] | | + | | | + |
| 567 | 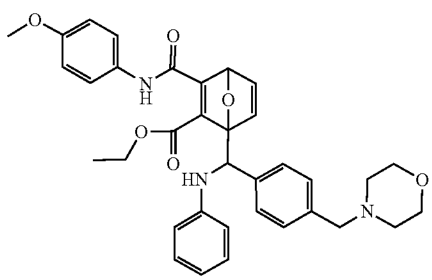 [SMILES: CCOC(=O)C1=C(C(=O)Nc2ccc(OC)cc2)C2C=CC1(C(Nc1ccccc1)c1ccc(CN3CCOCC3)cc1)O2] | | ++ | | | + |
| 569 | 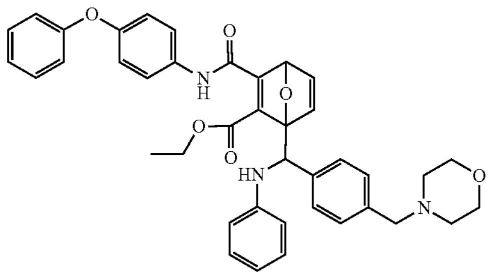 [SMILES: CCOC(=O)C1=C(C(=O)Nc2ccc(Oc3ccccc3)cc2)C2C=CC1(C(Nc1ccccc1)c1ccc(CN3CCOCC3)cc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 571 | 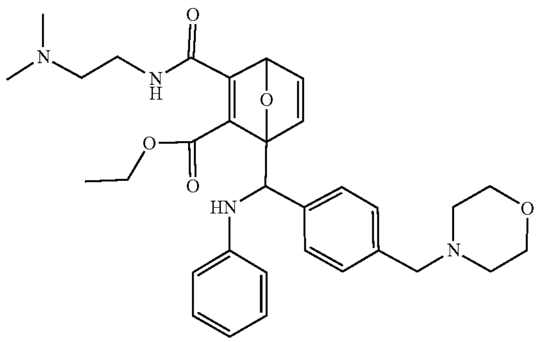 [SMILES: CCOC(=O)C1=C(C(=O)NCCN(C)C)C2C=CC1(C(Nc1ccccc1)c1ccc(CN3CCOCC3)cc1)O2] | | ++ | | | + |
| 573 | 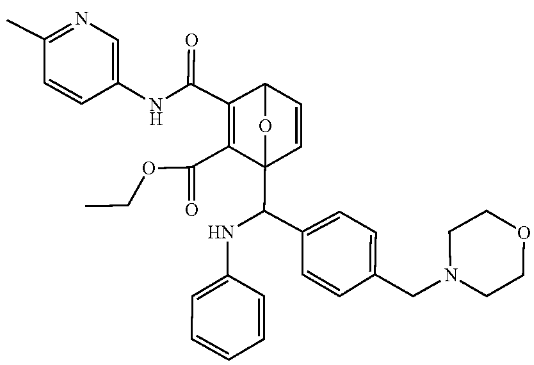 [SMILES: CCOC(=O)C1=C(C(=O)Nc2ccc(C)nc2)C2C=CC1(C(Nc1ccccc1)c1ccc(CN3CCOCC3)cc1)O2] | | + | | | + |
| 577 | 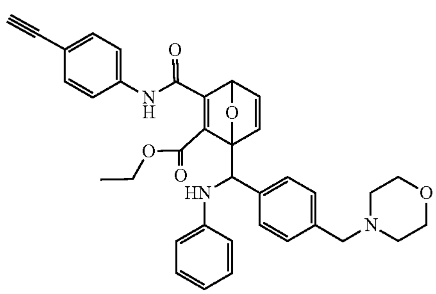 [SMILES: C#Cc1ccc(NC(=O)C2=C(C(=O)OCC)C3(C(Nc4ccccc4)c4ccc(CN5CCOCC5)cc4)C=CC2O3)cc1] | | ++ | | | ++ |
| 579 | 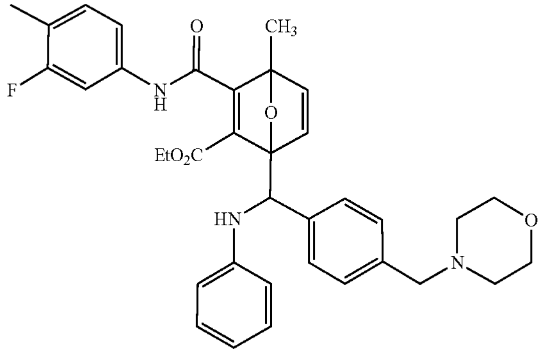 [SMILES: CCOC(=O)C1=C(C(=O)Nc2ccc(C)c(F)c2)C2(C)C=CC1(C(Nc1ccccc1)c1ccc(CN3CCOCC3)cc1)O2] | | + | | | + |

TABLE I-continued
compounds synthesized and biological activities.
| Compound number | Structure | SUMO | Nedd8 | Atg7 | Ubiquitin | c-Myc |
|---|---|---|---|---|---|---|
| 581 | 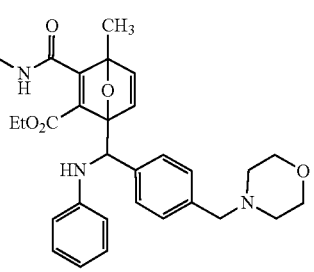 | + | | | | + |
| 582 | 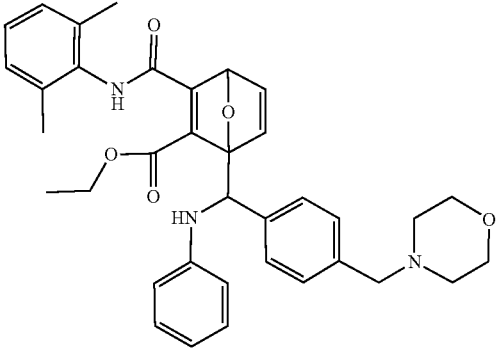 [SMILES: CCOC(=O)C1=C(C(=O)Nc2c(C)cccc2C)C2C=CC1(C(Nc1ccccc1)c1ccc(CN3CCOCC3)cc1)O2] | ++ | | | | ++ |
| 584 | 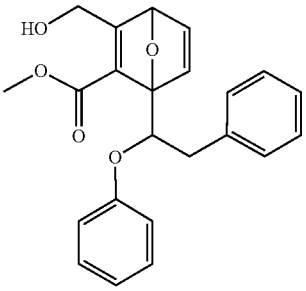 [SMILES: COC(=O)C1=C(CO)C2C=CC1(C(Cc1ccccc1)Oc1ccccc1)O2] | + | | ++ | | ++ |
| 585 | 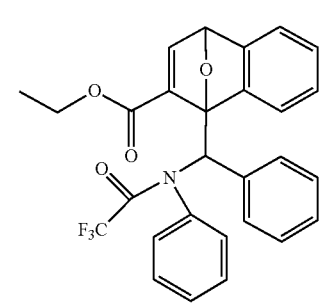 [SMILES: CCOC(=O)C1=CC2OC1(C(c1ccccc1)N(C(=O)C(F)(F)F)c1ccccc1)c1ccccc12] | + | | + | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 586 | 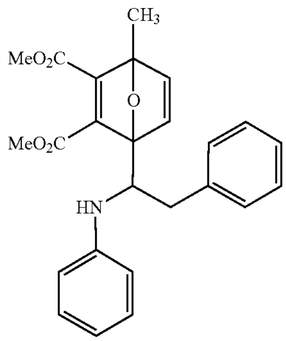 [SMILES: COC(=O)C1=C(C(=O)OC)C2(C(Cc3ccccc3)Nc3ccccc3)C=CC1(C)O2] | ++ | | | | + |
| 588 | 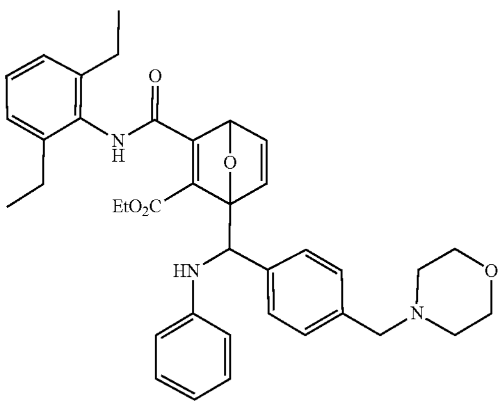 [SMILES: CCOC(=O)C1=C(C(=O)Nc2c(CC)cccc2CC)C2C=CC1(C(Nc1ccccc1)c1ccc(CN3CCOCC3)cc1)O2] | ++ | | | | ++ |
| 590 | 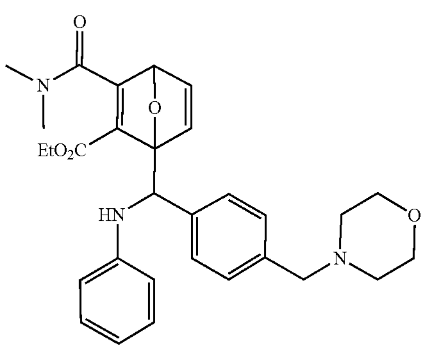 [SMILES: CCOC(=O)C1=C(C(=O)N(C)C)C2C=CC1(C(Nc1ccccc1)c1ccc(CN3CCOCC3)cc1)O2] | + | | | | + |
| 591 | 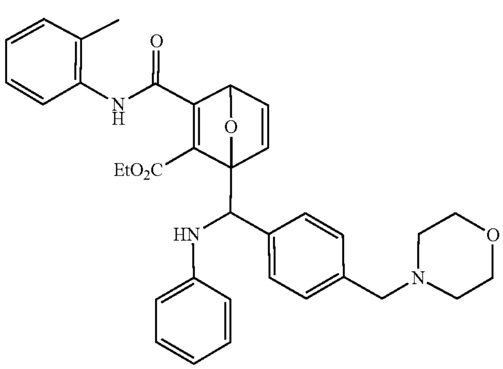 [SMILES: CCOC(=O)C1=C(C(=O)Nc2ccccc2C)C2C=CC1(C(Nc1ccccc1)c1ccc(CN3CCOCC3)cc1)O2] | ++ | | | | ++ |

TABLE I-continued compounds synthesized and biological activities.

| Compound number | Structure | SUMO | Nedd8 | Atg7 | Ubiquitin | c-Myc |
|---|---|---|---|---|---|---|
| 593 | 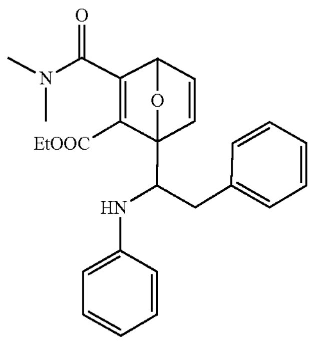 [SMILES: CCOC(=O)C1=C(C(=O)N(C)C)C2C=CC1(C(Cc1ccccc1)Nc1ccccc1)O2] | | | | + | + |
| 594 | 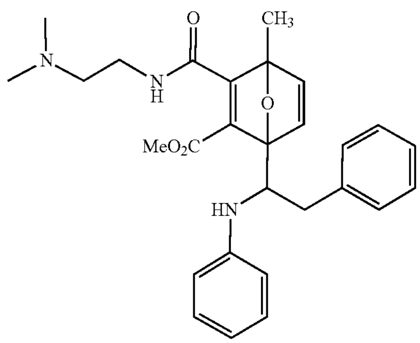 [SMILES: COC(=O)C1=C(C(=O)NCCN(C)C)C2(C)C=CC1(C(Cc1ccccc1)Nc1ccccc1)O2] | ++ | | | | + |
| 595 | 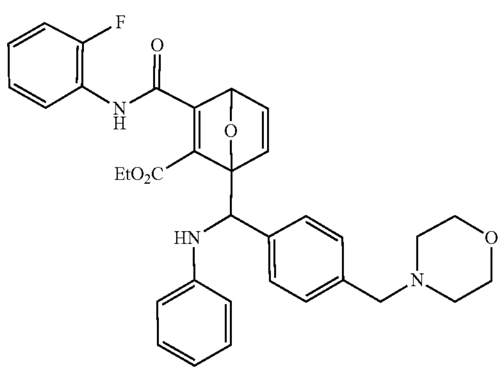 [SMILES: CCOC(=O)C1=C(C(=O)Nc2ccccc2F)C2C=CC1(C(Nc1ccccc1)c1ccc(CN3CCOCC3)cc1)O2] | ++ | | | | + |
| 597 | 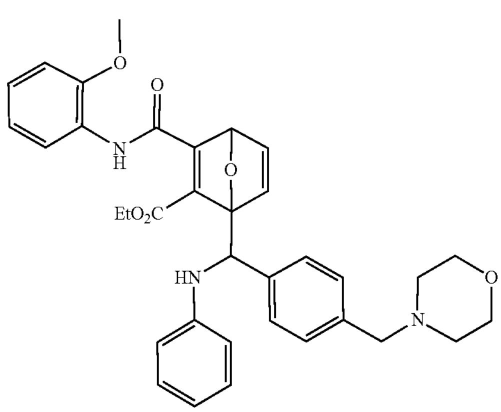 [SMILES: CCOC(=O)C1=C(C(=O)Nc2ccccc2OC)C2C=CC1(C(Nc1ccccc1)c1ccc(CN3CCOCC3)cc1)O2] | + | | | | ++ |

TABLE I-continued
compounds synthesized and biological activities.
| Compound number | Structure | SUMO | Nedd8 | Atg7 | Ubiquitin | c-Myc |
|---|---|---|---|---|---|---|
| 599 | 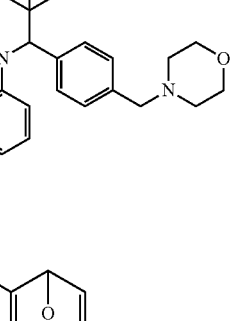 | ++ | | | | ++ |
| 601 | 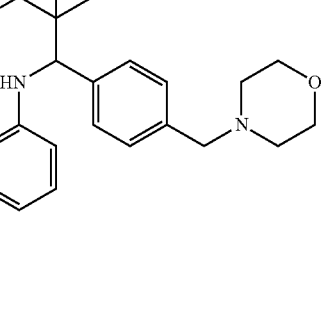 | ++ | | | | + |
| 603 | 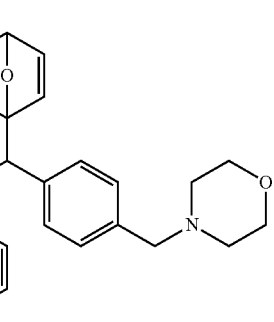 | ++ | | | | |
| 604 | 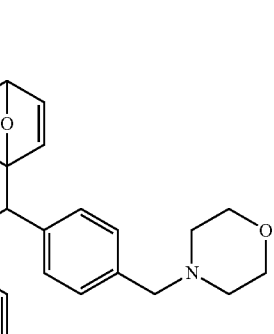 | ++ | | | | + |

TABLE I-continued
compounds synthesized and biological activities.
| Compound number | Structure | SUMO | Nedd8 | Atg7 | Ubiquitin | c-Myc |
|---|---|---|---|---|---|---|
| 606 | 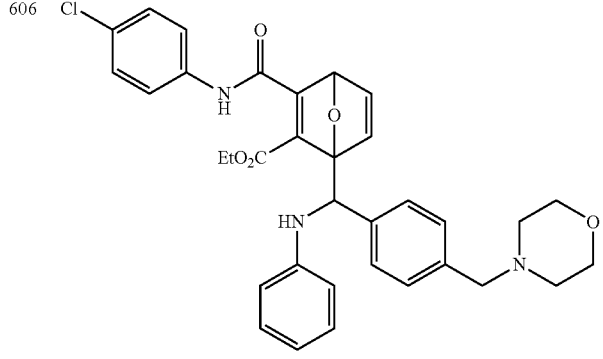 | | ++ | | | + |
| 608 | 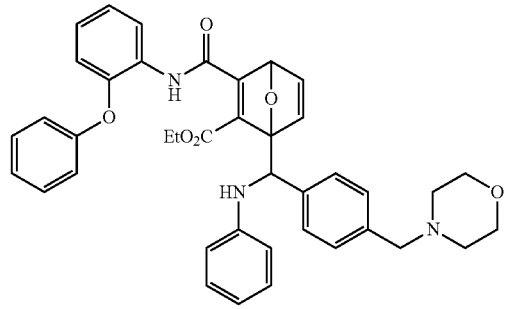 [SMILES: CCOC(=O)C1=C(C(=O)Nc2ccccc2Oc2ccccc2)C2C=CC1(C(Nc1ccccc1)c1ccc(CN3CCOCC3)cc1)O2] | | + | | | + |
| 610 | 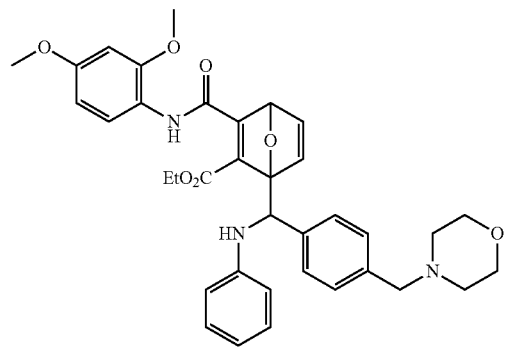 [SMILES: CCOC(=O)C1=C(C(=O)Nc2ccc(OC)cc2OC)C2C=CC1(C(Nc1ccccc1)c1ccc(CN3CCOCC3)cc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 612 | 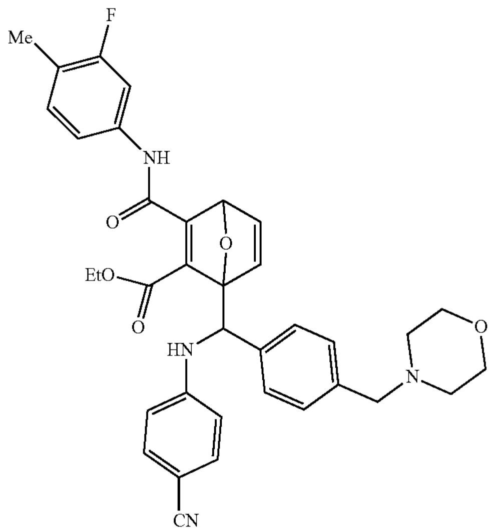 [SMILES: CCOC(=O)C1=C(C(=O)Nc2ccc(C)c(F)c2)C2C=CC1(C(Nc1ccc(C#N)cc1)c1ccc(CN3CCOCC3)cc1)O2] | | + | | | + |
| 613 | 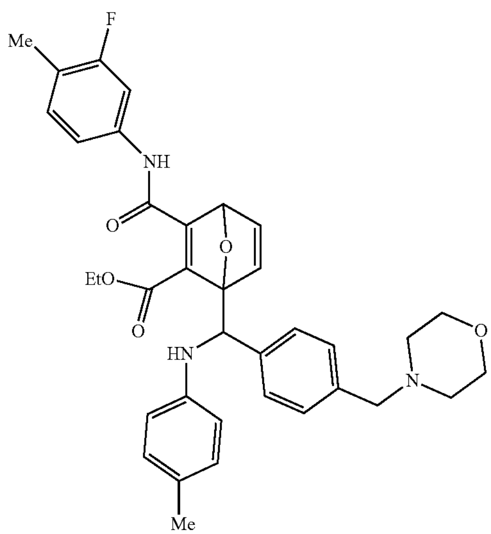 [SMILES: CCOC(=O)C1=C(C(=O)Nc2ccc(C)c(F)c2)C2C=CC1(C(Nc1ccc(C)cc1)c1ccc(CN3CCOCC3)cc1)O2] | | + | | | + |
| 615 | 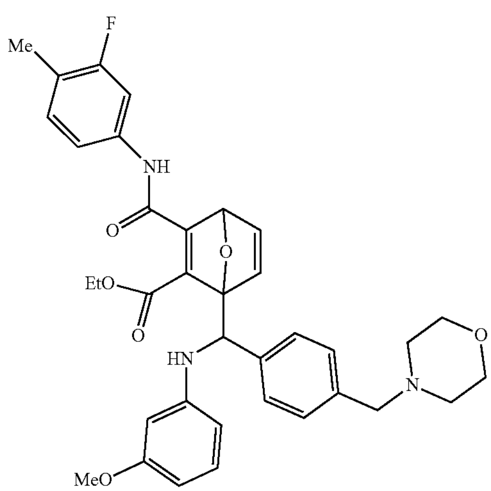 [SMILES: CCOC(=O)C1=C(C(=O)Nc2ccc(C)c(F)c2)C2C=CC1(C(Nc1cccc(OC)c1)c1ccc(CN3CCOCC3)cc1)O2] | | + | | | + |

TABLE I-continued compounds synthesized and biological activities.

| Compound number | Structure | SUMO | Nedd8 | Atg7 | Ubiquitin | c-Myc |
|---|---|---|---|---|---|---|
| 617 | 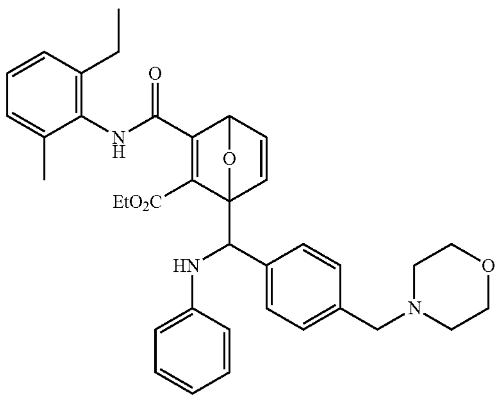 [SMILES: CCOC(=O)C1=C(C(=O)Nc2c(C)cccc2CC)C2C=CC1(C(Nc1ccccc1)c1ccc(CN3CCOCC3)cc1)O2] | ++ | | | | ++ |
| 619 | 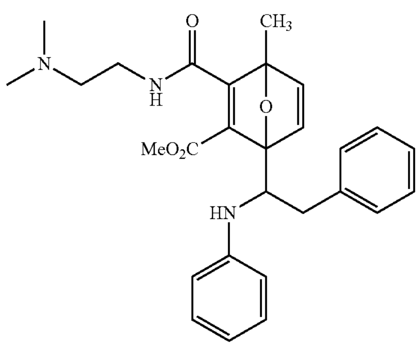 [SMILES: COC(=O)C1=C(C(=O)NCCN(C)C)C2(C)C=CC1(C(Cc1ccccc1)Nc1ccccc1)O2] | ++ | + | | | + |
| 621 | 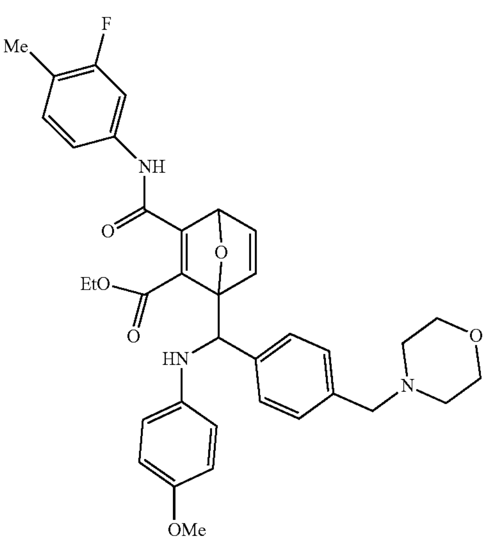 [SMILES: CCOC(=O)C1=C(C(=O)Nc2ccc(C)c(F)c2)C2C=CC1(C(Nc1ccc(OC)cc1)c1ccc(CN3CCOCC3)cc1)O2] | + | | | | + |

TABLE I-continued compounds synthesized and biological activities.

| Compound number | Structure | SUMO | Nedd8 | Atg7 | Ubiquitin | c-Myc |
|---|---|---|---|---|---|---|
| 623 | 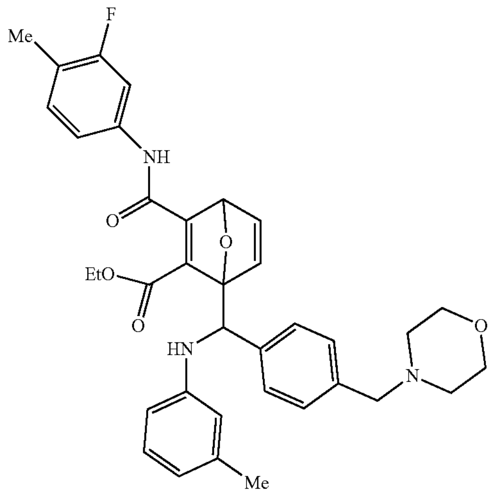 [SMILES: CCOC(=O)C1=C(C(=O)Nc2ccc(C)c(F)c2)C2C=CC1(C(Nc1cccc(C)c1)c1ccc(CN3CCOCC3)cc1)O2] | ++ | | | | + |
| 625 | 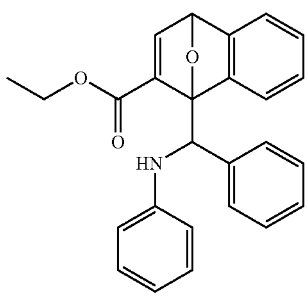 [SMILES: CCOC(=O)C1=CC2OC1(C(Nc1ccccc1)c1ccccc1)c1ccccc12] | + | | | | + |
| 626 | 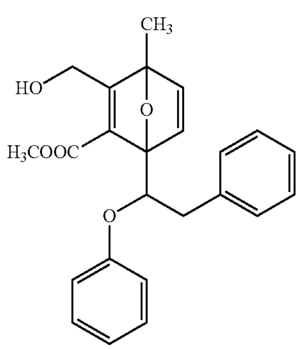 | + | ++ | | | |
| 627 | 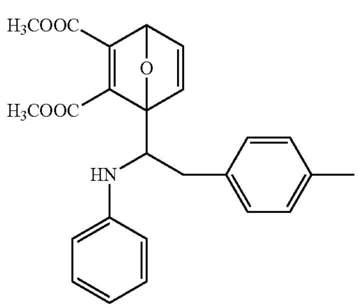 | +++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 629 | 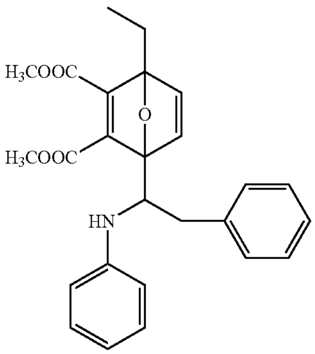 | ++ | | | | |
| 630 | 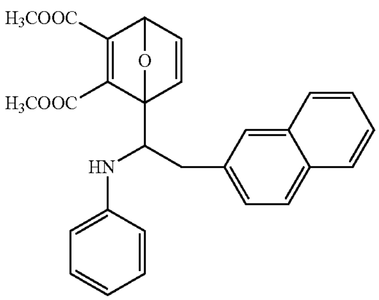 | +++ | | | | |
| 632 | 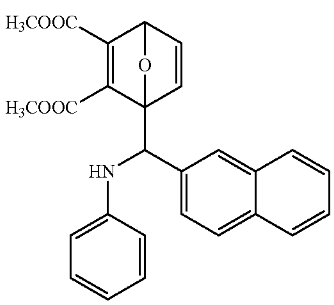 | +++ | | | | |
| 633 | 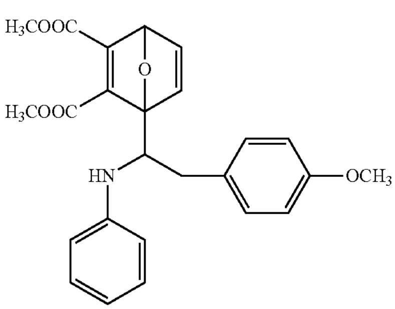 | +++ | | | | |

TABLE I-continued
compounds synthesized and biological activities.
| Compound number | Structure | SUMO | Nedd8 | Atg7 | Ubiquitin | c-Myc |
|---|---|---|---|---|---|---|
| 635 | 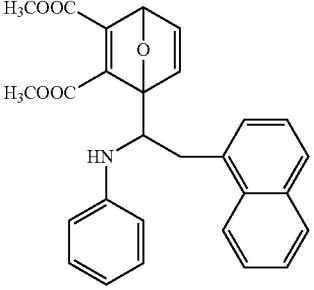 | ++ | | | | |
| 636 | 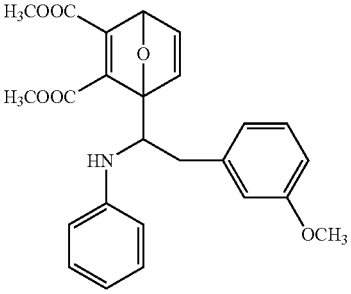 | +++ | | | | |
| 637 | 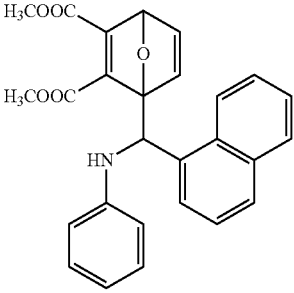 | +++ | | | | |
| 639 | 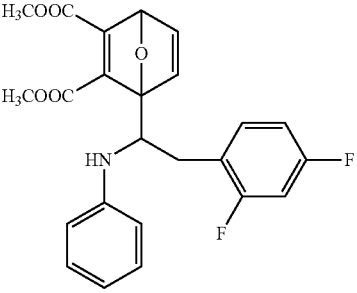 | ++ | | | | |
| 640 | 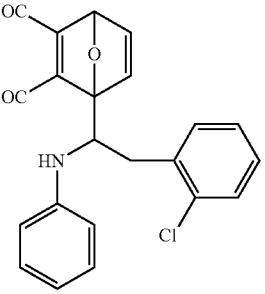 | +++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 641 | H3COOC, H3COOC-substituted oxabicyclic with CH(NHPh)CH2-(2,4-dichlorophenyl) | +++ | | | | |
| 642 | H3COOC, H3COOC-substituted oxabicyclic with CH(NHPh)CH2-(3,4-dichlorophenyl) | +++ | | | | |
| 643 | H3COOC, H3COOC-substituted oxabicyclic with CH(NHPh)CH2-(4-cyanophenyl) | ++ | | | | |
| 644 | H3COOC, H3COOC-substituted oxabicyclic with CH(NHPh)CH2-(4-ethoxyphenyl) | ++ | | | | |
| 647 | H3COOC, H3COOC-substituted oxabicyclic with CH(NHPh)CH2-(4-OCF3-phenyl) | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 648 | 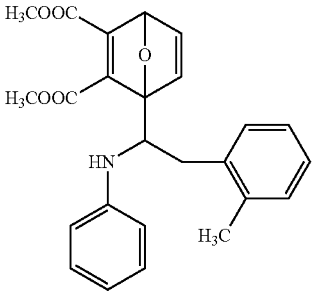 | ++ | | | | |
| 649 | 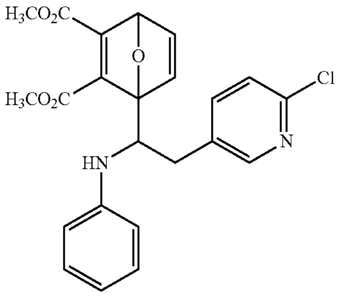 [SMILES: COC(=O)C1=C(C(=O)OC)C2(C(Cc3ccc(Cl)nc3)Nc3ccccc3)C=CC1O2] | ++ | | | | |
| 650 | 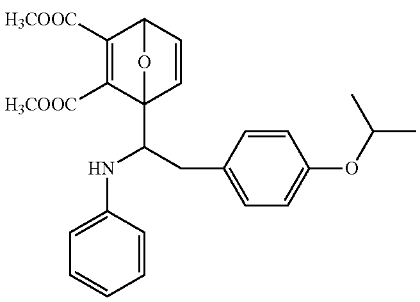 | ++ | | | | |
| 651 | 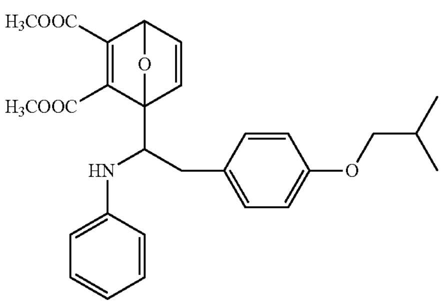 | ++ | | | | |
| 652 | 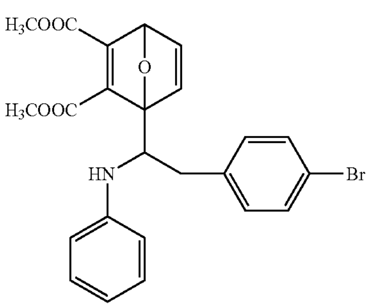 | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 653 | (structure) | ++ | | | | |
| 654 | (structure) | ++ | | | | |
| 655 | (structure) | ++ | | | | |
| 656 | (structure) | ++ | | | | |
| 657 | (structure) | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 658 | (structure) | | ++ | | | |
| 659 | (structure) | | ++ | | | |
| 660 | (structure) | | ++ | | | |
| 662 | (structure) | | + | | | |

TABLE I-continued compounds synthesized and biological activities.

| Compound number | Structure | SUMO | Nedd8 | Atg7 | Ubiquitin | c-Myc |
|---|---|---|---|---|---|---|
| 663 | (structure) | ++ | | | | |
| 664 | (structure) | ++ | | | | |
| 665 | (structure) | ++ | | | | |
| 667 | (structure) | ++ | | | | |
| 668 | (structure) | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 669 | 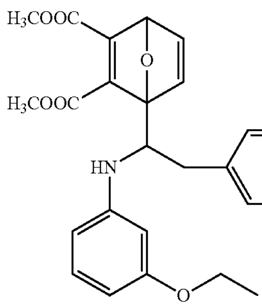 | ++ | | | | |
| 670 | 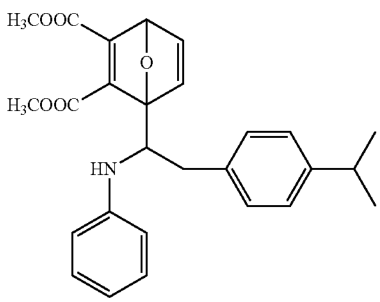 | ++ | | | | |
| 671 | 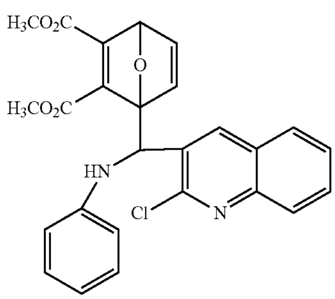 [SMILES: COC(=O)C1=C(C(=O)OC)C2(C(Nc3ccccc3)c3cc4ccccc4nc3Cl)C=CC1O2] | ++ | | | | |
| 672 | 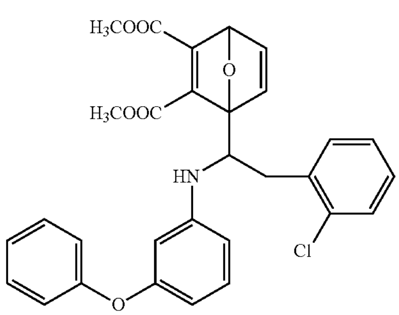 | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 673 | 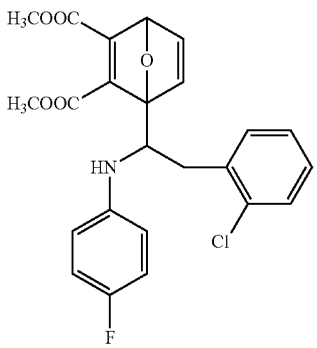 | ++ | | | | |
| 674 | 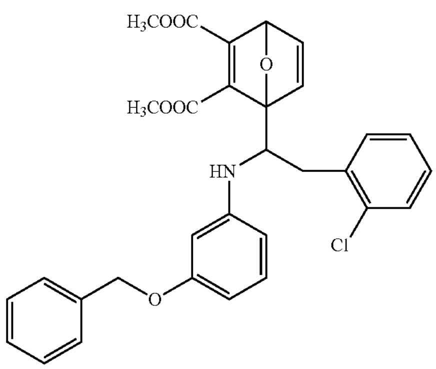 | ++ | | | | |
| 675 | 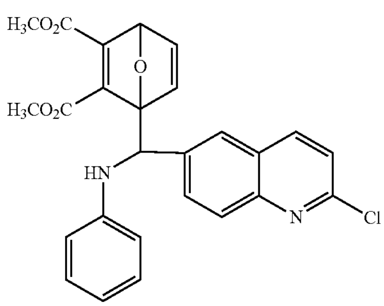 [SMILES: COC(=O)C1=C(C(=O)OC)C2(C(Nc3ccccc3)c3ccc4nc(Cl)ccc4c3)C=CC1O2] | ++ | | | | |
| 676 | 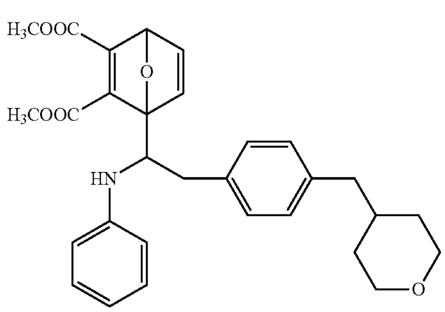 | ++ | | | | |

TABLE I-continued compounds synthesized and biological activities.

| Compound number | Structure | SUMO | Nedd8 | Atg7 | Ubiquitin | c-Myc |
|---|---|---|---|---|---|---|
| 677 | 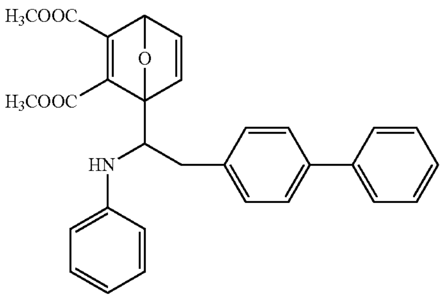 | | ++ | | | |
| 678 | 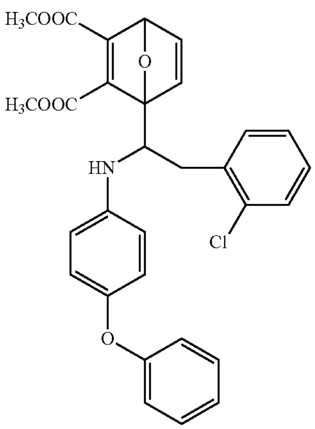 | | + | | | |
| 679 | 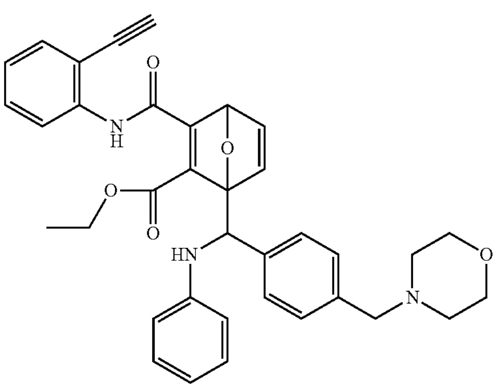 [SMILES: C#Cc1ccccc1NC(=O)C1=C(C(=O)OCC)C2(C(Nc3ccccc3)c3ccc(CN4CCOCC4)cc3)C=CC1O2] | | | | | |
| 681 | 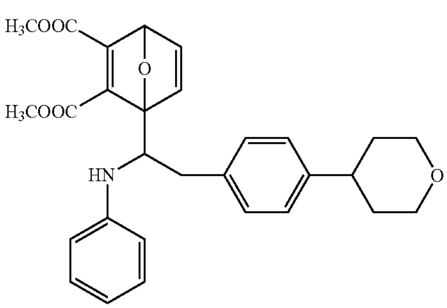 | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 682 | 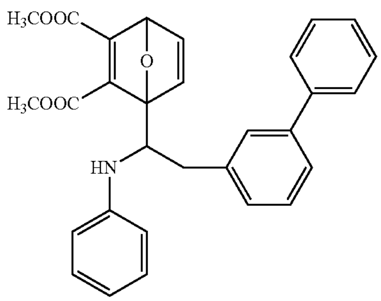 | + | | | | |
| 683 | 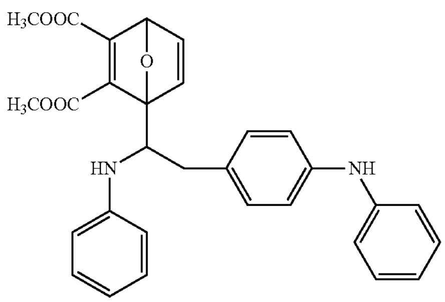 | + | | | | |
| 684 | 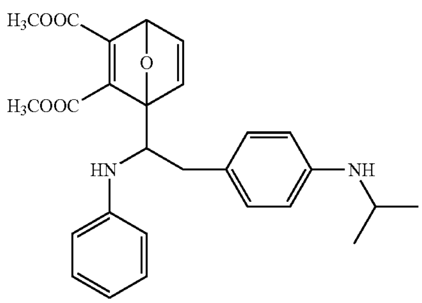 | + | | | | |
| 685 | 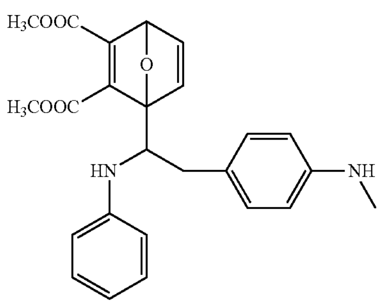 | ++ | | | | |
| 687 | 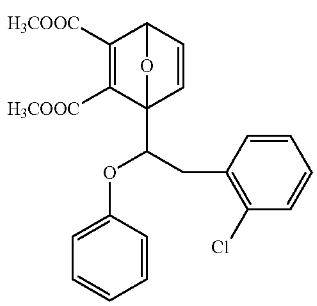 | + | | | | |

TABLE I-continued compounds synthesized and biological activities.

| Compound number | Structure | SUMO | Nedd8 | Atg7 | Ubiquitin | c-Myc |
|---|---|---|---|---|---|---|
| 688 | 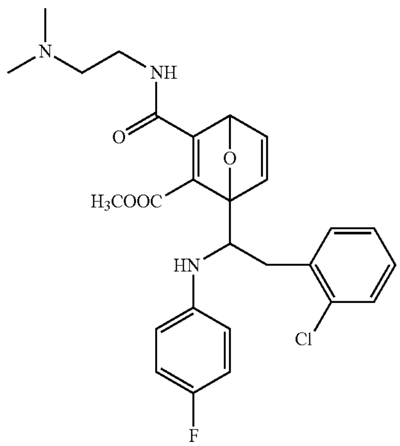 | | +++ | | | |
| 689 | 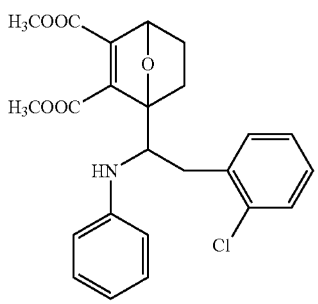 | | + | | | |
| 691 | 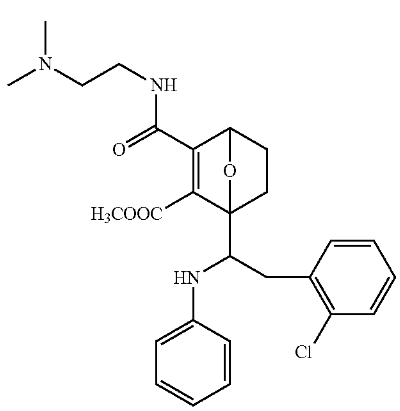 | | ++ | | | |

TABLE I-continued compounds synthesized and biological activities.

| Compound number | Structure | SUMO | Nedd8 | Atg7 | Ubiquitin | c-Myc |
|---|---|---|---|---|---|---|
| 692 | 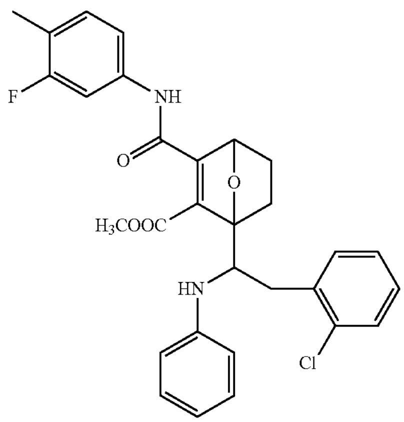 | | | + | | |
| 693 | 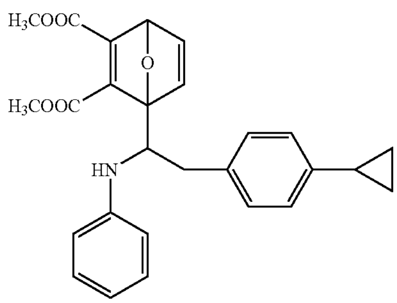 | | | ++ | | |
| 694 | 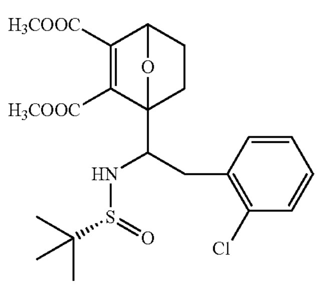 | | | ++ | | |
| 696 | 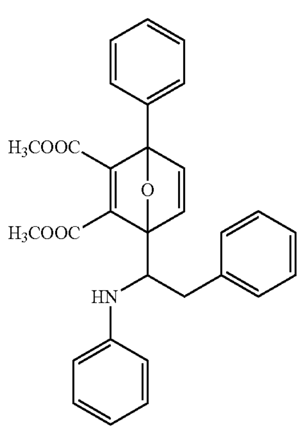 | | | + | | |

TABLE I-continued compounds synthesized and biological activities.

| Compound number | Structure | SUMO | Nedd8 | Atg7 | Ubiquitin | c-Myc |
|---|---|---|---|---|---|---|
| 698 | [structure] | | +++ | | | |

Activities are listed as + (less active), ++ (active), +++ (most active)

C. Example 3. Methods of Screening

More than 97% of the human proteome have not been addressed by FDA approved drugs of all diseases. An approach to accelerate the discovery of druggable sites and novel targets is by using compound libraries that can form covalent adducts with proteins in the proteome. Such a compound library can be used to screen a cellular disease model and compare with a non-disease model to identify compounds that have potential therapeutic benefit for the disease. Then, quantitative mass spectrometry approaches will be used to identify the specific site(s) in specific target(s) in the cells that the hit(s) covalently bind to through competition with an affinity labeled tool compound.

Such novel target and druggable site identification outcome is affected by the functional groups that form covalent bonds with proteins, known as "warhead" in these libraries. The warhead in the compound library provided herein is different from others used for such studies, and thus is unique. It led to the discovery of Cys30 of the SAE2/Uba2 as a novel druggable site in this novel target.

Ref: Counihan J L*, Wiggenhorn A*, Anderson K E, Nomura D K. (2018) Chemoproteomics-enabled covalent ligand screening reveals ALDH3A1 as a lung cancer target. AC S Chemical Biology doi:10.1021/acschembio.8b00381.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of formula:

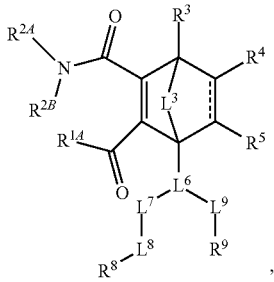

(II)

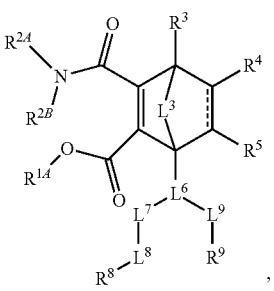

(III)

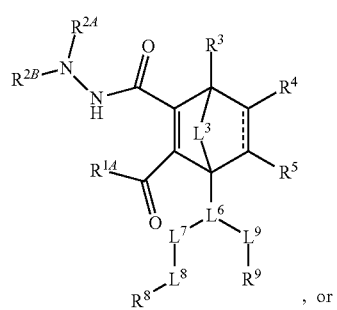

(IV)

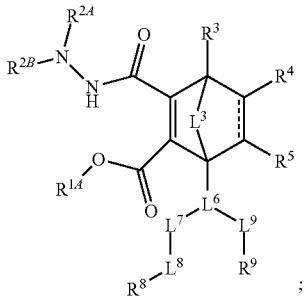

(V)

wherein

═ is a single bond or double bond;

$L^3$ is —O—, —S—, or —N(R$^7$)—;

$L^7$ is —O— or —N(R$^{10}$)—;

$R^{1A}$ is hydrogen, halogen, —CX$^{1A}_3$, —CHX$^{1A}_2$, —CH$_2$X$^{1A}$, —OCX$^{1A}_3$, —OCH$_2$X$^{1A}$, —OCHX$^{1A}_2$, —CN, —SO$_{n1A}$R$^{1AA}$, —SO$_{v1A}$NR$^{1AA}$R$^{1AB}$, —NHC(O)NR$^{1AA}$R$^{1AB}$, —N(O)$_{m1A}$, —NR$^{1AA}$R$^{1AB}$, —NHNR$^{1AA}$R$^{1AB}$, —C(O)R$^{1AA}$, —C(O)—OR$^{1AA}$, —C(O)NR$^{1AA}$R$^{1AB}$, —OR$^{1AA}$, —NR$^{1AA}$SO$_2$R$^{1AB}$, —NR$^{1AA}$C(O)R$^{1AB}$, —NR$^{1AA}$C(O)OR$^{1AB}$, —NR$^{1AA}$OR$^{1AB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —CX$^{2A}_3$, —CHX$^{2A}_2$, —CH$_2$X$^{2A}$, —OCX$^{2A}_3$, —OCH$_2$X$^{2A}$, —OCHX$^{2A}_2$, —CN, —SO$_{n2A}$R$^{2AA}$, —SO$_{v2A}$NR$^{2AA}$R$^{2AB}$, —NHC(O)NR$^{2AA}$R$^{2AB}$, —N(O)$_{m2A}$, —NR$^{2AA}$R$^{2AB}$, —NHNR$^{2AA}$R$^{2AB}$, —C(O)R$^{2AA}$, —C(O)—OR$^{2AA}$, —C(O)NR$^{2AA}$R$^{2AB}$, —OR$^{2AA}$, —NR$^{2AA}$SO$_2$R$^{2AB}$, —NR$^{2AA}$C(O)R$^{2AB}$, —NR$^{2AA}$C(O)OR$^{2AB}$, —NR$^{2AA}$OR$^{2AB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2B}$ is hydrogen, halogen, —CX$^{2B}_3$, —CHX$^{2B}_2$, —CH$_2$X$^{2B}$, —OCX$^{2B}_3$, —OCH$_2$X$^{2B}$, —OCHX$^{2B}_2$, —CN, —SO$_{n2B}$R$^{2BA}$, —SO$_{v2B}$NR$^{2BA}$R$^{2BB}$, —NHC(O)NR$^{2BA}$R$^{2BB}$, —N(O)$_{m2B}$, —NR$^{2BA}$R$^{2BB}$, —NHNR$^{2BA}$R$^{2BB}$, —C(O)R$^{2BA}$, —C(O)—OR$^{2BA}$, —C(O)NR$^{2BA}$R$^{2BB}$, —OR$^{2BA}$, —NR$^{2BA}$SO$_2$R$^{2BB}$, —NR$^{2BA}$C(O)R$^{2BB}$, —NR$^{2BA}$C(O)OR$^{2BB}$, —NR$^{2BA}$OR$^{2BB}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4A}$, —SO$_{v4}$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O) R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n5}$R$^{5A}$, —SO$_{v5}$NR$^{5A}$R$^{5B}$, —NHC(O)NR$^{5A}$R$^{5B}$, —N(O)$_{m5}$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O) NHNR$^{5A}$R$^{5B}$, —OR$^{5A}$, —NR$^{5A}$SO$_2$R$^{5B}$, —NR$^{5A}$C(O) R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted aryl, or substituted or unsubstituted heteroaryl;

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O) NHNR$^{7A}$R$^{7B}$, —OR$^{7A}$, —NR$^{7A}$SO$_2$R$^{7B}$, —NR$^{7A}$C(O) R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —CN, —SO$_{n8}$R$^{8A}$, —SO$_{v8}$NR$^{8A}$R$^{8B}$, —NHC(O)NR$^{8A}$R$^{8B}$, —N(O)$_{m8}$, —NR$^{8A}$R$^{8B}$, —NHNR$^{8A}$R$^{8B}$, —C(O)R$^{8A}$, —C(O)—OR$^{8A}$, —C(O)NR$^{8A}$R$^{8B}$, —C(O) NHNR$^{8A}$R$^{8B}$, —OR$^{8A}$, —NR$^{8A}$SO$_2$R$^{8B}$, —NR$^{8A}$C(O) R$^{8B}$, —NR$^{8A}$C(O)OR$^{8B}$, —NR$^{8A}$OR$^{8B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is halogen, —CX$^9_3$, —CHX$^9_2$, —CH$_2$X$^9$, —OCX$^9_3$, —OCH$_2$X$^9$, —OCHX$^9_2$, —CN, —SO$_{n9}$R$^{9A}$, —SO$_{v9}$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)— OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C (O)OR$^{9B}$, —NR$^{9A}$OR$^{9B}$, —N$_3$, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10A}$, —SO$_{v10}$NR$^{10A}$R$^{10B}$, —NHC(O) NR$^{10A}$R$^{10B}$, —N(O)$_{m10}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O) OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R$^{1AA}$, R$^{1AB}$, R$^{2AA}$, R$^{2AB}$, R$^{2BA}$, R$^{2BB}$, R$^{3A}$, R$^{3B}$, R$^{4A}$, R$^{4B}$, R$^{5A}$, R$^{5B}$, R$^{7A}$, R$^{7B}$, R$^{8A}$, R$^{8B}$, R$^{9A}$, R$^{9B}$, R$^{10A}$, and R$^{10B}$ is independently hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC= (O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1AA}$ and R$^{1AB}$ substituents bonded to the same nitrogen atom may optionally be joined to form a substituted or unsubstituted heterocycloalkyl or substituted or unsubstituted heteroaryl; R$^{2AA}$ and R$^{2AB}$ substituents bonded to the same nitrogen atom may optionally be joined to form a substituted or unsubstituted heterocycloalkyl or substituted or unsubstituted heteroaryl; R$^{2BA}$ and R$^{2BB}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{8A}$ and R$^{8B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl;

m1A, m2A, m2B, m3, m4, m5, m7, m8, m9, and m10 are independently 1 or 2;

v1A, v2A, v2B, v3, v4, v5, v7, v8, v9, and v10 are independently 1 or 2;

n1A, n2A, n2B, n3, n4, n5, n7, n8, n9, and n10 are independently an integer from 0 to 4;

X, $X^{1A}$, $X^{2A}$, $X^{2B}$, $X^3$, $X^4$, $X^5$, $X^7$, $X^8$, $X^9$, and $X^{10}$ are independently —Cl, —Br, —I, or —F;

$L^6$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^8$ is a bond, —C(O)—, —C(O)NH—, —C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^9$ is a bond, —O—, —S—, —NH—, —C(O)—, —C(O)O—, —C(O)NH—, —OC(O)—, —NHC(O)—, —NHC(O)NH—, —OC(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein $R^{2A}$ and $R^{2B}$ may optionally be joined to form a substituted or unsubstituted heterocycloalkyl or substituted or unsubstituted heteroaryl; and $R^4$ and $R^5$ may optionally be joined to form a substituted or unsubstituted cycloalkyl, substituted or unsubstituted heterocycloalkyl, substituted or unsubstituted aryl, or substituted or unsubstituted heteroaryl.

2. The compound of claim 1, having the formula:

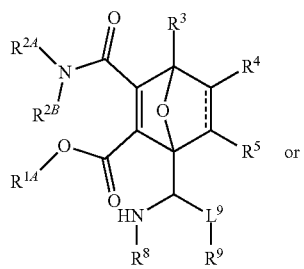

(IIIa)

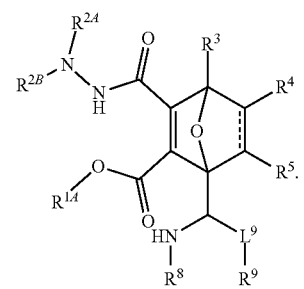

(Va)

3. The compound of claim 1, wherein $R^3$, $R^4$, or $R^5$ is hydrogen.

4. The compound of claim 1, wherein $R^8$ is substituted or unsubstituted cycloalkyl, substituted or unsubstituted heterocycloalkyl, substituted or unsubstituted aryl, or substituted or unsubstituted heteroaryl.

5. The compound of claim 1, wherein $R^8$ is substituted or unsubstituted phenyl.

6. The compound of claim 1, wherein $L^9$ is a bond, substituted or unsubstituted alkylene, or substituted or unsubstituted arylene.

7. The compound of claim 1, wherein $L^9$ is an unsubstituted phenylene.

8. The compound of claim 1, wherein $R^9$ is substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

9. The compound of claim 1, wherein $-L^9-R^9$ is

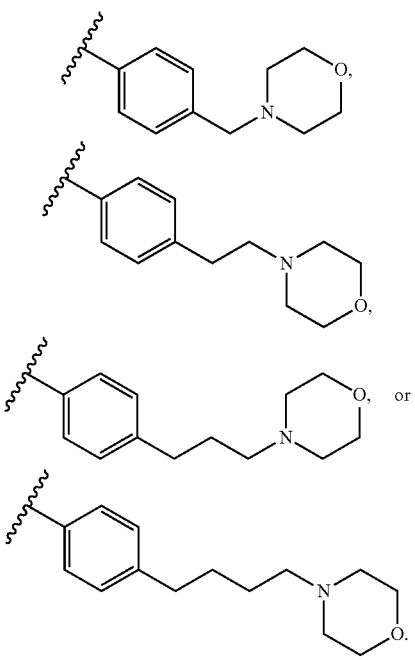

10. The compound of claim 1, wherein $R^{2A}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

11. The compound of claim 1, wherein $R^{2A}$ is substituted or unsubstituted phenyl.

12. The compound of claim 1, wherein $R^{2B}$ is hydrogen.

13. The compound of claim 1, wherein $R^{1A}$ is hydrogen, —$CX^{1A}_3$, —$CHX^{1A}_2$, —$CH_2X^{1A}$, or unsubstituted $C_1$-$C_3$ alkyl.

14. A pharmaceutical composition comprising a compound, or a pharmaceutically acceptable salt thereof, of claim 1 and a pharmaceutically acceptable excipient.

15. A method of inhibiting an E1 enzyme, said method comprising contacting an E1 enzyme with a compound of claim 1, thereby inhibiting said E1 enzyme.

16. The method of claim 15, wherein said method comprises allowing said compound to covalently bind said E1 enzyme.

17. The method of claim 15, further comprising administering to a cancer subject said compound.

18. The compound of claim 1, having the formula:
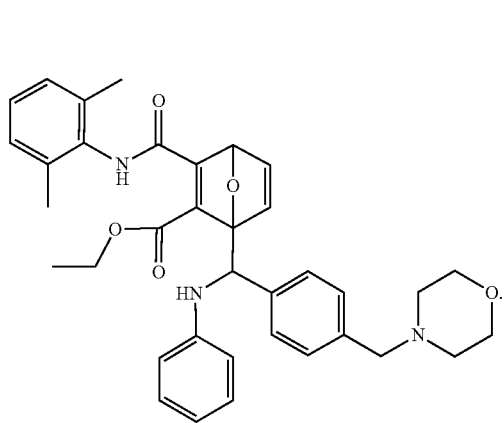 [SMILES: CCOC(=O)C1=C(C(=O)Nc2c(C)cccc2C)C2C=CC1(C(Nc1ccccc1)c1ccc(CN3CCOCC3)cc1)O2]
19. The compound of claim 1, having the formula:
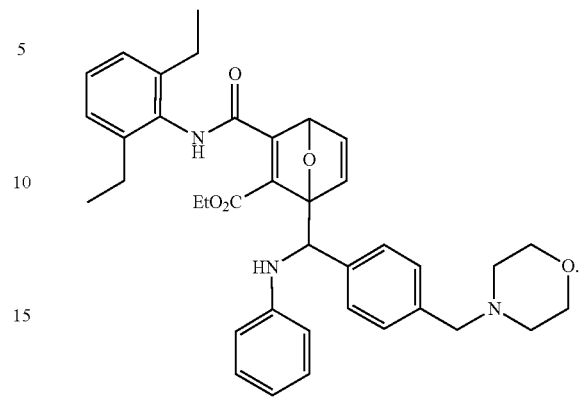
* * * * *

SEQUENCE LISTING

```
<160> NUMBER OF SEQ ID NOS: 7

<210> SEQ ID NO 1
<211> LENGTH: 640
<212> TYPE: PRT
<213> ORGANISM: Artificial Sequence
<220> FEATURE:
<223> OTHER INFORMATION: Synthetic polypeptide

<400> SEQUENCE: 1

Met Ala Leu Ser Arg Gly Leu Pro Arg Glu Leu Ala Glu Ala Val Ala
1               5                   10                  15

Gly Gly Arg Val Leu Val Val Gly Ala Gly Gly Ile Gly Cys Glu Leu
                20                  25                  30

Leu Lys Asn Leu Val Leu Thr Gly Phe Ser His Ile Asp Leu Ile Asp
            35                  40                  45

Leu Asp Thr Ile Asp Val Ser Asn Leu Asn Arg Gln Phe Leu Phe Gln
        50                  55                  60

Lys Lys His Val Gly Arg Ser Lys Ala Gln Val Ala Lys Glu Ser Val
65                  70                  75                  80

Leu Gln Phe Tyr Pro Lys Ala Asn Ile Val Ala Tyr His Asp Ser Ile
                85                  90                  95

Met Asn Pro Asp Tyr Asn Val Glu Phe Phe Arg Gln Phe Ile Leu Val
```

-continued

```
            100                 105                 110
Met Asn Ala Leu Asp Asn Arg Ala Arg Asn His Val Asn Arg Met
            115                 120             125
Cys Leu Ala Ala Asp Val Pro Leu Ile Glu Ser Gly Thr Ala Gly Tyr
    130                 135             140
Leu Gly Gln Val Thr Thr Ile Lys Lys Gly Val Thr Glu Cys Tyr Glu
145                 150                 155                 160
Cys His Pro Lys Pro Thr Gln Arg Thr Phe Pro Gly Cys Thr Ile Arg
                165                 170                 175
Asn Thr Pro Ser Glu Pro Ile His Cys Ile Val Trp Ala Lys Tyr Leu
            180                 185                 190
Phe Asn Gln Leu Phe Gly Glu Glu Asp Ala Asp Gln Glu Val Ser Pro
        195                 200             205
Asp Arg Ala Asp Pro Glu Ala Ala Trp Glu Pro Thr Glu Ala Glu Ala
    210                 215                 220
Arg Ala Arg Ala Ser Asn Glu Asp Gly Asp Ile Lys Arg Ile Ser Thr
225                 230                 235                 240
Lys Glu Trp Ala Lys Ser Thr Gly Tyr Asp Pro Val Lys Leu Phe Thr
                245                 250                 255
Lys Leu Phe Lys Asp Asp Ile Arg Tyr Leu Leu Thr Met Asp Lys Leu
                260                 265                 270
Trp Arg Lys Arg Lys Pro Pro Val Pro Leu Asp Trp Ala Glu Val Gln
            275                 280                 285
Ser Gln Gly Glu Glu Thr Asn Ala Ser Asp Gln Gln Asn Glu Pro Gln
        290                 295                 300
Leu Gly Leu Lys Asp Gln Gln Val Leu Asp Val Lys Ser Tyr Ala Arg
305                 310                 315                 320
Leu Phe Ser Lys Ser Ile Glu Thr Leu Arg Val His Leu Ala Glu Lys
                325                 330                 335
Gly Asp Gly Ala Glu Leu Ile Trp Asp Lys Asp Pro Ser Ala Met
            340                 345                 350
Asp Phe Val Thr Ser Ala Ala Asn Leu Arg Met His Ile Phe Ser Met
        355                 360                 365
Asn Met Lys Ser Arg Phe Asp Ile Lys Ser Met Ala Gly Asn Ile Ile
    370                 375                 380
Pro Ala Ile Ala Thr Thr Asn Ala Val Ile Ala Gly Leu Ile Val Leu
385                 390                 395                 400
Glu Gly Leu Lys Ile Leu Ser Gly Lys Ile Asp Gln Cys Arg Thr Ile
                405                 410                 415
Phe Leu Asn Lys Gln Pro Asn Pro Arg Lys Lys Leu Leu Val Pro Cys
                420                 425                 430
Ala Leu Asp Pro Pro Asn Pro Asn Cys Tyr Val Cys Ala Ser Lys Pro
            435                 440                 445
Glu Val Thr Val Arg Leu Asn Val His Lys Val Thr Val Leu Thr Leu
    450                 455                 460
Gln Asp Lys Ile Val Lys Glu Lys Phe Ala Met Val Ala Pro Asp Val
465                 470                 475                 480
Gln Ile Glu Asp Gly Lys Gly Thr Ile Leu Ile Ser Ser Glu Glu Gly
                485                 490                 495
Glu Thr Glu Ala Asn Asn His Lys Lys Leu Ser Glu Phe Gly Ile Arg
                500                 505                 510
Asn Gly Ser Arg Leu Gln Ala Asp Asp Phe Leu Gln Asp Tyr Thr Leu
            515                 520                 525
```

```
Leu Ile Asn Ile Leu His Ser Glu Asp Leu Gly Lys Asp Val Glu Phe
        530                 535                 540

Glu Val Val Gly Asp Ala Pro Glu Lys Val Gly Pro Lys Gln Ala Glu
545                 550                 555                 560

Asp Ala Ala Lys Ser Ile Thr Asn Gly Ser Asp Asp Gly Ala Gln Pro
                565                 570                 575

Ser Thr Ser Thr Ala Gln Glu Gln Asp Asp Val Leu Ile Val Asp Ser
                580                 585                 590

Asp Glu Glu Asp Ser Ser Asn Asn Ala Asp Val Ser Glu Glu Glu Arg
            595                 600                 605

Ser Arg Lys Arg Lys Leu Asp Glu Lys Glu Asn Leu Ser Ala Lys Arg
        610                 615                 620

Ser Arg Ile Glu Gln Lys Glu Glu Leu Asp Asp Val Ile Ala Leu Asp
625                 630                 635                 640

<210> SEQ ID NO 2
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 2

Leu Val Gly Ala Gly Ala Ile Gly Cys Glu Leu Leu Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Val Val Gly Ala Gly Gly Ile Gly Cys Glu Leu Leu Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 4

Val Ile Gly Ala Gly Gly Leu Gly Cys Glu Leu Leu Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 5

Ile Val Gly Cys Gly Gly Leu Gly Cys Pro Leu Ala Gln
1               5                   10

<210> SEQ ID NO 6
<211> LENGTH: 13
<212> TYPE: PRT
<213> ORGANISM: Artificial Sequence
```

```
<220> FEATURE:
<223> OTHER INFORMATION: Synthetic polypeptide

<400> SEQUENCE: 6

Leu Val Gly Ala Gly Ala Ile Gly Cys Glu Leu Leu Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 7

Leu Leu Gly Ala Gly Thr Leu Gly Cys Asn Val Ala Arg
1               5                   10
```